(12) United States Patent
Kaldor et al.

(10) Patent No.: US 10,927,111 B2
(45) Date of Patent: Feb. 23, 2021

(54) INHIBITORS OF RAF KINASES

(71) Applicant: Kinnate Biopharma Inc., San Diego, CA (US)

(72) Inventors: Stephen W. Kaldor, San Diego, CA (US); Toufike Kanouni, Rancho Santa Fe, CA (US); Lee Arnold, Rancho Santa Fe, CA (US)

(73) Assignee: KINNATE BIOPHARMA INC., San Diego, CA (US)

( * ) Notice: Subject to any disclaimer, the term of this patent is extended or adjusted under 35 U.S.C. 154(b) by 0 days.

(21) Appl. No.: 16/863,553

(22) Filed: Apr. 30, 2020

(65) Prior Publication Data

US 2020/0347052 A1  Nov. 5, 2020

Related U.S. Application Data

(60) Provisional application No. 62/843,197, filed on May 3, 2019.

(51) Int. Cl.
 *C07D 471/04* (2006.01)
 *C07D 519/00* (2006.01)
(52) U.S. Cl.
 CPC ......... *C07D 471/04* (2013.01); *C07D 519/00* (2013.01)
(58) Field of Classification Search
 CPC .................................................. C07D 471/04
 See application file for complete search history.

(56) References Cited

U.S. PATENT DOCUMENTS

| | | | |
|---|---|---|---|
| 5,846,514 | A | 12/1998 | Foster et al. |
| 6,334,997 | B1 | 1/2002 | Foster et al. |
| 2004/0157827 | A1 | 8/2004 | Pevarello et al. |
| 2005/0256174 | A1 | 11/2005 | Wood et al. |
| 2007/0054916 | A1 | 3/2007 | Patel et al. |
| 2007/0244120 | A1 | 10/2007 | Dumas et al. |
| 2008/0114006 | A1 | 5/2008 | Flynn et al. |
| 2011/0183997 | A1 | 7/2011 | Chianelli et al. |
| 2015/0119392 | A1 | 4/2015 | Flynn et al. |
| 2017/0260207 | A1 | 9/2017 | Aversa et al. |

FOREIGN PATENT DOCUMENTS

| | | |
|---|---|---|
| WO | WO-03068229 A1 | 8/2003 |
| WO | WO-2006071940 A2 | 7/2006 |
| WO | WO-2008034008 A2 | 3/2008 |
| WO | WO-2013184119 A1 | 12/2013 |
| WO | WO-2016038581 A1 | 3/2016 |
| WO | WO-2020198058 A1 | 10/2020 |

OTHER PUBLICATIONS

CAS Chemical Structure Search #3191415 Updated (Apr. 2020).
CAS Chemical Structure Search dated Apr. 24, 2019.
Anastassiadis et al. Comprehensive assay of kinase catalytic activity reveals features of kinase inhibitor selectivity. Nat Biotechnol. 29(11):1039-45 (2011).
Berge et al. Pharmaceutical Salts. Journal of Pharmaceutical Sciences 66(1):1-19 (Jan. 1977).
Evans. Synthesis of radiolabeled compounds. J Radioanal Chem 64(1-2):9-32 (1981).
Kabalka et al. The Synthesis of Radiolabeled Compounds via Organometallic Intermediates. Tetrahedron 45(21):6601-6621 (1989).
PCT/US2020/024009 International Search Report and Written Opinion dated Jul. 28, 2020.
PCT/US2020/030786 Invitation to Pay Additional Fees dated Jul. 14, 2020.
Rosse. Pyridyl Isonicotinamide Inhibitors of RAF Kinase. ACS Med. Chem. Lett. 7:1022-1023 (2016).
PCT/US2020/024009 Invitation to Pay Additional Fees dated Jun. 2, 2020.
Henry et al. Discovery of 1-(3,3-dimethylbutyl)-3-(2-fluoro-4-methyl-5-(7-methyl-2-(methylamino)pyrido[2,3-d]pyrimidin-6-yl)phenyl)urea (LY3009120) as a pan-RAF inhibitor with minimal paradoxical activation and activity against BRAF or RAS mutant tumor cells. J Med Chem 58:4165-4179 (2015).
PCT/US2020/030786 International Search Report and Written Opinion dated Sep. 14, 2020.

*Primary Examiner* — Paul V Ward
(74) *Attorney, Agent, or Firm* — Wilson Sonsini Goodrich & Rosati

(57) ABSTRACT

Provided herein are heteroaryl inhibitors of receptor tyrosine kinase effector (RAF), pharmaceutical compositions comprising said compounds, and methods for using said compounds for the treatment of disease.

29 Claims, No Drawings

INHIBITORS OF RAF KINASES

CROSS REFERENCE TO RELATED APPLICATIONS

This application claims the benefit of U.S. Provisional Application No. 62/843,197, filed May 3, 2019, which is incorporated by reference in the disclosure of this application.

BACKGROUND

RAF kinase functions in the Ras-Raf-MEK-ERK mitogen activated protein kinase (MAPK) pathway (also known as MAPK/ERK pathway) by phosphorylating and activating MEK. By altering the levels and activities of transcription factors, MAPK leads to altered transcription of genes that are important for the cell cycle. Deregulation of MAPK activity occurs frequently in tumors. Accordingly, therapies that target RAF kinase activity are desired for use in the treatment of cancer and other disorders characterized by aberrant MAPK/ERK pathway signaling.

BRIEF SUMMARY OF THE INVENTION

Provided herein are inhibitors of the receptor tyrosine kinase effector Raf (RAF), pharmaceutical compositions comprising said compounds, and methods for using said compounds for the treatment of diseases.

One embodiment provides a compound, or pharmaceutically acceptable salt or solvate thereof, having the structure of Formula (I):

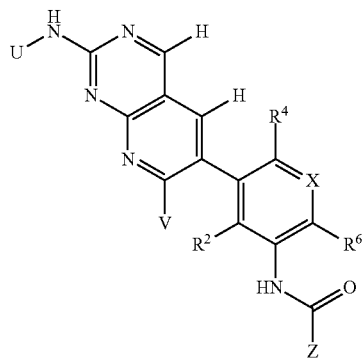

(I)

wherein,
V is hydrogen, halogen, —CN, optionally substituted C1-C4 alkyl, —CD$_3$, optionally substituted C1-C4 alkoxy, optionally substituted C1-C4 alkenyl, or optionally substituted C1-C4 alkynyl;
U is selected from optionally substituted alkyl, —CD$_3$, optionally substituted cycloalkyl, optionally substituted cycloalkylalkyl, optionally substituted heterocyclyl, optionally substituted heterocyclylalkyl, optionally substituted heteroaryl, optionally substituted heteroaralkyl group, optionally substituted —COalkyl, optionally substituted —COcycloalkyl;
X is N, C—H, C-D, or C—F
$R^2$ is H, D or F;
$R^4$ is halogen, optionally substituted C1-C3 alkyl, —CD$_3$, or optionally substituted C1-C3 alkoxy;
$R^6$ is H, D, Cl or F;
Z is selected from:
(a)

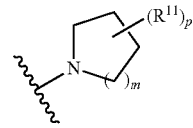

wherein m is 0, 1, 2, or 3; p is 0, 1, 2, 3, or 4; and
each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl; or two $R^{11}$ groups together form an oxo;
(b)

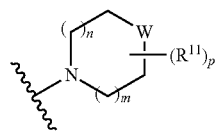

wherein m is 0, 1, 2, or 3; p is 0, 1, 2, 3, or 4;
W is O, S, S(O), SO$_2$, NH or N (optionally substituted C1-C6 alkyl); and
each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two $R^{11}$ groups together form an oxo;
(c)

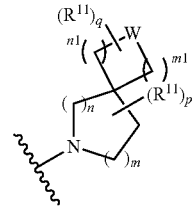

wherein m is 0, 1, or 2; n is 0, 1, or 2; m1 is 0, 1, or 2; n1 is 0, 1, or 2 provided both m1 and n1 are not both 0; p is 0, 1, or 2; and q is 0, 1 or 2;
W is O, S, S(O), SO$_2$, NH or N (optionally substituted C1-C6 alkyl), CH$_2$, CHR$^{11}$, or C(R$^{11}$)$_2$; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two $R^{11}$ groups together form an oxo;

(d)

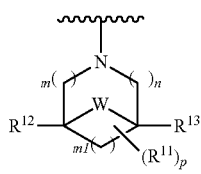

wherein m is 0, 1, or 2; n is 0, 1, or 2; m1 is 1, or 2; p is 0, 1, 2, or 3; W is O, S, S(O), SO$_2$, NH or N (optionally substituted C1-C6 alkyl), CH$_2$, CHR$^{11}$, —CH$_2$—CH$_2$—, —CH$_2$—CHR$^{11}$—, —CH$_2$—C(R$^{11}$)$_2$—, —CHR$^{11}$—CH$_2$—, —C(R$^{11}$)$_2$—CH$_2$—, —NH—CH$_2$—, —NH—CHR$^{11}$—, —NH—C(R$^{11}$)$_2$—, —CH$_2$—NH—, —CHR$^{11}$—NH—, —C(R$^{11}$)$_2$—NH—, —N(R$^{11}$)—CH$_2$—, —N(R$^{11}$)—CHR$^{11}$—, —N(R$^{11}$)—C(R$^{11}$)$_2$—, —CH$_2$—N(R$^{11}$)—, —CHR$^{11}$—N(R$^{11}$)—, —C(R$^{11}$)$_2$—N(R$^{11}$)—; each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo; and R$^{12}$ and R$^{13}$ are each independently selected from H, or optionally substituted C1-C6 alkyl;

(e)

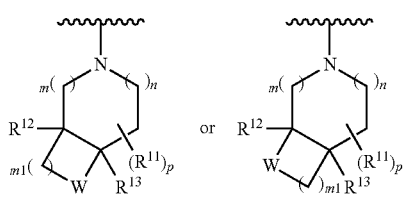

wherein m is 0, 1, or 2; n is 0, 1, or 2; m1 is 0, 1, or 2; p is 0, 1, or 2;
W is O, S, S(O), SO$_2$, NH or N (optionally substituted C1-C6 alkyl), CH$_2$, CHR$^{11}$, or C(R$^{11}$)$_2$ each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo;
and R$^{12}$ and R$^{13}$ are each independently selected from H, or optionally substituted C1-C6 alkyl;

(f)

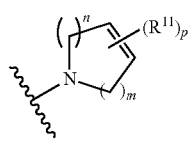

wherein m is 0, 1, 2, or 3; n is 0, 1, 2, or 3 provided both m and n are not both 0; p is 0, 1, 2, 3, or 4; and each R$^{11}$ is independently selected from —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo;

(g)

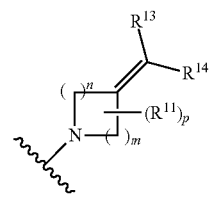

wherein m is 1, 2, or 3; n is 1, 2, or 3; p is 0, 1, or 2; and each R$^{13}$ or R$^{14}$ is independently selected from hydrogen, halogen, —CN, optionally substituted C1-C6 alkyl, or optionally substituted C3-C6 cycloalkyl; each R$^{11}$ is independently selected from —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl;

(h)

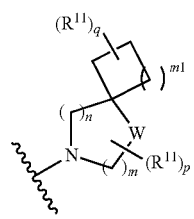

wherein m is 0, 1, or 2; n is 0, 1, or 2; m1 is 0, 1, or 2; p is 0, 1, or 2; and q is 0, 1 or 2; W is O, S, S(O), SO$_2$, NH or N (optionally substituted C1-C6 alkyl), CH$_2$, CHR$^{11}$, or C(R$^{11}$)$_2$; and each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two geminal R$^{11}$ groups together form an oxo; or (i) optionally substituted heteroaryl group.

One embodiment provides a pharmaceutical composition comprising a compound of Formula (I), or pharmaceutically acceptable salt or solvate thereof, and at least one pharmaceutically acceptable excipient.

One embodiment provides a method of treating a disease or disorder in a patient in need thereof comprising administering to the patient a compound of Formula (I), or pharmaceutically acceptable salt or solvate thereof. Another embodiment provides the method wherein the disease or disorder is cancer.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises two carbon atoms (e.g., $C_2$ alkenylene). In other embodiments, an alkenylene comprises five to eight carbon atoms (e.g., $C_5$-$C_8$ alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)R$^a$ (where t is 1 or 2), —R$^b$—S(O)OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$R^a$ (where t is 1 or 2), —$R^b$—S(O)$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

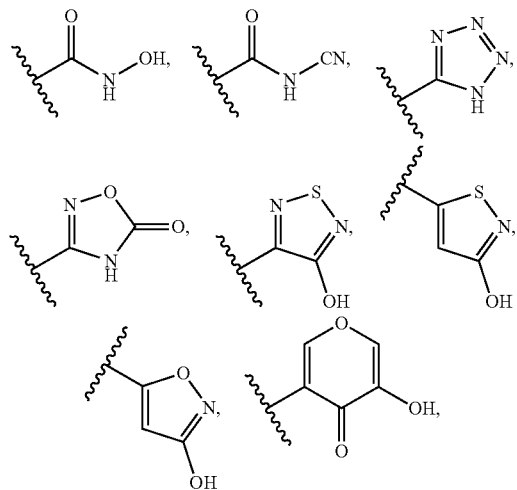

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$R^a$ (where t is 1 or 2), —$R^b$—S(O)$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$R^a$ (where t is 1 or 2), —$R^b$—S(O)$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

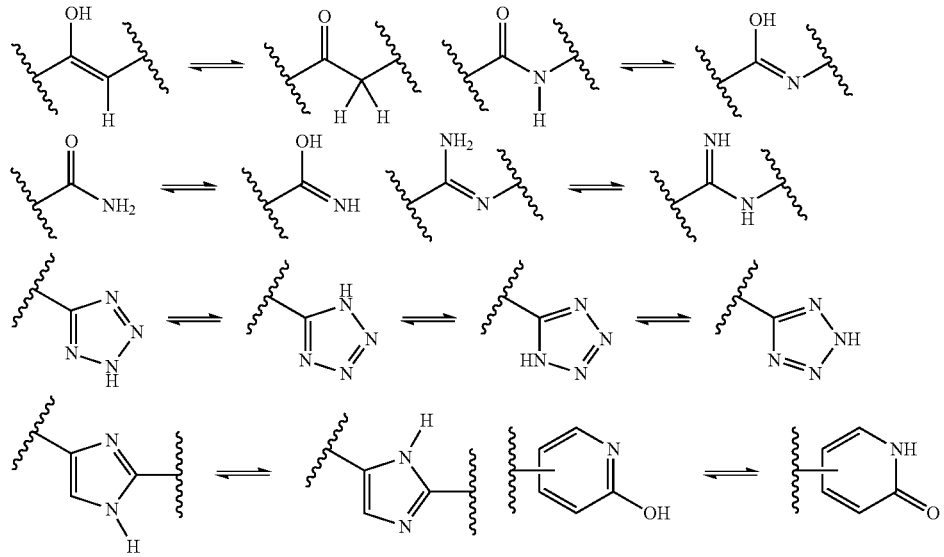

The compounds disclosed herein, in some embodiments, are used in different enriched isotopic forms, e.g., enriched in the content of $^2$H, $^3$H, $^{11}$C, $^{13}$C and/or $^{14}$C. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. In some embodiments, isotopic substitution with $^{18}$F is contemplated. All isotopic variations of the compounds of the present invention, whether radioactive or not, are encompassed within the scope of the present invention.

In certain embodiments, the compounds disclosed herein have some or all of the $^1$H atoms replaced with $^2$H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-$d_3$ ($CD_3I$), are readily available and may be employed to transfer a deuterium-substituted carbon atom under nucleophilic substitution reaction conditions to the reaction substrate. The use of $CD_3I$ is illustrated, by way of example only, in the reaction schemes below.

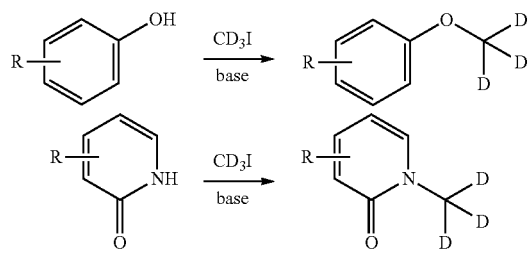

Deuterium-transfer reagents, such as lithium aluminum deuteride ($LiAlD_4$), are employed to transfer deuterium under reducing conditions to the reaction substrate. The use of $LiAD_4$ is illustrated, by way of example only, in the reaction schemes below.

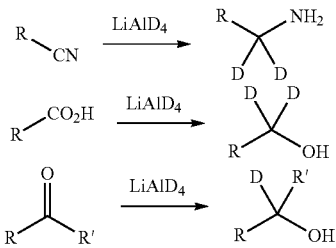

Deuterium gas and palladium catalyst are employed to reduce unsaturated carbon-carbon linkages and to perform a reductive substitution of aryl carbon-halogen bonds as illustrated, by way of example only, in the reaction schemes below.

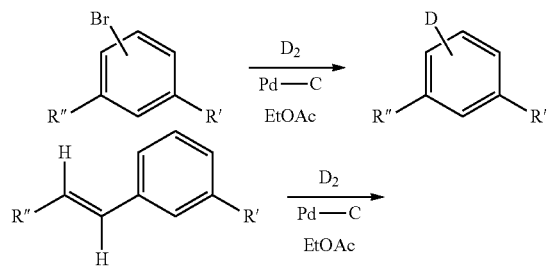

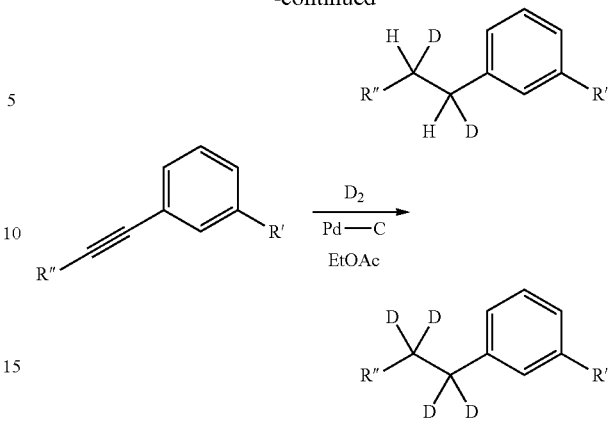

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1H$ hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the heteroaromatic RAF inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein optionally exist in either unsolvated as well as solvated forms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

The RAF Family of Kinases

The RAF kinases are a family of serine/threonine protein kinases constitute core components of the RAS-RAF-MEK-ERK mitogen activated protein kinase (MAPK) signalling cascade (also known as the MAPK/ERK pathway), a pathway that mediates signals from cell surface receptors to the nucleus to regulate cell growth, differentiation and survival. The RAF proteins are related to retroviral oncogenes and are structurally conserved from metazoans to mammals, as is the MAPK/ERK pathway. Their dysregulation leads to uncontrolled cellular proliferation, survival and dedifferentiation. Consequently, RAF kinases are altered or inappropriately activated in a majority of cancers.

The MAPK/ERK signalling pathway is a network of proteins in the cell that communicates a signal from a receptor on the surface of the cell to the DNA in the nucleus of the cell. The signal starts when a signaling molecule binds to the receptor on the cell surface and ends when the DNA in the nucleus expresses a protein and produces some change in the cell, such as cell division. The pathway includes many proteins, which communicate by adding phosphate groups to a neighboring protein, which acts as a molecular "on" or "off" switch, and overall the pathway can be divided into 3 steps: (i) Ras activation, (ii) a kinase signal transduction cascade, and (iii) regulation of translation and transcription. Briefly, an extracellular mitogen or a signaling molecule binds to the membrane receptor. This allows Ras (a small GTPase) to swap its GDP for a GTP and become active. Activated Ras activates the protein kinase activity of RAF kinase. RAF kinase phosphorylates and activates MEK (MEK1 and MEK2). MEK then phosphorylates and activates a MAPK (also known as ERK). MAPK activation regulates activities of several transcription factors and also alters the translation of mRNA to proteins. By altering the levels and activities of transcription factors, MAPK leads to altered transcription of genes that are important for the cell cycle.

There are three known mammalian RAF isoforms: C-RAF (also known as RAF-1, or c-RAF-1), B-RAF, and A-RAF. All RAF kinases share a common modular structure consisting of 3 conserved regions (CR1, CR2, and CR3) with distinct functions. CR1 contains (i) a Ras-binding domain (RBD), which is necessary for the interaction with Ras and with membrane phospholipids required for membrane recruitment, and (ii) a cysteine-rich domain (CRD), which is a secondary Ras-binding site and also necessary for the interaction of CR1 with the kinase domain for RAF autoinhibition. CR2 contains important inhibitory phosphorylation sites participating in the negative regulation of Ras binding and RAF activation. CR3 features the kinase domain, including the activation segment, whose phosphorylation is crucial for kinase activation.

Functionally, the RAF structure can be split into a regulatory N-terminal region, containing the RBD, which is critical for activation as well as inhibitory phosphorylation sites, and a catalytic C-terminal region, which includes phosphorylation sites necessary for the kinase activation. The regulatory domain restrains the activity of the kinase domain, and its removal results in constitutive oncogenic activation. However, the activity of the isolated C-RAF kinase domain is subjected to further regulation and can be stimulated by phorbol esters, v-Src, and phosphorylation.

The common and key step in the activation of all 3 RAF kinase isoforms is membrane recruitment by a Ras family protein. The RAF kinases are located in the cytosol in their inactive state when bound to 14-3-3 proteins. In the presence of active Ras, they translocate to the plasma membrane. Membrane translocation triggers further activation events, such as the binding of PP2A to dephosphorylate the inhibitory pS259 site in RAF-1 (and presumably the corresponding sites in A-RAF and B-RAF) and the co-localization with the kinases responsible for the multiple activating phosphorylations. The sequences forming the binding interface are well conserved in the RAF as well as Ras family indicating that several members of the Ras family have the ability to bind RAF kinases. H-Ras, N-Ras, and K-Ras stimulate all 3 RAF isoforms and are the only Ras proteins that activate B-RAF. In contrast, A-RAF is also activated by R-Ras3, while C-RAF responds weakly to R-Ras3, Rit, and TC21 as well. But, all RAF kinases share MEK1/2 kinases as substrates. MEK1/2 in turn activate ERK1/2, and this pathway regulates many cellular functions such as cell proliferation, differentiation, migration, or apoptosis.

C-RAF

C-RAF was first to be identified and is a ubiquitously expressed isoform. In humans, C-RAF is encoded by the RAF gene. C-RAF also has a known splice variant preferentially expressed in the muscle and brain. C-RAF plays a critical role in mediating the cellular effects of growth factor signals. In the inactive state, C-RAF exists in a closed conformation in which the N-terminal regulatory region folds over and occludes the catalytic region. This conformation is stabilized by a 14-3-3 dimer binding to an N-terminal site, phospho-S259 (pS259), and a C-terminal site, pS621. Dephosphorylation of pS259 at the cell membrane by specific phosphatases (PP2A, PP1) releases 14-3-3 from its N-terminal binding site in C-RAF, thereby allowing conformational changes to occur that unmask the RBD and CRD domains in the CR1 region to enable Ras binding and membrane recruitment.

B-RAF

B-RAF is encoded in humans by the BRAF gene, also known as proto-oncogene B-RAF and v-RAF murine sarcoma viral oncogene homolog B. Alternative splicing gives rise to multiple B-RAF isoforms which are differentially expressed in various tissues. Whereas activation of A-RAF and C-RAF requires both phosphorylation and dephosphorylation of certain residues, as well as binding to other proteins, B-RAF becomes activated immediately upon translocation to the plasma membrane. B-RAF exhibits higher basal kinase activity than A-RAF and C-RAF. B-RAF requires Ras and 14-3-3 binding for its activation and is inhibited or activated by PKA depending on the levels of 14-3-3 expression, which need to be high for permitting activation. B-RAF activity is also regulated by splicing. B-RAF isoforms containing exon 8b are more phosphorylated on the inhibitory S365 site, leading to an increased interaction with 14-3-3 and strengthening the inhibitory interaction between N-terminal regulatory domain and kinase domain, altogether resulting in lower kinase activity.

A-RAF

Serine/threonine-protein kinase A-RAF or A-RAF is an enzyme encoded by the ARAF gene in humans. There are 2 known splice isoforms of A-RAF-DA-RAF1 and D-RAF2. They lack the kinase domain and act as dominant inhibitory mutants of Ras and ARF GTPases. DA-RAF1 is a positive regulator of myogenic differentiation by mediating the inhibition of the ERK pathway required for differentiation. There are several ways A-RAF is different from the other RAF kinases. A-RAF is the only steroid hormone-regulated Raf isoform. In addition, the A-RAFprotein has amino acid substitutions in a negatively charged region upstream of the kinase domain (N-region), which contributes to its low basal activity. A-RAF is also only weakly activated by oncogenic H-Ras and Src and also displays low kinase activity towards MEK (the lowest kinase activity towards MEK proteins in the Raf kinase family). In addition to phosphorylating MEK, A-RAF also inhibits MST2, a tumor suppressor and pro-apoptotic kinase not found in the MAPK pathway. By inhibiting MST2, A-RAF prevents apoptosis from occurring. However, this inhibition only occurs when the splice factor heterogenous nuclear ribonucleoprotein H (hnRNP H) maintains the expression of a full-length A-RAF protein. Tumorous cells often overexpress hnRNP H which leads to full-length expression of A-Raf which then inhibits apoptosis, allowing cancerous cells that should be destroyed to stay alive. A-RAF also binds to pyruvate kinase M2 (PKM2), again outside the MAPK pathway. PKM2 is an isozyme of pyruvate kinase that is responsible for the Warburg effect in cancer cells. A-RAF upregulates the activity of PKM2 by promoting a conformational change in PKM2. This causes PKM2 to transition from its low-activity dimeric form to a highly active tetrameric form. This causes more glucose carbons to be converted to pyruvate and lactate, producing energy for the cell, linking A-Raf to energy metabolism regulation and cell transformation, both of which are very important in tumorigenesis.

RAF Kinase Inhibitors

Aberrant activation of the MAPK/ERK pathway is frequently found in various cancers and is a target for cancer therapeutics. In particular, B-RAF has emerged as one of the most attractive molecular targets for cancer therapeutics because somatic mutations of B-RAF have frequently been found in human tumors. Approximately 20% of all cancer samples tested to date harbor mutations in B-RAF. B-RAF-V600E, a missense mutation in the kinase domain generated by the substitution of glutamic acid with valine at position 600 is the most common B-RAF mutation. C-RAF is mutated in ~1% of the various tumor types tested and the rate of mutations in A-RAF is even lower. B-RAF and C-RAF form both homo- and heterodimers as part of their activation mechanism and A-RAF stabilizes the B-RAF:C-RAF complexes to sustain signaling efficiency. Also, it is C-RAF, not B-RAF, that transmits signals from oncogenic RAS to MEK. Therefore, in different contexts, each of the RAF isoforms act as a potential therapeutic target.

Sorafenib was the first RAF inhibitor to enter clinical trials. Sorafenib is a broad specificity drug that inhibits additional kinases, including vascular endothelial growth factor receptor family (VEGFR-2 and VEGFR-3), platelet-derived growth factor receptor family (PDGFR-b and KIT) and FLT3. Clinical trials showed no correlation between the clinical responses with B-RAF mutation status, indicating it is a poor inhibitor of B-RAF. This led to the development of a new generation of B-RAF inhibitors, including, but not limited to vemurafenib, SB-590885, and dabrafenib (GSK2118436). Although the initial results of the clinical studies in B-RAF-mutant melanoma were encouraging, as clinical testing began in other B-RAF-mutated cancers (such as thyroid and colorectal cancers) it became apparent that tumors of different cell types harboring B-RAF mutations responded differently to selective B-RAF inhibition. Moreover, the existence of both primary and secondary resistance to RAF inhibition poses one of the greatest challenges to the progress of RAF kinase inhibitor therapy. The mechanisms of resistance fall into two broad categories. Intrinsic/primary resistance is displayed by approximately 50% of patients. The other 50% of the patients initially respond (>30% tumor shrinkage) to RAF inhibitor but subsequently develop progressive disease associated with acquired/secondary resistance to RAF inhibitor. These two categories are not mutually exclusive because nearly all responders have remaining disease and, thus, may display intrinsic resistance. The determinants of primary RAF inhibitor resistance seem to vary with tumor type, with alteration in RTK signaling also being involved. Potential mechanisms of secondary B-RAF inhibitor resistance include, but are not limited to, reactivation of ERK1/2 pathways, upregulation of RTK signaling, the upregulation of receptor tyrosine kinases, mutations in RAS, and upregulation of COT. B-Raf alternative splicing and amplification of B-RAF-V600E have also been implicated in 30 and 20% of patients, respectively. Moreover, RAF kinase inhibitors cause paradoxical activation of the MAPK pathway, which, in some instances, leads to the development of secondary RAS mutation-driven malignancies. As such, there is a need in the field for new RAF kinase inhibitors that overcome the existing pitfalls and challenges posed by the current inhibitors.

Heteroaromatic RAF Inhibitory Compounds

In one aspect, provided herein is a heteroaromatic RAF inhibitory compound.

One embodiment provides a compound, or pharmaceutically acceptable salt or solvate thereof, having the structure of Formula (I):

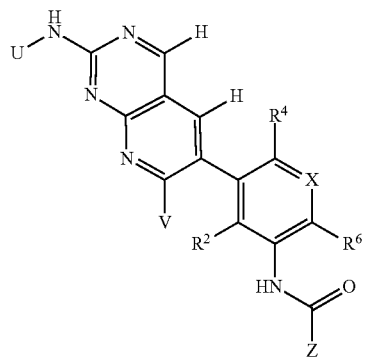

(I)

wherein,

V is hydrogen, halogen, —CN, optionally substituted C1-C4 alkyl, —CD$_3$, optionally substituted C1-C4 alkoxy, optionally substituted C1-C4 alkenyl, or optionally substituted C1-C4 alkynyl;

U is selected from optionally substituted alkyl, —CD$_3$, optionally substituted cycloalkyl, optionally substituted cycloalkylalkyl, optionally substituted heterocyclyl, optionally substituted heterocyclylalkyl, optionally substituted heteroaryl, optionally substituted heteroaralkyl group, optionally substituted —COalkyl, optionally substituted —COcycloalkyl;

X is N, C—H, C-D, or C—F

R$^2$ is H, D or F;

R$^4$ is halogen, optionally substituted C1-C3 alkyl, —CD$_3$, or optionally substituted C1-C3 alkoxy;

R$^6$ is H, D, Cl or F;

Z is selected from:

(a)

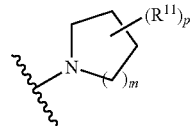

wherein m is 0, 1, 2, or 3; p is 0, 1, 2, 3, or 4; and each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl; or two R$^{11}$ groups together form an oxo;

(b)

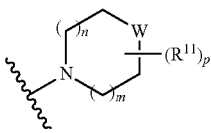

wherein m is 0, 1, 2, or 3; p is 0, 1, 2, 3, or 4;

W is O, S, S(O), SO$_2$, NH or N (optionally substituted C1-C6 alkyl); and each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo;

(c)

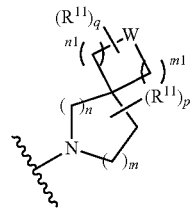

wherein m is 0, 1, or 2; n is 0, 1, or 2; m1 is 0, 1, or 2; n is 0, 1, or 2 provided both m1 and n1 are not both 0; p is 0, 1, or 2; and q is 0, 1 or 2;

W is O, S, S(O), SO$_2$, NH or N (optionally substituted C1-C6 alkyl), CH$_2$, CHR$^{11}$, or C(R$^{11}$)$_2$; and each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo;

(d)

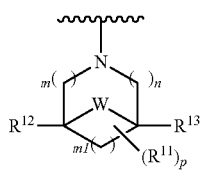

wherein m is 0, 1, or 2; n is 0, 1, or 2; m1 is 1, or 2; p is 0, 1, 2, or 3; W is O, S, S(O), SO$_2$, NH or N (optionally substituted C1-C6 alkyl), CH$_2$, CHR$^{11}$, —CH$_2$—CH$_2$—, —CH$_2$—CHR$^{11}$—, —CH$_2$—C(R$^1$)$_2$—, —CHR$^{11}$—CH$_2$—, —C(R$^1$)$_2$—CH$_2$—, —NH—CH$_2$—, —NH—CHR$^{11}$—, —NH—C(R$^{11}$)$_2$—, —CH$_2$—NH—, —CHR$^{11}$—NH—, —C(R$^{11}$)$_2$—NH—, —N(R$^{11}$)—CH$_2$—, —N(R$^{11}$)—CHR$^{11}$—, —N(R$^{11}$)—C(R$^{11}$)$_2$—, —CH$_2$—N(R$^{11}$)—, —CHR$^{11}$—N(R$^{11}$)—, —C(R$^{11}$)$_2$—N(R$^{11}$)—; each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo; and R$^{12}$ and R$^{13}$ are each independently selected from H, or optionally substituted C1-C6 alkyl;

(e)

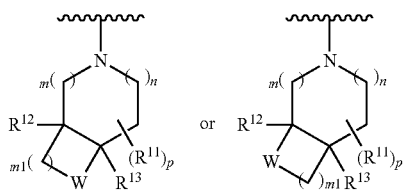

wherein m is 0, 1, or 2; n is 0, 1, or 2; ml is 0, 1, or 2; p is 0, 1, or 2;
W is O, S, S(O), SO$_2$, NH or N (optionally substituted C1-C6 alkyl), CH$_2$, CHR$^{11}$, or C(R$^{11}$)$_2$;
each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo; and R$^{12}$ and R$^{13}$ are each independently selected from H, or optionally substituted C1-C6 alkyl;

(f)

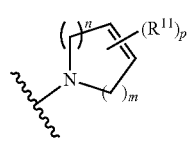

wherein m is 0, 1, 2, or 3; n is 0, 1, 2, or 3 provided both m and n are not both 0; p is 0, 1, 2, 3, or 4; and each R$^{11}$ is independently selected from —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo;

(g)

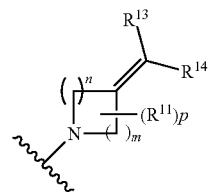

wherein m is 1, 2, or 3; n is 1, 2, or 3; p is 0, 1, or 2; and each R$^{13}$ or R$^{14}$ is independently selected from hydrogen, halogen, —CN, optionally substituted C1-C6 alkyl, or optionally substituted C3-C6 cycloalkyl; each R$^1$ is independently selected from —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl;

(h)

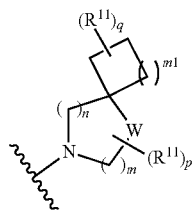

wherein m is 0, 1, or 2; n is 0, 1, or 2; m1 is 0, 1, or 2; p is 0, 1, or 2; and q is 0, 1 or 2; W is O, S, S(O), SO$_2$, NH or N (optionally substituted C1-C6 alkyl), CH$_2$, CHR$^{11}$, or C(R$^{11}$)$_2$; and each R$^1$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two geminal R$^{11}$ groups together form an oxo; or (i) optionally substituted heteroaryl group.

One embodiment provides a compound, or pharmaceutically acceptable salt or solvate thereof, of Formula (I) having the structure of Formula (Ia):

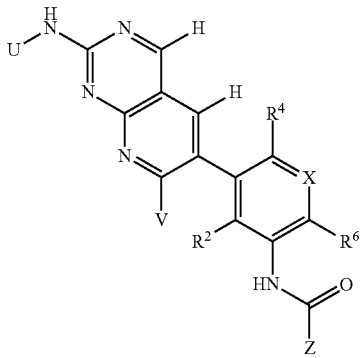

(Ia)

wherein,
V is H or Me;
U is selected from optionally substituted alkyl, optionally substituted cycloalkyl, optionally substituted cycloalkylalkyl, optionally substituted heterocyclyl, optionally substituted heterocyclylalkyl, optionally substituted heteroaryl, or optionally substituted heteroaralkyl group;
X is N, C—H, C-D, or C—F
$R^2$ is H, D or F;
$R^4$ is halogen, optionally substituted C1-C3 alkyl, —CD$_3$, or optionally substituted C1-C3 alkoxy;
$R^6$ is H, D, Cl or F;
Z is selected from:
(a)

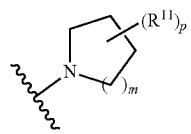

wherein m is 0, 1, 2, or 3; p is 0, 1, 2, 3, or 4; and
each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl; or two $R^{11}$ groups together form an oxo;
(b)

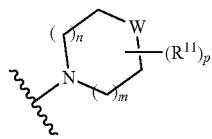

wherein m is 0, 1, 2, or 3; p is 0, 1, 2, 3, or 4;
W is O, S, S(O), SO$_2$, NH or N (optionally substituted C1-C6 alkyl); and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two $R^{11}$ groups together form an oxo;
(c)

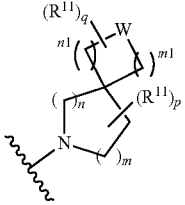

wherein m is 0, 1, or 2; n is 0, 1, or 2; m1 is 0, 1, or 2; n1 is 0, 1, or 2 provided both m1 and n1 are not both 0; p is 0, 1, or 2; and q is 0, 1 or 2;
W is O, S, S(O), SO$_2$, NH or N (optionally substituted C1-C6 alkyl), CH$_2$, CHR$^{11}$, or C(R$^{11}$)$_2$; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two $R^{11}$ groups together form an oxo;
(d)

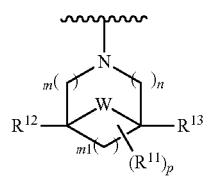

wherein m is 0, 1, or 2; n is 0, 1, or 2; m1 is 1, or 2; p is 0, 1, 2, or 3; W is O, S, S(O), SO$_2$, NH or N (optionally substituted C1-C6 alkyl), CH$_2$, CHR$^{11}$, —CH$_2$—CH$_2$—, —CH$_2$—CHR$^{11}$—, —CH$_2$—C(R$^{11}$)$_2$—, —CHR$^{11}$—CH$_2$—, —C(R$^{11}$)$_2$—CH$_2$—, —NH—CH$_2$—, —NH—CHR$^{11}$—, —NH—C(R$^{11}$)$_2$—, —CH$_2$—NH—, —CHR$^{11}$—NH—, —C(R$^{11}$)$_2$—NH—, —N(R$^{11}$)—CH$_2$—, —N(R$^{11}$)—CHR$^{11}$—, —N(R$^{11}$)—C(R$^{11}$)$_2$—, —CH$_2$—N(R$^{11}$)—, —CHR$^{11}$—N(R$^{11}$)—, —C(R$^{11}$)$_2$—N(R$^{11}$)—; each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two $R^{11}$ groups together form an oxo; and $R^{12}$ and $R^{13}$ are each independently selected from H, or optionally substituted C1-C6 alkyl;
(e)

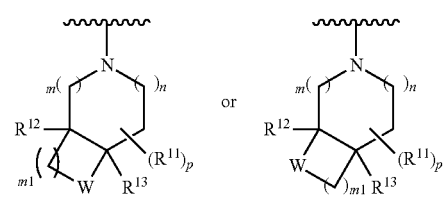

wherein m is 0, 1, or 2; n is 0, 1, or 2; m1 is 0, 1, or 2; p is 0, 1, or 2;
W is O, S, S(O), SO$_2$, NH or N (optionally substituted C1-C6 alkyl), CH$_2$, CHR$^{11}$, or C(R$^{11}$)$_2$;
each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo;
and R$^{12}$ and R$^{13}$ are each independently selected from H, or optionally substituted C1-C6 alkyl;

(f)

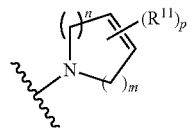

wherein m is 0, 1, 2, or 3; n is 0, 1, 2, or 3 provided both m and n are not both 0; p is 0, 1, 2, 3, or 4; and
each R$^{11}$ is independently selected from —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two R$^{11}$ groups together form an oxo;

(g)

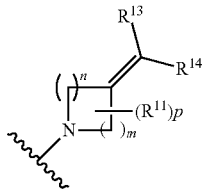

wherein m is 1, 2, or 3; n is 1, 2, or 3; p is 0, 1, or 2; and each R$^{13}$ or R$^{14}$ is independently selected from hydrogen, halogen, —CN, optionally substituted C1-C6 alkyl, or optionally substituted C3-C6 cycloalkyl; each R$^{11}$ is independently selected from —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl;

(h)

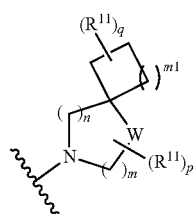

wherein m is 0, 1, or 2; n is 0, 1, or 2; m1 is 0, 1, or 2; p is 0, 1, or 2; and q is 0, 1 or 2; W is O, S, S(O), SO$_2$, NH or N (optionally substituted C1-C6 alkyl), CH$_2$, CHR$^{11}$, or C(R$^{11}$)$_2$; and each R$^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two geminal R$^{11}$ groups together form an oxo; or (i) optionally substituted heteroaryl group.

One embodiment provides the compound of Formula (I) or (Ia), or pharmaceutically acceptable salt or solvate thereof, wherein V is H. One embodiment provides the compound of Formula (I) or (Ia), or pharmaceutically acceptable salt or solvate thereof, wherein V is Me.

One embodiment provides the compound of Formula (I) or (Ia), or pharmaceutically acceptable salt or solvate thereof, wherein X is N. One embodiment provides the compound of Formula (I) or (Ia), or pharmaceutically acceptable salt or solvate thereof, wherein X is C—H. One embodiment provides the compound of Formula (I) or (Ia), or pharmaceutically acceptable salt or solvate thereof, wherein X is C—F.

One embodiment provides the compound of Formula (I) or (Ia), or pharmaceutically acceptable salt or solvate thereof, wherein R$^2$ is H. One embodiment provides the compound of Formula (I) or (Ia), or pharmaceutically acceptable salt or solvate thereof, wherein R$^2$ is F.

One embodiment provides the compound of Formula (I) or (Ia), or pharmaceutically acceptable salt or solvate thereof, wherein R$^4$ is halogen. One embodiment provides the compound of Formula (I) or (Ia), or pharmaceutically acceptable salt or solvate thereof, wherein R$^4$ is optionally substituted C1-C3 alkyl. One embodiment provides the compound of Formula (I) or (Ia), or pharmaceutically acceptable salt or solvate thereof, wherein R$^4$ is methyl.

One embodiment provides the compound of Formula (I) or (Ia), or pharmaceutically acceptable salt or solvate thereof, wherein R$^6$ is H. One embodiment provides the compound of Formula (I) or (Ia), or pharmaceutically acceptable salt or solvate thereof, wherein R$^6$ is F.

One embodiment provides the compound of Formula (I) or (Ia), or pharmaceutically acceptable salt or solvate thereof, wherein U is optionally substituted alkyl. One embodiment provides the compound of Formula (I) or (Ia), or pharmaceutically acceptable salt or solvate thereof, wherein U is optionally substituted cycloalkyl. One embodiment provides the compound of Formula (I) or (Ia), or pharmaceutically acceptable salt or solvate thereof, wherein U is optionally substituted cycloalkylalkyl. One embodiment provides the compound of Formula (I) or (Ia), or pharmaceutically acceptable salt or solvate thereof, wherein U is optionally substituted heterocyclyl. One embodiment provides the compound of Formula (I) or (Ia), or pharmaceutically acceptable salt or solvate thereof, wherein U is optionally substituted heterocyclylalkyl. One embodiment provides the compound of Formula (I) or (Ia), or pharmaceutically acceptable salt or solvate thereof, wherein U is optionally substituted heteroaryl. One embodiment provides the compound of Formula (I) or (Ia), or pharmaceutically acceptable salt or solvate thereof, wherein U is optionally substituted heteroaralkyl group.

One embodiment provides the compound of Formula (I) or (Ia), or pharmaceutically acceptable salt or solvate thereof, wherein Z is

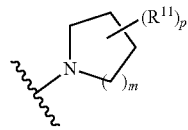

wherein m is 0, 1, 2, or 3; p is 0, 1, 2, 3, or 4; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl; or two $R^{11}$ groups together form an oxo. One embodiment provides the compound of Formula (I) or (Ia), or pharmaceutically acceptable salt or solvate thereof, wherein m is 0. Another embodiment provides the compound of Formula (I) or (Ia), or pharmaceutically acceptable salt or solvate thereof, wherein m is 1. Another embodiment provides the compound of Formula (I) or (Ia), or pharmaceutically acceptable salt or solvate thereof, wherein m is 2. Another embodiment provides the compound of Formula (I) or (Ia), or pharmaceutically acceptable salt or solvate thereof, wherein m is 3. Another embodiment provides the compound of Formula (I) or (Ia), or pharmaceutically acceptable salt or solvate thereof, wherein p is 0. Another embodiment provides the compound of Formula (I) or (Ia), or pharmaceutically acceptable salt or solvate thereof, wherein p is 1. Another embodiment provides the compound of Formula (I) or (Ia), or pharmaceutically acceptable salt or solvate thereof, wherein p is 2. Another embodiment provides the compound of Formula (I) or (Ia), or pharmaceutically acceptable salt or solvate thereof, wherein p is 1. Another embodiment provides the compound of Formula (I) or (Ia), or pharmaceutically acceptable salt or solvate thereof, wherein $R^{11}$ is optionally substituted C1-C6 alkyl, or optionally substituted C3-C6 cycloalkyl. Another embodiment provides the compound of Formula (I) or (Ia), or pharmaceutically acceptable salt or solvate thereof, wherein the optionally substituted C1-C6 alkyl, or optionally substituted C3-C6 cycloalkyl is substituted with at least a halogen.

One embodiment provides the compound of Formula (I) or (Ia), or pharmaceutically acceptable salt or solvate thereof, wherein Z is

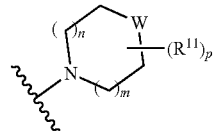

wherein m is 0, 1, 2, or 3; p is 0, 1, 2, 3, or 4;
W is O, S, S(O), SO$_2$, NH or N (optionally substituted C1-C6 alkyl); and
each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two $R^{11}$ groups together form an oxo. Another embodiment provides the compound of Formula (I) or (Ia), or pharmaceutically acceptable salt or solvate thereof, wherein W is O. Another embodiment provides the compound of Formula (I) or (Ia), or pharmaceutically acceptable salt or solvate thereof, wherein W is S. Another embodiment provides the compound of Formula (I) or (Ia), or pharmaceutically acceptable salt or solvate thereof, wherein m is 1, and n is 1. Another embodiment provides the compound of Formula (I) or (Ia), or pharmaceutically acceptable salt or solvate thereof, wherein m is 1, and n is 2. Another embodiment provides the compound of Formula (I) or (Ia), or pharmaceutically acceptable salt or solvate thereof, wherein $R^{11}$ is optionally substituted C1-C6 alkyl, or optionally substituted C3-C6 cycloalkyl. Another embodiment provides the compound of Formula (I) or (Ia), or pharmaceutically acceptable salt or solvate thereof, wherein $R^1$ is optionally substituted C1-C6 alkyl, or optionally substituted C3-C6 cycloalkyl, and the optionally substituted C1-C6 alkyl, or optionally substituted C3-C6 cycloalkyl is substituted with at least a halogen.

One embodiment provides the compound of Formula (I) or (Ia), or pharmaceutically acceptable salt or solvate thereof, wherein Z is

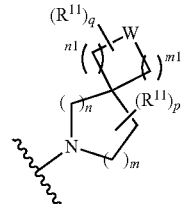

wherein m is 0, 1, or 2; n is 0, 1, or 2; m1 is 0, 1, or 2; n1 is 0, 1, or 2 provided both m1 and n1 are not both 0; p is 0, 1, or 2; and q is 0, 1 or 2; W is O, S, S(O), SO$_2$, NH or N (optionally substituted C1-C6 alkyl), CH$_2$, CHR$^{11}$, or C(R$^1$)$_2$; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO$_2$alkyl, optionally substituted C3-C6 cycloalkylalkyl, optionally substituted heterocyclyl, or optionally substituted heterocyclylalkyl, or two $R^{11}$ groups together form an oxo. Another embodiment provides the compound of Formula (I) or (Ia), or pharmaceutically acceptable salt or solvate thereof, wherein m is 1, and n is 1. Another embodiment provides the compound of Formula (I) or (Ia), or pharmaceutically acceptable salt or solvate thereof, wherein m is 0, and n is 2. Another embodiment provides the compound of Formula (I) or (Ia), or pharmaceutically acceptable salt or solvate thereof, wherein m1 is 0, and n1 is 2. Another embodiment provides the compound of Formula (I) or (Ia), or pharmaceutically acceptable salt or solvate thereof, wherein m1 is 1, and n1 is 1. Another embodiment provides the compound of Formula (I) or (Ia), or pharmaceutically acceptable salt or solvate thereof, wherein W is O. Another embodiment provides the compound of Formula (I) or (Ia), or pharmaceutically acceptable salt or solvate thereof, wherein W is CH$_2$. Another embodiment provides the compound of Formula (I) or (Ia), or pharmaceutically acceptable salt or solvate thereof, wherein W is CHR¹¹. Another embodiment provides the compound of Formula (I) or (Ia), or pharmaceutically acceptable salt or solvate thereof, wherein W is C(R¹¹)₂. Another embodiment provides the compound of Formula (I) or (Ia), or pharmaceutically acceptable salt or solvate thereof, wherein R¹¹ is halogen and q is 1.

One embodiment provides the compound of Formula (I) or (Ia), or pharmaceutically acceptable salt or solvate thereof, wherein Z is

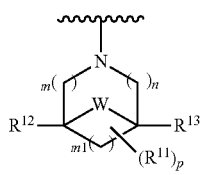

wherein m is 0, 1, or 2; n is 0, 1, or 2; m1 is 1, or 2; p is 0, 1, 2, or 3; W is O, S, S(O), SO₂, NH or N (optionally substituted C1-C6 alkyl), CH₂, CHR¹¹, —CH₂—CH₂—, —CH₂—CHR¹¹—, —CH₂—C(R¹¹)₂—, —CHR¹¹—CH₂—, —C(R¹¹)₂—CH₂—, —NH—CH₂—, —NH—CHR¹¹—, —NH—C(R¹¹)₂—, —CH₂—NH—, —CHR¹¹—NH—, —C(R¹¹)₂—NH—, —N(R¹¹)—CH₂—, —N(R¹¹)—CHR¹¹—, —N(R¹¹)—C(R¹¹)₂—, —CH₂—N(R¹¹)—, —CHR¹¹—N(R¹¹)—, —C(R¹¹)₂—N(R¹¹)—; each R¹¹ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO₂alkyl, optionally substituted C3-C6 cycloalkylalkyl, optionally substituted heterocyclyl, or optionally substituted heterocyclylalkyl, or two R¹¹ groups together form an oxo; and R¹² and R¹³ are each independently selected from H, or optionally substituted C1-C6 alkyl. Another embodiment provides the compound of Formula (I) or (Ia), or pharmaceutically acceptable salt or solvate thereof, wherein m is 0, n is 1, and m1 is 1; and W is —O—CH₂—, or —CH₂—O—.

One embodiment provides the compound of Formula (I) or (Ia), or pharmaceutically acceptable salt or solvate thereof, wherein Z is

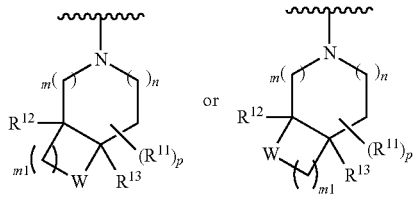

wherein m is 0, 1, or 2; n is 0, 1, or 2; m1 is 0, 1, or 2; p is 0, 1, or 2; W is O, S, S(O), SO2, NH or N (optionally substituted C1-C6 alkyl), CH₂, CHR11, or C(R11)2; each R11 is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO2alkyl, optionally substituted C3-C6 cycloalkylalkyl, optionally substituted heterocyclyl, or optionally substituted heterocyclylalkyl, or two R11 groups together form an oxo; and R12 and R13 are each independently selected from H, or optionally substituted C1-C6 alkyl. Another embodiment provides the compound of Formula (I) or (Ia), or pharmaceutically acceptable salt or solvate thereof, wherein W is O. Another embodiment provides the compound of Formula (I) or (Ia), or pharmaceutically acceptable salt or solvate thereof, wherein W is CH2, or CHR11. Another embodiment provides the compound of Formula (I) or (Ia), or pharmaceutically acceptable salt or solvate thereof, wherein m1 is 0. Another embodiment provides the compound of Formula (I) or (Ia), or pharmaceutically acceptable salt or solvate thereof, wherein m1 is 1. Another embodiment provides the compound of Formula (I) or (Ia), or pharmaceutically acceptable salt or solvate thereof, wherein m is 1 and n is 1. Another embodiment provides the compound of Formula (I) or (Ia), or pharmaceutically acceptable salt or solvate thereof, wherein m is 1 and n is 0. Another embodiment provides the compound of Formula (I) or (Ia), or pharmaceutically acceptable salt or solvate thereof, wherein m is 0 and n is 1.

One embodiment provides the compound of Formula (I) or (Ia), or pharmaceutically acceptable salt or solvate thereof, wherein Z is

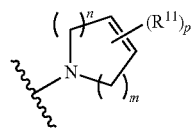

wherein m is 0, 1, 2, or 3; n is 0, 1, 2, or 3 provided both m and n are not both 0; p is 0, 1, 2, 3, or 4; and each R¹¹ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —SO₂alkyl, optionally substituted C3-C6 cycloalkylalkyl, optionally substituted heterocyclyl, or optionally substituted heterocyclylalkyl. Another embodiment provides the compound of Formula (I) or (Ia), or pharmaceutically acceptable salt or solvate thereof, wherein m is 1, and n is 1. Another embodiment provides the compound of Formula (I) or (Ia), or pharmaceutically acceptable salt or solvate thereof, wherein m is 1, and n is 2. Another embodiment provides the compound of Formula (I) or (Ia), or pharmaceutically acceptable salt or solvate thereof, wherein p is 1. Another embodiment provides the compound of Formula (I) or (Ia), or pharmaceutically acceptable salt or solvate thereof, wherein p is 2. Another embodiment provides the compound of Formula (I) or (Ia), or pharmaceutically acceptable salt or solvate thereof, wherein p is 0. Another embodiment provides the compound of Formula (I) or (Ia), or pharmaceutically acceptable salt or solvate thereof, wherein at least one R¹¹ is attached to an alkene carbon. Another embodiment provides the compound of Formula (I) or (Ia), or pharmaceutically acceptable salt or solvate thereof, wherein at least one R¹¹ is not attached to an alkene carbon. Another embodiment provides the compound of Formula (I) or (Ia), or pharmaceutically acceptable salt or solvate thereof, wherein R¹¹ is optionally substituted C1-C6 alkyl, or optionally substituted C3-C6 cycloalkyl.

One embodiment provides the compound of Formula (I) or (Ia), or pharmaceutically acceptable salt or solvate thereof, wherein Z is

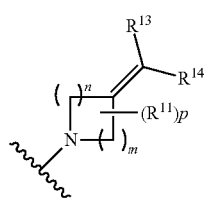

wherein m is 1, 2, or 3; n is 1, 2, or 3; p is 0, 1, or 2; and each $R^{13}$ or $R^{14}$ is independently selected from hydrogen, halogen, —CN, optionally substituted C1-C6 alkyl, or optionally substituted C3-C6 cycloalkyl; each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —$SO_2$alkyl, optionally substituted C3-C6 cycloalkylalkyl, optionally substituted heterocyclyl, or optionally substituted heterocyclylalkyl. Another embodiment provides the compound of Formula (I) or (Ia), or pharmaceutically acceptable salt or solvate thereof, wherein m is 2, and n is 1. Another embodiment provides the compound of Formula (I) or (Ia), or pharmaceutically acceptable salt or solvate thereof, wherein p is 0. Another embodiment provides the compound of Formula (I) or (Ia), or pharmaceutically acceptable salt or solvate thereof, wherein p is 1. Another embodiment provides the compound of Formula (I) or (Ia), or pharmaceutically acceptable salt or solvate thereof, wherein one of $R^{13}$ or $R^{14}$ is not hydrogen. Another embodiment provides the compound of Formula (I) or (Ia), or pharmaceutically acceptable salt or solvate thereof, wherein one of $R^{13}$ or $R^{14}$ is optionally substituted C1-C6 alkyl. Another embodiment provides the compound of Formula (I) or (Ia), or pharmaceutically acceptable salt or solvate thereof, wherein $R^{13}$ is optionally substituted C1-C6 alkyl. Another embodiment provides the compound of Formula (I) or (Ia), or pharmaceutically acceptable salt or solvate thereof, wherein $R^{14}$ is optionally substituted C1-C6 alkyl.

One embodiment provides the compound of Formula (I) or (Ia), or pharmaceutically acceptable salt or solvate thereof, wherein Z is

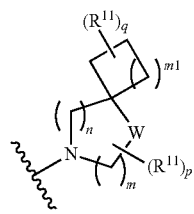

wherein m is 0, 1, or 2; n is 0, 1, or 2; m1 is 0, 1, or 2; p is 0, 1, or 2; and q is 0, 1 or 2; W is O, S, S(O), $SO_2$, NH or N (optionally substituted C1-C6 alkyl), $CH_2$, $CHR^{11}$, or $C(R^{11})_2$; and each $R^{11}$ is independently selected from amino, alkylamino, dialkylamino, —OH, halogen, optionally substituted C1-C6 alkyl, optionally substituted C3-C6 cycloalkyl, optionally substituted C1-C6 alkoxy, optionally substituted C2-C6 alkynyl, optionally substituted —$SO_2$alkyl, optionally substituted C3-C6 cycloalkylalkyl, optionally substituted heterocyclyl, or optionally substituted heterocyclylalkyl, or two geminal $R^{11}$ groups together form an oxo. Another embodiment provides the compound of Formula (I) or (Ia), or pharmaceutically acceptable salt or solvate thereof, wherein W is O. Another embodiment provides the compound of Formula (I) or (Ia), or pharmaceutically acceptable salt or solvate thereof, wherein m is 2, and n is 1. Another embodiment provides the compound of Formula (I) or (Ia), or pharmaceutically acceptable salt or solvate thereof, wherein m1 is 1 or 2. Another embodiment provides the compound of Formula (I) or (Ia), or pharmaceutically acceptable salt or solvate thereof, wherein p is 0 or 1, and q is 0 or 1.

One embodiment provides the compound of Formula (I) or (Ia), or pharmaceutically acceptable salt or solvate thereof, wherein Z is an optionally substituted heteroaryl group. Another embodiment provides the compound of Formula (I) or (Ia), or pharmaceutically acceptable salt or solvate thereof, wherein Z is an optionally substituted nitrogen-containing heteroaryl group. Another embodiment provides the compound of Formula (I) or (Ia), or pharmaceutically acceptable salt or solvate thereof, wherein the optionally substituted nitrogen-containing heteroaryl group is an optionally substituted monocyclic nitrogen-containing heteroaryl group. Another embodiment provides the compound of Formula (I) or (Ia), or pharmaceutically acceptable salt or solvate thereof, wherein the optionally substituted monocyclic nitrogen-containing heteroaryl group is a 5-membered optionally substituted monocyclic nitrogen-containing heteroaryl group. Another embodiment provides the compound of Formula (I) or (Ia), or pharmaceutically acceptable salt or solvate thereof, wherein the 5-membered optionally substituted monocyclic nitrogen-containing heteroaryl group is selected from an optionally substituted pyrrole, optionally substituted oxazole, optionally substituted thiazole, optionally substituted imidazole, optionally substituted pyrazole, optionally substituted isoxazole, or optionally substituted isothiazole. Another embodiment provides the compound of Formula (I) or (Ia), or pharmaceutically acceptable salt or solvate thereof, wherein the 5-membered optionally substituted monocyclic nitrogen-containing heteroaryl group is an optionally substituted pyrazole. Another embodiment provides the compound of Formula (I) or (Ia), or pharmaceutically acceptable salt or solvate thereof, wherein the optionally substituted monocyclic nitrogen-containing heteroaryl group is a 6-membered optionally substituted monocyclic nitrogen-containing heteroaryl group. Another embodiment provides the compound of Formula (I) or (Ia), or pharmaceutically acceptable salt or solvate thereof, wherein the 6-membered optionally substituted monocyclic nitrogen-containing heteroaryl group is selected from an optionally substituted pyridine, optionally substituted pyridazine, optionally substituted pyrimidine, optionally substituted pyrazine or optionally substituted triazene. Another embodiment provides the compound of Formula (I) or (Ia), or pharmaceutically acceptable salt or solvate thereof, wherein the 6-membered optionally substituted monocyclic nitrogen-containing heteroaryl group is an optionally substituted pyridine. Another embodiment provides the compound of Formula (I) or (Ia), or pharmaceutically acceptable salt or solvate thereof, wherein the optionally substituted nitrogen-containing heteroaryl group is substituted with a halogen, or an optionally substituted C1-C4 alkyl. Another embodiment provides the compound of Formula (I) or (Ia), or pharmaceutically acceptable salt or solvate thereof, wherein the optionally substituted C1-C4 alkyl is an optionally substituted C1-C2 alkyl. Another embodiment provides the compound of Formula (I) or (Ia), or pharmaceutically acceptable salt or solvate thereof, wherein the optionally substituted C1-C4 alkyl is an optionally substituted C1 alkyl. Another embodiment provides the compound of Formula (I) or (Ia), or pharmaceutically acceptable salt or solvate thereof, wherein the optionally substituted C1 alkyl is a —CF₃ group. Another embodiment provides the compound of Formula (I) or (Ia), or pharmaceutically acceptable salt or solvate thereof, wherein the optionally substituted pyridine is substituted with at least a —CF₃ group. Another embodiment provides the compound of Formula (I) or (Ia), or pharmaceutically acceptable salt or solvate thereof, wherein the optionally substituted pyridine is a 2-trifluoromethylpyridin-4-yl group.

In some embodiments, the heteroaromatic RAF kinase inhibitory compound as described herein has a structure provided in Table 1.

TABLE 1

| Synthetic Chemistry Example | Compound Structure | Compound Name |
| --- | --- | --- |
| 1 | 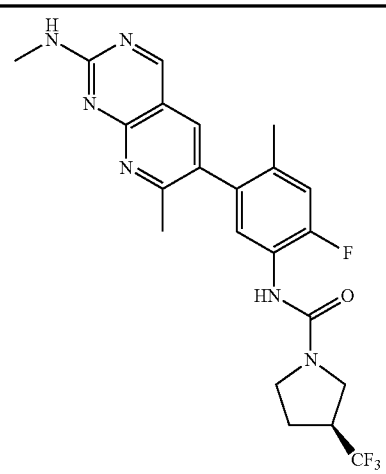 | (S)-N-(2-fluoro-4-methyl-5-(7-methyl-2-(methylamino)pyrido[2,3-d]pyrimidin-6-yl)phenyl)-3-(trifluoromethyl)pyrrolidine-1-carboxamide |
| 2 | 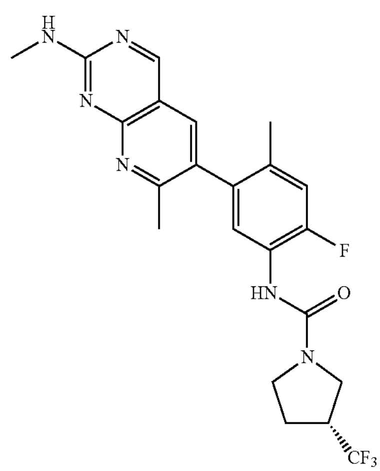 [SMILES: CNc1ncc2cc(-c3cc(NC(=O)N4CC[C@@H](C(F)(F)F)C4)c(F)cc3C)c(C)nc2n1] | (R)-N-(2-fluoro-4-methyl-5-(7-methyl-2-(methylamino)pyrido[2,3-d]pyrimidin-6-yl)phenyl)-3-(trifluoromethyl)pyrrolidine-1-carboxamide |
| 3 | 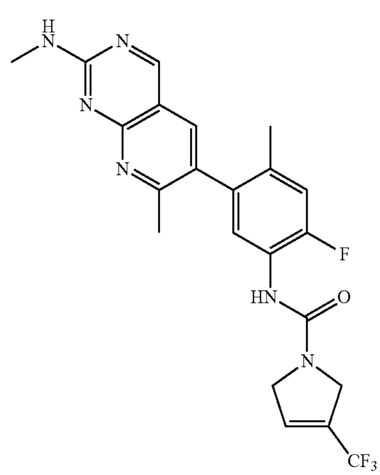 [SMILES: CNc1ncc2cc(-c3cc(NC(=O)N4CC=C(C(F)(F)F)C4)c(F)cc3C)c(C)nc2n1] | N-(2-fluoro-4-methyl-5-(7-methyl-2-(methylamino)pyrido[2,3-d]pyrimidin-6-yl)phenyl)-3-(trifluoromethyl)-2,5-dihydro-1H-pyrrole-1-carboxamide |

TABLE 1-continued

| Synthetic Chemistry Example | Compound Structure | Compound Name |
|---|---|---|
| 4 and 5 | 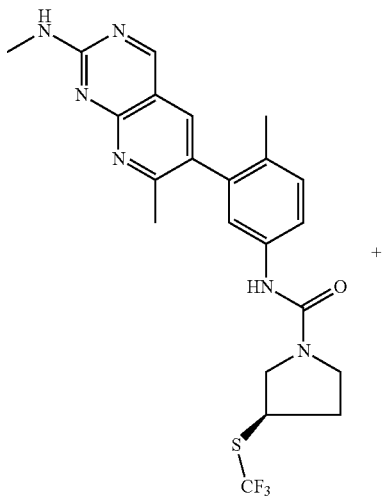 [SMILES: CNc1ncc2cc(-c3cc(NC(=O)N4CC[C@@H](SC(F)(F)F)C4)ccc3C)c(C)nc2n1] + | (3R)-N-methyl-3-[7-methyl-2-(methylamino)pyrido[2,3-d]pyrimidin-6-yl]phenyl]-3-[(trifluoromethyl)sulfanyl]pyrrolidine-1-carboxamide And (3S)-N-methyl-3-[7-methyl-2-(methylamino)pyrido[2,3-d]pyrimidin-6-yl]phenyl]-3-[(trifluoromethyl)sulfanyl]pyrrolidine-1-carboxamide |
| 6 | 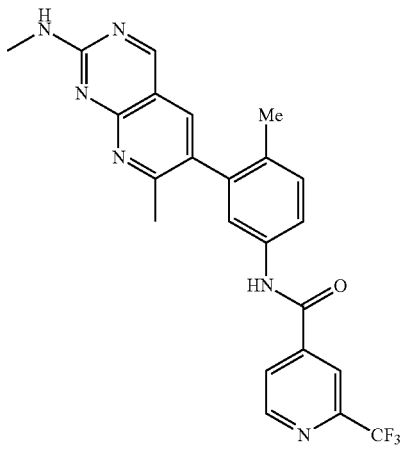 [SMILES: CNc1ncc2cc(-c3cc(NC(=O)c4ccnc(C(F)(F)F)c4)ccc3C)c(C)nc2n1] | N-[4-methyl-3-[7-methyl-2-(methylamino)pyrido[2,3-d]pyrimidin-6-yl]phenyl]-2-(trifluoromethyl)pyridine-4-carboxamide |

TABLE 1-continued

| Synthetic Chemistry Example | Compound Structure | Compound Name |
|---|---|---|
| 7 | 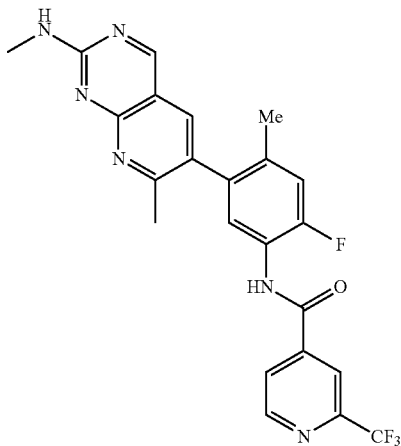 [SMILES: CNc1ncc2cc(-c3cc(NC(=O)c4ccnc(C(F)(F)F)c4)c(F)cc3C)c(C)nc2n1] | N-[2-fluoro-4-methyl-5-[7-methyl-2-(methylamino)pyrido[2,3-d]pyrimidin-6-yl]phenyl]-2-(trifluoromethyl)pyridine-4-carboxamide |
| 8 and 9 | 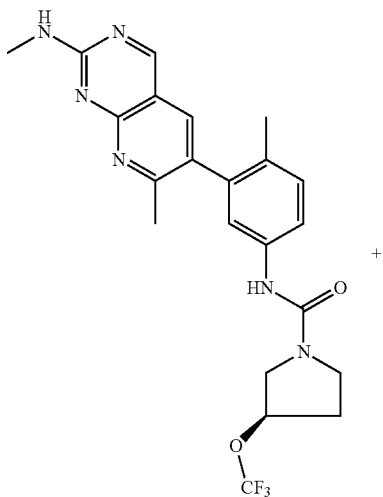 [SMILES: CNc1ncc2cc(-c3cc(NC(=O)N4CC[C@@H](OC(F)(F)F)C4)ccc3C)c(C)nc2n1] + 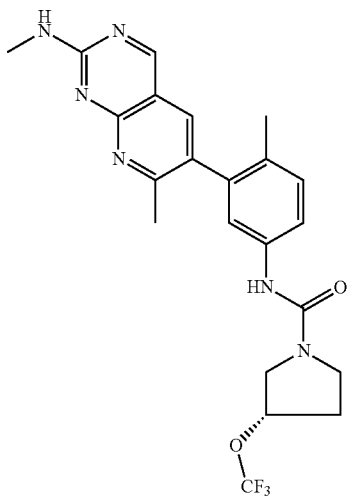 [SMILES: CNc1ncc2cc(-c3cc(NC(=O)N4CC[C@H](OC(F)(F)F)C4)ccc3C)c(C)nc2n1] | (3R)-N-[2-fluoro-4-methyl-5-[7-methyl-2-(methylamino)pyrido[2,3-d]pyrimidin-6-yl]phenyl]-3-(trifluoromethoxy)pyirolidine-1-carboxamide and and (3S)-N-[2-fluoro-4-methyl-5-[7-methyl-2-(methylamino)pyrido[2,3-d]pyrimidin-6-yl]phenyl]-3-(trifluoromethoxy)pyrrolidine-1-carboxamide |

TABLE 1-continued

| Synthetic Chemistry Example | Compound Structure | Compound Name |
|---|---|---|
| 10 | 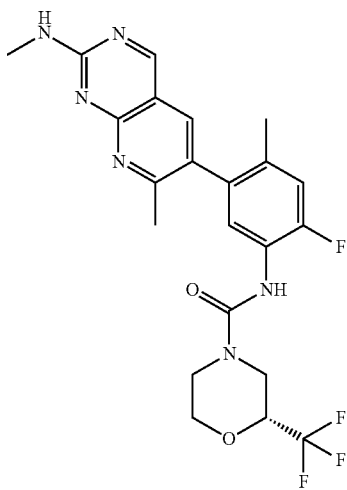 [SMILES: CNc1ncc2cc(-c3cc(NC(=O)N4CCO[C@@H](C(F)(F)F)C4)c(F)cc3C)c(C)nc2n1] | (2R)-N-[2-fluoro-4-methyl-5-[7-methyl-2-(methylamino)pyrido[2,3-d]pyrimidin-6-yl]phenyl]-2-(trifluoromethyl)morpholine-4-carboxamide |
| 11 | 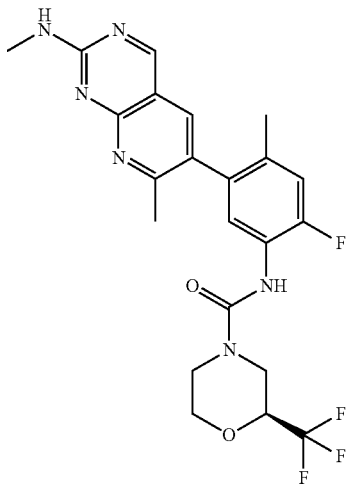 [SMILES: CNc1ncc2cc(-c3cc(NC(=O)N4CCO[C@H](C(F)(F)F)C4)c(F)cc3C)c(C)nc2n1] | (2S)-N-[2-fluoro-4-methyl-5-[7-methyl-2-(methylamino)pyrido[2,3-d]pyrimidin-6-yl]phenyl]-2-(trifluoromethyl)morpholine-4-carboxamide |
| 12 | 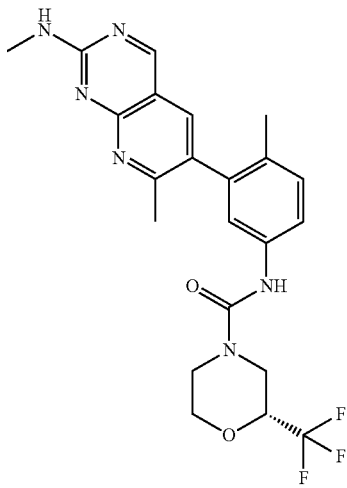 [SMILES: CNc1ncc2cc(-c3cc(NC(=O)N4CCO[C@@H](C(F)(F)F)C4)ccc3C)c(C)nc2n1] | (2R)-N-[4-methyl-3-[7-methyl-2-(methylamino)pyrido[2,3-d]pyrimidin-6-yl]phenyl]-2-(trifluoromethyl)morpholine-4-carboxamide |

TABLE 1-continued

| Synthetic Chemistry Example | Compound Structure | Compound Name |
|---|---|---|
| 13 | 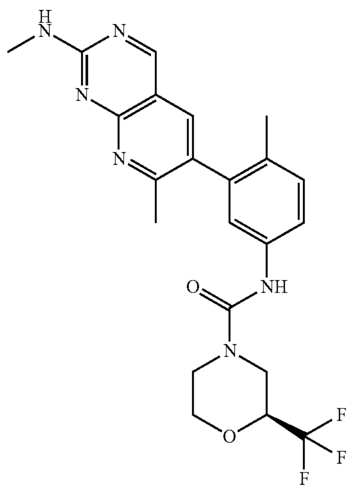 [SMILES: CNc1ncc2cc(-c3cc(NC(=O)N4CCO[C@H](C(F)(F)F)C4)ccc3C)c(C)nc2n1] | (2S)-N-methyl-3-[7-methyl-2-(methylamino)pyrido[2,3-d]pyrimidin-6-yl]phenyl]-2-(trifluoromethyl)morpholine-4-carboxamide |
| 14 | 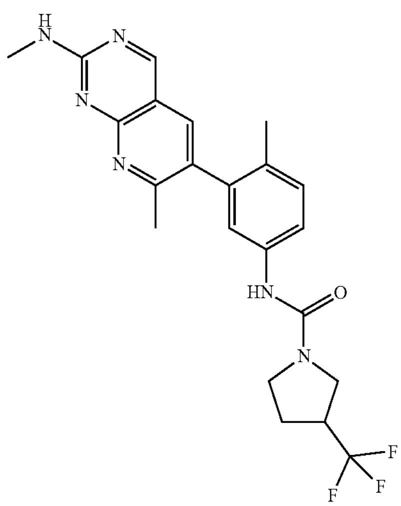 [SMILES: CNc1ncc2cc(-c3cc(NC(=O)N4CCC(C(F)(F)F)C4)ccc3C)c(C)nc2n1] | N-(4-methyl-3-(7-methyl-2-(methylamino)pyrido[2,3-d]pyrimidin-6-yl)phenyl)-3-(trifluoromethyl)pyrrolidine-1-carboxamide |
| 15 | 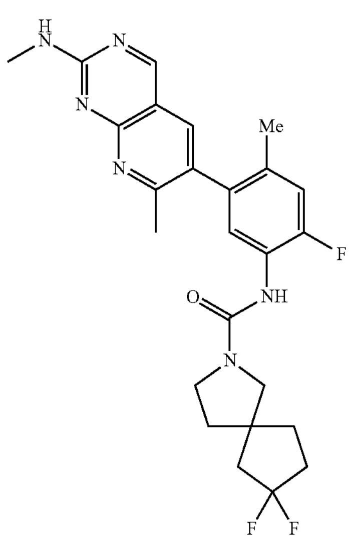 [SMILES: CNc1ncc2cc(-c3cc(NC(=O)N4CCC5(CCC(F)(F)C5)C4)c(F)cc3C)c(C)nc2n1] | 7,7-difluoro-N-(2-fluoro-4-methyl-5-(7-methyl-2-(methylamino)pyrido[2,3-d]pyrimidin-6-yl)phenyl)-2-azaspiro[4.4]nonane-2-carboxamide |

TABLE 1-continued

| Synthetic Chemistry Example | Compound Structure | Compound Name |
|---|---|---|
| 16 | 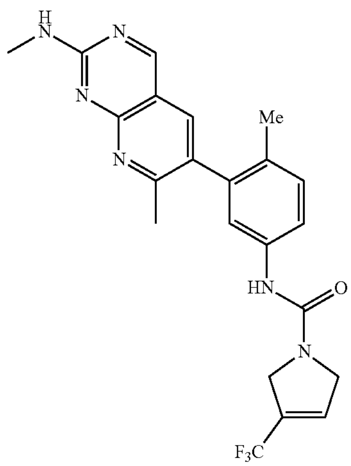 [SMILES: CNc1ncc2cc(-c3cc(NC(=O)N4CC=C(C(F)(F)F)C4)ccc3C)c(C)nc2n1] | N-(4-methyl-3-(7-methyl-2-(methylamino)pyrido[2,3-d]pyrimidin-6-yl)phenyl)-3-(trifluoromethyl)-2,5-dihydro-1H-pyrrole-1-carboxamide |
| 17 and 18 | | (R)-N-(2-fluoro-4-methyl-5-(7-methyl-2-(methylamino)pyrido[2,3-d]pyrimidin-6-yl)phenyl)-3-(2,2,2-trifluoroethyl)pyrrolidine-1-carboxamide and (S)-N-(2-fluoro-4-methyl-5-(7-methyl-2-(methylamino)pyrido[2,3-d]pyrimidin-6-yl)phenyl)-3-(2,2,2-trifluoroethyl)pyrrolidine-1-carboxamide |

TABLE 1-continued

| Synthetic Chemistry Example | Compound Structure | Compound Name |
|---|---|---|
| 19 and 20 | 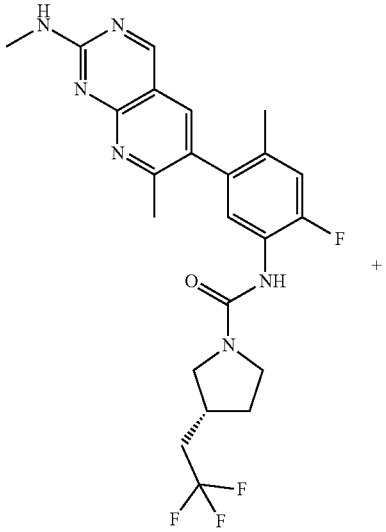 [SMILES: CNc1ncc2cc(-c3cc(NC(=O)N4CC[C@H](CC(F)(F)F)C4)c(F)cc3C)c(C)nc2n1] | (R)-N-(4-methyl-3-(7-methyl-2-(methylamino)pyrido[2,3-d]pyrimidin-6-yl)phenyl)-3-(2,2,2-trifluoroethyl)pyrrolidine-1-carboxamide and (S)-N-(4-methyl-3-(7-methyl-2-(methylamino)pyrido[2,3-d]pyrimidin-6-yl)phenyl)-3-(2,2,2-trifluoroethyl)pyrrolidine-1-carboxamide |
| 21 | 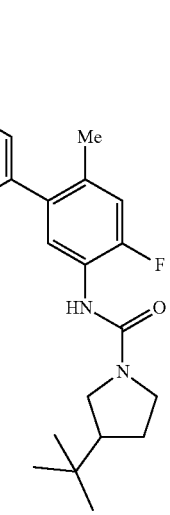 | 3-(tert-butyl)-N-(2-fluoro-4-methyl-5-(7-methyl-2-(methylamino)pyrido[2,3-d]pyrimidin-6-yl)phenyl)pyrrolidine-1-carboxamide |

TABLE 1-continued

| Synthetic Chemistry Example | Compound Structure | Compound Name |
|---|---|---|
| 22 and 23 | 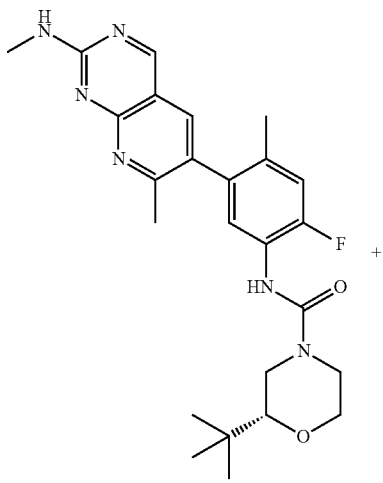 [SMILES: CNc1ncc2cc(-c3cc(NC(=O)N4CCO[C@H](C(C)(C)C)C4)c(F)cc3C)c(C)nc2n1] | (R)-2-(tert-butyl)-N-(2-fluoro-4-methyl-5-(7-methyl-2-(methylamino)pyrido[2,3-d]pyrimidin-6-yl)phenyl)morpholine-4-carboxamide and (S)-2-(tert-butyl)-N-(2-fluoro-4-methyl-5-(7-methyl-2-(methylamino)pyrido[2,3-d]pyrimidin-6-yl)phenyl)morpholine-4-carboxamide |
| 24 | 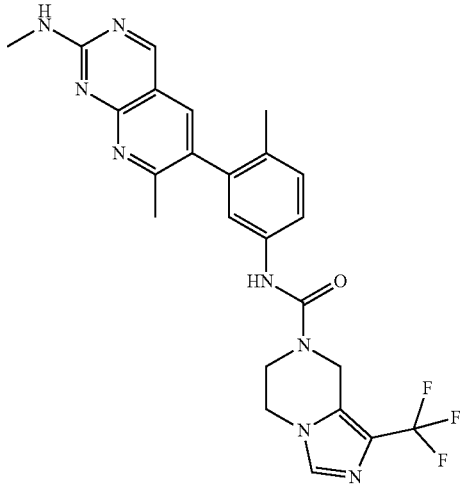 [SMILES: CNc1ncc2cc(-c3cc(NC(=O)N4CCn5cnc(C(F)(F)F)c5C4)ccc3C)c(C)nc2n1] | N-(4-methyl-3-(7-methyl-2-(methylamino)pyrido[2,3-d]pyrimidin-6-yl)phenyl)-1-(trifluoromethyl)-5,6-dihydroimidazo[1,5-a]pyrazine-7(8H)-carboxamide |

TABLE 1-continued

| Synthetic Chemistry Example | Compound Structure | Compound Name |
|---|---|---|
| 25 and 26 | 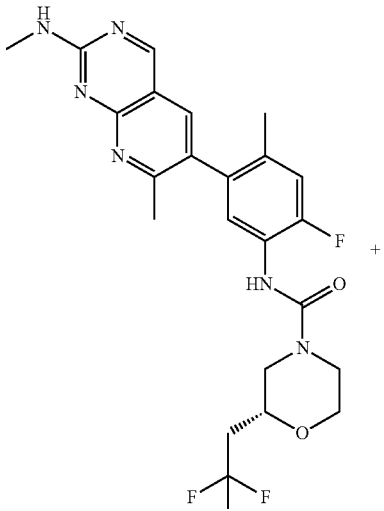 | (R)-N-(2-fluoro-4-methyl-5-(7-methyl-2-(methylamino)pyrido[2,3-d]pyrimidin-6-yl)phenyl)-2-(2,2,2-trifluoroethyl)morpholine-4-carboxamide and (S)-N-(2-fluoro-4-methyl-5-(7-methyl-2-(methylamino)pyrido[2,3-d]pyrimidin-6-yl)phenyl)-2-(2,2,2-trifluoroethyl)morpholine-4-carboxamide |
| 27 | 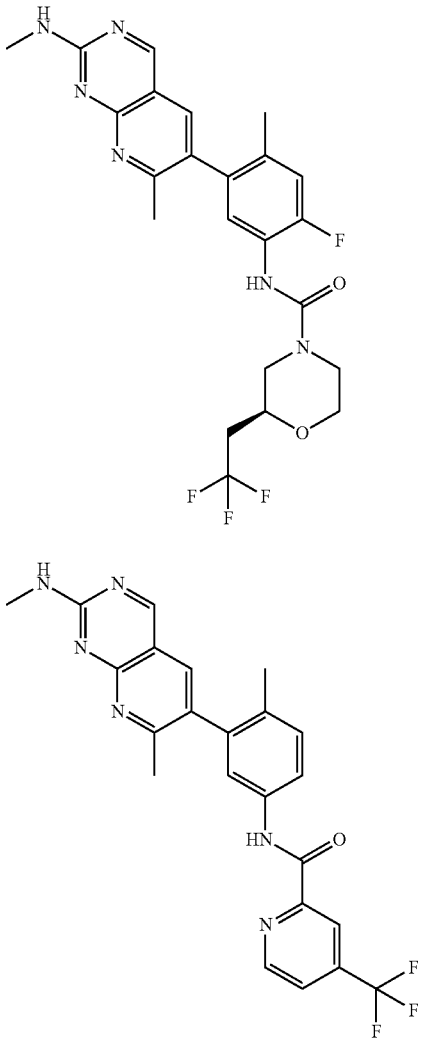 | N-(4-methyl-3-(7-methyl-2-(methylamino)pyrido[2]3-d]pyrimidin-6-yl)phenyl)-4-(trifluoromethyl)picolinamide |

TABLE 1-continued
| Synthetic Chemistry Example | Compound Structure | Compound Name |
|---|---|---|
| 28 | 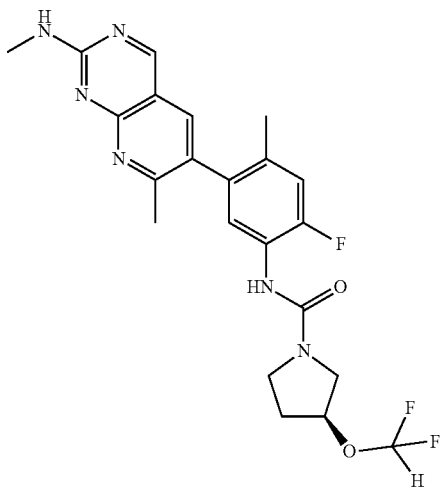 [SMILES: CNc1ncc2cc(-c3cc(NC(=O)N4CC[C@H](OC(F)F)C4)c(F)cc3C)c(C)nc2n1] | (S)-3-(difluoromethoxy)-N-(2-fluoro-4-methyl-5-(2-(methylamino)pyrido[2,3-d]pyrimidin-6-yl)phenyl)pyrrolidine-1-carboxamide |
| 29 | 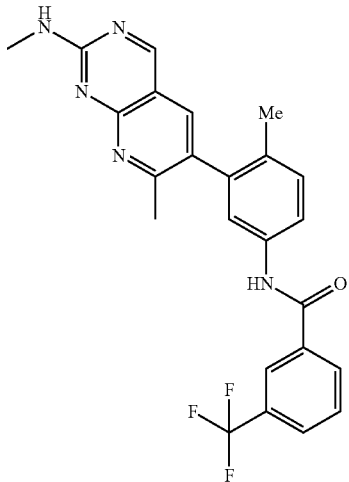 | N-(4-methyl-3-(7-methyl-2-(methylamino)pyrido[2,3-d]pyrimidin-6-yl)phenyl)-3-(trifluoromethyl)benzamide |

TABLE 1-continued

| Synthetic Chemistry Example | Compound Structure | Compound Name |
|---|---|---|
| 30 and 31 | 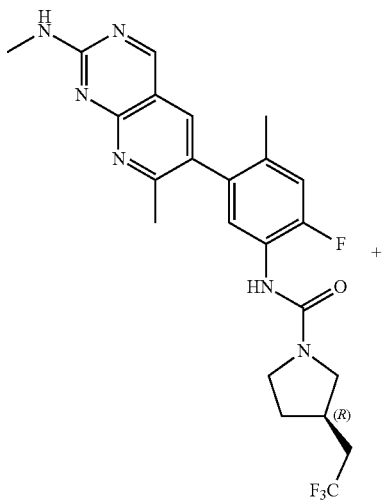 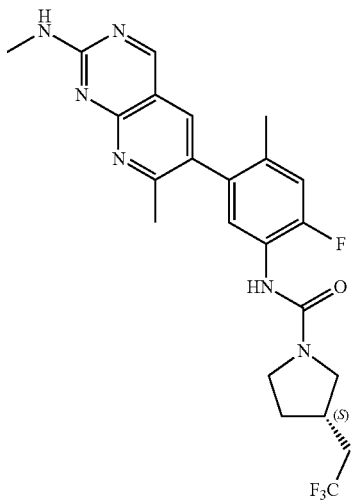 | (R)-N-(2-fluoro-4-methyl-5-(2-(methylamino)pyrido[2,3-d]pyrimidin-6-yl)phenyl)-3-(2,2,2-trifluoroethyl)pyrrolidine-1-carboxamide and (S)-N-(2-fluoro-4-methyl-5-(2-(methylamino)pyrido[2,3-d]pyrimidin-6-yl)phenyl)-3-(2,2,2-trifluoroethyl)pyrrolidine-1-carboxamide |
| 32 | 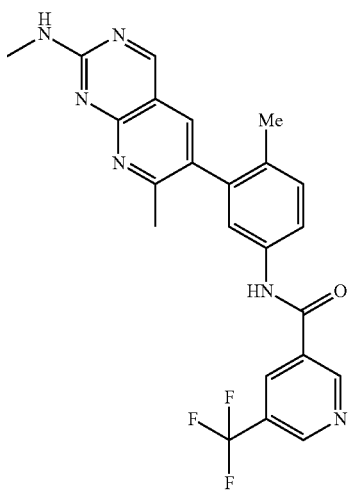 [SMILES: CNc1ncc2cc(-c3cc(NC(=O)c4cncc(C(F)(F)F)c4)ccc3C)c(C)nc2n1] | N-(4-methyl-3-(7-methyl-2-(methylamino)pyrido[2,3-d]pyrimidin-6-yl)phenyl)-5-(trifluoromethyl)nicotinamide |

TABLE 1-continued

| Synthetic Chemistry Example | Compound Structure | Compound Name |
|---|---|---|
| 33 | 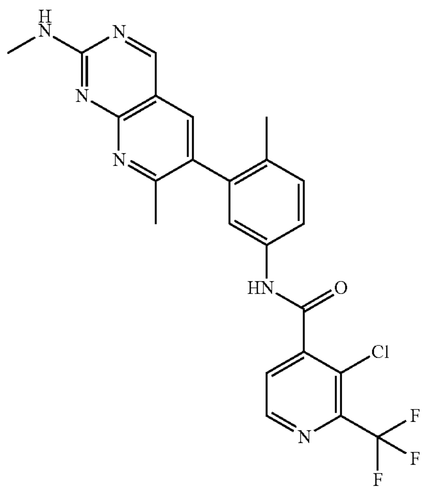 [SMILES: CNc1ncc2cc(-c3cc(NC(=O)c4ccnc(C(F)(F)F)c4Cl)ccc3C)c(C)nc2n1] | 3-chloro-N-(4-methyl-3-(7-methyl-2-(methylamino)pyrido[2,3-d]pyrimidin-6-yl)phenyl)-2-(trifluoromethyl)isonicotinamide |
| 34 | 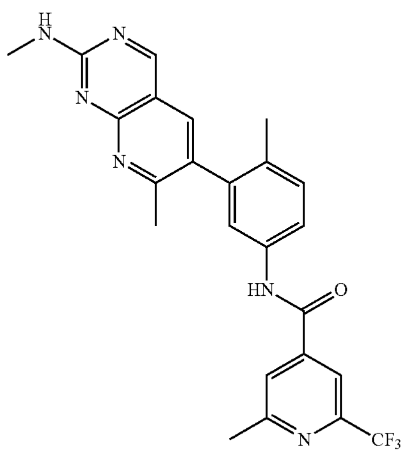 [SMILES: CNc1ncc2cc(-c3cc(NC(=O)c4cc(C)nc(C(F)(F)F)c4)ccc3C)c(C)nc2n1] | 2-methyl-N-(4-methyl-3-(7-methyl-2-(methylamino)pyrido[2,3-d]pyrimidin-6-yl)phenyl)-6-(trifluoromethyl)isonicotinamide |
| 35 | 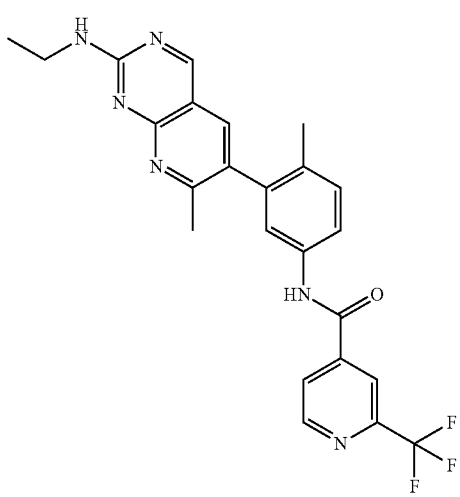 [SMILES: CCNc1ncc2cc(-c3cc(NC(=O)c4ccnc(C(F)(F)F)c4)ccc3C)c(C)nc2n1] | N-(3-(2-(ethylamino)-7-methylpyrido[2,3-d]pyrimidin-6-yl)-4-methylphenyl)-2-(trifluoromethyl)isonicotinamide |

TABLE 1-continued

| Synthetic Chemistry Example | Compound Structure | Compound Name |
|---|---|---|
| 36 | 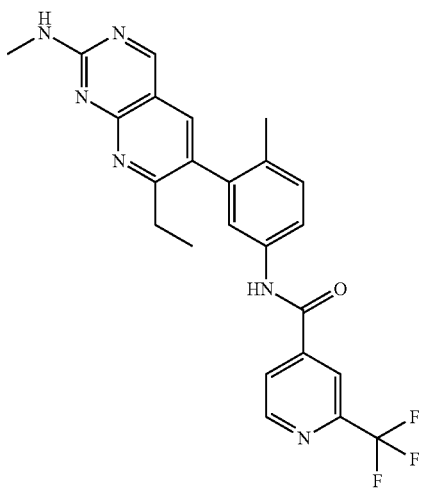 [SMILES: CCc1nc2nc(NC)ncc2cc1-c1cc(NC(=O)c2ccnc(C(F)(F)F)c2)ccc1C] | N-(3-(7-ethyl-2-(methylamino)pyrido[2,3-d]pyrimidin-6-yl)-4-methylphenyl)-2-(trifluoromethyl)isonicotinamide |
| 37 | 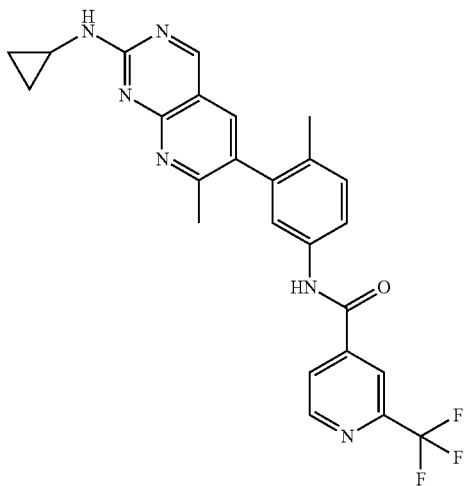 [SMILES: Cc1ccc(NC(=O)c2ccnc(C(F)(F)F)c2)cc1-c1cc2cnc(NC3CC3)nc2nc1C] | N-(3-(2-(cyclopropylamino)-7-methylpyrido[2,3-d]pyrimidin-6-yl)-4-methylphenyl)-2-(trifluoromethyl)isonicotinamide |
| 38 | 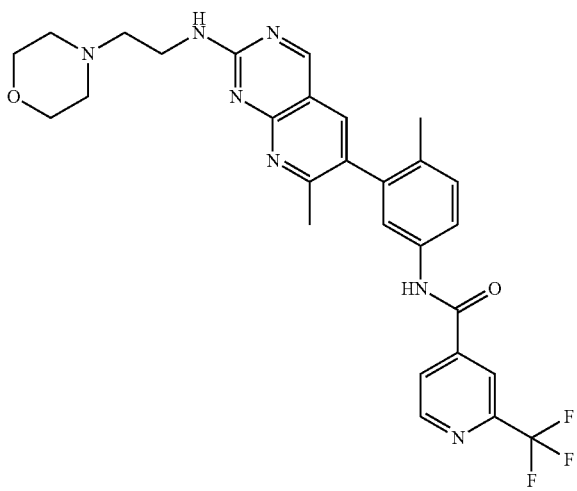 [SMILES: Cc1ccc(NC(=O)c2ccnc(C(F)(F)F)c2)cc1-c1cc2cnc(NCCN3CCOCC3)nc2nc1C] | N-(4-methyl-3-(7-methyl-2-((2-morpholinoethyl)amino)pyrido[2,3-d]pyrimidin-6-yl)phenyl)-2-(trifluoromethyl)isonicotinamide |

TABLE 1-continued

| Synthetic Chemistry Example | Compound Structure | Compound Name |
|---|---|---|
| 39 | 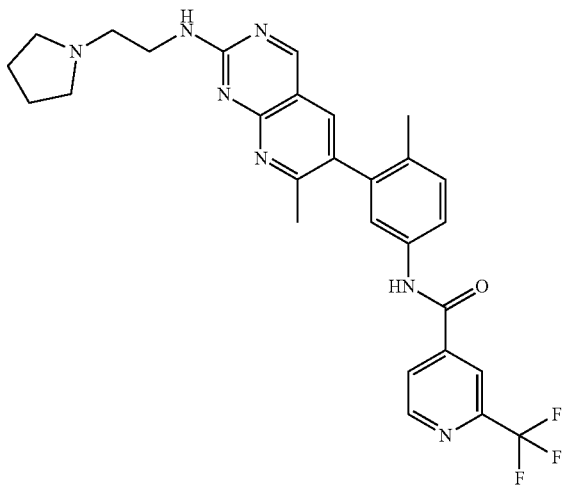 [SMILES: Cc1ccc(NC(=O)c2ccnc(C(F)(F)F)c2)cc1-c1cc2cnc(NCCN3CCCC3)nc2nc1C] | N-(4-methyl-3-(7-methyl-2-((2-(pyrrolidin-1-yl)ethyl)amino)pyrido[2,3-d]pyrimidin-6-yl)phenyl)-2-(trifluoromethyl)isonicotinamide |
| 40 | 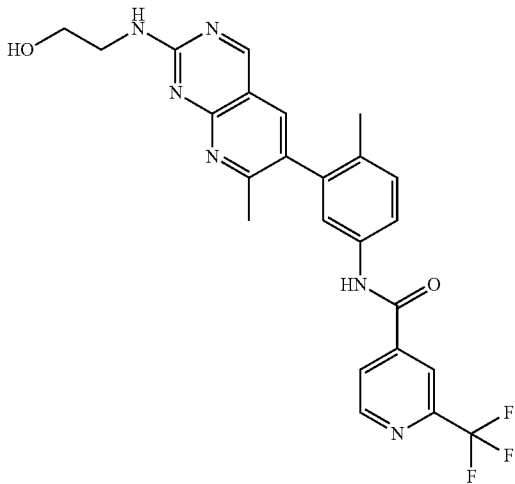 [SMILES: Cc1ccc(NC(=O)c2ccnc(C(F)(F)F)c2)cc1-c1cc2cnc(NCCO)nc2nc1C] | N-(3-(2-((2-hydroxyethyl)amino)-7-methylpyrido[2,3-d]pyrimidin-6-yl)-4-methylphenyl)-2-(trifluoromethyl)isonicotinamide |
| 41 | 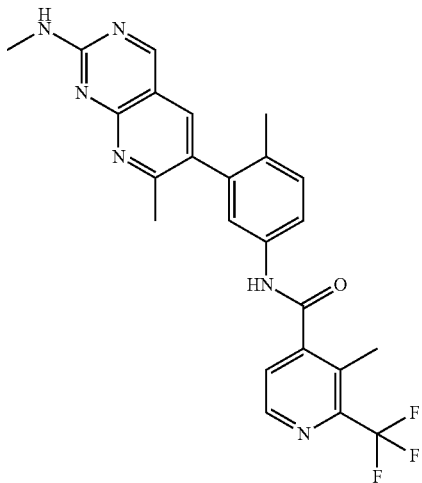 [SMILES: CNc1ncc2cc(-c3cc(NC(=O)c4ccnc(C(F)(F)F)c4C)ccc3C)c(C)nc2n1] | 3-methyl-N-(4-methyl-3-(7-methyl-2-(methylamino)pyrido[2,3-d]pyrimidin-6-yl)phenyl)-2-(trifluoromethyl)isonicotinamide |

TABLE 1-continued

| Synthetic Chemistry Example | Compound Structure | Compound Name |
|---|---|---|
| 42 | 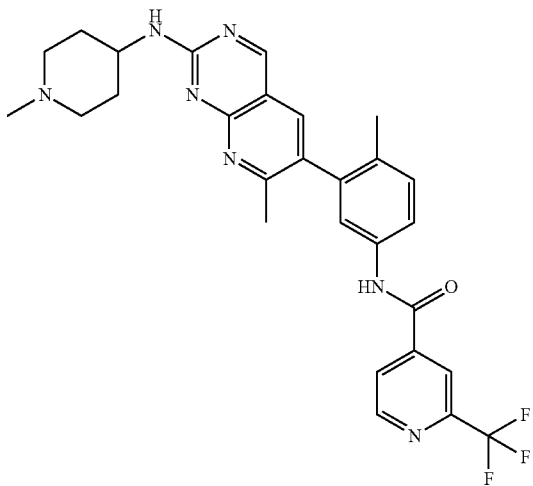 [SMILES: Cc1ccc(NC(=O)c2ccnc(C(F)(F)F)c2)cc1-c1cc2cnc(NC3CCN(C)CC3)nc2nc1C] | N-(4-methyl-3-(7-methyl-2-((1-methylpiperidin-4-yl)amino)pyrido[2,3-d]pyrimidin-6-yl)phenyl)-2-(trifluoromethyl)isonicotinamide |
| 43 | 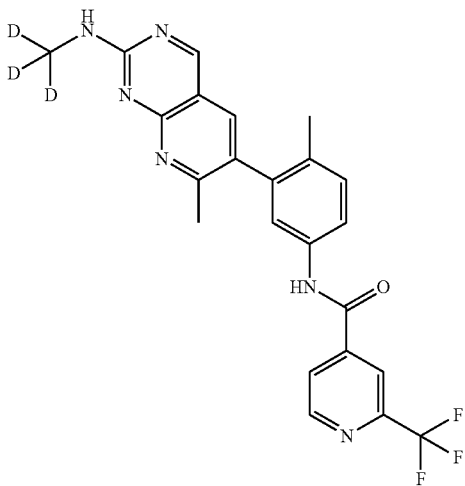 [SMILES: [2H]C([2H])([2H])Nc1ncc2cc(-c3cc(NC(=O)c4ccnc(C(F)(F)F)c4)ccc3C)c(C)nc2n1] | N-(4-methyl-3-(7-methyl-2-((trideuteromethyl)amino)pyrido[2,3-d]pyrimidin-6-yl)phenyl)-2-(trifluoromethyl)isonicotinamide |
| 44 | 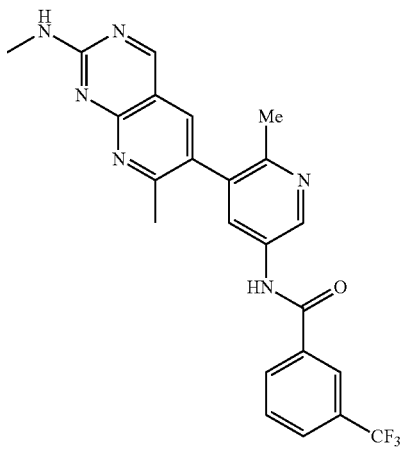 | N-(6-methyl-5-(7-methyl-2-(methylamino)pyrido[2,3-d]pyrimidin-6-yl)pyridin-3-yl)-3-(trifluoromethyl)benzamide |

TABLE 1-continued

| Synthetic Chemistry Example | Compound Structure | Compound Name |
|---|---|---|
| 45 | 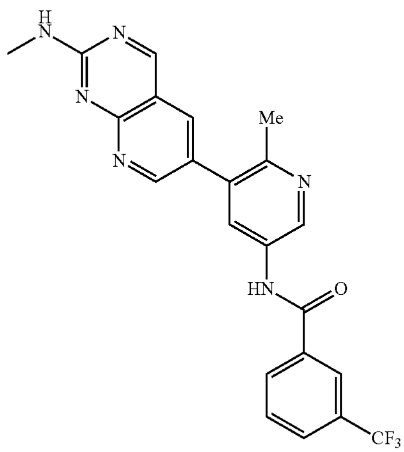 [SMILES: CNc1ncc2cc(-c3cc(NC(=O)c4cccc(C(F)(F)F)c4)cnc3C)cnc2n1] | N-(6-methyl-5-(2-(methylamino)pyrido[2,3-d]pyrimidin-6-yl)pyridin-3-yl)-3-(trifluoromethyl)benzamide |
| 46 | 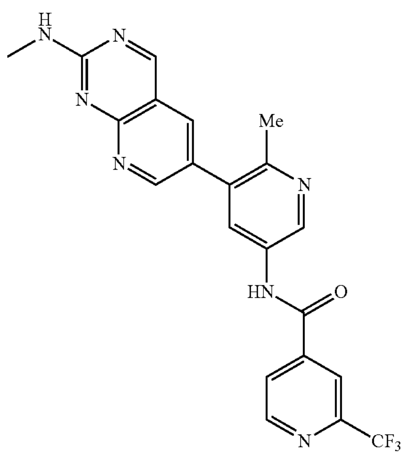 [SMILES: CNc1ncc2cc(-c3cc(NC(=O)c4ccnc(C(F)(F)F)c4)cnc3C)cnc2n1] | N-(6-methyl-5-(2-(methylamino)pyrido[2,3-d]pyrimidin-6-yl)pyridin-3-yl)-2-(trifluoromethyl)isonicotinamide |
| 47 | 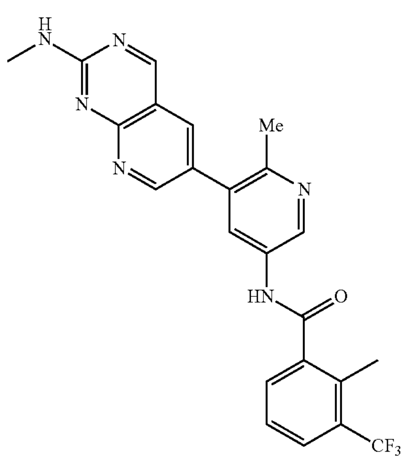 [SMILES: CNc1ncc2cc(-c3cc(NC(=O)c4cccc(C(F)(F)F)c4C)cnc3C)cnc2n1] | 2-methyl-N-(6-methyl-5-(2-(methylamino)pyrido[2,3-d]pyrimidin-6-yl)pyridin-3-yl)-3-(trifluoromethyl)benzamide |

TABLE 1-continued

| Synthetic Chemistry Example | Compound Structure | Compound Name |
|---|---|---|
| 48 | 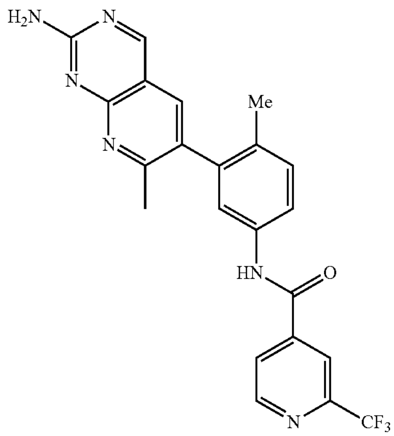 [SMILES: Cc1ccc(NC(=O)c2ccnc(C(F)(F)F)c2)cc1-c1cc2cnc(N)nc2nc1C] | N-(3-(2-amino-7-methylpyrido[2,3-d]pyrimidin-6-yl)-4-methylphenyl)-2-(trifluoromethyl)isonicotinamide |
| 49 | 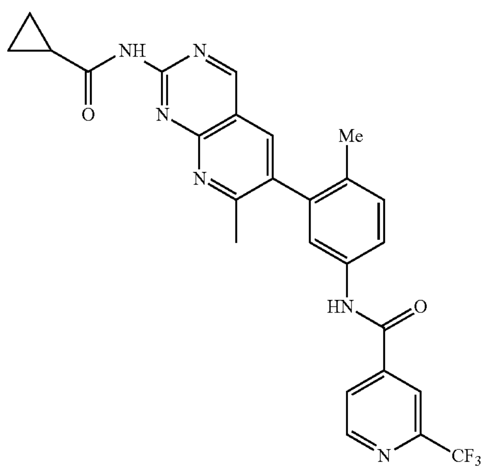 [SMILES: Cc1ccc(NC(=O)c2ccnc(C(F)(F)F)c2)cc1-c1cc2cnc(NC(=O)C3CC3)nc2nc1C] | N-(3-(2-(cyclopropanecarboxamido)-7-methylpyrido[2,3-d]pyrimidin-6-yl)-4-methylphenyl)-2-(trifluoromethyl)isonicotinamide |
| 50 | 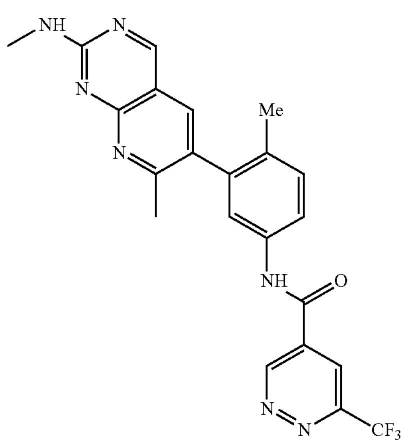 [SMILES: CNc1ncc2cc(-c3cc(NC(=O)c4cnnc(C(F)(F)F)c4)ccc3C)c(C)nc2n1] | N-(4-methyl-3-(7-methyl-2-(methylamino)pyrido[2,3-d]pyrimidin-6-yl)phenyl)-6-(trifluoromethyl)pyridazine-4-carboxamide |

TABLE 1-continued

| Synthetic Chemistry Example | Compound Structure | Compound Name |
|---|---|---|
| 51 | 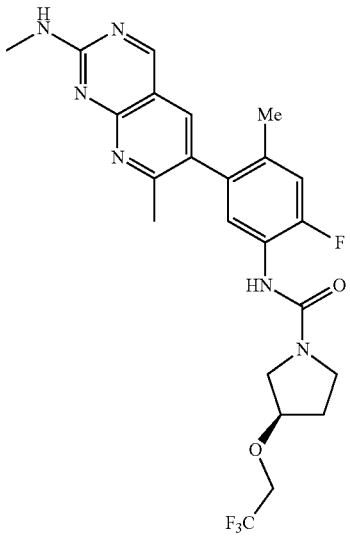 [SMILES: CNc1ncc2cc(-c3cc(NC(=O)N4CC[C@@H](OCC(F)(F)F)C4)c(F)cc3C)c(C)nc2n1] | (3R)-N-[2-fluoro-4-methyl-5-[7-methyl-2-(methylamino)pyrido[2,3-d]pyrimidin-6-yl]phenyl]-3-(2,2,2-trifluoroethoxy)pyrrolidine-1-carboxamide |
| 52 | 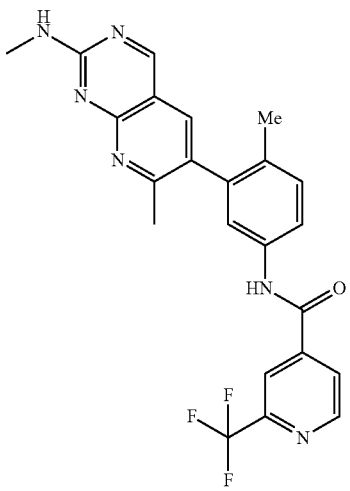 | 2-(1,1-difluoroethyl)-N-[4-methyl-3-[7-methyl-2-(methylamino)pyrido[2,3-d]pyrimidin-6-yl]phenyl]pyridine-4-carboxamide |
| 53 | 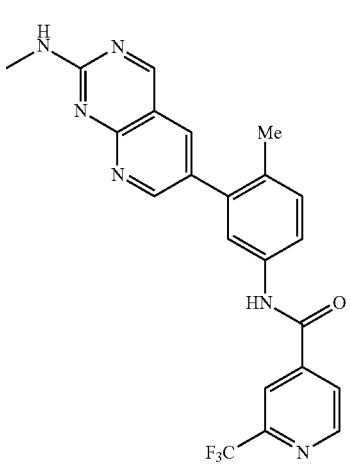 [SMILES: CNc1ncc2cc(-c3cc(NC(=O)c4ccnc(C(F)(F)F)c4)ccc3C)cnc2n1] | N-[4-methyl-3-[2-(methylamino)pyrido[2,3-d]pyrimidin-6-yl]phenyl]-2-(trifluoromethyl)pyridine-4-carboxamide |

TABLE 1-continued

| Synthetic Chemistry Example | Compound Structure | Compound Name |
|---|---|---|
| 54 and 55 | 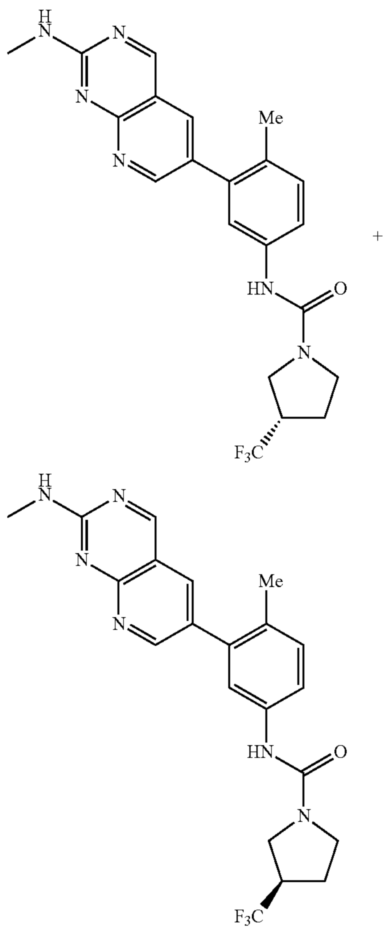 | (3R)-[4-methyl-3-[2-(methylamino)pyrido[2,3-d]pyrimidin-6-yl]phenyl]3(trifluoromethyl)pyrrolidine-1-carboxamide and (3S)-N-[4-methyl-3-[2-(methylamino)pyrido[2,3-d]pyrimidin-6-yl]phenyl]-3-(trifluoromethyl)pyrrolidine-1-carboxamide |
| 56 | 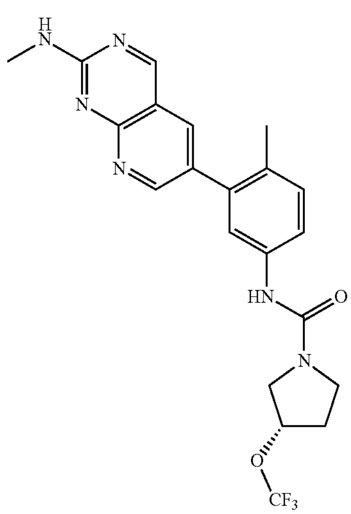 [SMILES: CNc1ncc2cc(-c3cc(NC(=O)N4CC[C@H](OC(F)(F)F)C4)ccc3C)cnc2n1] | 3S-N-[4-methyl-3-[2-(methylamino)pyrido[2,3-d]pyrimidin-6-yl]phenyl]-3-(trifluoromethoxy)pyrrolidine-1-carboxamide |

| Synthetic Chemistry Example | Compound Structure | Compound Name |
|---|---|---|
| 57 | 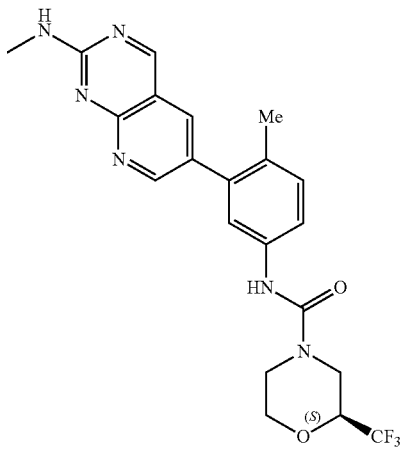 | (2S)-N--[4-methyl-3-[2-(methylamino)pyrido[2,3-d]pyrimidin-6-yl]phenyl-2-(trifluoromethyl)morpholine-4-carboxamide |
| 58 | 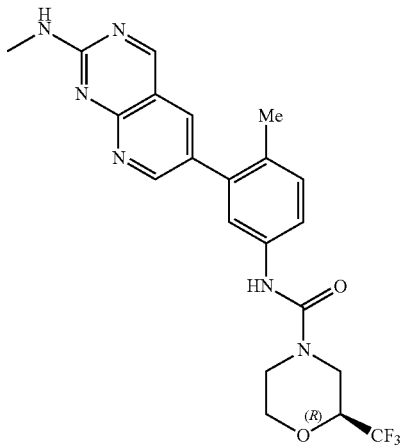 | (2S)-N-[4-methyl-3-[2-(methylamino)pyrido[2,3-d]pyrimidin-6-yl]phenyl]-2-(trifluoromethyl)morpholine-4-carboxamide |
| 59 | 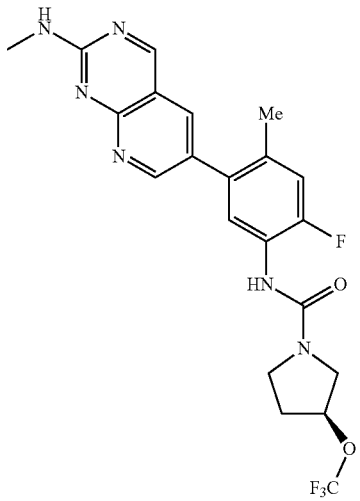 [SMILES: CNc1ncc2cc(-c3cc(NC(=O)N4CC[C@H](OC(F)(F)F)C4)c(F)cc3C)cnc2n1] | (3S)-N-[2-fluoro-4-methyl-5-[2-(methylamino)pyrido[2,3-d]pyrimidin-6-yl]phenyl]-3-(trifluoromethoxy)pyrrolidine-1-carboxamide |

TABLE 1-continued

| Synthetic Chemistry Example | Compound Structure | Compound Name |
|---|---|---|
| 60 | 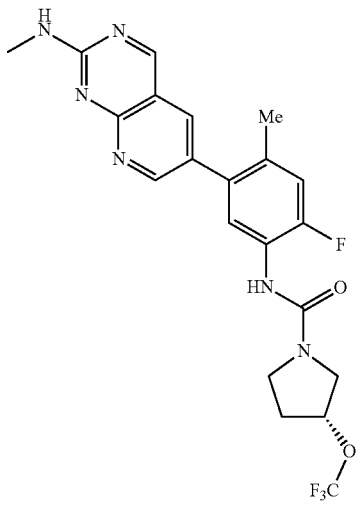 [SMILES: CNc1ncc2cc(-c3cc(NC(=O)N4CC[C@@H](OC(F)(F)F)C4)c(F)cc3C)cnc2n1] | (3R)-N-[2-fluoro-4-methyl-5-[2-(methylamino)pyrido[2,3-d]pyrimidin-6-yl]phenyl]-3-(trifluoromethoxy)pyrrolidine-1-carboxamide |
| 61 | 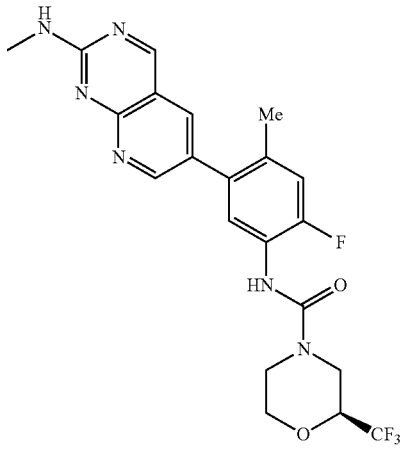 [SMILES: CNc1ncc2cc(-c3cc(NC(=O)N4CCO[C@H](C(F)(F)F)C4)c(F)cc3C)cnc2n1] | (2S)-N-[2-fluoro-4-methyl-5-[2-(methylamino)pyrido[2,3-d]pyrimidin-6-yl]phenyl]-2-(trifluoromethyl)morpholine-4-carboxamide |
| 62 | 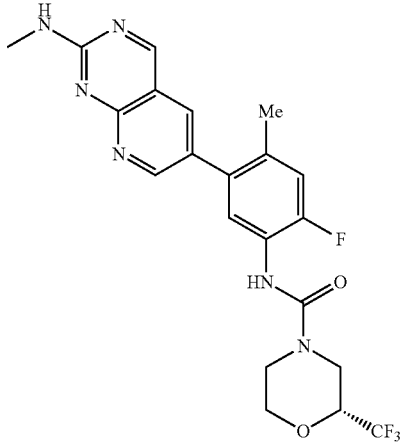 [SMILES: CNc1ncc2cc(-c3cc(NC(=O)N4CCO[C@@H](C(F)(F)F)C4)c(F)cc3C)cnc2n1] | (2R)-N-[2-fluoro-4-methyl-5-[2-(methylamino)pyrido[2,3-d]pyrimidin-6-yl]phenyl]-2-(trifluoromethyl)morpholine-4-carboxamide |

TABLE 1-continued

| Synthetic Chemistry Example | Compound Structure | Compound Name |
|---|---|---|
| 63 | 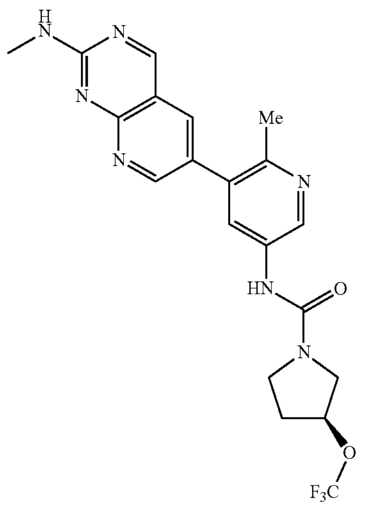 [SMILES: CNc1ncc2cc(-c3cc(NC(=O)N4CC[C@H](OC(F)(F)F)C4)cnc3C)cnc2n1] | (3S)-N/-[6-methyl-5-[2-(methylamino)pyrido[2,3-d]pyrimidin-6-yl]pyridin-3-yl]-3-(trifluoromethoxy)pyrrolidine-1-carboxamide |
| 64 | 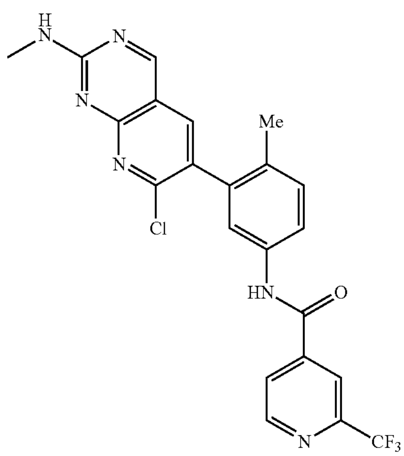 [SMILES: CNc1ncc2cc(-c3cc(NC(=O)c4ccnc(C(F)(F)F)c4)ccc3C)c(Cl)nc2n1] | N-[3-[7-chloro-2-(methylamino)pyrido[2,3-d]pyrimidin-6-yl]-4-methylphenyl]-2-(trifluoromethyl)pyridine-4-carboxamide |
| 65 | 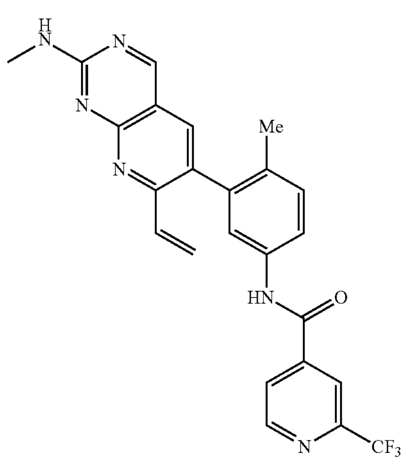 [SMILES: C=Cc1nc2nc(NC)ncc2cc1-c1cc(NC(=O)c2ccnc(C(F)(F)F)c2)ccc1C] | N-[3-[7-ethenyl-2-(methylamino)pyrido[2,3-d]pyrimidin-6-yl]-4-methylphenyl]-2-(trifluoromethyl)pyridine-4-carboxamide |

TABLE 1-continued

| Synthetic Chemistry Example | Compound Structure | Compound Name |
|---|---|---|
| 66 | 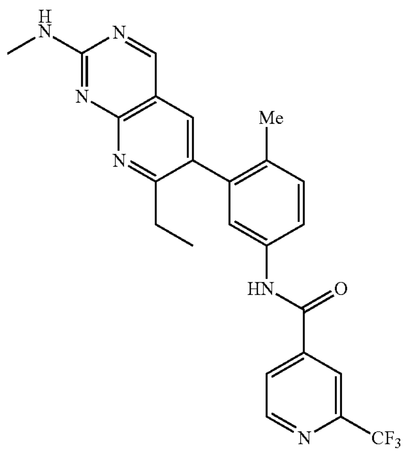 [SMILES: CCc1nc2nc(NC)ncc2cc1-c1cc(NC(=O)c2ccnc(C(F)(F)F)c2)ccc1C] | N-[3-[7-ethyl-2-(methylamino)pyrido[2,3-d]pyrimidin-6-yl]-4-methylphenyl]-2-(trifluoromethyl)pyridine-4-carboxamide |
| 67 | 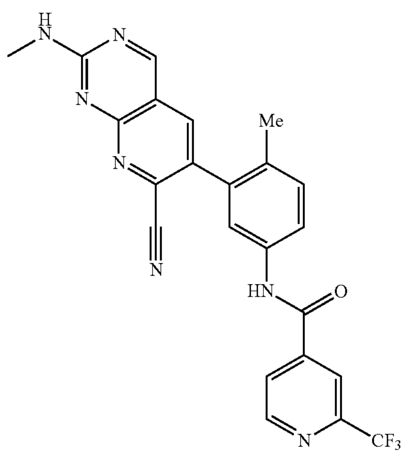 [SMILES: CNc1ncc2cc(-c3cc(NC(=O)c4ccnc(C(F)(F)F)c4)ccc3C)c(C#N)nc2n1] | N-[3-[7-ethynyl-2-(methylamino)pyrido[2,3-d]pyrimidin-6-yl]-4-methylphenyl]-2-(trifluoromethyl)pyridine-4-carboxamide |
| 68 | 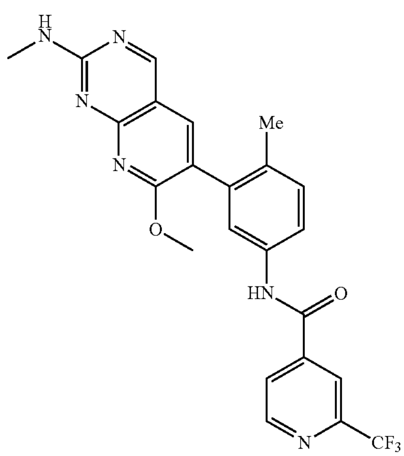 [SMILES: CNc1ncc2cc(-c3cc(NC(=O)c4ccnc(C(F)(F)F)c4)ccc3C)c(OC)nc2n1] | N-[3-[7-methoxy-2-(methylamino)pyrido[2,3-d]pyrimidin-6-yl]-4-methylphenyl]-2-(trifluoromethy)pyridine-4-carboxamide |

TABLE 1-continued

| Synthetic Chemistry Example | Compound Structure | Compound Name |
|---|---|---|
| 69 | 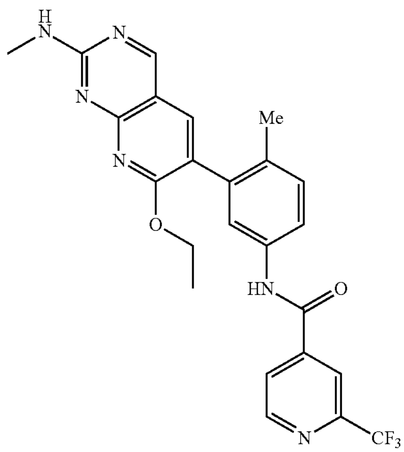 [SMILES: CCOc1nc2nc(NC)ncc2cc1-c1cc(NC(=O)c2ccnc(C(F)(F)F)c2)ccc1C] | N-[3-[7-ethoxy-2-(methylamino)pyrido[2,3-d]pyrimidin-6-yl]-4-methylphenyl]-2-(trifluoromethyl)pyridine-4-carboxamide |
| 70 | 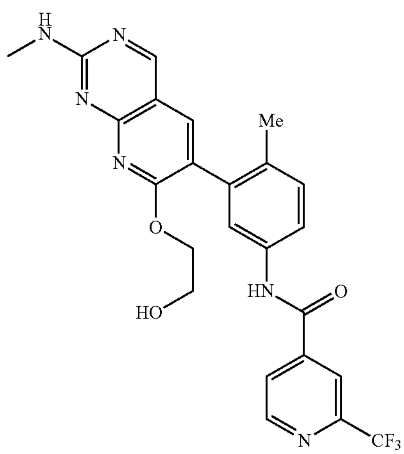 [SMILES: CNc1ncc2cc(-c3cc(NC(=O)c4ccnc(C(F)(F)F)c4)ccc3C)c(OCCO)nc2n1] | N-[3-[7-(2-hydroxyethoxy)-2-(methylamino)pyrido[2,3-d]pyrimidin-6-yl]-4-methylphenyl]-2-(trifluoromethyl)pyridine-4-carboxamide |
| 71 | 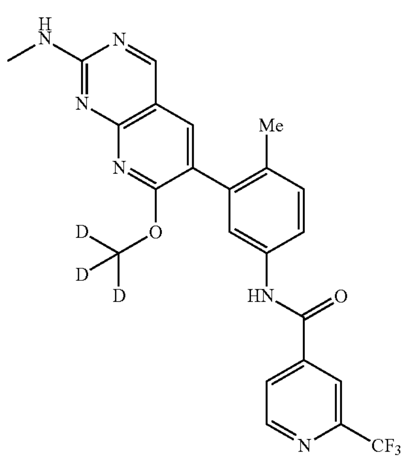 [SMILES: [2H]C([2H])([2H])Oc1nc2nc(NC)ncc2cc1-c1cc(NC(=O)c2ccnc(C(F)(F)F)c2)ccc1C] | N-(3-(7-(methoxy-$d_3$)-2-(methylamino)pyrido[2,3-d]pyrimidin-6-yl)-4-methylphenyl)-2-(trifluoromethyl)isonicotinamide |

TABLE 1-continued

| Synthetic Chemistry Example | Compound Structure | Compound Name |
|---|---|---|
| 72 | 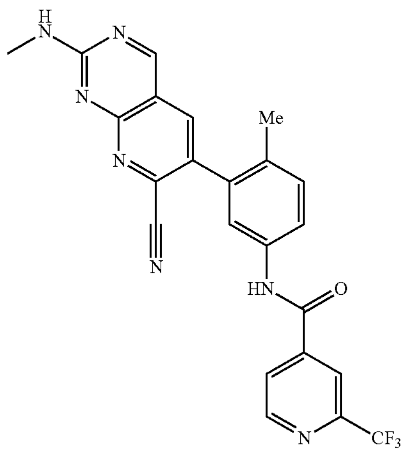 [SMILES: CNc1ncc2cc(-c3cc(NC(=O)c4ccnc(C(F)(F)F)c4)ccc3C)c(C#N)nc2n1] | N-[3-[7-cyano-2-(methylamino)pyrido[2,3-d]pyrimidin-6-yl]-4-methylphenyl]-2-(trifluoromethyl)pyridine-4-carboxamide |
| 73 | 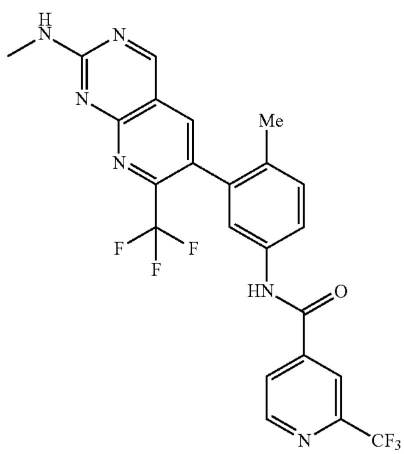 [SMILES: CNc1ncc2cc(-c3cc(NC(=O)c4ccnc(C(F)(F)F)c4)ccc3C)c(C(F)(F)F)nc2n1] | N-[4-methyl-3-[2-(methylamino)-7-(trifluoromethyl)pyrido[2,3-d]pyrimidin-6-yl]phenyl]-2-(trifluoromethyl)pyridine-4-carboxamide |
| 74 | 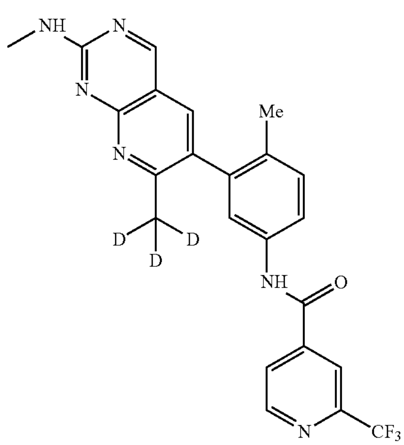 [SMILES: [2H]C([2H])([2H])c1nc2nc(NC)ncc2cc1-c1cc(NC(=O)c2ccnc(C(F)(F)F)c2)ccc1C] | N-(4-methyl-3-(7-(methyl-$d_3$)-2-(methylamino)pyrido[2,3-d]pyrimidin-6-yl)phenyl)-2-(trifluoromethyl)isonicotinamide |

TABLE 1-continued

| Synthetic Chemistry Example | Compound Structure | Compound Name |
|---|---|---|
| 75 | 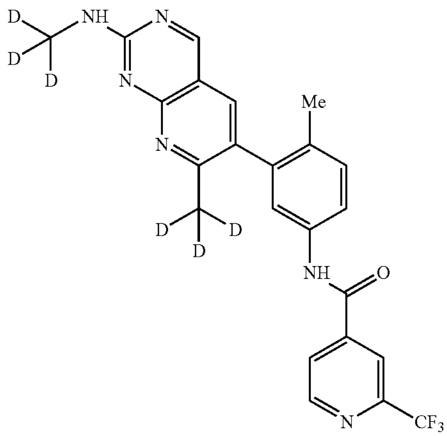 [SMILES: [2H]C([2H])([2H])Nc1ncc2cc(-c3cc(NC(=O)c4ccnc(C(F)(F)F)c4)ccc3C)c(C([2H])([2H])[2H])nc2n1] | N-(4-methyl-3-(7-(methyl-d$_3$)-2-((methyl-d$_3$)amino)pyrido[2,3-d]pyrimidin-6-yl)phenyl)-2-(trifluoromethyl)isonicotinamide |
| 76 | 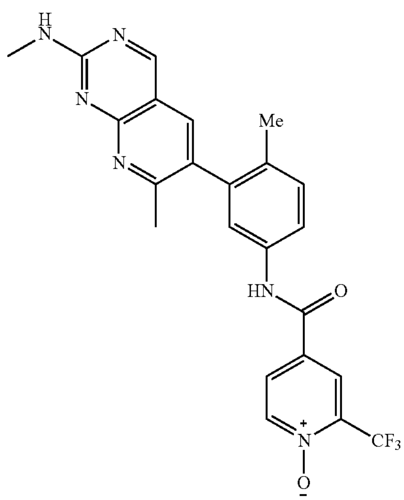 [SMILES: CNc1ncc2cc(-c3cc(NC(=O)c4cc[n+]([O-])c(C(F)(F)F)c4)ccc3C)c(C)nc2n1] | 4-([4-methyl-3-[7-methyl-2-rnethylamino)pyrido[2,3-d]pyrimidin-6-yl]phenyl]carbamoyl)-2-(trifluoromethyl)pyridin-1-ium-1-olate |
| 77 | 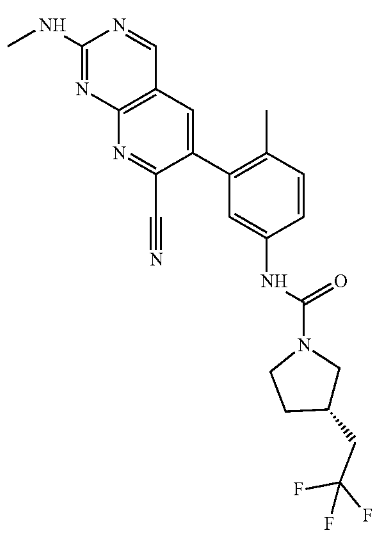 [SMILES: CNc1ncc2cc(-c3cc(NC(=O)N4CC[C@@H](CC(F)(F)F)C4)ccc3C)c(C#N)nc2n1] | (3S)-N-[7-cyano-2-(methylamino)pyrido[2,3-d]pyrimidin-6-yl]-4-methylphenyl]-3-(2,2,2-trifluoroethyl)pyrrolidine-1-carboxamide |

TABLE 1-continued

| Synthetic Chemistry Example | Compound Structure | Compound Name |
|---|---|---|
| 78 | 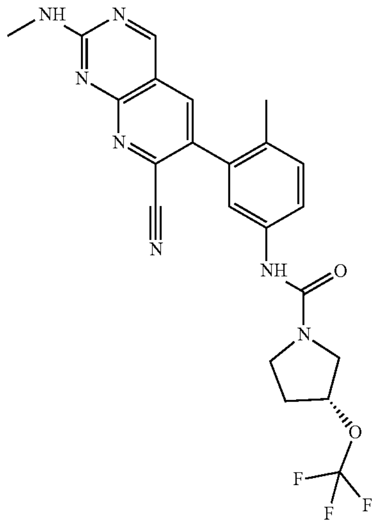 [SMILES: CNc1ncc2cc(-c3cc(NC(=O)N4CC[C@@H](OC(F)(F)F)C4)ccc3C)c(C#N)nc2n1] | (3R)-N-[3-[7-cyano-2-(methylamino)pyrido[2,3-d]pyrimidin-6-yl]-4-methylphenyl]-3-(trifluoromethoxy)pyrrolidine-1-carboxamide |

In some embodiments, the heteroaromatic RAF kinase inhibitory compound as described herein has a structure provided in Table 2A, wherein Z is selected from a substituent illustrated in Table 2B.

TABLE 2A

TABLE 2A-continued

TABLE 2A-continued
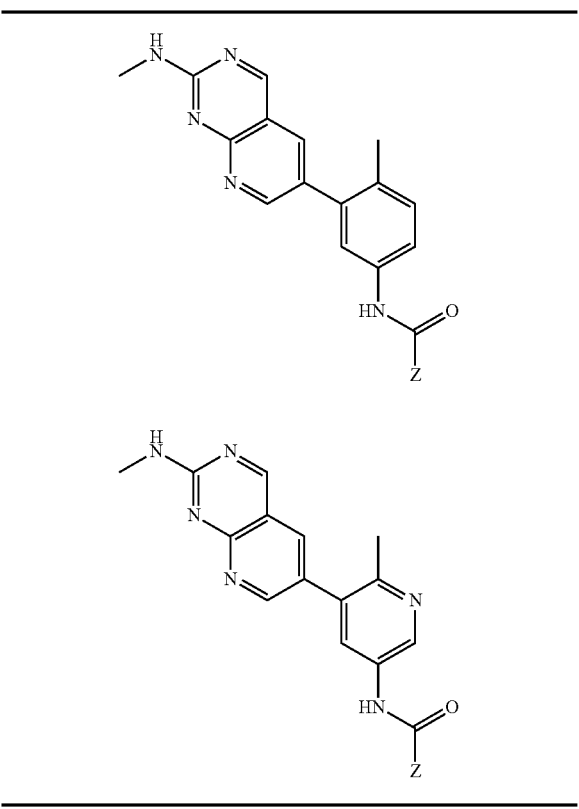
TABLE 2B
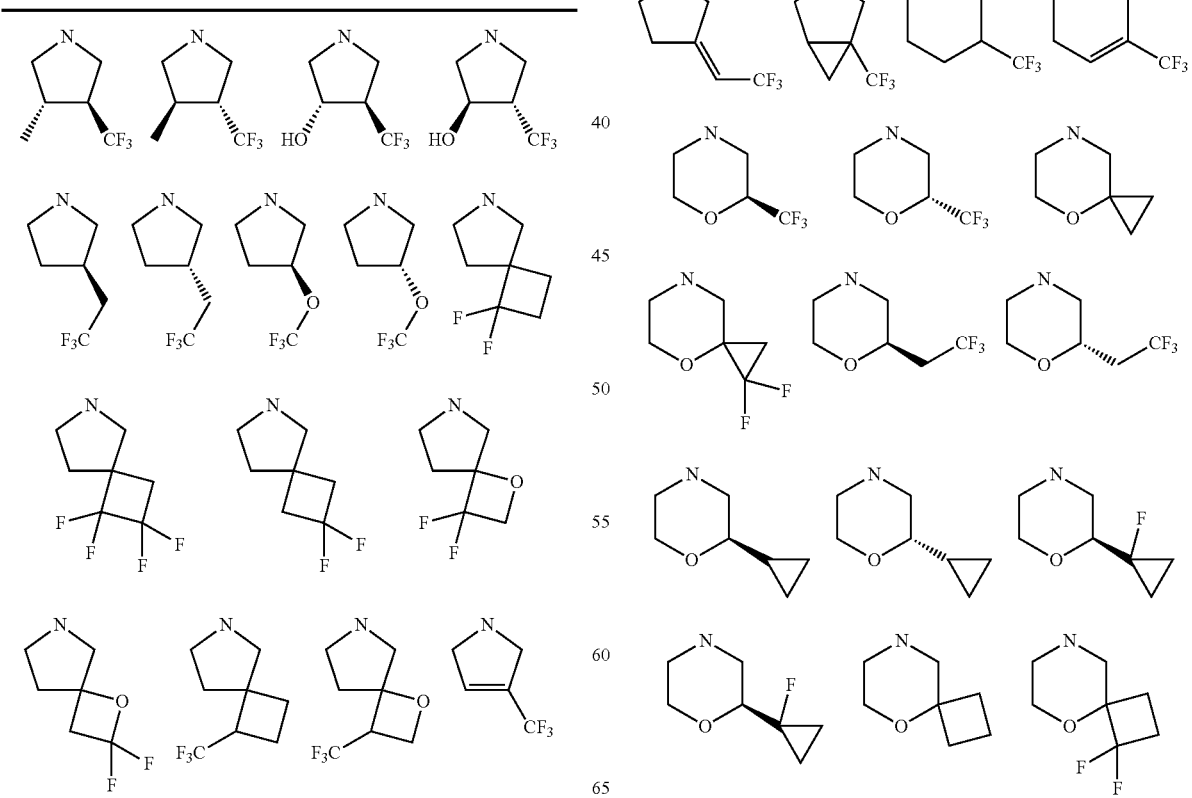
TABLE 2B-continued
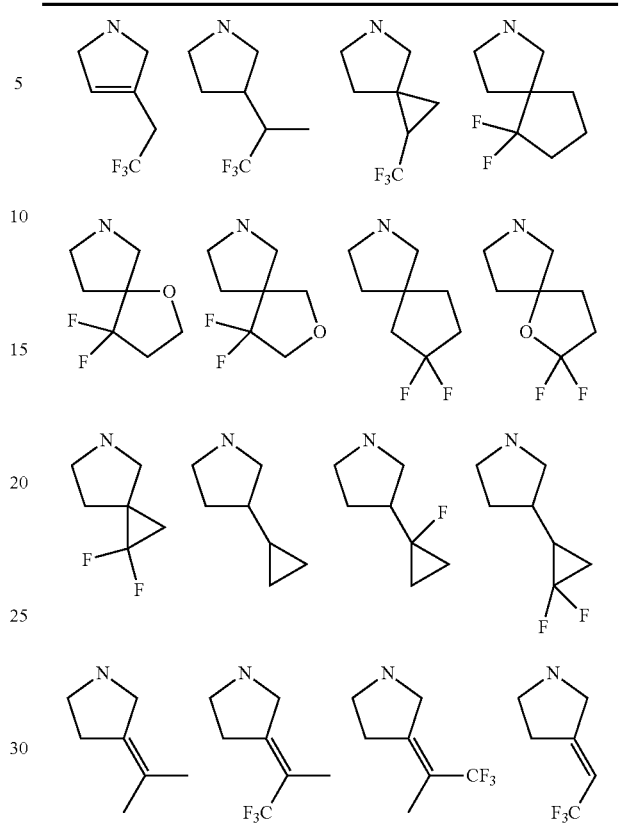

TABLE 2B-continued
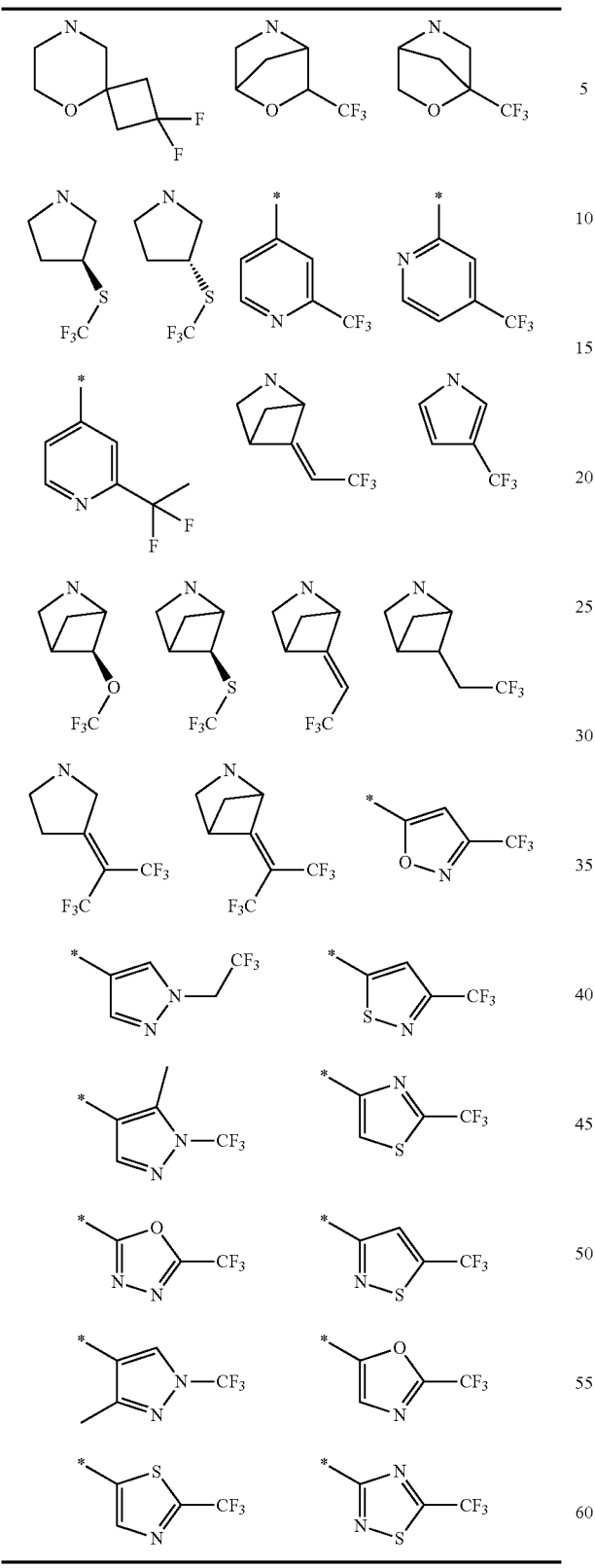
TABLE 3A
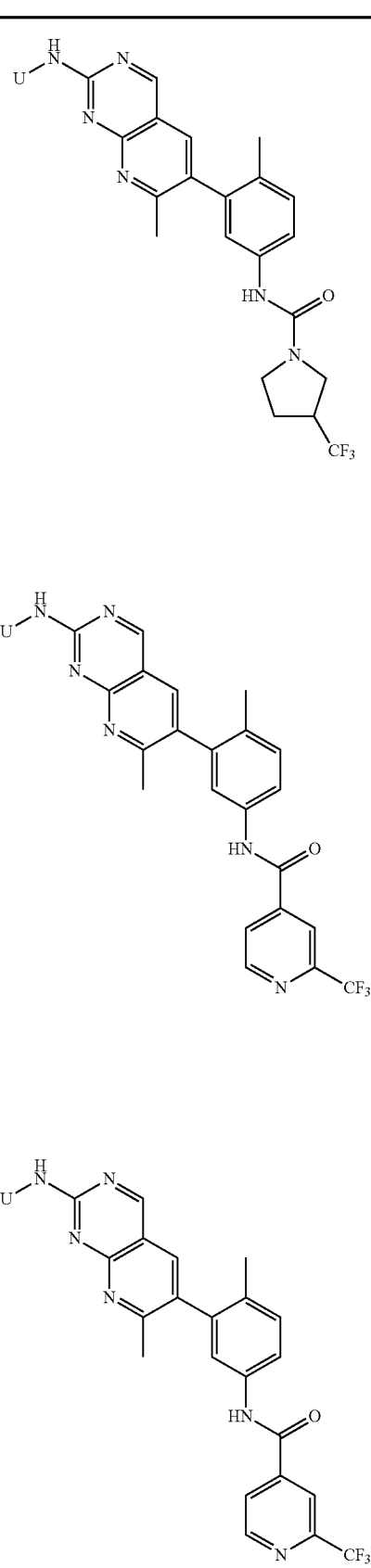
In some embodiments, the heteroaromatic RAE kinase inhibitory compound as described herein has a structure provided in Table 3A, wherein W is selected from a substituent illustrated in

TABLE 3B

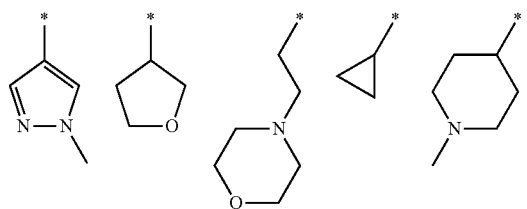

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Pharmaceutical Compositions

In certain embodiments, the heteroaromatic RAF kinase inhibitory compound described herein is administered as a pure chemical. In other embodiments, the heteroaromatic RAF kinase inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, $21^{st}$ Ed. Mack Pub. Co., Easton, Pa. (2005)).

Provided herein is a pharmaceutical composition comprising at least one heteroaromatic RAF kinase inhibitory compound as described herein, or a stereoisomer, pharmaceutically acceptable salt, hydrate, or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and a compound of Formula (I) or (Ia), or a pharmaceutically acceptable salt or solvate thereof.

One embodiment provides a method of preparing a pharmaceutical composition comprising mixing a compound of Formula (I) or (Ia), or a pharmaceutically acceptable salt or solvate thereof, and a pharmaceutically acceptable carrier.

In certain embodiments, the heteroaromatic RAF kinase inhibitory compound as described by Formula (I) or (Ia), or a pharmaceutically acceptable salt or solvate thereof, is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

In some embodiments, the heteroaromatic RAF kinase inhibitory compound as described by Formula (I) or (Ia), or pharmaceutically acceptable salt or solvate thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one heteroaromatic RAF kinase inhibitory compound as described herein differs depending upon the subject or patient's (e.g., human) condition. In some embodiments, such factors include general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.
Methods of Treatment One embodiment provides a compound of Formula (I), or a pharmaceutically acceptable salt or solvate thereof, for use in a method of treatment of the human or animal body.

One embodiment provides a compound of Formula (I), or a pharmaceutically acceptable salt or solvate thereof, for use in a method of treatment of cancer or neoplastic disease.

One embodiment provides a use of a compound of Formula (I), or a pharmaceutically acceptable salt or solvate thereof, in the manufacture of a medicament for the treatment of cancer or neoplastic disease.

In some embodiments, described herein is a method of treating cancer in a patient in need thereof comprising administering to the patient a compound of Formula (I), or a pharmaceutically acceptable salt or solvate thereof. In some embodiments, described herein is a method of treating cancer in a patient in need thereof comprising administering to the patient a pharmaceutical composition comprising a compound of Formula (I), or a pharmaceutically acceptable salt or solvate thereof, and a pharmaceutically acceptable excipient. In some embodiments, the cancer is breast cancer, colorectal cancer, ovarian cancer, pancreatic cancer, prostate cancer, or lung cancer.

One embodiment provides a compound of Formula (Ia), or a pharmaceutically acceptable salt or solvate thereof, for use in a method of treatment of the human or animal body.

One embodiment provides a compound of Formula (Ia), or a pharmaceutically acceptable salt or solvate thereof, for use in a method of treatment of cancer or neoplastic disease.

One embodiment provides a use of a compound of Formula (Ia), or a pharmaceutically acceptable salt or solvate thereof, in the manufacture of a medicament for the treatment of cancer or neoplastic disease.

In some embodiments, described herein is a method of treating cancer in a patient in need thereof comprising administering to the patient a compound of Formula (Ia), or a pharmaceutically acceptable salt or solvate thereof. In some embodiments, described herein is a method of treating cancer in a patient in need thereof comprising administering to the patient a pharmaceutical composition comprising a compound of Formula (Ia), or a pharmaceutically acceptable salt or solvate thereof, and a pharmaceutically acceptable excipient. In some embodiments, the cancer is breast cancer, colorectal cancer, ovarian cancer, pancreatic cancer, prostate cancer, or lung cancer.

Provided herein is the method wherein the pharmaceutical composition is administered orally. Provided herein is the method wherein the pharmaceutical composition is administered by injection.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

In some embodiments, the heteroaromatic RAF kinase inhibitory compounds disclosed herein are synthesized according to the following examples. As used below, and throughout the description of the invention, the following abbreviations, unless otherwise indicated, shall be understood to have the following meanings:
° C. degrees Celsius
$\delta_H$ chemical shift in parts per million downfield from tetramethylsilane
DCM dichloromethane ($CH_2Cl_2$)
DMF dimethylformamide
DMSO dimethylsulfoxide
EA ethyl acetate
ESI electrospray ionization
Et ethyl
g gram(s)
h hour(s)
HPLC high performance liquid chromatography
Hz hertz
J coupling constant (in NMR spectrometry)
LCMS liquid chromatography mass spectrometry
μ micro
m multiplet (spectral); meter(s); milli
M molar
M$^+$ parent molecular ion
Me methyl
MHz megahertz
min minute(s)
mol mole(s); molecular (as in mol wt)
mL milliliter
MS mass spectrometry
nm nanometer(s)
NMR nuclear magnetic resonance pH potential of hydrogen; a measure of the acidity or basicity of an aqueous solution
PE petroleum ether
RT room temperature
s singlet (spectral)
t triplet (spectral)
T temperature
TFA trifluoroacetic acid
THF tetrahydrofuran Intermediate 1: 2-fluoro-4-methyl-5-(4,4,5,5-tetramethyl-1,3,2-dioxaborolan-2-yl)aniline

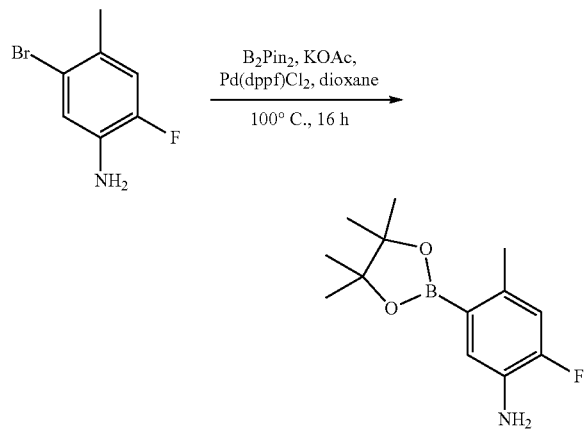

To a solution of 5-bromo-2-fluoro-4-methylaniline (2.0 g, 9.8 mmol), 4,4,4',4',5,5,5',5'-octamethyl-2,2'-bi(1,3,2-dioxaborolane) (2.7 g, 10.8 mmol) and KOAc (2.9 g, 29.4 mmol) in dioxane (20 mL) was added Pd(dppf)Cl2 (359 mg, 0.49 mmol) under $N_2$, and the mixture was stirred at 100° C. for 16 h. The reaction was cooled down to RT and the mixture was filtered. The filtrate was concentrated to give 2-fluoro-4-methyl-5-(4,4,5,5-tetramethyl-1,3,2-dioxaborolan-2-yl)aniline (crude), which was used in the next step without any further purification. MS Calcd.: 251, MS Found: 252 ([M+H]+).

Intermediate 2: N-[2-fluoro-4-methyl-5-(4,4,5,5-tetramethyl-1,3,2-dioxaborolan-2-yl)phenyl]-3-(trifluoromethyl)pyrrolidine-1-carboxamide

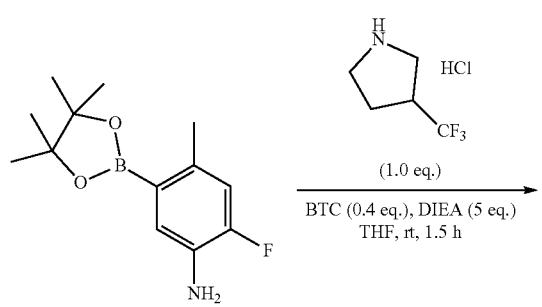

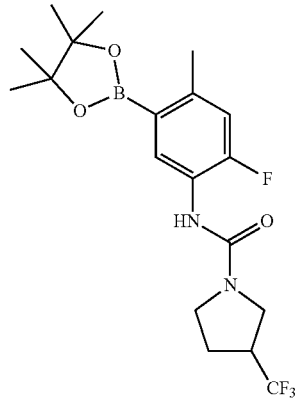

To a stirred solution of 2-fluoro-4-methyl-5-(4,4,5,5-tetramethyl-1,3,2-dioxaborolan-2-yl)aniline (800 mg, 3.19 mmol) and ditrichloromethyl carbonate (378.16 mg, 1.27 mmol) in THF (40 mL) was added DIEA (2.63 mL, 20.37 mmol) dropwise at 0° C. After stirring for 0.5 h, 3-(trifluoromethyl)pyrrolidine hydrochloride (559.37 mg, 3.19 mmol) in THF (1 mL) was added to the reaction mixture. The reaction mixture was stirred for 0.5 h at ambient temperature. The resulting mixture was concentrated under reduced pressure. The residue was purified by silica gel column chromatography, eluted with 33% EA in PE. The fractions contained desired product were concentrated to afford N-[2-fluoro-4-methyl-5-(4,4,5,5-tetramethyl-1,3,2-dioxaborolan-2-yl)phenyl]-3-(trifluoromethyl)pyrrolidine-1-carboxamide (0.928 g, 64%) as an off-white solid. MS ESI calculated for $C_{19}H_{25}BF_4N_2O_3$ [M+H]+, 417.19, found 417.15. 1H NMR (400 MHz, CDCl3) δ 8.34 (d, J=9.2 Hz, 1H), 6.86 (d, J=12.0 Hz, 1H), 6.17 (s, 1H), 3.81-3.53 (m, 4H), 3.06-2.96 (m, 1H), 2.47 (s, 3H), 2.32-2.16 (m, 2H), 1.31 (s, 12H).

Intermediate 3: 7-Methyl-2-(methylamino)pyrido[2,3-d]pyrimidin-6-yl trifluoromethanesulfonate

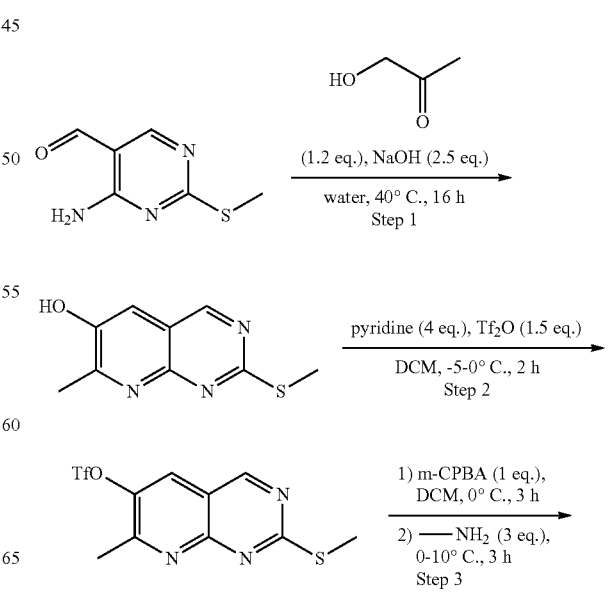

-continued

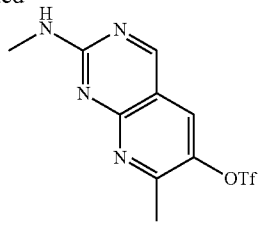

Step 1

To a solution of NaOH (4.13 g, 103.43 mmol) in water (56.00 mL) were added 4-amino-2-(methylsulfanyl)pyrimidine-5-carbaldehyde (7.00 g, 41.37 mmol) and acetone alcohol (3.68 g, 49.65 mmol). The reaction mixture was stirred at 40° C. for 16 h. The resulting mixture was cooled to 5~10° C. To the above mixture was added HCl (105 mL, 1 M in water) drop wise below 15° C. (pH=3-4). The reaction mixture was stirred at 10-15° C. for 1 h and filtered. The filter cake was washed with water (10 mL) and dried under reduced pressure at 55° C. for 16 h to provide 7-methyl-2-(methylsulfanyl)pyrido[2,3-d]pyrimidin-6-ol (8.00 g, 93%) as a brown solid. MS ESI calculated for $C_9H_9N_3OS$ [M+H]$^+$, 208.05, found 208.15. $^1$H NMR (400 MHz, d$_6$-DMSO) δ 10.86 (s, 1H), 9.29 (s, 1H), 7.55 (s, 1H), 2.60 (s, 3H), 2.59 (s, 3H).

Step 2

To a stirred solution of 7-methyl-2-(methylsulfanyl)pyrido[2,3-d]pyrimidin-6-ol (8.00 g, 38.60 mmol) in DCM (160.00 mL) was added pyridine (12.21 g, 154.40 mmol) below 20° C. The reaction mixture was cooled to −5~0° C. To the above mixture was added a solution of triflic anhydride (16.33 g, 57.90 mmol) in DCM (80 mL) drop wise below 0° C. The reaction mixture was stirred at 0° C. for 2 h. The resulting mixture was quenched with HCl (80 mL, 2M in water) and washed with water (20 mL×2). To the organic layer was added 5 g of silica gel. The resulting mixture was stirred at 10-20° C. for 1 h and filtered through diatomaceous earth. The filtrate was concentrated under reduced pressure. The residue was slurried with PE (40 mL) at 10-20° C. for 2 h and filtered. The filter cake was dried under reduced pressure to provide 7-methyl-2-(methylsulfanyl)pyrido[2,3-d]pyrimidin-6-yl trifluoromethanesulfonate (11.00 g, 84%) as a brown solid. MS ESI calculated for $C_{10}H_8F_3N_3O_3S_2$[M+H]$^+$, 340.00, found 340.00. $^1$H NMR (400 MHz, CDCl$_3$) δ 9.20 (s, 1H), 8.10 (s, 1H), 2.88 (s, 3H), 2.77 (s, 3H).

Step 3

To a solution of 7-methyl-2-(methylsulfanyl)pyrido[2,3-d]pyrimidin-6-yl trifluoromethane sulfonate (10.00 g, 29.47 mmol) in DCM (200.00 mL) was added m-CPBA (5.98 g, 29.472 mmol, 85%) in portions below 5° C. The reaction mixture was stirred at 0° C. for 3 h. To the above mixture was added methylamine (44.21 mL, 88.416 mmol) (2 M in THF) drop wise below 10° C. The reaction mixture was stirred at 0-10° C. for 3 h. The resulting mixture was diluted with DCM (100 mL) and washed with water (50 mL×5). The organic layer was concentrated under reduced pressure. The residue was slurried by DCM/PE (1:5) (200 mL) at 20° C. for 1 h and filtered. The filter cake was dried under reduced pressure to provide 7-methyl-2-(methylamino)pyrido[2,3-d]pyrimidin-6-yl trifluoromethanesulfonate (5.56 g, 58%) as a light yellow solid. MS ESI calculated for $C_{10}H_9F_3N_4O_3S$ [M+H]$^+$, 323.03, found 323.00. $^1$H NMR (400 MHz, CDCl$_3$) δ 8.95 (s, 1H), 7.87 (s, 1H), 5.90 (s, 1H), 3.20 (s, 3H), 2.76 (s, 3H).

Intermediate 4: N-[2-fluoro-4-methyl-5-(4,4,5,5-tetramethyl-1,3,2-dioxaborolan-2-yl)phenyl]-3-(trifluoromethyl)pyrrolidine-1-carboxamide

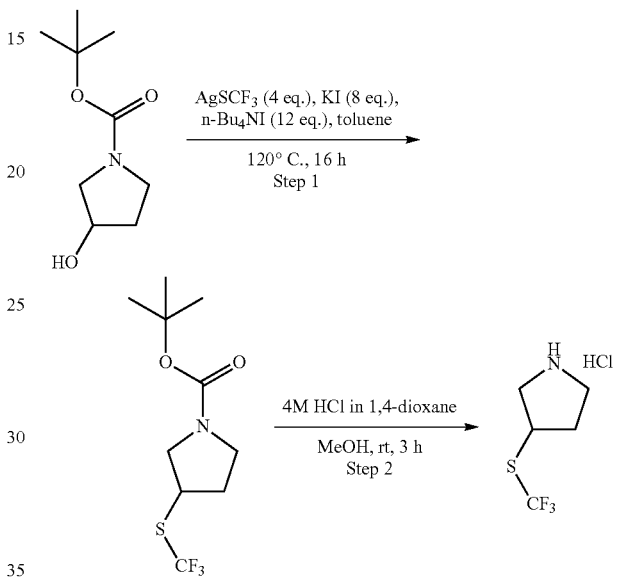

Step 1

To a mixture of tert-butyl 3-hydroxypyrrolidine-1-carboxylate (0.60 g, 3.20 mmol), tetrabutylammonium iodide (14.2 g, 38.45 mmol, 12.00 equiv), KI (4.2 g, 25.64 mmol) in toluene (30 mL) was added [(trifluoromethyl)sulfanyl] silver (892.68 mg, 4.27 mmol). The reaction mixture was stirred for 16 h at 120° C. The resulting mixture was concentrated under reduced pressure. The residue was purified by silica gel column chromatography, eluted with EA/PE (0 to 15%). The fractions contained desired product were combined and concentrated to afford tert-butyl 3-[(trifluoromethyl)sulfanyl]pyrrolidine-1-carboxylate (1 g, crude) as brown oil. MS ESI calculated for $C_{10}H_{16}F_3NO_2S$ [M+H−t-Bu]$^+$, 216.09, found 215.95.

Step 2

To a mixture of tert-butyl 3-[(trifluoromethyl)sulfanyl] pyrrolidine-1-carboxylate (1.00 g, 3.69 mmol) in MeOH (4.00 mL) was added HCl (gas) in 1,4-dioxane (4.00 mL, 131.65 mmol). The reaction mixture was stirred for 16 h at room temperature. The resulting mixture was concentrated under reduced pressure to afford 3-[(trifluoromethyl)sulfanyl]pyrrolidine hydrochloride (1 g, crude) as brown oil. The crude product was used directly to next step without further purification. MS ESI calculated for $C_5H_9ClF_3NS$ [M+H−HCl]$^+$, 172.03, found 172.05.

Intermediate 5: 4-methyl-3-(4,4,5,5-tetramethyl-1,3,2-dioxaborolan-2-yl)-N-[1-[2-(trifluoromethyl)pyridin-4-yl]ethenyl]aniline

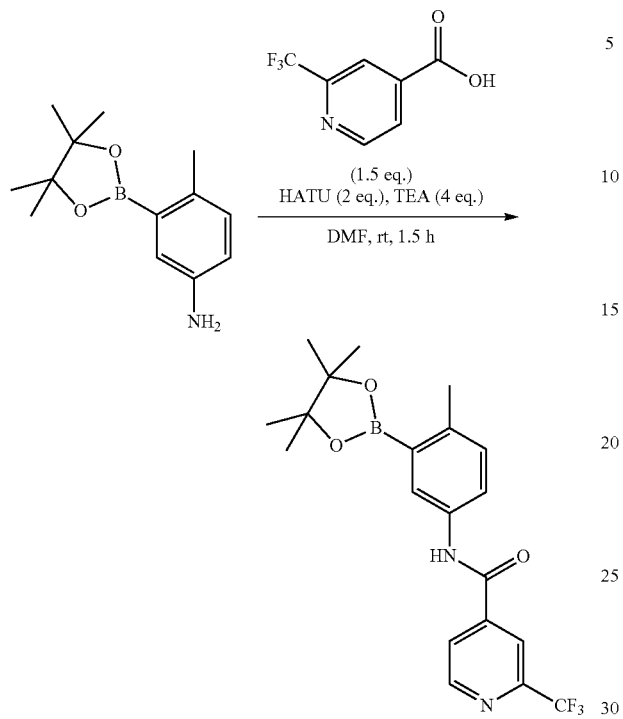

To a stirred solution of 2-(trifluoromethyl)pyridine-4-carboxylic acid (1.23 g, 6.43 mmol) and HATU (3.26 g, 8.58 mmol) in DMF (10 mL) were added TEA (2.38 mL, 23.57 mmol) and 4-methyl-3-(4,4,5,5-tetramethyl-1,3,2-dioxaborolan-2-yl)aniline (1 g, 4.29 mmol) at 0° C. under nitrogen atmosphere. The reaction mixture was stirred for 1.5 h at ambient temperature. The resulting mixture was diluted with water (30 mL) and extracted with EA (3×80 mL). The combined organic layers was washed with brine (5×40 mL), dried over anhydrous $Na_2SO_4$ and filtered. The filtrate was concentrated under reduced pressure. The residue was purified by silica gel column chromatography, eluted with 25% EA in PE. The fraction contained desired product were combined and concentrated to afford 4-methyl-3-(4,4,5,5-tetramethyl-1,3,2-dioxaborolan-2-yl)-N-[1-[2-(trifluoromethyl)pyridin-4-yl]ethenyl]aniline (1.45 g, 83%) as an off-white solid. MS ESI calculated for $C_{30}H_{39}F_3N_4O_5$ $[M+H]^+$, 407.17, found 406.90. H-NMR (400 MHz, $CDCl_3$) δ 8.93 (s, 1H), 8.12 (s, 1H), 7.70 (d, J=2.4 Hz, 1H), 7.25-7.23 (m, 1H), 2.56 (s, 3H), 1.37 (s, 12H). F-NMR (376 MHz, $CDCl_3$) δ −68.01.

Intermediate 6: 2-(ethylamino)-7-methylpyrido[2,3-d]pyrimidin-6-yl trifluoromethanesulfonate

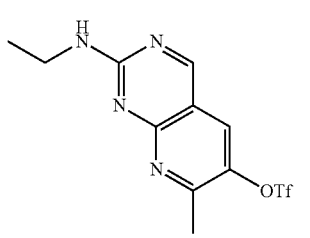 [SMILES: CCNc1ncc2cc(OS(=O)(=O)C(F)(F)F)c(C)nc2n1]

The title compound was prepared using procedures similar to those described in Intermediate 3 using ethylamine instead of methylamine to afford the title compound as a solid.

Intermediate 7: 2-[(2-hydroxyethyl)amino]-7-methylpyrido[2,3-d]pyrimidin-6-yl trifluoromethanesulfonate

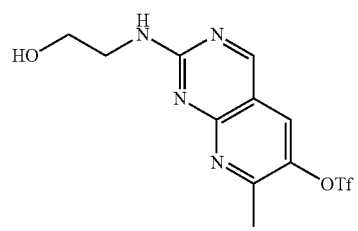 [SMILES: Cc1nc2nc(NCCO)ncc2cc1OS(=O)(=O)C(F)(F)F]

The title compound was prepared using procedures similar to those described in Intermediate 3 using ethanolamine instead of methylamine to afford the title compound as a solid.

Intermediate 8: N-[2-fluoro-4-methyl-5-(4,4,5,5-tetramethyl-1,3,2-dioxaborolan-2-yl)phenyl]-3-(trifluoromethyl)pyrrolidine-1-carboxamide

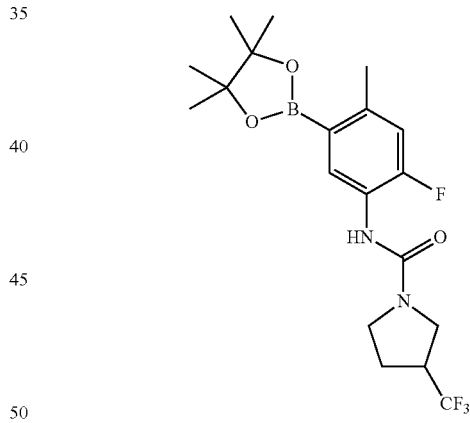

Step 1

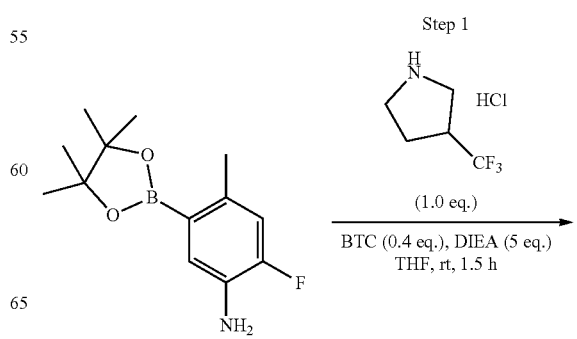

105
-continued

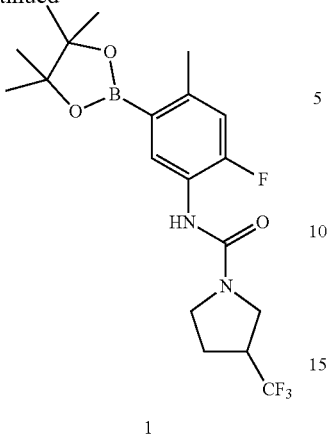

Step 1: N-[2-fluoro-4-methyl-5-(4,4,5,5-tetramethyl-1,3,2-dioxaborolan-2-yl)phenyl]-3-(trifluoromethyl)pyrrolidine-1-carboxamide

106
-continued

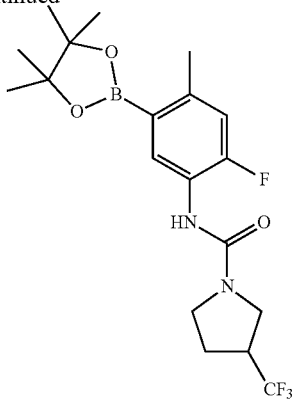

To a stirred solution of 2-fluoro-4-methyl-5-(4,4,5,5-tetramethyl-1,3,2-dioxaborolan-2-yl)aniline (0.80 g, 3.19 mmol) and ditrichloromethyl carbonate (0.38 g, 1.27 mmol) in THF (40 mL) was added DIEA (2.63 mL, 20.37 mmol) dropwise at 0° C. After stirring for 0.5 h, 3-(trifluoromethyl)pyrrolidine hydrochloride (0.56 g, 3.19 mmol) in THF (1 mL) was added to the above mixture. The reaction mixture was stirred for 0.5 h at ambient temperature. The resulting mixture was concentrated under reduced pressure. The residue was purified by silica gel column chromatography, eluted with 33% EA in PE. The fractions contained desired product were combined and concentrated to afford N-[2-fluoro-4-methyl-5-(4,4,5,5-tetramethyl-1,3,2-dioxaborolan-2-yl)phenyl]-3-(trifluoromethyl)pyrrolidine-1-carboxamide (0.928 g, 640) as an off-white solid. MS ESI calculated for $C_{19}H_{25}BF_4N_2O_3[M+H]^+$, 417.19, found 417.15. H-NMR (400 MHz, CDCl$_3$) δ 8.34 (d, J=9.2 Hz, 1H), 6.86 (d, J=12.0 Hz, 1H), 6.17 (s, 1H), 3.81-3.53 (m, 4H), 3.06-2.96 (m, 1H), 2.47 (s, 3H), 2.32-2.16 (m, 2H), 1.31 (s, 12H).

The compounds in Table 4 were prepared using procedures similar to those described in Intermediate 8 using appropriate starting materials.

TABLE 4

| Intermediate | Structure | IUPAC Name | Exact Mass [M + H]⁺ |
|---|---|---|---|
| 9 | 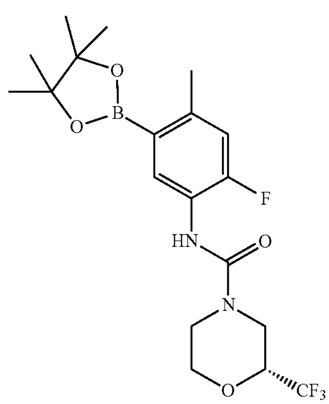 [SMILES: Cc1cc(F)c(NC(=O)N2CCO[C@@H](C(F)(F)F)C2)cc1B1OC(C)(C)C(C)(C)O1] | (2R)-N-[2-fluoro-4-methyl-5-(4,4,5,5-tetramethyl-1,3,2-dioxaborolan-2-yl)phenyl]-2-(trifluoromethyl)morpholine-4-carboxamide | Calc'd 433.18, found 433.10 |

TABLE 4-continued

| Intermediate | Structure | IUPAC Name | Exact Mass [M + H]+ |
|---|---|---|---|
| 10 | 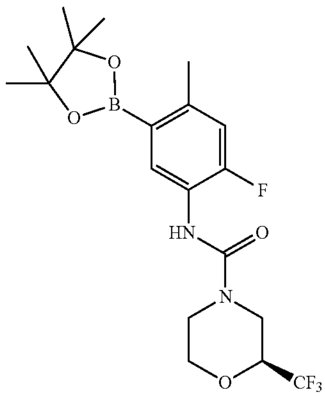 [SMILES: Cc1cc(F)c(NC(=O)N2CCO[C@H](C(F)(F)F)C2)cc1B1OC(C)(C)C(C)(C)O1] | (2S)-N-[2-fluoro-4-methyl-5-(4,4,5,5-tetramethyl-1,3,2-dioxaborolan-2-yl)phenyl]-2-(trifluoromethyl)morpholine-4-carboxamide | Calc'd 433.18, found 433.55 |
| 11 | 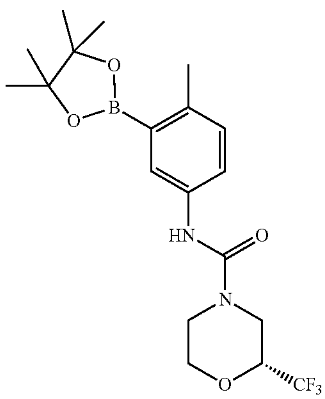 [SMILES: Cc1ccc(NC(=O)N2CCO[C@@H](C(F)(F)F)C2)cc1B1OC(C)(C)C(C)(C)O1] | (2R)-N-[4-methyl-3-(4,4,5,5-tetramethyl-1,3,2-dioxaborolan-2-yl)phenyl]-2-(trifluoromethyl)morpholine-4-carboxamide | Calc'd 415.19; found 415.25 |
| 12 | 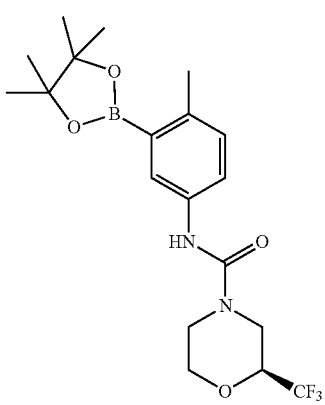 [SMILES: Cc1ccc(NC(=O)N2CCO[C@H](C(F)(F)F)C2)cc1B1OC(C)(C)C(C)(C)O1] | (2S)-N-[4-methyl-3-(4,4,5,5-tetramethyl-1,3,2-dioxaborolan-2-yl)phenyl]-2-(trifluoromethyl)morpholine-4-carboxamide | Calc'd 415.19; found 414.80 |

TABLE 4-continued

| Intermediate | Structure | IUPAC Name | Exact Mass [M + H]⁺ |
|---|---|---|---|
| 13 | 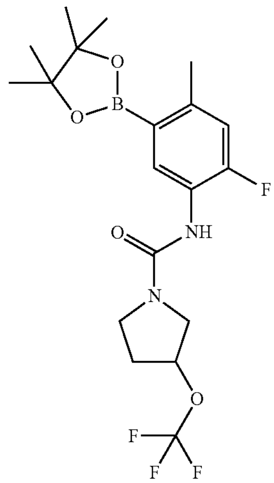 [SMILES: Cc1cc(F)c(NC(=O)N2CCC(OC(F)(F)F)C2)cc1B1OC(C)(C)C(C)(C)O1] | N-[2-fluoro-4-methyl-5-(4,4,5,5-tetramethyl-1,3,2-dioxaborolan-2-yl)phenyl]-3-(trifluoromethoxy)pyrrolidine-1-carboxamide | Calc'd 433.18, found 433.10 |
| 14 | 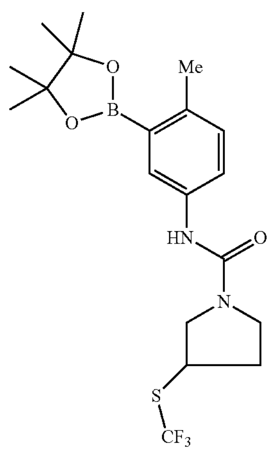 [SMILES: Cc1ccc(NC(=O)N2CCC(SC(F)(F)F)C2)cc1B1OC(C)(C)C(C)(C)O1] | N-[4-methyl-3-(4,4,5,5-tetramethyl-1,3,2-dioxaborolan-2-yl)phenyl]-3-[(trifluoromethyl)sulfanyl]pyrrolidine-1-carboxamide | Calc'd 431.17, found 431.15 |
| 15 | 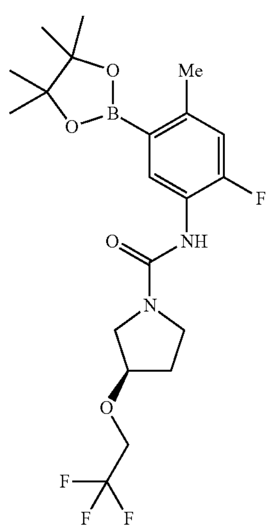 [SMILES: Cc1cc(F)c(NC(=O)N2CC[C@@H](OCC(F)(F)F)C2)cc1B1OC(C)(C)C(C)(C)O1] | 3R)-N-[2-fluoro-4-methyl-5-(4,4,5,5-tetramethyl-1,3,2-dioxaborolan-2-yl)phenyl]-3-(2,2,2-trifluoroethoxy)pyrrolidine-1-carboxamide | Calc'd 447.20, found 447.20 |

The compounds in Table 5 were prepared using procedures similar to those described in Intermediate 5 using appropriate starting materials.

TABLE 5

| Intermediate | Structure | IUPAC Name | Exact Mass [M + H]+ |
|---|---|---|---|
| 16 | 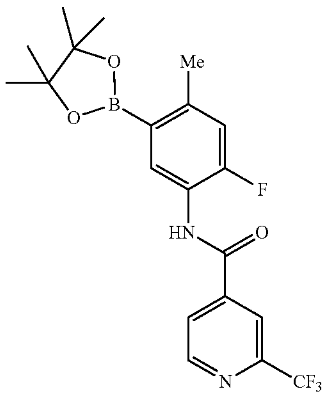 [SMILES: Cc1cc(F)c(NC(=O)c2ccnc(C(F)(F)F)c2)cc1B1OC(C)(C)C(C)(C)O1] | N-[2-fluoro-4-methyl-5-(4,4,5,5-tetramethyl-1,3,2-dioxaborolan-2-yl)phenyl]-2-(trifluoromethyl)pyridine-4-carboxamide | Calc'd 425.16, found 425.20 |
| 17 | 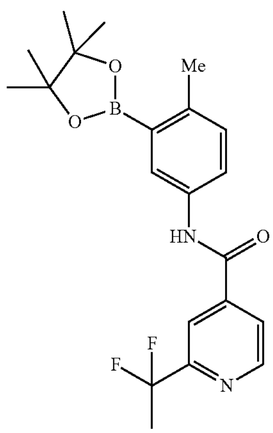 [SMILES: Cc1ccc(NC(=O)c2ccnc(C(C)(F)F)c2)cc1B1OC(C)(C)C(C)(C)O1] | 2-(1,1-difluoroethyl)-N-[4-methyl-3-(4,4,5,5-tetramethyl-1,3,2-dioxaborolan-2-yl)phenyl]pyridine-4-carboxamide | Calc'd 403.19, found 403.15 |

Intermediate 18: 6-bromo-N-[(4-methoxyphenyl)methyl]-N-methylpyrido[2,3-d]pyrimidin-2-amine

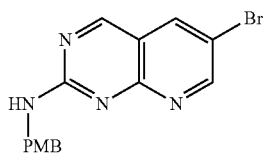

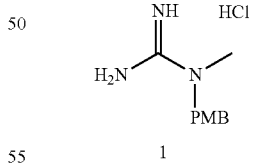

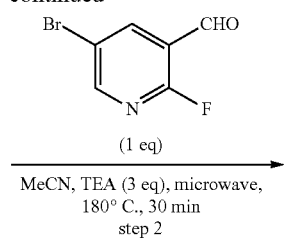

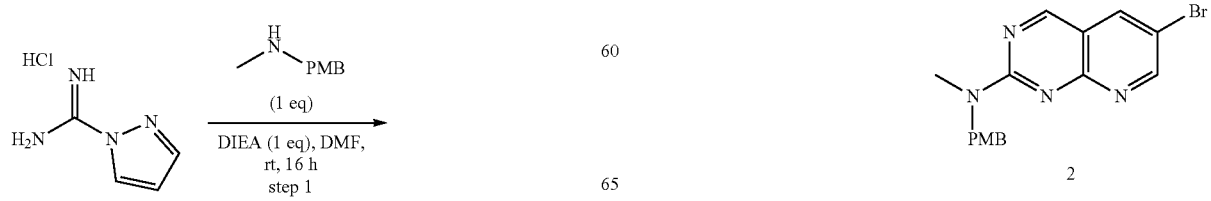

Step 1: N-[(4-methoxyphenyl)methyl]-N-methyl-guanidine hydrochloride

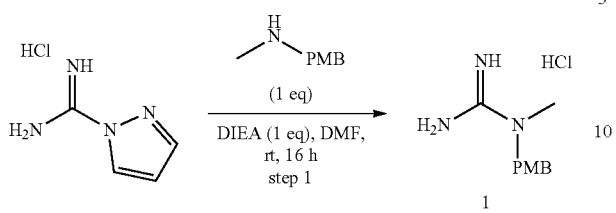

To a stirred solution of pyrazole-1-carboximidamide hydrochloride (48.00 g, 0.7 mmol) and [(4-methoxyphenyl)methyl](methyl)amine (49.52 g, 327.47 mmol) in DMF (480 mL) was added DIEA (44.44 g, 343.84 mmol) at room temperature. The resulting mixture was stirred for 16 h at room temperature. $Et_2O$ (500 mL) was added, and the desired product became an oil at the bottom of the flask. The mixture was sonicated and the top ether layer was decanted. This process was repeated several times until the desired product solidified. The solid was dried under high vacuum to afford N-[(4-methoxyphenyl)methyl]-N-methylguanidine hydrochloride (37.3 g, 45%) as an off-white solid. MS ESI calculated for $C_{10}H_{16}ClN_3O$ [M+H–HCl]$^+$, 194.12, found 194.10. H NMR (400 MHz, $CD_3OD$) δ 7.24-7.21 (m, 2H), 7.02-7.21 (m, 2H), 4.56 (s, 2H), 3.81 (s, 3H), 2.99 (s, 3H).

Step 2: 6-bromo-N-[(4-methoxyphenyl)methyl]-N-methylpyrido[2,3-d]pyrimidin-2-amine

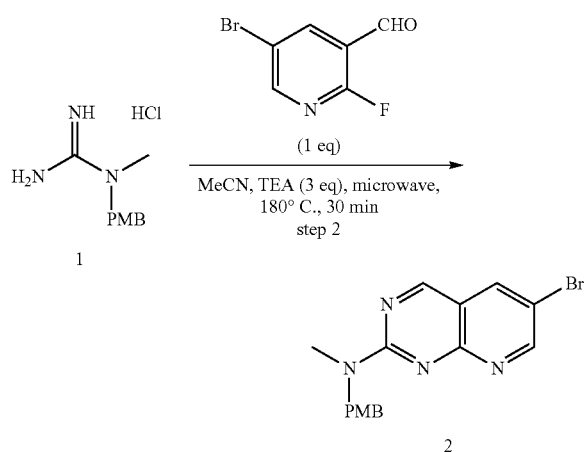

To a stirred mixture of N-[(4-methoxyphenyl)methyl]-N-methylguanidine hydrochloride (15.00 g, 65.30 mmol) and 5-bromo-2-fluoropyridine-3-carbaldehyde (13.32 g, 65.30 mmol) in ACN (150 mL) was added TEA (19.8 mL, 195.90 mmol) at room temperature under nitrogen atmosphere. The resulting mixture was stirred for 30 min at 180° C. microwave under nitrogen atmosphere. The resulting mixture was concentrated under reduced pressure. The residue was purified by silica gel column chromatography, eluted with PE/EtOAc (7:3) to afford 6-bromo-N-[(4-methoxyphenyl)methyl]-N-methylpyrido[2,3-d]pyrimidin-2-amine (10 g, 38%) as a brown solid. MS ESI calculated for $C_{15}H_{13}BrN_4O$ [M+H]$^+$, 359.04, 361.04, found 358.95, 360.95. H NMR (400 MHz, DMSO-$d_6$) δ 9.28 (s, 1H), 8.95-8.94 (m, 1H), 8.58-8.57 (m, 1H), 7.27-7.21 (m, 2H), 6.92-6.87 (m, 2H), 4.96 (s, 1H), 3.73 (s, 3H), 3.19 (s, 3H).

Intermediate 19: 6-(5-amino-2-methylphenyl)-N-[(4-methoxyphenyl)methyl]-N-methylpyrido[2,3-d]pyrimidin-2-amine

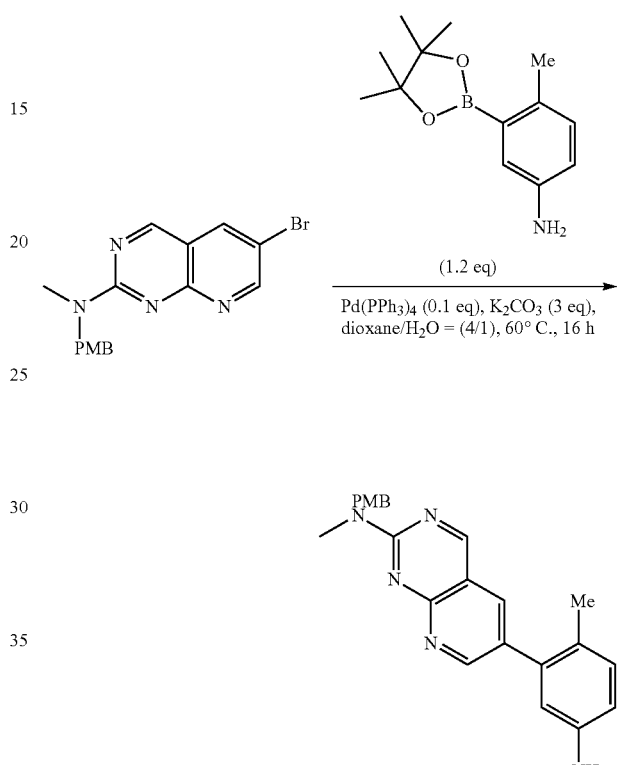

To a solution of 6-bromo-N-[(4-methoxyphenyl)methyl]-N-methylpyrido[2,3-d]pyrimidin-2-amine (9.90 g, 27.55 mmol) and 4-methyl-3-(4,4,5,5-tetramethyl-1,3,2-dioxaborolan-2-yl)aniline (7.71 g, 33.07 mmol) in 1,4-dioxane (100.00 mL) and water (25.00 mL) were added $K_2CO_3$ (11.43 g, 82.67 mmol) and Pd(PPh$_3$)$_4$ (3.18 g, 2.75 mmol). The mixture was stirred for 16 h at 65 degrees C. under a nitrogen atmosphere. The reaction mixture was allowed to cool down to ambient temperature, diluted with water (200 mL) and extracted with ethyl acetate (3×200 mL). The combined organic fractions was washed with brine (200 mL), dried over anhydrous sodium sulfate and filtered. The filtrate was concentrated under reduced pressure. The residue was purified by silica gel column chromatography, eluted with PE/EtOAc (1:5). The fractions contained desired product was concentrated to afford 6-(5-amino-2-methylphenyl)-N-[(4-methoxyphenyl)methyl]-N-methylpyrido[2,3-d]pyrimidin-2-amine (9.2 g, 87%) as a yellow solid. MS ESI calculated for $C_{23}H_{23}N_5O$ [M+H]$^+$, 386.19; found 386.05. H-NMR (400 MHz, $d_6$-DMSO) δ 9.34 (s, 1H), 8.85 (d, J=2.8 Hz, 1H), 8.28-8.12 (m, 1H), 7.25 (s, 2H), 7.00 (d, J=8.0 Hz, 1H), 6.90 (d, J=8.4 Hz, 2H), 6.57 (d, J=8.0 Hz, 2H), 5.04 (s, 2H), 4.98 (s, 2H), 3.73 (d, J=1.2 Hz, 3H), 3.21 (s, 3H), 2.12 (s, 3H).

Intermediate 20: 5-(2-[[(4-methoxyphenyl)methyl](methyl)amino]pyrido[2,3-d]pyrimidin-6-yl)-6-methylpyridin-3-amine

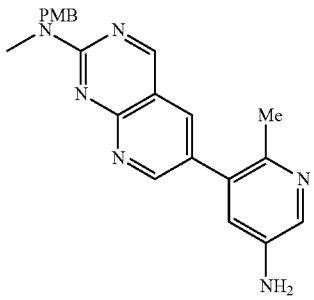

The title compound was prepared using procedures similar to those described in Intermediate 17 using 6-bromo-N-[(4-methoxyphenyl)methyl]-N-methylpyrido[2,3-d]pyrimidin-2-amine and 6-methyl-5-(4,4,5-trimethyl-1,3,2-dioxaborolan-2-yl)pyridin-3-amine to afford the title compound as a yellow solid.

Intermediate 21: 6-bromo-N-methyl-7-(trifluoromethyl)pyrido[2,3-d]pyrimidin-2-amine

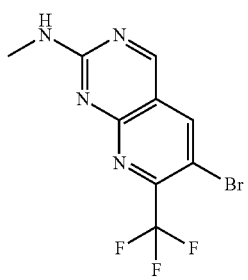 [SMILES: CNc1ncc2cc(Br)c(C(F)(F)F)nc2n1]

Step 1: 2-(methylsulfanyl)-7-(trifluoromethyl)pyrido[2,3-d]pyrimidine

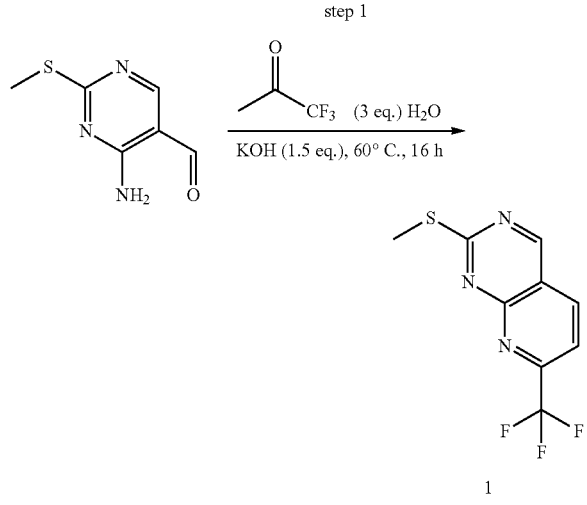

To a stirred mixture of 4-amino-2-(methylsulfanyl)pyrimidine-5-carbaldehyde (2.00 g, 11.82 mmol) and 1,1,1-trifluoroacetone (2.65 g, 23.64 mmol) in H$_2$O (16.00 mL) was added KOH (0.99 g, 17.73 mmol) in portions at 0° C. The reaction mixture was stirred for 16 h at 60° C. The precipitated solids were collected by filtration, washed with water (3×30 ml) and dried in vacuum drying oven. This resulted in 2-(methylsulfanyl)-7-(trifluoromethyl)pyrido[2,3-d]pyrimidine (1.76 g, 61%) as an off-white solid. MS ESI calculated for C$_9$H$_6$F$_3$N$_3$S [M+H]$^+$, 246.02, found 246.15.

Step 2: N-[2-fluoro-4-methyl-5-[2-(morpholin-4-yl)-6-[2-(oxan-2-yloxy)ethoxy]pyridin-4-yl]phenyl]-3-(1,1,2,2,2-pentafluoroethyl)-2,5-dihydropyrrole-1-carboxamide

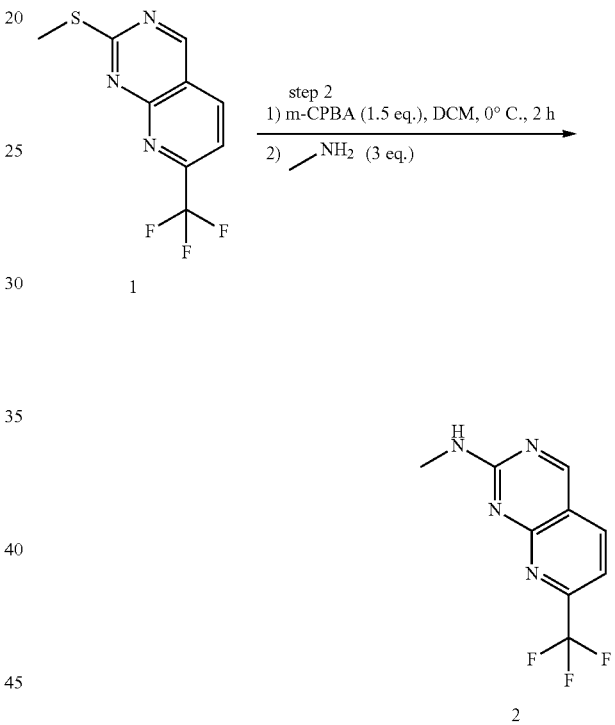

To a stirred solution of 2-(methylsulfanyl)-7-(trifluoromethyl)pyrido[2,3-d]pyrimidine (1.70 g, 6.93 mmol) in DCM (48.00 mL) was added m-CPBA (1.79 g, 10.40 mmol) dropwise at 0° C. The reaction mixture was stirred for 2 h at 0° C. To the above mixture was added methylamine (0.65 g, 20.93 mmol) dropwise at 0° C. The reaction mixture was stirred for additional 5 h at room temperature. The resulting mixture was diluted with water (50 mL) at room temperature and extracted with DCM (3×50 mL). The combined organic layers was washed with brine (3×40 mL), dried over anhydrous Na$_2$SO$_4$ and filtered. The filtrate was concentrated under reduced pressure. The residue was purified by silica gel column chromatography, eluted with PE/(EA/EtOH=3:1) (1.5:1). The fractions contained desired product were combined and concentrated to afford N-methyl-7-(trifluoromethyl)pyrido[2,3-d]pyrimidin-2-amine (1 g, 63%) as an off-white solid. MS ESI calculated for C$_9$H$_7$F$_3$N$_4$ [M+H]$^+$, 229.06, found 229.20.

117

Step 3: 6-bromo-N-methyl-7-(trifluoromethyl)pyrido[2,3-d]pyrimidin-2-amine

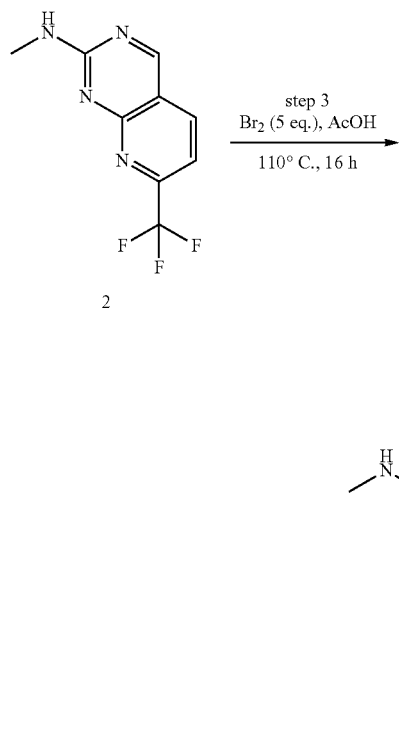

To a stirred solution of N-methyl-7-(trifluoromethyl)pyrido[2,3-d]pyrimidin-2-amine (0.55 g, 2.41 mmol) in AcOH (11.00 mL) was added $Br_2$ (1.93 g, 12.05 mmol) dropwise at room temperature. The reaction mixture was stirred at 110° C. for 16 h. The resulting mixture was concentrated under reduced pressure. The residue was diluted with saturated aqueous $NaHCO_3$ (150 mL) at 0° C. The resulting mixture was extracted with DCM (3×100 mL). The combined organic layers was washed with brine (3×50 mL), dried over anhydrous $Na_2SO_4$ and filtered. The filtrate was concentrated under reduced pressure. The residue was purified by reverse phase column chromatography with the following conditions: Column: XBridge C18 OBD Prep Column, 100 Å, 5 um, 19 mm×250 mm; Mobile Phase A: Water (10 mmol/L $NH_4HCO_3$), Mobile Phase B: ACN; Flow rate: 20 mL/min; Gradient: 40 B to 70 B in 5.8 min. The fractions contained desired product were combined and concentrated to afford 6-bromo-N-methyl-7-(trifluoromethyl)pyrido[2,3-d]pyrimidin-2-amine (85.2 mg, 11%) as an off-white solid. MS ESI calculated for $C_9H_6BrF_3N_4$ [M+H]$^+$, 306.97, 308.97, found 308.05, 310.05.

The compounds in Table 6 were prepared using procedures similar to those described in Intermediate 21 using appropriate starting materials.

118

TABLE 6

| Intermediate | Structure | IUPAC Name | Exact Mass [M + H]$^+$ |
|---|---|---|---|
| 22 | (structure) | 6-bromo-N-methyl-7-(methyl-d$_3$)pyrido[2,3-d]pyrimidin-2-amine | Calc'd 256.02, 258.02; found 255.95, 257.95 |
| 23 | (structure) | 6-bromo-N,7-bis(methyl-d$_3$)pyrido[2,3-d]pyrimidin-2-amine | Calc'd 259.04, 261.04, found 258.95, 260.95 |

Example 1 and Example 2: Synthesis of (3S)—N-[2-fluoro-4-methyl-5-[7-methyl-2-(methylamino)pyrido[2,3-d]pyrimidin-6-yl]phenyl]-3-(trifluoromethyl)pyrrolidine-1-carboxamide; (3R)—N-[2-fluoro-4-methyl-5-[7-methyl-2-(methylamino)pyrido[2,3-d]pyrimidin-6-yl]phenyl]-3-(trifluoromethyl)pyrrolidine-1-carboxamide

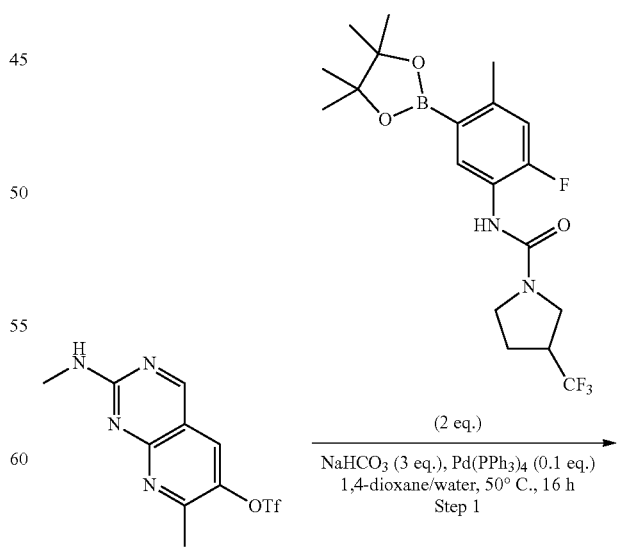

-continued

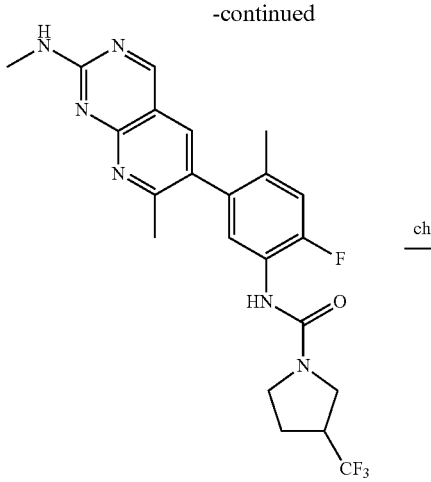

EA (3×30 mL). The combined organic layers was washed with brine (2×15 mL), dried over anhydrous $Na_2SO_4$ and filtered. The filtrate was concentrated under reduced pressure. The residue was purified by reverse phase-flash chromatography, eluted with 25% ACN in water (0.1% FA) to afford 400 mg product which was further purified by Prep-HPLC with the following conditions (Column: SunFire Prep C18 OBD Column, 19×150 mm Sum 10 nm; Mobile Phase A:Water (0.05% TFA), Mobile Phase B: ACN; Flow rate: 20 mL/min; Gradient: 25 B to 35 B in 6 min; 210/254 nm) to afford N-[2-fluoro-4-methyl-5-[7-methyl-2-(methylamino) pyrido[2,3-d]pyrimidin-6-yl]phenyl]-3-(trifluoromethyl) pyrrolidine-1-carboxamide (200 mg, 51%) as a yellow solid. MS ESI calculated for $C_{22}H_{22}F_4N_6O$ [M+H]$^+$, 463.18, found 463.20.

Step 2

N-[2-fluoro-4-methyl-5-[7-methyl-2-(methylamino) pyrido[2,3-d]pyrimidin-6-yl]phenyl]-3-(trifluoromethyl) pyrrolidine-1-carboxamide (220 mg, 0.48 mmol) was separated by chiral SFC with following conditions: Column: CHIRALPAK IE, 3*25 cm, 5 um; Mobile Phase A: Hex: DCM=3:1 (10 mM $NH_3$-MEOH)—HPLC, Mobile Phase B: EtOH—HPLC; Flow rate: 40 mL/min; Gradient: 20 B to 20 B in 21 min; 220/254 nm. The fractions contained desired product were concentrated to give the two enantiomers: (66.5 mg, 30%) of the first isomer eluted at 15.19 min (ee>98%) and (66.3 mg, 30%) of the second isomer eluted at 18.44 min (ee>98%). $^1$H NMR (400 MHz, DMSO-$d_6$) of the first eluted isomer: δ 9.08 (s, 1H), 8.07 (s, 1H), 7.91 (s, 1H), 7.68 (s, 1H), 7.31 (d, J=8.0 Hz, 1H), 7.22 (d, J=11.6 Hz, 1H), 3.67 (t, J=9.4 Hz, 1H), 3.52-3.41 (m, 3H), 3.31-3.27 (m, 1H), 2.92 (d, J=4.8 Hz, 3H), 2.31 (s, 3H), 2.23-2.15 (m, 1H), 2.05-2.01 (m, 4H). $^1$H NMR (400 MHz, DMSO-$d_6$) of the second eluted isomer: δ 9.08 (s, 1H), 8.07 (s, 1H), 7.91 (s, 1H), 7.68 (s, 1H), 7.31 (d, J=8.0 Hz, 1H), 7.22 (d, J=11.6 Hz, 1H), 3.67 (t, J=9.4 Hz, 1H), 3.52-3.41 (m, 3H), 3.31-3.27 (m, 1H), 2.92 (d, J=4.8 Hz, 3H), 2.31 (s, 3H), 2.23-2.15 (m, 1H), 2.05-2.01 (m, 4H). MS ESI calculated for $C_{22}H_{22}F_4N_6O$ [M+H]$^+$, 463.18, found 463.15.

Example 3: N-(2-fluoro-4-methyl-5-(7-methyl-2-(methylamino)pyrido[2,3-d]pyrimidin-6-yl)phenyl)-3-(trifluoromethyl)-2,5-dihydro-1H-pyrrole-1-carboxamide Step 1

To a solution of 7-methyl-2-(methylamino)pyrido[2,3-d] pyrimidin-6-yl trifluoromethanesulfonate (270 mg, 0.84 mmol) and N-[2-fluoro-4-methyl-5-(4,4,5,5-tetramethyl-1, 3,2-dioxaborolan-2-yl)phenyl]-3-(trifluoromethyl)pyrrolidine-1-carboxamide (697.45 mg, 1.68 mmol) in 1,4-dioxane (4.00 mL) and water (1.00 mL) were added $NaHCO_3$ (211.15 mg, 2.51 mmol) and Pd(PPh$_3$)$_4$ (96.82 mg, 0.084 mmol). The reaction mixture was degassed with nitrogen for three times and stirred for 16 h at 50° C. The resulting mixture was diluted with water (10 mL) and extracted with

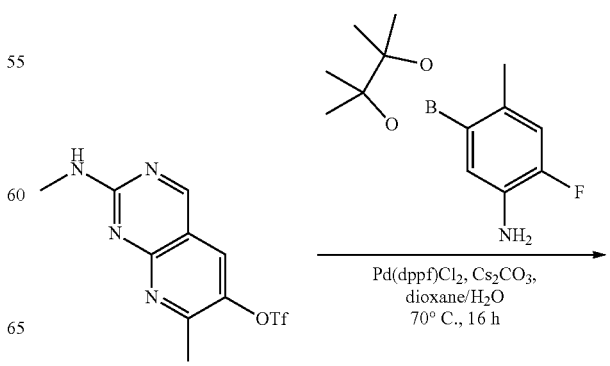

-continued

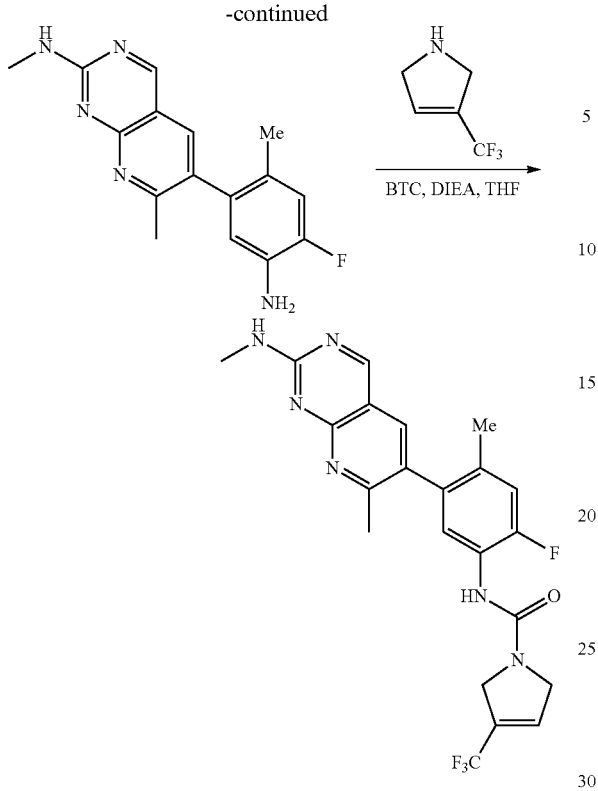

Step 1

To a solution of 7-methyl-2-(methylamino)pyrido[2,3-d]pyrimidin-6-yltrifluoromethanesulfonate (1.5 g, 4.9 mmol), 2-fluoro-4-methyl-5-(4,4,5,5-tetramethyl-1,3,2-dioxaborolan-2-yl)aniline (1.6 g, 6.3 mmol) and Cs₂CO₃ (3.2 g, 9.7 mmol) in dioxane (30 mL) and water (5 mL) was added Pd(dppf)C12 (356 mg, 0.5 mmol) under N₂, and the mixture was stirred at 70° C. for 16 h. The mixture was cooled down to RT diluted with water (100 mL) and extracted with DCM (100 mL*3). The combined organic layers were washed with H₂O (100 mL*2) and brine (200 mL), dried over Na₂SO₄, filtered and concentrated. The residue was purified by flash chromatography on silica gel (PE:EA=10:1 to PE:EA=2:1) to afford 6-(5-amino-4-fluoro-2-methylphenyl)-N,7-dimethylpyrido[2,3-d]pyrimidin-2-amine (1.0 g, 72%). MS Calcd.: 297, MS Found: 298 ([M+H]⁺).

Step 2

To a solution of 6-(5-amino-4-fluoro-2-methylphenyl)-N,7-dimethylpyrido[2,3-d]pyrimidin-2-amine (80 mg, 0.2 mmol), DIEA (274 mg, 2.1 mmol) in THF (10 mL) was added BTC (32 mg, 0.1 mmol) in THF at 0° C. under N₂ atmosphere, and the mixture was stirred at 0° C. for 0.5 h. 3-(Trifluoromethyl)-2,5-dihydro-1H-pyrrole trifluoroacetate (crude, 0.5 mmol) was then added and the reaction was stirred at 0° C. for 1 h. The mixture was concentrated and the residue was purified by prep-HPLC to afford N-(2-fluoro-4-methyl-5-(7-methyl-2-(methylamino)pyrido[2,3-d]pyrimidin-6-yl)phenyl)-3-(trifluoromethyl)-2,5-dihydro-1H-pyrrole-1-carboxamide (22.1 mg, 17.9%). ¹H NMR (400 MHz, DMSO-d₆): δ 2.01 (s, 3H), 2.31 (s, 3H), 2.92 (d, J=4.4 Hz, 3H), 4.39 (s, 4H), 6.72 (d, J=1.6 Hz, 1H), 7.23 (d, J=12.0 Hz, 1H), 7.33 (d, J=8.0 Hz, 1H), 7.68 (brs, 1H), 7.92 (s, 1H), 8.16 (s, 1H), 9.08 (s, 1H). MS Calcd.: 460 Found: 461 ([M+H]⁺).

Example 6: N-[4-methyl-3-[7-methyl-2-(methylamino)pyrido[2,3-d]pyrimidin-6-yl]phenyl]-2-(trifluoromethyl)pyridine-4-carboxamide

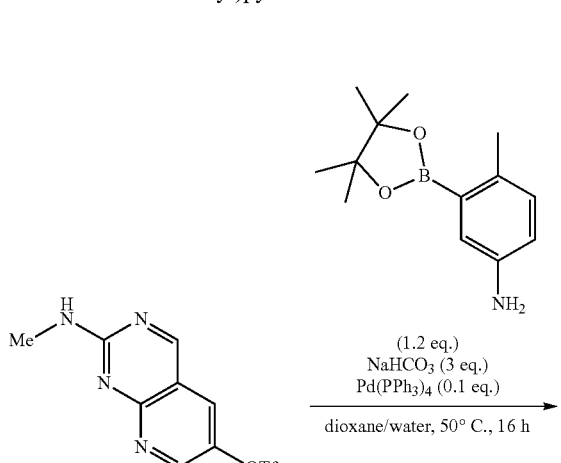

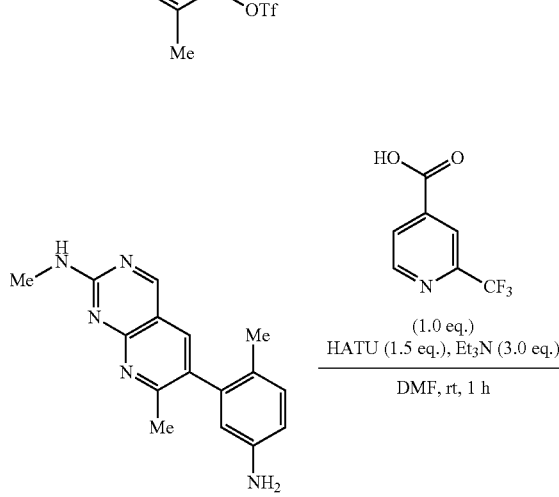

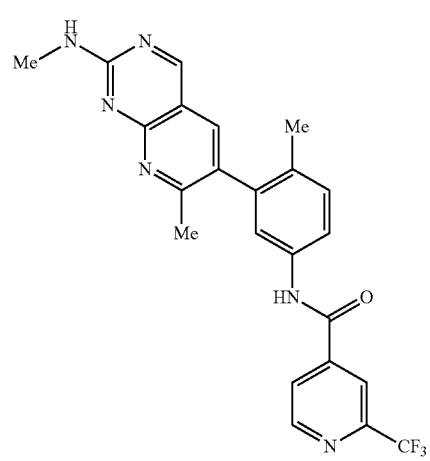

Step 1

To a stirred mixture of 7-methyl-2-(methylamino)pyrido[2,3-d]pyrimidin-6-yl trifluoromethanesulfonate (6.00 g, 18.63 mmol) and 4-methyl-3-(4,4,5,5-tetramethyl-1,3,2-dioxaborolan-2-yl)aniline (5.20 g, 22.32 mmol) in 1,4-dioxane (80 mL) and water (40 mL) were added Pd(PPh$_3$)$_4$ (2.16 g, 1.87 mmol) and NaHCO$_3$ (4.7 g, 55.90 mmol) at room temperature under nitrogen atmosphere. The reaction mixture was degassed with nitrogen three times and stirred for 16 h at 50° C. The resulting mixture was diluted with water (80 mL) and extracted with EA (3×300 mL). The combined organic layer was washed with brine (3×100 mL), dried over anhydrous Na$_2$SO$_4$ and filtered. The filtrate was concentrated under reduced pressure. The residue was purified by silica gel column chromatography, eluted with 52% EA/EtOH (3/1) in PE. The fractions contained desired product were combined and concentrated to afford 6-(5-amino-2-methylphenyl)-N,7-dimethylpyrido[2,3-d]pyrimidin-2-amine (4.6 g, 88%) as a yellow solid. MS ESI calculated for C$_{16}$H$_{17}$N$_5$ [M+H]$^+$, 280.15, found 280.20. H-NMR (300 MHz, d$_6$-DMSO) δ 9.08 (s, 1H), 7.86 (s, 1H), 7.64 (s, 1H), 6.98 (d, J=8.1 Hz, 1H), 6.57-6.53 (m, 1H), 6.38 (d, J=2.4 Hz, 1H), 4.99 (s, 2H), 2.92 (d, J=4.8 Hz, 3H), 2.32 (s, 3H), 1.85 (s, 3H).

Step 2

To a stirred solution of 6-(5-amino-2-methylphenyl)-N,7-dimethylpyrido[2,3-d]pyrimidin-2-amine (4.76 g, 17.06 mmol) and 2-(trifluoromethyl)pyridine-4-carboxylic acid (3.26 g, 17.06 mmol) in DMF (48 mL) was added HATU (9.72 g, 25.57 mmol) and TEA (7.1 mL, 51.08 mmol) at 0° C. under nitrogen atmosphere. The reaction mixture was stirred for 1 h at room temperature under nitrogen atmosphere. The resulting mixture was diluted with water (100 ml) and extracted with EA (3×300 mL). The combined organic layer was washed with brine (6×150 mL), dried over anhydrous Na$_2$SO$_4$ and filtered. The filtrate was concentrated under reduced pressure. The residue was purified by silica gel column chromatography, eluted with 55% EA/EtOH (3/1) in PE to afford 6 g product which was further purified by trituration with EA/n-hexane (150 mL) to afford N-[4-methyl-3-[7-methyl-2-(methylamino)pyrido[2,3-d]pyrimidin-6-yl]phenyl]-2-(trifluoromethyl)pyridine-4-carboxamide (4.89 g, 63%) as a yellow solid. MS ESI calculated for C$_{23}$H$_{19}$F$_3$N$_6$O [M+H]$^+$, 453.16, found 453.25. $^1$H-NM/R (400 MHz, d$_6$-DMSO) δ 10.70 (s, 1H), 9.11 (s, 1H), 8.99 (d, J=4.8 Hz, 1H), 8.37 (s, 1H), 8.19 (d, J=4.8 Hz, 1H), 7.97 (s, 1H), 7.78-7.71 (m, 2H), 7.63 (d, J=2.0 Hz, 1H), 7.39 (d, J=8.8 Hz, 1H), 2.93 (d, J=4.4 Hz, 3H), 2.34 (s, 3H), 2.05 (s, 3H). $^{19}$F-NMR (400 MHz, d$_6$-DMSO) δ −66.46 (s).

The compounds in Table 7 were prepared using appropriate starting materials and the procedures described in Examples 1 and 2, or Example 3. Racemic products were separated using chiral columns specified in the table.

TABLE 7

| Ex. # | Structure | Exact Mass [M + H]$^+$ | Preparation using procedures from Example(s) | Chiral column |
|---|---|---|---|---|
| 4 and 5 | 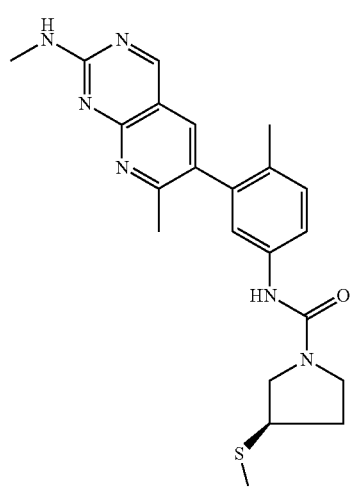 | Calc'd 477.16, found 477.20 | 1 and 2 | CHIRALPAK IG, 2.0 cm I.D x 25 cm L (5 um) |

TABLE 7-continued
| Ex. # | Structure | Exact Mass [M + H]+ | Preparation using procedures from Example(s) | Chiral column |
|---|---|---|---|---|
| | 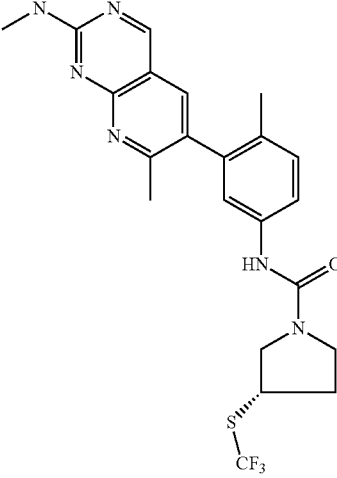 | | | |
| 7 | 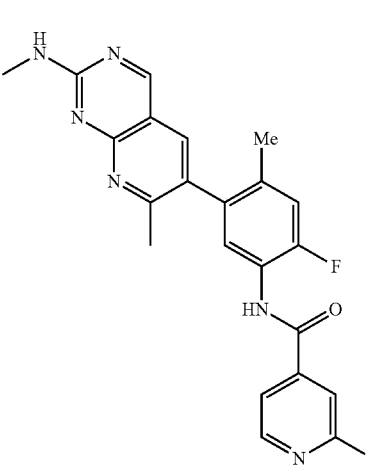 | Calc'd 471.15, found 471.20 | 1 and 2 | NA |
| 8 and 9 | 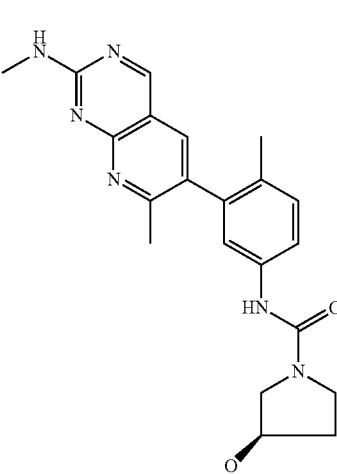 | Calc'd 479.17; found 479.15 | 1 and 2 | CHIRAL ART Cellulose-SB, 2 x 25 cm, 5 um |

TABLE 7-continued
| Ex. # | Structure | Exact Mass [M + H]+ | Preparation using procedures from Example(s) | Chiral column |
|---|---|---|---|---|
| | 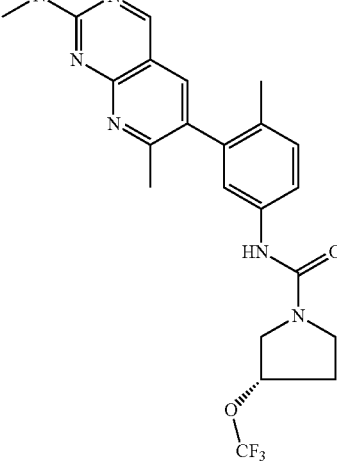 | | | |
| 10 | 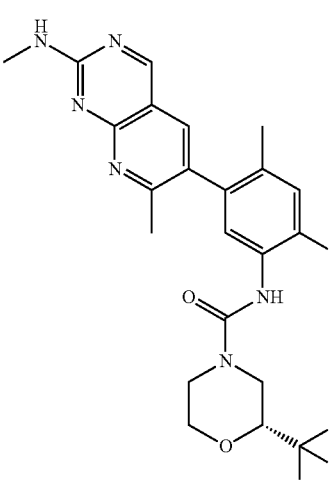 | Calc'd 479.17; found 479.15 | 1 and 2 | NA |
| 11 | 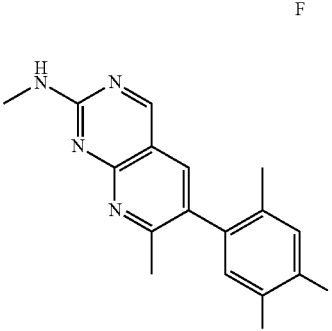 | Calc'd 479.17; found 479.15 | 1 and 2 | NA |

TABLE 7-continued

| Ex. # | Structure | Exact Mass [M + H]+ | Preparation using procedures from Example(s) | Chiral column |
|---|---|---|---|---|
| 12 | 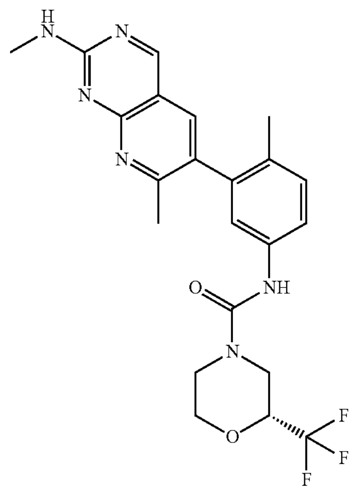 [SMILES: CNc1ncc2cc(-c3cc(NC(=O)N4CCO[C@@H](C(F)(F)F)C4)ccc3C)c(C)nc2n1] | Calc'd 461.18, found 461.20 | 1 and 2 | NA |
| 13 | 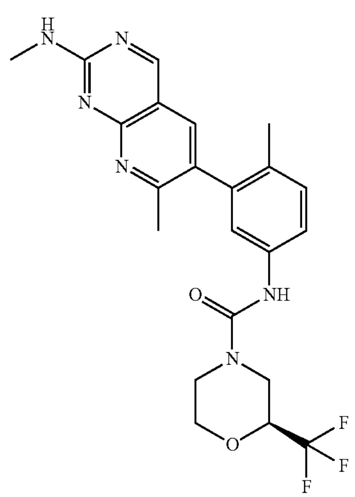 [SMILES: CNc1ncc2cc(-c3cc(NC(=O)N4CCO[C@H](C(F)(F)F)C4)ccc3C)c(C)nc2n1] | Calc'd 461.18, found 461.25 | 1 and 2 | NA |

TABLE 7-continued
| Ex. # | Structure | Exact Mass [M + H]+ | Preparation using procedures from Example(s) | Chiral column |
|---|---|---|---|---|
| 14 | 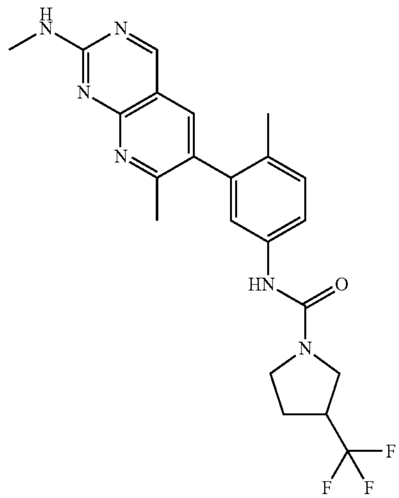 [SMILES: CNc1ncc2cc(-c3cc(NC(=O)N4CCC(C(F)(F)F)C4)ccc3C)c(C)nc2n1] | Calc'd 445, found 445 | 3 | NA |
| 15 | 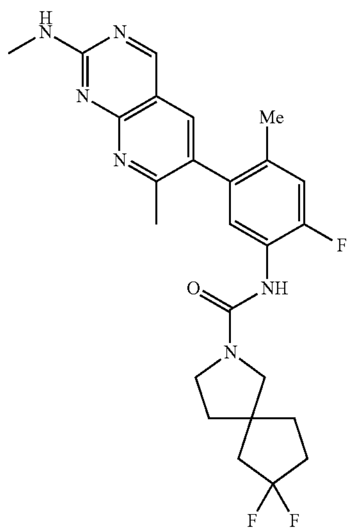 [SMILES: CNc1ncc2cc(-c3cc(NC(=O)N4CCC5(CCC(F)(F)C5)C4)c(F)cc3C)c(C)nc2n1] | Calc'd 485, found 485 | 3 | NA |
Example 16: Synthesis of N-(4-methyl-3-(7-methyl-2-(methylamino)pyrido[2,3-d]pyrimidin-6-yl)phenyl)-3-(trifluoromethyl)-2,5-dihydro-1H-pyrrole-1-carboxamide
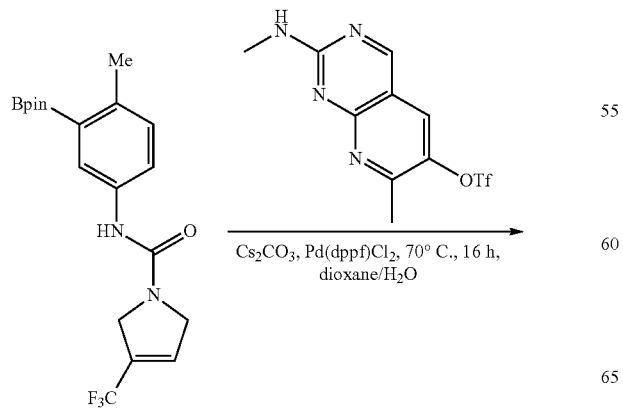
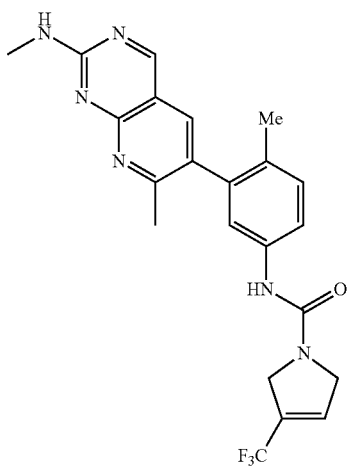

Step 1

To a solution of 7-methyl-2-(methylamino)pyrido[2,3-d]pyrimidin-6-yl trifluoromethanesulfonate (180 mg, 0.58 mmol) and N-(4-methyl-3-(4,4,5,5-tetramethyl-1,3,2-dioxaborolan-2-yl)phenyl)-3-(trifluoromethyl)-2,5-dihydro-1H-pyrrole-1-carboxamide (301 mg, 0.75 mmol) in dioxane (12 mL) and H$_2$O (2 mL) was added Pd(dppf)Cl2 (43 mg, 0.06 mmol) and Cs$_2$CO$_3$ (381 mg, 1.16 mmol) at room temperature. The reaction mixture was stirred at 70° C. for 16 hrs under N$_2$. The reaction mixture was cooled down to room temperature, quenched with water (20 mL) and extracted with DCM (20 mL*3). The combined organic layers were washed with brine (100 mL), dried over Na$_2$SO$_4$, filtered and concentrated. The residue purified by prep-HPLC to give N-(4-methyl-3-(7-methyl-2-(methylamino)pyrido[2,3-d]pyrimidin-6-yl)phenyl)-3-(trifluoromethyl)-2,5-dihydro-1H-pyrrole-1-carboxamide (84.5 mg, 32.7%). $^1$H NMR (400 MHz, DMSO-d$_6$): δ 9.08 (s, 1H), 8.34 (s, 1H), 7.91 (s, 1H), 7.66 (br s, 1H), 7.50 (dd, J=2.4, 8.4 Hz, 1H), 7.36 (d, J=2.4 Hz, 1H), 7.23 (d, J=8.4 Hz, 1H), 6.73 (d, J=1.6 Hz, 1H), 4.41-4.37 (m, 4H), 2.92 (d, J=4.4 Hz, 3H), 2.32 (s, 3H), 1.98 (s, 3H). MS Calcd.: 442, MS Found: 443 ([M+H]$^+$).

Example 17 & 18: Synthesis of (R)—N-(2-fluoro-4-methyl-5-(7-methyl-2-(methylamino)pyrido[2,3-d]pyrimidin-6-yl)phenyl)-3-(2,2,2-trifluoroethyl)pyrrolidine-1-carboxamide and (S)—N-(2-fluoro-4-methyl-5-(7-methyl-2-(methylamino)pyrido[2,3-d]pyrimidin-6-yl)phenyl)-3-(2,2,2-trifluoroethyl)pyrrolidine-1-carboxamide

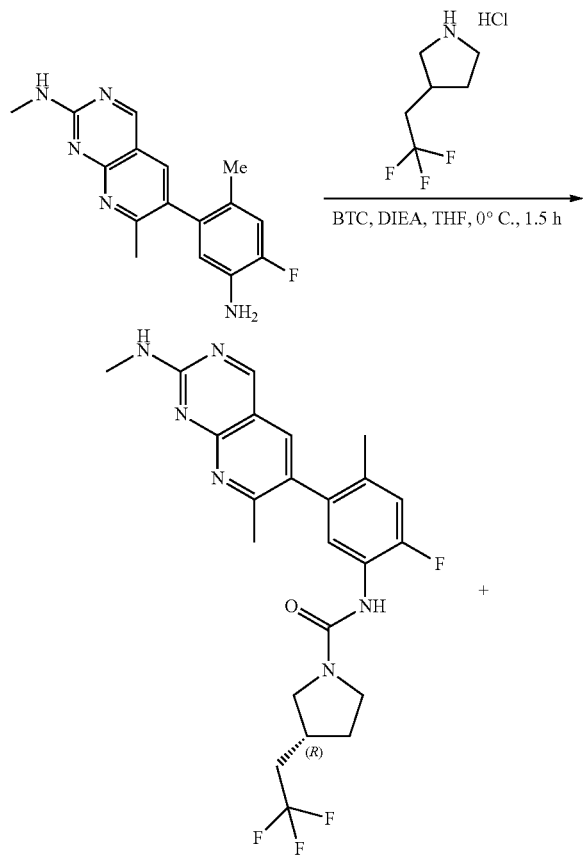

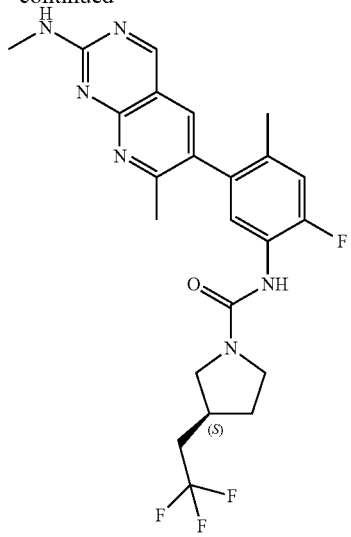

Step 1

To a solution of 6-(5-amino-4-fluoro-2-methylphenyl)-N,7-dimethylpyrido[2,3-d]pyrimidin-2-amine (400 mg, 1.35 mmol) and DIEA (869 mg, 6.73 mmol) in THF (30 mL) was added a solution of BTC (160 mg, 0.53 mmol) in THF (1 mL) at 0° C. The reaction mixture was stirred at 0° C. for 30 min. Then 3-(2,2,2-trifluoroethyl)pyrrolidine hydrochloride (383 mg, 2.02 mmol) was added at 0° C. The reaction mixture was stirred at 0° C. for 1 h. The reaction mixture was concentrated. The residue was purified by FCC (PE:EA=1:1) to afford a mixture which was separated by chiral prep-SFC (Column: Chiralpak IB 5 μm 20*250 mm; Mobile Phase: CO$_2$:MeOH:DEA=80:20:0.2% at 50 g/min; Temp: 40° C.; Wavelength: 214 nm) to give two enatiomers.

First eluting peak: 142.6 mg, 22.2%, RT=6.65 min, ee>98%. $^1$H NMR (400 MHz, DMSO-d$_6$): δ 9.08 (s, 1H), 7.90 (s, 1H), 7.89 (s, 1H), 7.68 (br s, 1H), 7.33 (dd, J=2.8, 8.4 Hz, 1H), 7.20 (d, J=11.6 Hz, 1H), 3.66 (t, J=8.0 Hz, 1H), 3.52 (t, J=9.2 Hz, 1H), 3.28-3.26 (m, 1H), 3.02 (t, J=9.2 Hz, 1H), 2.92 (d, J=4.4 Hz, 3H), 2.45-2.35 (m, 3H), 2.31 (s, 3H), 2.11-2.05 (m, 1H), 2.00 (s, 3H), 1.70-1.60 (m, 1H). MS Calcd.: 476, M Found: 477 ([M+H]$^+$).

Second eluting peak: 103.8 mg, 16.2%, RT=7.72 min, ee>98%. $^1$H NMR (400 MHz, DMSO-d$_6$): δ 9.08 (s, 1H), 7.90 (s, 1H), 7.89 (s, 1H), 7.68 (br s, 1H), 7.33 (dd, J=2.8, 8.4 Hz, 1H), 7.20 (d, J=11.6 Hz, 1H), 3.66 (t, J=8.0 Hz, 1H), 3.52 (t, J=9.2 Hz, 1H), 3.28-3.26 (m, 1H), 3.02 (t, J=9.2 Hz, 1H), 2.92 (d, J=4.4 Hz, 3H), 2.45-2.35 (m, 3H), 2.31 (s, 3H), 2.11-2.05 (m, 1H), 2.00 (s, 3H), 1.70-1.60 (m, 1H).

MS Calcd.: 476, M Found: 477 ([M+H]$^+$).

Examples 19 and 20: Synthesis of (R)—N-(4-methyl-3-(7-methyl-2-(methylamino)pyrido[2,3-d]pyrimidin-6-yl)phenyl)-3-(2,2,2-trifluoroethyl)pyrrolidine-1-carboxamide and (S)—N-(4-methyl-3-(7-methyl-2-(methylamino)pyrido[2,3-d]pyrimidin-6-yl)phenyl)-3-(2,2,2-trifluoroethyl)pyrrolidine-1-carboxamide

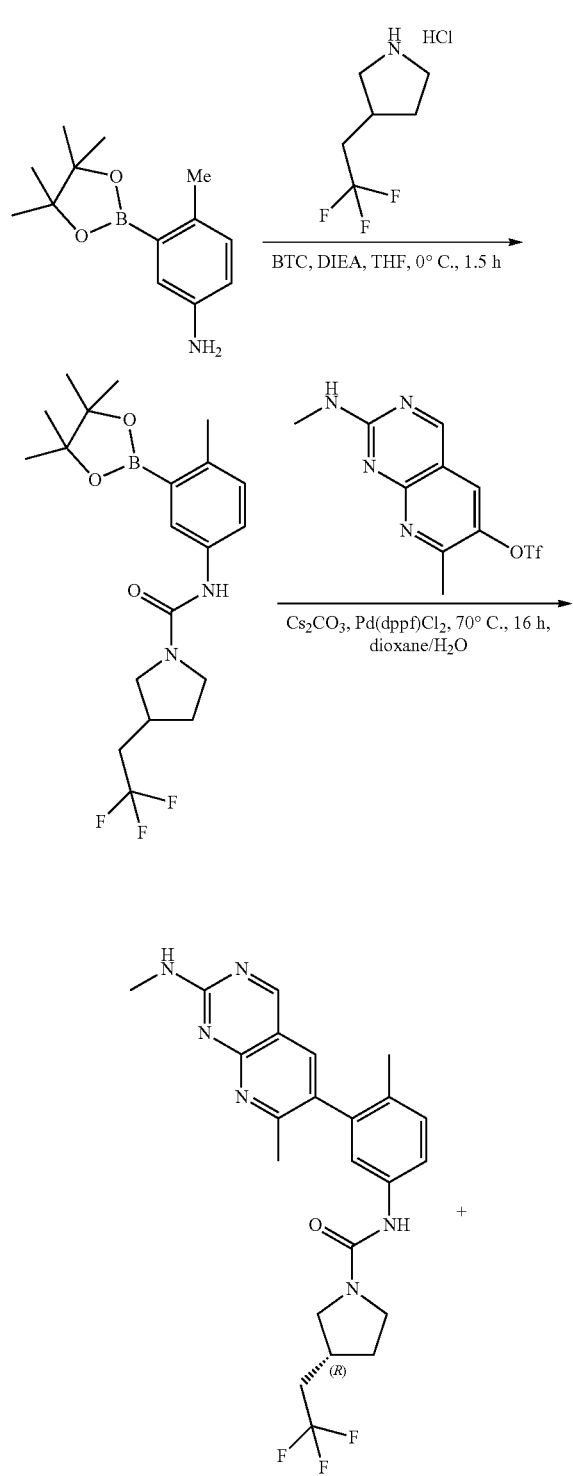

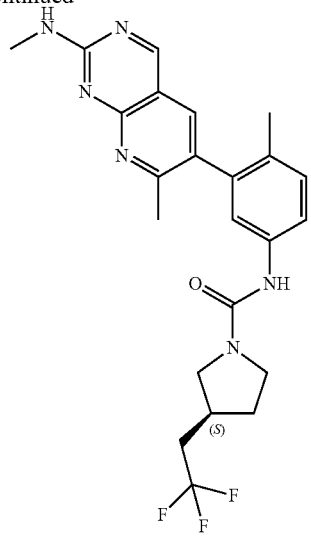

Step 1

To a solution of 4-methyl-3-(4,4,5,5-tetramethyl-1,3,2-dioxaborolan-2-yl)aniline (400 mg, 1.72 mmol) and DIEA (1.1 g, 8.62 mmol) in THF (20 mL) was added a solution of BTC (204 mg, 0.68 mmol) in THF (1 mL) at 0° C. The reaction mixture was stirred at 0° C. for 30 min. Then 3-(2,2,2-trifluoroethyl)pyrrolidine hydrochloride (489 mg, 2.58 mmol) was added at 0° C. The reaction mixture was stirred at 0° C. for 1 h. The reaction mixture was concentrated. The residue was purified by FCC (PE:EA=2:1) to afford N-(4-methyl-3-(4,4,5,5-tetramethyl-1,3,2-dioxaborolan-2-yl)phenyl)-3-(2,2,2-trifluoroethyl)pyrrolidine-1-carboxamide (700 mg, 99%). MS Calcd.: 412, MS Found: 413 ([M+H]$^+$).

Step 2

To a solution of N-(4-methyl-3-(4,4,5,5-tetramethyl-1,3,2-dioxaborolan-2-yl)phenyl)-3-(2,2,2-trifluoroethyl)pyrrolidine-1-carboxamide (720 mg, 1.75 mmol) and 7-methyl-2-(methylamino)pyrido[2,3-d]pyrimidin-6-yl trifluoromethanesulfonate (385 mg, 1.25 mmol) in dioxane (60 mL) and H$_2$O (10 mL) was added Pd(dppf)Cl$_2$ (92 mg, 0.12 mmol) and Cs$_2$CO$_3$ (815 mg, 2.50 mmol) at room temperature. The reaction mixture was stirred at 70° C. for 16 h under N$_2$. The reaction mixture was cooled to room temperature, quenched with water (50 mL) and extracted with DCM (30 mL*3). The combined organic layers were washed with brine (100 mL), dried over Na$_2$SO$_4$, filtered and concentrated. The residue purified by FCC (PE:EA=1:1) to give a mixture which was separated by chiral prep-SCF (Column: Chiralpak IG 5 μm 20*250 mm; Mobile Phase: CO$_2$:IPA:DEA=60:40:0.2 at 50 g/min; Temp: 40° C.; Wavelength: 254 nm) to give both enantiomers.

First eluting peak: 108.3 mg, 18.9%, RT=8.45 min, ee>98. $^1$H NMR (400 MHz, DMSO-d$_6$): δ 9.08 (s, 1H), 8.17 (s, 1H), 7.90 (s, 1H), 7.67 (br s, 1H), 7.48 (dd, J=2.0, 8.0 Hz, 1H), 7.35 (s, 1H), 7.19 (d, J=8.4 Hz, 1H), 3.66 (t, J=8.0 Hz, 1H), 3.51 (t, J=9.6 Hz, 1H), 3.30-3.26 (m, 1H), 3.01 (t, J=8.8 Hz, 1H), 2.92 (d, J=4.4 Hz, 3H), 2.47-2.37 (m, 3H), 2.31 (s, 3H), 2.10-2.04 (m, 1H), 1.96 (s, 3H), 1.69-1.59 (m, 1H). MS Calcd.: 458, M Found: 459 ([M+H]$^+$).

Second eluting peak: 132.2 mg, 23.1%, RT=10.37 min, ee>98%. $^1$H NMR (400 MHz, DMSO-$d_6$): δ 9.08 (s, 1H), 8.17 (s, 1H), 7.90 (s, 1H), 7.67 (br s, 1H), 7.48 (dd, J=2.0, 8.0 Hz, 1H), 7.35 (s, 1H), 7.19 (d, J=8.4 Hz, 1H), 3.66 (t, J=8.0 Hz, 1H), 3.51 (t, J=9.6 Hz, 1H), 3.30-3.26 (m, 1H), 3.01 (t, J=8.8 Hz, 1H), 2.92 (d, J=4.4 Hz, 3H), 2.47-2.37 (m, 3H), 2.31 (s, 3H), 2.10-2.04 (m, 1H), 1.96 (s, 3H), 1.69-1.59 (m, 1H). MS Calcd.: 458, M Found: 459 ([M+H]$^+$).

Example 21: Synthesis of 3-(tert-butyl)-N-(2-fluoro-4-methyl-5-(7-methyl-2-(methylamino)pyrido[2,3-d]pyrimidin-6-yl)phenyl)pyrrolidine-1-carboxamide

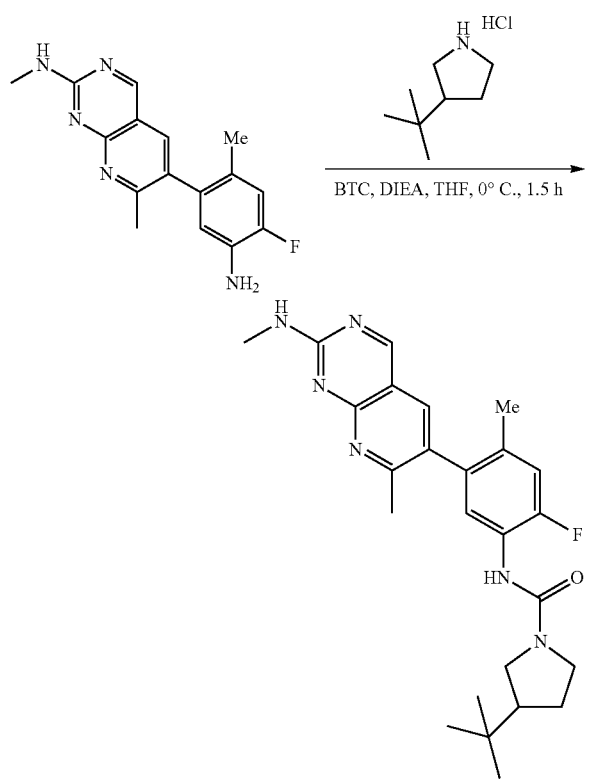

Step 1

To a solution of 6-(5-amino-4-fluoro-2-methylphenyl)-N,7-dimethylpyrido[2,3-d]pyrimidin-2-amine (320 mg, 1.08 mmol) and DIEA (0.88 mL, 5.38 mmol) in THF (20 mL) was added a solution of BTC (128 mg, 0.43 mmol) in THF (1 mL) at 0° C. The reaction mixture was stirred at 0° C. for 30 min. Then 3-(tert-butyl)pyrrolidine hydrochloride (211 mg, 1.29 mmol) was added at 0° C. The reaction mixture was stirred at 0° C. for 1 h. The reaction mixture was concentrated. The residue was purified by prep-HPLC to afford 3-(tert-butyl)-N-(2-fluoro-4-methyl-5-(7-methyl-2-(methylamino)pyrido[2,3-d]pyrimidin-6-yl)phenyl)pyrrolidine-1-carboxamide (61.4 mg, 12.6%). $^1$H NMR (400 MHz, DMSO-$d_6$): δ 9.08 (s, 1H), 7.91 (s, 1H), 7.83 (s, 1H), 7.69 (d, J=3.6 Hz, 1H), 7.34 (dd, J=4.0, 8.0 Hz, 1H), 7.20 (d, J=11.6 Hz, 1H), 3.54 (t, J=8.4 Hz, 1H), 3.44 (t, J=8.8 Hz, 1H), 3.33-3.30 (m, 1H), 3.05 (t, J=10.0 Hz, 1H), 2.91 (d, J=4.4 Hz, 3H), 2.31 (s, 3H), 2.03-2.00 (m, 4H), 1.85-1.79 (m, 1H), 1.62-1.56 (m, 1H), 0.90 (s, 9H). MS Calcd.: 450, MS Found: 451 ([M+H]$^+$).

Examples 22 and 23: Synthesis of (R)-2-(tert-butyl)-N-(2-fluoro-4-methyl-5-(7-methyl-2-(methylamino)pyrido[2,3-d]pyrimidin-6-yl)phenyl)morpholine-4-carboxamide and (S)-2-(tert-butyl)-N-(2-fluoro-4-methyl-5-(7-methyl-2-(methylamino)pyrido[2,3-d]pyrimidin-6-yl)phenyl)morpholine-4-carboxamide

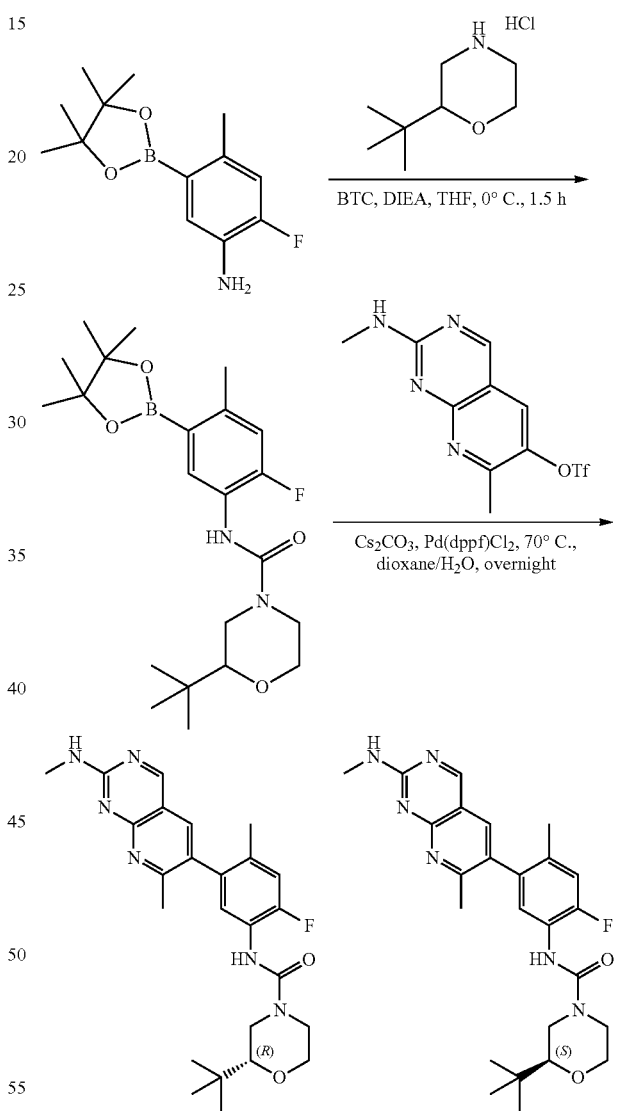

Step 1

To a solution of 2-fluoro-4-methyl-5-(4,4,5,5-tetramethyl-1,3,2-dioxaborolan-2-yl)aniline (400 mg, 1.59 mmol) and DIEA (1.0 g, 7.75 mmol) in THF (20 mL) was added a solution of BTC (191 mg, 0.64 mmol) in THF (5 mL) at 0° C. The reaction mixture was stirred at 0° C. for 30 min. Then 2-(tert-butyl)morpholine hydrochloride (344 mg, 1.91 mmol) was added at 0° C. The reaction mixture was stirred at 0° C. for 1 h. The reaction mixture was concentrated. The residue was purified by FCC (PE:EA=2:1) to afford 2-(tert-butyl)-N-(2-fluoro-4-methyl-5-(4,4,5,5-tetramethyl-1,3,2-dioxaborolan-2-yl)phenyl)morpholine-4-carboxamide (460 mg, 62%). MS Calcd.: 420, MS Found: 421 ([M+H]+).

Step 2

To a solution of 2-(tert-butyl)-N-(2-fluoro-4-methyl-5-(4,4,5,5-tetramethyl-1,3,2-dioxaborolan-2-yl)phenyl)morpholine-4-carboxamide (460 mg, 1.09 mmol) and 7-methyl-2-(methylamino)pyrido[2,3-d]pyrimidin-6-yl trifluoromethanesulfonate (260 mg, 0.84 mmol) in dioxane (24 mL) and H₂O (4 mL) was added Pd(dppf)C12 (62 mg, 0.08 mmol) and Cs₂CO₃ (548 mg, 1.68 mmol) at room temperature. The reaction mixture was stirred at 70° C. overnight under N₂. The reaction mixture was cooled to room temperature, quenched with water (50 mL) and extracted with DCM (20 mL*3). The combined organic layers were washed with brine (20 mL), dried over Na₂SO₄, filtered and concentrated. The residue purified by FCC (100% EA) to give a mixture which was separated by chiralprep-HPLC (Column: Chiralpak IG 5 μm 20*250 mm; Mobile Phase: Hex:EtOH=50:50 at 15 mL/min; Temp: 30° C.; Wavelength: 254 nm) to give both enatiomers.

First eluting peak: 69.7 mg, 17.8%, RT=8.216 min, ee>98%.

$^1$H NMR (400 MHz, DMSO-$d_6$): δ 9.08 (s, 1H), 8.35 (s, 1H), 7.91 (s, 1H), 7.68 (br s, 1H), 7.24-7.19 (m, 2H), 3.98 (d, J=12.8 Hz, 1H), 3.91-3.85 (m, 2H), 3.41 (t, J=11.2 Hz, 1H), 2.98-2.84 (m, 5H), 2.64 (t, J=12.0 Hz, 1H), 2.31 (s, 3H), 2.01 (s, 3H), 0.90 (s, 9H). MS Calcd.: 466, MS Found: 467 ([M+H]+).

Second eluting peak: 67.3 mg, 17.2%, RT=10.798 min, ee>98%. $^1$H NMR (400 MHz, DMSO-$d_6$): δ 9.08 (s, 1H), 8.35 (s, 1H), 7.91 (s, 1H), 7.68 (br s, 1H), 7.24-7.19 (m, 2H), 3.98 (d, J=12.8 Hz, 1H), 3.91-3.85 (m, 2H), 3.41 (t, J=11.2 Hz, 1H), 2.98-2.84 (m, 5H), 2.64 (t, J=12.0 Hz, 1H), 2.31 (s, 3H), 2.01 (s, 3H), 0.90 (s, 9H). MS Calcd.: 466, MS Found: 467 ([M+H]+).

Example 24: Synthesis of N-(4-methyl-3-(7-methyl-2-(methylamino)pyrido[2,3-d]pyrimidin-6-yl)phenyl)-1-(trifluoromethyl)-5,6-dihydroimidazo[1,5-a]pyrazine-7(8H)-carboxamide

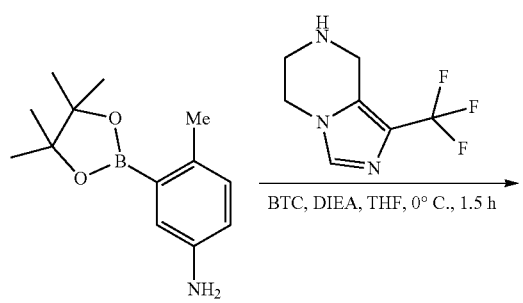

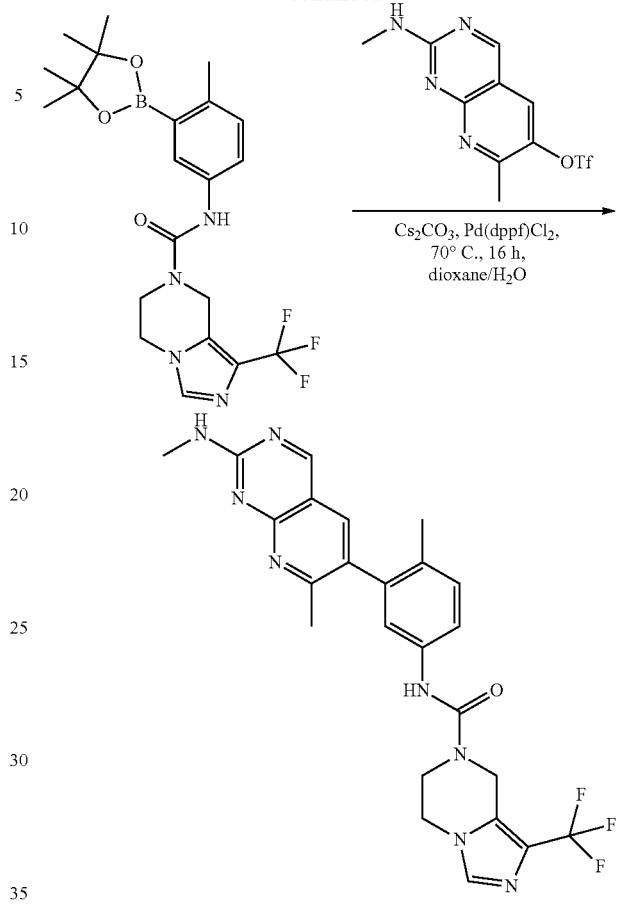

Step 1

To a solution of 4-methyl-3-(4,4,5,5-tetramethyl-1,3,2-dioxaborolan-2-yl)aniline (233 mg, 1.00 mmol) and DIEA (646 mg, 5.00 mmol) in THF (20 mL) was added a solution of BTC (119 mg, 0.40 mmol) in THF (1 mL) at 0° C. The reaction mixture was stirred at 0° C. for 30 min. Then 1-(trifluoromethyl)-5,6,7,8-tetrahydroimidazo[1,5-a]pyrazine (287 mg, 1.50 mmol) was added at 0° C. The reaction mixture was stirred at 0° C. for 1 h. The reaction mixture was concentrated. The residue was purified by FCC (PE:EA=5:1) to afford N-(4-methyl-3-(4,4,5,5-tetramethyl-1,3,2-dioxaborolan-2-yl)phenyl)-1-(trifluoromethyl)-5,6-dihydroimidazo[1,5-a]pyrazine-7(8H)-carboxamide (395 mg, 88%). MS Calcd.: 450, MS Found: 451 ([M+H]+).

Step 2

To a solution of N-(4-methyl-3-(4,4,5,5-tetramethyl-1,3,2-dioxaborolan-2-yl)phenyl)-1-(trifluoromethyl)-5,6-dihydroimidazo[1,5-a]pyrazine-7(8H)-carboxamide (395 mg, 0.88 mmol) and 7-methyl-2-(methylamino)pyrido[2,3-d]pyrimidin-6-yl trifluoromethanesulfonate (235 mg, 0.73 mmol) in dioxane (30 mL) and H₂O (5 mL) was added Pd(dppf)Cl₂ (53 mg, 0.07 mmol) and Cs₂CO₃ (476 mg, 1.46 mmol) at room temperature. The reaction mixture was stirred at 70° C. for 16 h under N₂. The reaction mixture was cooled to room temperature, quenched with water (50 mL) and extracted with DCM (20 mL*3). The combined organic layers were washed with brine (20 mL), dried over Na₂SO₄, filtered and concentrated. The residue purified by prep-HPLC to give N-(4-methyl-3-(7-methyl-2-(methylamino)pyrido[2,3-d]pyrimidin-6-yl)phenyl)-1-(trifluoromethyl)-5,6-dihydroimidazo[1,5-a]pyrazine-7(8H)-carboxamide (136.0 mg, 37.6%) as a yellow solid. $^1$H NMR (400 MHz, DMSO-$d_6$): δ 9.08 (s, 1H), 8.87 (s, 1H), 7.92 (s, 1H), 7.82 (s, 1H), 7.70 (br s, 1H), 7.45 (dd, J=2.4, 8.4 Hz, 1H), 7.30 (d, J=2.4 Hz, 1H), 7.24 (d, J=8.4 Hz, 1H), 4.81 (s, 2H), 4.14 (t, J=4.8 Hz, 2H), 3.89 (t, J=5.2 Hz, 2H), 2.91 (d, J=4.8 Hz, 3H), 2.31 (s, 3H), 1.98 (s, 3H). MS Calcd.: 496, MS Found: 497 ([M+H]$^+$).

Examples 25 and 26 Synthesis of (R)—N-(2-fluoro-4-methyl-5-(7-methyl-2-(methylamino)pyrido[2,3-d]pyrimidin-6-yl)phenyl)-2-(2,2,2-trifluoroethyl)morpholine-4-carboxamide and (S)—N-(2-fluoro-4-methyl-5-(7-methyl-2-(methylamino)pyrido[2,3-d]pyrimidin-6-yl)phenyl)-2-(2,2,2-trifluoroethyl)morpholine-4-carboxamide

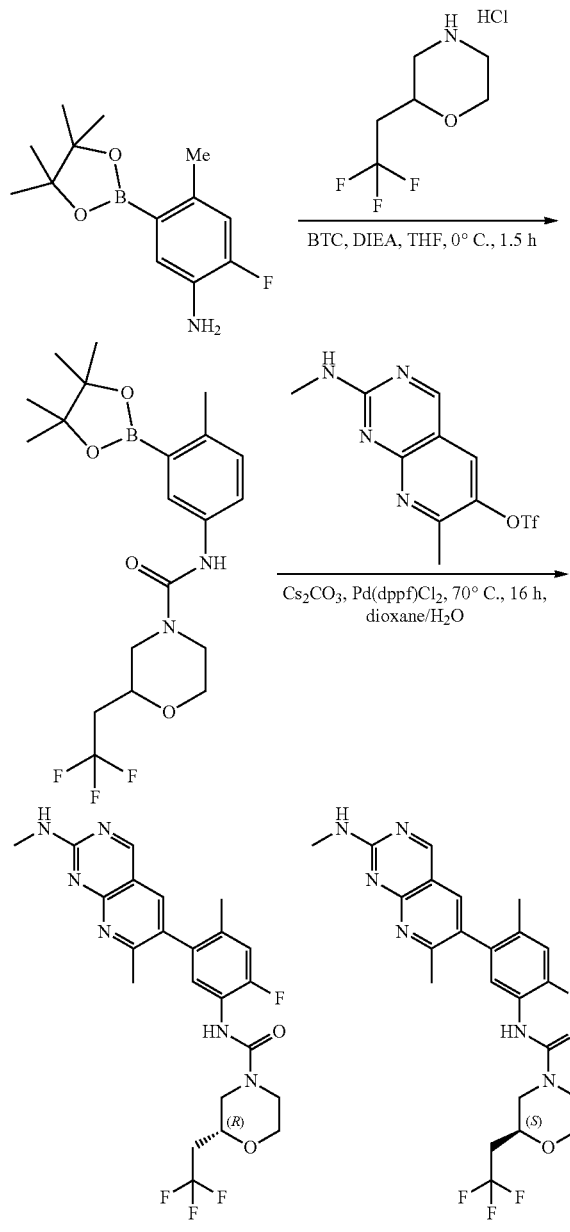

Step 1

To a solution of 2-fluoro-4-methyl-5-(4,4,5,5-tetramethyl-1,3,2-dioxaborolan-2-yl)aniline (251 mg, 1.00 mmol) and DIEA (646 mg, 5.00 mmol) in THF (20 mL) was added a solution of BTC (119 mg, 0.40 mmol) in THF (1 mL) at 0° C. The reaction mixture was stirred at 0° C. for 30 min. Then 2-(2,2,2-trifluoroethyl)morpholine hydrochloride (308 mg, 1.50 mmol) was added at 0° C. The reaction mixture was stirred at 0° C. for 1 h. The reaction mixture was concentrated. The residue was purified by FCC (PE:EA=2:1) to afford N-(4-methyl-3-(4,4,5,5-tetramethyl-1,3,2-dioxaborolan-2-yl)phenyl)-2-(2,2,2-trifluoroethyl)morpholine-4-carboxamide (286 mg, 64%). MS Calcd.: 428, MS Found: 429 ([M+H]$^+$).

Step 2

To a solution of N-(4-methyl-3-(4,4,5,5-tetramethyl-1,3,2-dioxaborolan-2-yl)phenyl)-2-(2,2,2-trifluoroethyl)morpholine-4-carboxamide (286 mg, 0.64 mmol) and 7-methyl-2-(methylamino)pyrido[2,3-d]pyrimidin-6-yl trifluoromethanesulfonate (187 mg, 0.58 mmol) in dioxane (30 mL) and H$_2$O (5 mL) was added Pd(dppf)Cl2 (42 mg, 0.06 mmol) and Cs$_2$CO$_3$ (378 mg, 1.16 mmol) at room temperature. The reaction mixture was stirred at 70° C. for 16 h under N$_2$. The reaction mixture was cooled down to room temperature, quenched with water (50 mL) and extracted with DCM (20 mL*3). The combined organic layers were washed with brine (20 mL), dried over Na$_2$SO$_4$, filtered and concentrated. The residue purified by prep-HPLC to give a mixture which was separated by chiralprep-SFC (Column: Chiralpak IA 5 μm 20*250 mm; Mobile Phase: CO$_2$:IPA:DEA=70:30:0.2 at 50 g/min; Temp: 40° C.; Wavelength: 230 nm) to give two enatiomers.

First eluting peak: 77.2 mg, 10.3%, RT=7.28 min, ee=97%. $^1$H NMR (400 MHz, DMSO-$d_6$): δ 9.07 (s, 1H), 8.39 (s, 1H), 7.91 (s, 1H), 7.67 (br s, 1H), 7.27-7.20 (m, 2H), 4.00 (d, J=13.2 Hz, 1H), 3.88-3.85 (m, 2H), 3.69-3.66 (m, 1H), 3.48 (t, J=11.2 Hz, 1H), 3.29 (s, 2H), 2.98-2.91 (m, 4H), 2.73-2.67 (m, 1H), 2.31 (s, 3H), 2.01 (s, 3H).
MS Calcd.: 492, MS Found: 493 ([M+H]$^+$).

Second eluting peak: 91.0 mg, 12.1%, RT=10.15 min, ee=92%. $^1$H NMR (400 MHz, DMSO-$d_6$): δ 9.07 (s, 1H), 8.39 (s, 1H), 7.91 (s, 1H), 7.67 (br s, 1H), 7.27-7.20 (m, 2H), 4.00 (d, J=13.2 Hz, 1H), 3.88-3.85 (m, 2H), 3.69-3.66 (m, 1H), 3.48 (t, J=11.2 Hz, 1H), 3.29 (s, 2H), 2.98-2.91 (m, 4H), 2.73-2.67 (m, 1H), 2.31 (s, 3H), 2.01 (s, 3H).
MS Calcd.: 492, MS Found: 493 ([M+H]$^+$).

Example 27: Synthesis of N-(4-methyl-3-(7-methyl-2-(methylamino)pyrido[2,3-d]pyrimidin-6-yl)phenyl)-4-(trifluoromethyl)picolinamide

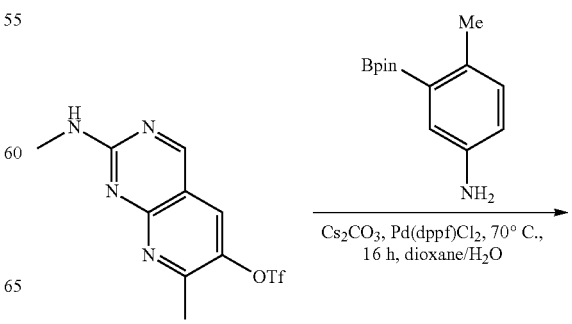

-continued

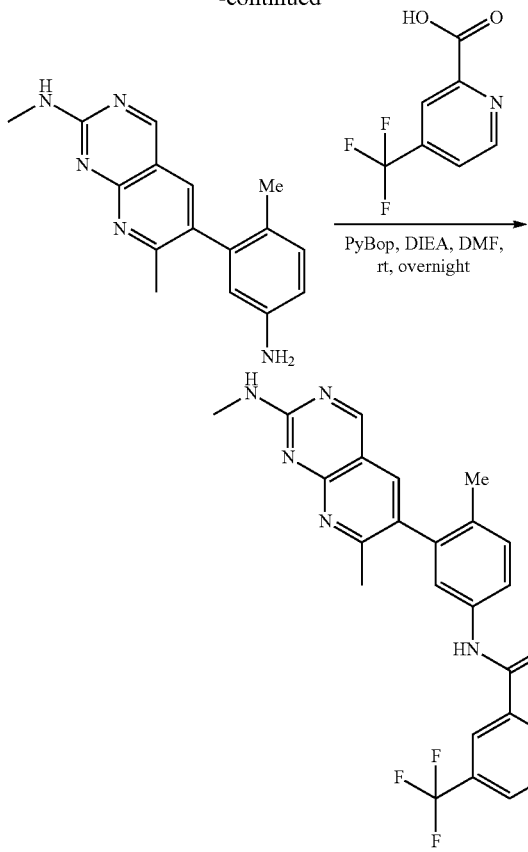

1H), 8.33 (s, 1H), 8.08 (dd, J=1.2, 5.2 Hz, 1H), 7.96 (s, 1H), 7.89 (dd, J=2.4, 8.4 Hz, 1H), 7.79 (d, J=2.0 Hz, 1H), 7.68 (br s, 1H), 7.37 (d, J=8.4 Hz, 1H), 2.93 (d, J=4.4 Hz, 3H), 2.35 (s, 3H), 2.04 (s, 3H). MS Calcd.: 452, MS Found: 453 ([M+H]$^+$).

Example 28: Synthesis of (S)-3-(difluoromethoxy)-N-(2-fluoro-4-methyl-5-(2-(methylamino)pyrido[2,3-d]pyrimidin-6-yl)phenyl)pyrrolidine-1-carboxamide

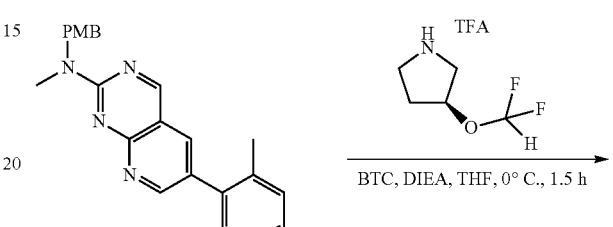

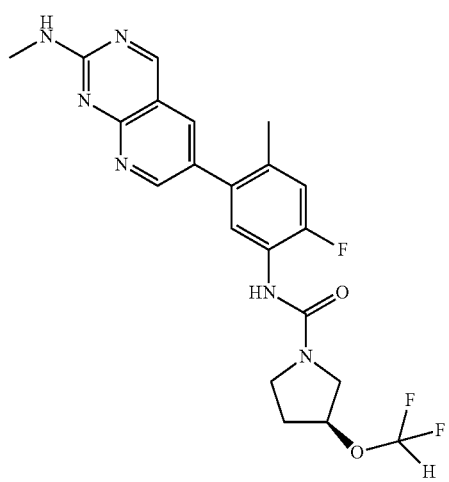

Step 1

To a solution of 7-methyl-2-(methylamino)pyrido[2,3-d]pyrimidin-6-yl trifluoromethanesulfonate (200 mg, 0.62 mmol) and 4-methyl-3-(4,4,5,5-tetramethyl-1,3,2-dioxaborolan-2-yl)aniline (159 mg, 0.68 mmol) in dioxane (30 mL) and H$_2$O (5 mL) was added Pd(dppf)Cl2 (49 mg, 0.06 mmol) and Cs$_2$CO$_3$ (404 mg, 1.24 mmol) at room temperature. The reaction mixture was stirred at 70° C. for 16 h under N$_2$. The reaction mixture was cooled to room temperature, quenched with water (30 mL) and extracted with DCM (20 mL*3). The combined organic layers were washed with brine (20 mL), dried over Na$_2$SO$_4$, filtered and concentrated. The residue purified by FCC (100% EA) to give 6-(5-amino-2-methylphenyl)-N,7-dimethylpyrido[2,3-d]pyrimidin-2-amine (190 mg, >100%). MS Calcd.: 279, MS Found: 280 ([M+H]$^+$).

Step 2

To a solution of 6-(5-amino-2-methylphenyl)-N,7-dimethylpyrido[2,3-d]pyrimidin-2-amine (190 mg, 0.681 mmol) and 4-(trifluoromethyl)picolinic acid (143 mg, 0.74 mmol) in DMF (15 mL) was added DIEA (439 mg, 3.40 mmol) and PyBop (389 mg, 0.74 mmol). The reaction mixture was stirred at room temperature overnight. The reaction mixture was concentrated in vacuum and purified by FCC (PE: EA=1:1) to afford N-(4-methyl-3-(7-methyl-2-(methylamino)pyrido[2,3-d]pyrimidin-6-yl)phenyl)-4-(trifluoromethyl)picolinamide (75.5 mg, 24.4%). $^1$H NMR (400 MHz, DMSO-d$_6$): δ 10.82 (s, 1H), 9.10 (s, 1H), 9.03 (d, J=5.2 Hz,

Step 1

To a solution of 6-(5-amino-4-fluoro-2-methylphenyl)-N-(4-methoxybenzyl)-N-methylpyrido[2,3-d]pyrimidin-2-amine (403 mg, 1.00 mmol) and DIEA (0.82 mL, 5.00 mmol) in THF (30 mL) was added a solution of BTC (119 mg, 0.40 mmol) in THF (5 mL) at 0° C. The reaction mixture was stirred at 0° C. for 30 min. Then the TFA salt of (S)-3-(difluoromethoxy)pyrrolidine (504 mg, 2.00 mmol) was added at 0° C. The reaction mixture was stirred at 0° C. for 1 h. The reaction mixture was concentrated. The residue was purified by FCC (100% EA) to afford (S)-3-(difluoromethoxy)-N-(2-fluoro-5-(2-((4-methoxybenzyl)(methyl)amino)pyrido[2,3-d]pyrimidin-6-yl)-4-methylphenyl)pyrrolidine-1-carboxamide (100 mg, 17.7%). MS Calcd.: 566, MS Found: 567 ([M+H]⁺).

Step 2

To a solution of (S)-3-(difluoromethoxy)-N-(2-fluoro-5-(2-((4-methoxybenzyl)(methyl)amino)pyrido[2,3-d]pyrimidin-6-yl)-4-methylphenyl)pyrrolidine-1-carboxamide (80 mg, 0.14 mmol) in DCM (5 mL) was added TFA (5 mL). The reaction mixture was stirred at 40° C. for 4 h. The reaction mixture was cooled to room temperature and concentrated in vacuum. The residue was dissolved in ice water (20 mL), basified to pH 7-8 with saturated sodium bicarbonate aqueous solution and extracted with DCM (20 mL*3). The combined organic layers were washed with brine (20 mL), dried over Na₂SO₄, filtered and concentrated. The residue was purified by C18 column (acetonitrile: water=05% to 95%) to give (S)-3-(difluoromethoxy)-N-(2-fluoro-4-methyl-5-(2-(methylamino)pyrido[2,3-d]pyrimidin-6-yl)phenyl)pyrrolidine-1-carboxamide (5.3 mg, 7.5%). ¹H NMR (400 MHz, DMSO-d₆): δ 9.18 (s, 1H), 8.82 (d, J=2.0 Hz, 1H), 8.20 (d, J=2.8 Hz, 1H), 8.03 (s, 1H), 7.78 (br s, 1H), 7.47 (d, J=8.0 Hz, 1H), 7.21 (d, J=11.6 Hz, 1H), 6.77 (t, J=75.6 Hz, 1H), 4.85-4.83 (m, 1H), 3.58-3.41 (m, 4H), 2.93 (d, J=4.4 Hz, 3H), 2.25 (s, 3H), 2.13-2.06 (m, 2H). MS Calcd.: 446, MS Found: 447 ([M+H]⁺).

Example 29: Synthesis of N-(4-methyl-3-(7-methyl-2-(methylamino)pyrido[2,3-d]pyrimidin-6-yl)phenyl)-3-(trifluoromethyl)benzamide

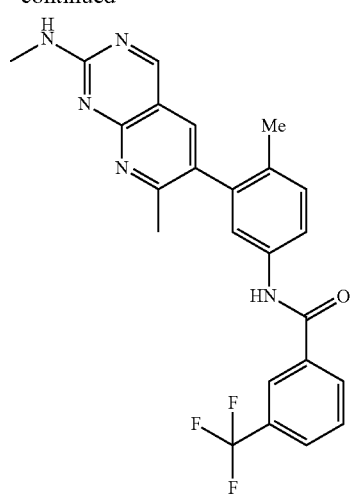

Step 1

To a solution of 6-(5-amino-2-methylphenyl)-N,7-dimethylpyrido[2,3-d]pyrimidin-2-amine (250 mg, 0.896 mmol) and 3-(trifluoromethyl)benzoic acid (186 mg, 0.97 mmol) in DMF (5 mL) was added DIEA (574 mg, 4.45 mmol) and PyBop (509 mg, 0.980 mmol) at rt. The reaction mixture was stirred at room temperature overnight. The reaction mixture was concentrated in vacuum and purified by FCC (PE: EA=1:1) to afford N-(4-methyl-3-(7-methyl-2-(methylamino)pyrido[2,3-d]pyrimidin-6-yl)phenyl)-3-(trifluoromethyl)benzamide (104.4 mg, 25.9%).

¹H NMR (400 MHz, DMSO-d₆): δ 10.48 (s, 1H), 9.10 (s, 1H), 8.29-8.25 (m, 2H), 7.96-7.95 (m, 2H), 7.80-7.75 (m, 2H), 7.68-7.62 (m, 2H), 7.36 (d, J=8.4 Hz, 1H), 2.93 (d, J=4.4 Hz, 3H), 2.35 (s, 3H), 2.04 (s, 3H).

MS Calcd.: 451, MS Found: 452 ([M+H]⁺).

Examples 30 & 31: Synthesis of (R)—N-(2-fluoro-4-methyl-5-(2-(methylamino)pyrido[2,3-d]pyrimidin-6-yl)phenyl)-3-(2,2,2-trifluoroethyl)pyrrolidine-1-carboxamide and (S)—N-(2-fluoro-4-methyl-5-(2-(methylamino)pyrido[2,3-d]pyrimidin-6-yl)phenyl)-3-(2,2,2-trifluoroethyl)pyrrolidine-1-carboxamide

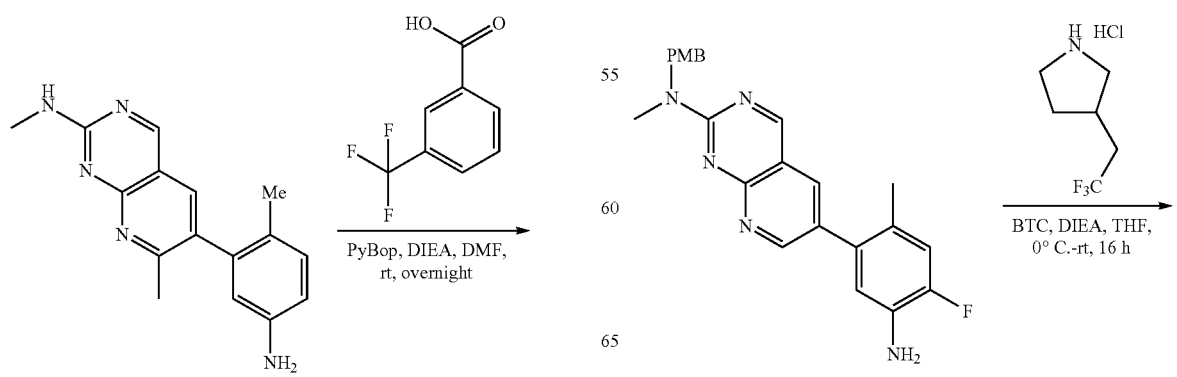

-continued

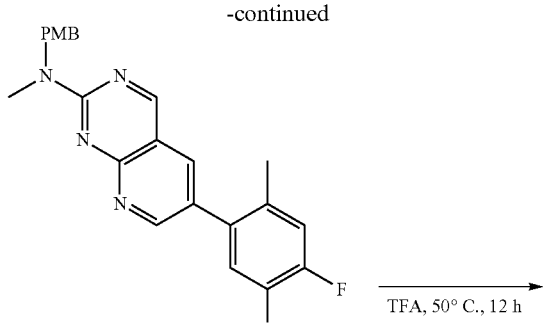

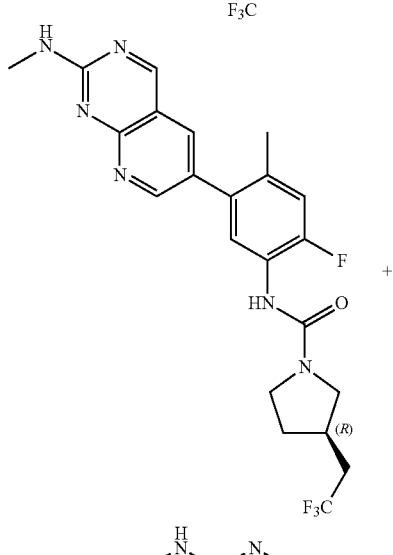

Step 1

To a solution of 6-(5-amino-4-fluoro-2-methylphenyl)-N-(4-methoxybenzyl)-N-methylpyrido[2,3-d]pyrimidin-2-amine (600 mg, 1.48 mmol) and DIEA (1.21 mL, 7.40 mmol) in THF (100 mL) was added a solution of BTC (176 mg, 0.59 mmol) in THF (5 mL) at 0° C. The reaction mixture was stirred at 0° C. for 30 min. Then 3-(2,2,2-trifluoroethyl) pyrrolidine hydrochloride (310 mg, 1.63 mmol) was added at 0° C. The reaction mixture was stirred at 0° C. to rt for 16 hrs. The reaction mixture was concentrated. The residue was purified by FCC (DCM:MeOH=10:1) to afford N-(2-fluoro-5-(2-((4-methoxybenzyl)(methyl)amino)pyrido[2,3-d]pyrimidin-6-yl)-4-methylphenyl)-3-(2,2,2-trifluoroethyl)pyrrolidine-1-carboxamide (650 mg, 75%) MS Calcd.: 582, MS Found: 583 ([M+H]$^+$).

Step 2

A solution of N-(2-fluoro-5-(2-((4-methoxybenzyl)(methyl)amino)pyrido[2,3-d]pyrimidin-6-yl)-4-methylphenyl)-3-(2,2,2-trifluoroethyl)pyrrolidine-1-carboxamide (1.45 g, 2.45 mmol) in TFA (5 mL) was stirred at 50° C. for 12 h. The reaction mixture was cooled down to room temperature and concentrated in vacuum. The residue was dissolved in ice water (50 mL), basified to pH 7-8 with saturated sodium bicarbonate aqueous solution and extracted with DCM (50 mL*3). The combined organic layers were washed with brine (20 mL), dried over Na$_2$SO$_4$, filtered and concentrated. The residue was purified by FCC (DCM:MeOH=10:1) to give a mixture which was seperated by chiralprep-HPLC (Column: Chiralpak OD-H 5 μm 20*250 mm; Mobile Phase: Hex:EtOH=70:30 at 15 mL/min; Temp: 30° C.; Wavelength: 230 nm) to give two enatiomers.

First eluting peak: 357.7 mg, 31.1%, RT=11.448 min, ee>98%. $^1$H NMR (400 MHz, DMSO-d$_6$): δ 9.18 (s, 1H), 8.82 (d, J=2.0 Hz, 1H), 8.20 (d, J=2.4 Hz, 1H), 7.93 (s, 1H), 7.79-7.78 (m, 1H), 7.47 (d, J=8.4 Hz, 1H), 7.21 (d, J=11.6 Hz, 1H), 3.69-3.65 (m, 1H), 3.55-3.51 (m, 1H), 3.35-3.28 (m, 1H), 3.03 (t, J=9.2 Hz, 1H), 2.94 (d, J=4.4 Hz, 3H), 2.49-2.38 (m, 3H), 2.25 (s, 3H), 2.10-2.07 (m, 1H), 1.69-1.64 (m, 1H). MS Calcd.: 462, MS Found: 463 ([M+H]$^+$).

Second eluting peak: 325.7 mg, 28.3%, RT=9.801 min, ee>98%. $^1$H NMR (400 MHz, DMSO-d$_6$): δ 9.18 (s, 1H), 8.82 (d, J=2.0 Hz, 1H), 8.20 (d, J=2.4 Hz, 1H), 7.93 (s, 1H), 7.79-7.78 (m, 1H), 7.47 (d, J=8.4 Hz, 1H), 7.21 (d, J=11.6 Hz, 1H), 3.69-3.65 (m, 1H), 3.55-3.51 (m, 1H), 3.35-3.28 (m, 1H), 3.03 (t, J=9.2 Hz, 1H), 2.94 (d, J=4.4 Hz, 3H), 2.49-2.38 (m, 3H), 2.25 (s, 3H), 2.10-2.07 (m, 1H), 1.69-1.64 (m, 1H). MS Calcd.: 462, MS Found: 463 ([M+H]$^+$).

Example 32: Synthesis of N-(4-methyl-3-(7-methyl-2-(methylamino)pyrido[2,3-d]pyrimidin-6-yl)phenyl)-3-(trifluoromethyl)benzamide

Step 1

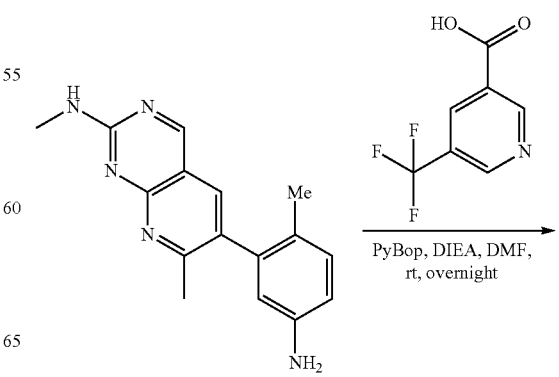

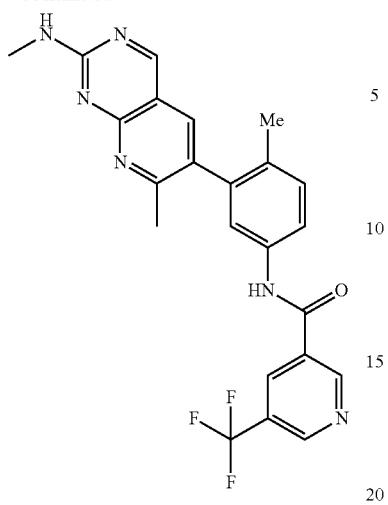

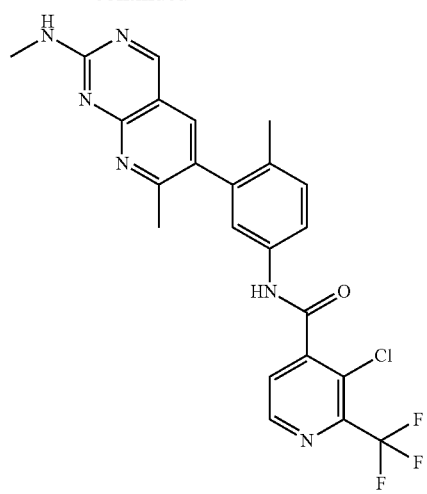

To a solution of 6-(5-amino-2-methylphenyl)-N,7-dimethylpyrido[2,3-d]pyrimidin-2-amine (250 mg, 0.89 mmol) and 5-(trifluoromethyl)nicotinic acid (186 mg, 0.97 mmol) in DMF (5 mL) was added DIEA (574 mg, 4.45 mmol) and PyBop (509 mg, 0.98 mmol) at rt. The reaction mixture was stirred at room temperature overnight. The reaction mixture was concentrated in vacuum and purified by FCC (PE:EA=1:1) to afford N-(4-methyl-3-(7-methyl-2-(methylamino)pyrido[2,3-d]pyrimidin-6-yl)phenyl)-5-(trifluoromethyl)nicotinamide (99.5 mg, 24.6%). $^1$H NMR (400 MHz, DMSO-$d_6$): δ 10.64 (s, 1H), 9.36 (d, J=1.6 Hz, 1H), 9.17-9.09 (m, 2H), 8.68 (s, 1H), 7.96 (s, 1H), 7.75 (dd, J=2.0, 8.0 Hz, 1H), 7.68 (br s, 1H), 7.62 (d, J=2.0 Hz, 1H), 7.38 (d, J=8.4 Hz, 1H), 2.93 (d, J=4.8 Hz, 3H), 2.34 (s, 3H), 2.04 (s, 3H). MS Calcd.: 452, MS Found: 453 ([M+H]$^+$).

Example 33: Synthesis of N-(4-methyl-3-(7-methyl-2-(methylamino)pyrido[2,3-d]pyrimidin-6-yl)phenyl)-3-(trifluoromethyl)benzamide

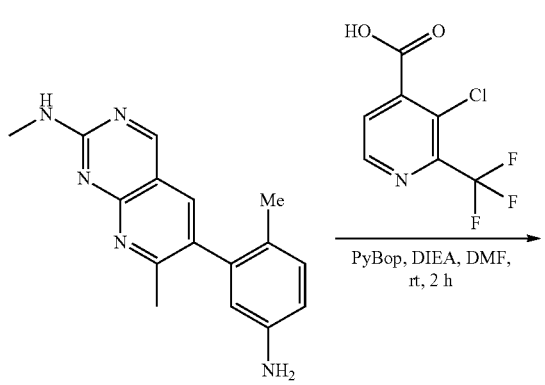

Step 1

To a solution of 6-(5-amino-2-methylphenyl)-N,7-dimethylpyrido[2,3-d]pyrimidin-2-amine (186 mg, 0.66 mmol) and 3-chloro-2-(trifluoromethyl)isonicotinic acid (150 mg, 0.66 mmol) in DMF (5 mL) was added DIEA (429 mg, 3.33 mmol) and PyBop (380 mg, 0.73 mmol) at rt. The reaction mixture was stirred at room temperature for 2 h. The reaction mixture was pour into water (10 mL) and extracted with EA (10 mL) for three times. The combined organic layers were washed with brine (20 mL), dried over Na$_2$SO$_4$, filtered and concentrated in vacuum and purified by prep-HPLC to afford 3-chloro-N-(4-methyl-3-(7-methyl-2-(methylamino)pyrido[2,3-d]pyrimidin-6-yl)phenyl)-2-(trifluoromethyl)isonicotinamide (92.8 mg, 28.7%).

$^1$H NMR (400 MHz, DMSO-$d_6$): 10.85 (s, 1H), 9.09 (s, 1H), 8.83 (d, J=4.8 Hz, 1H), 8.04 (d, J=4.8 Hz, 1H), 7.96 (s, 1H), 7.68 (br s, 1H), 7.61-7.56 (m, 2H), 7.38 (d, J=8.4 Hz, 1H), 2.92 (d, J=4.8 Hz, 3H), 2.33 (s, 3H), 2.03 (s, 3H). MS Calcd.: 486, MS Found: 487 ([M+H]$^+$).

Example 34: Synthesis of 2-methyl-N-(4-methyl-3-(7-methyl-2-(methylamino)pyrido[2,3-d]pyrimidin-6-yl)phenyl)-6-(trifluoromethyl)isonicotinamide

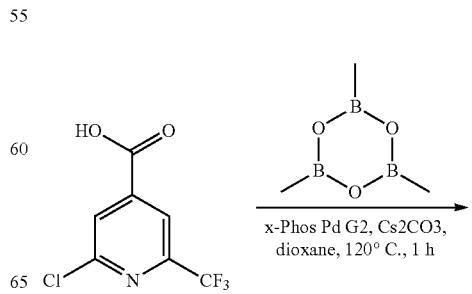

1H), 7.38 (d, J=8.4 Hz, 1H), 2.92 (d, J=4.8 Hz, 3H), 2.66 (s, 3H), 2.34 (s, 3H), 2.04 (s, 3H). MS Calcd.: 466, MS Found: 467 ([M+H]⁺).

Example 35: Synthesis of N-(3-(2-(ethylamino)-7-methylpyrido[2,3-d]pyrimidin-6-yl)-4-methylphenyl)-2-(trifluoromethyl)isonicotinamide

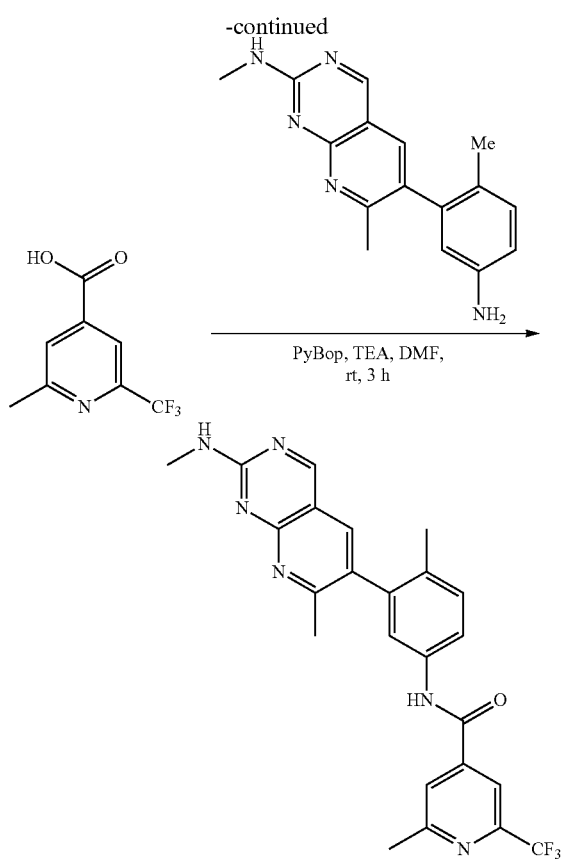

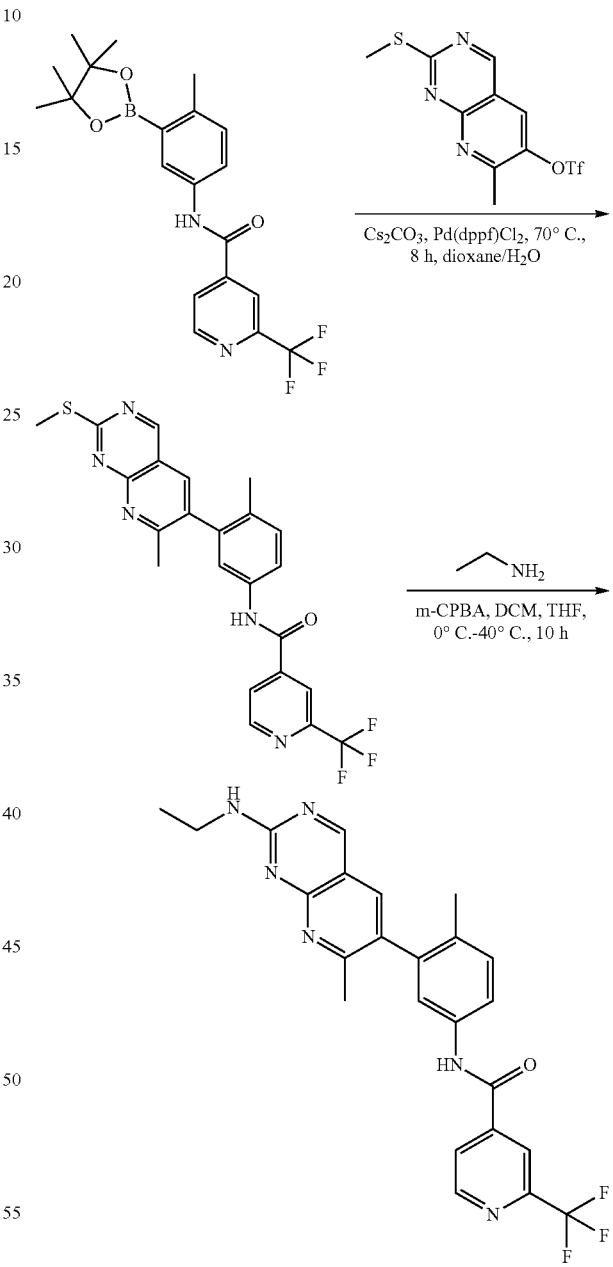

Step 1:

To a solution of N-(4-methyl-3-(4,4,5,5-tetramethyl-1,3,2-dioxaborolan-2-yl)phenyl)-2-(trifluoromethyl)isonicotinamide (500 mg, 2.22 mmol) and 2,4,6-trimethyl-1,3,5,2,4,6-trioxatriborinane (1.3 mL, 4.44 mmol) in dioxane (50 mL) was added $Cs_2CO_3$ (1.4 g, 4.44 mmol) and x-Phos Pd G2 (17 mg, 0.022 mmol). The reaction mixture was stirred at 120° C. for 1 h under $N_2$. The reaction mixture was diluted with water (30 mL) and extracted with EA (30 mL) for three times. The combined organic layers were washed with brine (30 mL), dried over $Na_2SO_4$, filtered and concentrated. The residue was purified by silica gel column chromatography (100% EA) to afford 2-methyl-6-(trifluoromethyl)isonicotinic acid (400 mg, 88%). MS Calcd.: 205, MS Found: 206 ([M+H]⁺).

Step 2

To a solution of 6-(5-amino-2-methylphenyl)-N,7-dimethylpyrido[2,3-d]pyrimidin-2-amine (200 mg, 0.71 mmol) and 2-methyl-6-(trifluoromethyl)isonicotinic acid (176 mg, 0.85 mmol) in DMF (20 mL) was added TEA (145 mg, 1.43 mmol) and PyBop (447 mg, 0.86 mmol) at rt. The reaction mixture was stirred at room temperature for 3 h. The reaction mixture was pour into water (10 mL) and extracted with EA (10 mL) for three times. The combined organic layers were washed with brine (20 mL), dried over $Na_2SO_4$, filtered and concentrated in vacuum and purified by FCC (100% EA) to afford 2-methyl-N-(4-methyl-3-(7-methyl-2-(methylamino)pyrido[2,3-d]pyrimidin-6-yl)phenyl)-6-(trifluoromethyl)isonicotinamide (129.7 mg, 38.6%). ¹H NMR (400 MHz, DMSO-d₆): δ 10.63 (s, 1H), 9.10 (s, 1H), 8.15 (s, 1H), 8.06 (s, 1H), 7.96 (s, 1H), 7.75-7.69 (m, 2H), 7.61 (d, J=2.0 Hz, Step 1

To a solution of N-(4-methyl-3-(4,4,5,5-tetramethyl-1,3,2-dioxaborolan-2-yl)phenyl)-2-(trifluoromethyl)isonicotinamide (1.4 g, 3.5 mmol) and 7-methyl-2-(methylthio)pyrido[2,3-d]pyrimidin-6-yl trifluoromethanesulfonate (2.0 g, 2.9 mmol) in dioxane (60 mL) and $H_2O$ (10 mL) was added $Cs_2CO_3$ (1.9 g, 5.9 mmol) and Pd(dppf)Cl₂ (216 mg, 0.29 mmol), The reaction mixture was stirred at 70° C. for 8 h under $N_2$. The reaction mixture was diluted with water (100 mL) and extracted with EA (100 mL) for three times. The combined organic layers were washed with brine (100 mL), dried over $Na_2SO_4$, filtered and concentrated. The residue was purified by silica gel column chromatography (PE:EA=1:1) to afford N-(4-methyl-3-(7-methyl-2-(methylthio)pyrido[2,3-d]pyrimidin-6-yl)phenyl)-2-(trifluoromethyl)isonicotinamide (1.61 g, 58%).

Step 2

A mixture of N-(4-methyl-3-(7-methyl-2-(methylthio)pyrido[2,3-d]pyrimidin-6-yl)phenyl)-2-(trifluoromethyl)isonicotinamide (250 mg, 0.53 mmol) in DCM (10 mL) was cooled to −5° C. and added m-CPBA (108 mg, 0.53 mmol). The reaction mixture was stirred at room temperature for 2 h. A solution of ethanamine (0.8 mL) in THF (10 mL) was dropwised to the mixture which was stirred at 40° C. for 8 h. The reaction mixture was diluted with water (20 mL) and extracted with DCM (20 mL) for four times. The combined organic layers were washed with brine (20 mL), dried over $Na_2SO_4$, filtered and concentrated. The residue was purified by prep-HPLC to afford N-(3-(2-(ethylamino)-7-methylpyrido[2,3-d]pyrimidin-6-yl)-4-methylphenyl)-2-(trifluoromethyl)isonicotinamide (121.0 mg, 48.8%). $^1$H NMR (400 MHz, DMSO-$d_6$): δ 10.69 (s, 1H), 9.10 (s, 1H), 8.99 (d, J=5.2 Hz, 1H), 8.36 (s, 1H), 8.18 (dd, J=0.8, 4.8 Hz, 1H), 7.95 (s, 1H), 7.76 (dd, J=2.0, 8.0 Hz, 1H), 7.62 (d, J=2.0 Hz, 1H), 7.38 (d, J=8.4 Hz, 1H), 3.46-3.39 (m, 2H), 2.33 (s, 3H), 2.04 (s, 3H), 1.20 (t, J=7.2 Hz, 3H). MS Calcd.: 466, MS Found: 467 ([M+H]$^+$).

Example 36: Synthesis of N-(3-(7-ethyl-2-(methylamino)pyrido[2,3-d]pyrimidin-6-yl)-4-methylphenyl)-2-(trifluoromethyl)isonicotinamide

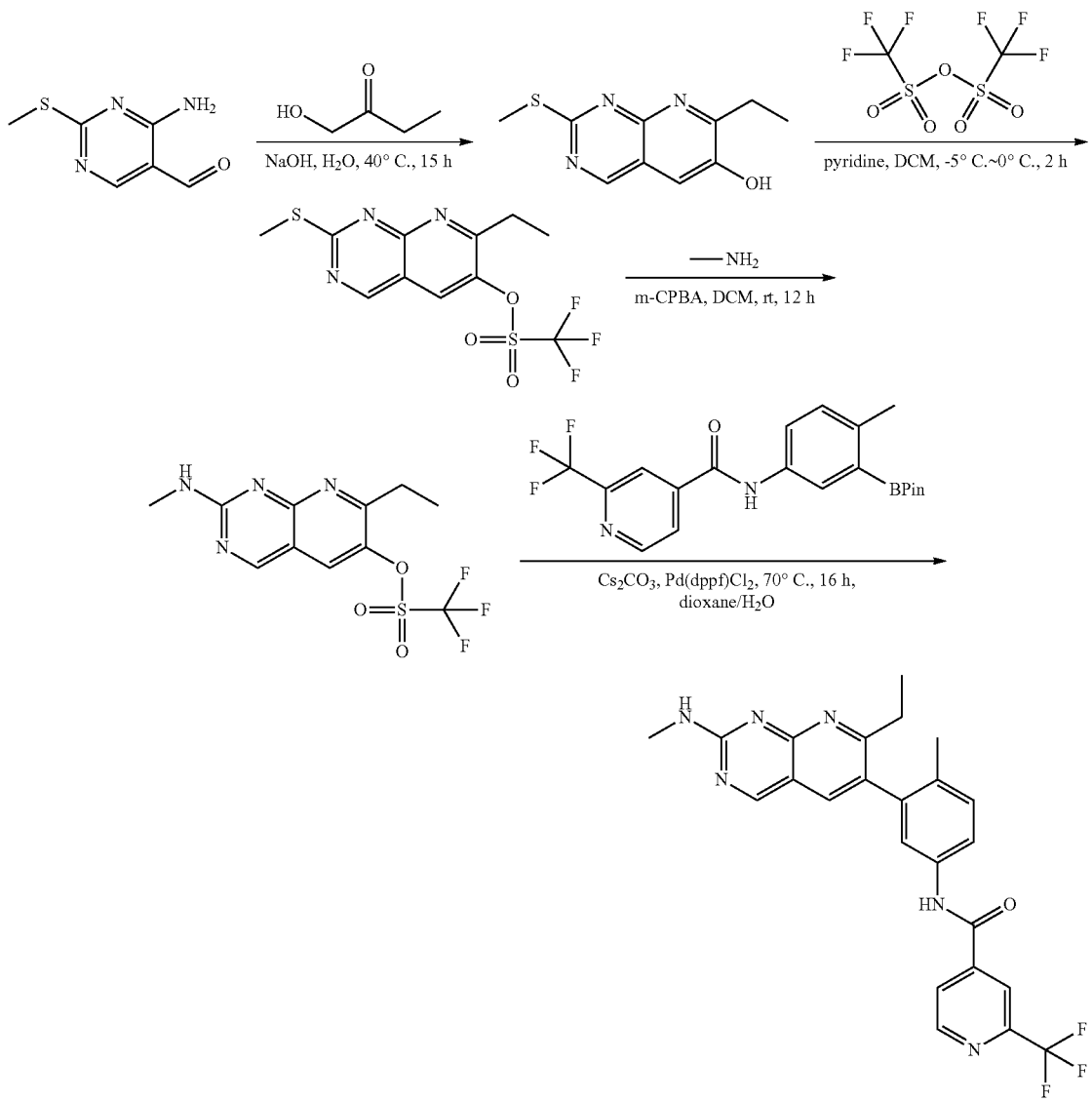

155

Step 1

To a solution of NaOH (0.6 g, 14.8 mmol) in H₂O (8.2 mL) was added 4-amino-2-(methylthio)pyrimidine-5-carbaldehyde (8.0 g, 47.3 mmol) and 1-hydroxybutan-2-one (5.0 g, 56.8 mmol) at rt. The reaction mixture was stirred at 40° C. for 15 h. The mixture was cooled down to rt, diluted with ice water (200 mL) and acidified with 1 M hydrochloride aqueous solution to pH 7-8. The product was separated out, filtered and concentrated. The filtered cake was dried to afford 7-ethyl-2-(methylthio)pyrido[2,3-d]pyrimidin-6-ol (7.4 g, 71%).
MS Calcd.: 221, MS Found: 222 ([M+H]⁺).

Step 2

To a solution of 7-ethyl-2-(methylthio)pyrido[2,3-d]pyrimidin-6-ol (1.0 g, 4.5 mmol) and pyridine (1.4 g, 18.1 mmol) in DCM (40 mL) was added a solution of trifluoromethanesulfonic anhydride (1.9 g, 6.7 mmol) in DCM (10 mL) slowly at −5° C. The reaction mixture was stirred at −5° C. for 2 h. The reaction mixture was allowed to warm to room temperature, quenched with water (50 mL) and extracted with EA (50 mL) for three times. The combined organic layers were washed with brine (100 mL), dried over Na₂SO₄, filtered and concentrated. The residue purified by silica gel column chromatography (PE:EA=3:1) to afford 7-ethyl-2-(methylthio)pyrido[2,3-d]pyrimidin-6-yl trifluoromethanesulfonate (1.0 g, 65%). MS Calcd.: 353, MS Found: 354 ([M+H]⁺).

Step 3

A mixture of 7-ethyl-2-(methylthio)pyrido[2,3-d]pyrimidin-6-yl trifluoromethanesulfonate (1.0 g, 2.83 mmol) and m-CPBA (0.5 g, 2.83 mmol) in DCM (20 mL) was stirred at room temperature for 1 h. Then to the reaction mixture was added a solution of methanamine in THF (2 M, 4.25 mL, 8.50 mmol). The reaction mixture was stirred at room temperature for 12 h. The reaction mixture was diluted with water (20 mL) and extracted with EA (50 mL) for four times. The combined organic layers were washed with brine (50 mL), dried over Na₂SO₄, filtered and concentrated. The residue was purified by silica gel column chromatography (PE:EA=3:1) to afford 7-ethyl-2-(methylamino)pyrido[2,3-d]pyrimidin-6-yl trifluoromethanesulfonate (660 mg, 70%). MS Calcd.: 336, MS Found: 337 ([M+H]⁺).

Step 4

To a solution of 7-ethyl-2-(methylthio)pyrido[2,3-d]pyrimidin-6-yl trifluoromethanesulfonate (660 mg, 1.96 mmol) and N-(4-methyl-3-(4,4,5,5-tetramethyl-1,3,2-dioxaborolan-2-yl)phenyl)-2-(trifluoromethyl)isonicotinamide (960 mg, 2.36 mmol) in dioxane (30 mL) and H₂O (5 mL) was added Cs₂CO₃ (1.3 g, 3.93 mmol) and Pd(dppf)Cl₂ (145 mg, 0.198 mmol). The reaction mixture was stirred at 70° C. for 16 h under N₂. The reaction mixture was diluted with water (50 mL) and extracted with EA (50 mL) for three times. The combined organic layers were washed with brine (50 mL), dried over Na₂SO₄, filtered and concentrated. The residue was purified by silica gel column chromatography (100% EA) to afford N-(3-(7-ethyl-2-(methylamino)pyrido[2,3-d]pyrimidin-6-yl)-4-methylphenyl)-2-(trifluoromethyl)isonicotinamide (565.9 mg, 62%). ¹H NMR (400 MHz, DMSO-d₆): δ 10.69 (s, 1H), 9.09 (s, 1H), 8.98 (d, J=4.8 Hz, 1H), 8.36 (s, 1H), 8.19-8.18 (m, 1H), 7.94 (s, 1H), 7.76 (dd, J=2.4, 8.4 Hz, 1H), 7.68-7.63 (m, 2H), 7.38 (d, J=8.4, 1H), 2.94 (d, J=4.4, 3H), 2.67-2.57 (m, 2H), 2.03 (s, 3H), 1.14 (t, J=7.6 Hz, 3H). MS Calcd.: 466, MS Found: 467 ([M+H]⁺).

Example 37: Synthesis of N-(3-(2-(cyclopropylamino)-7-methylpyrido[2,3-d]pyrimidin-6-yl)-4-methylphenyl)-2-(trifluoromethyl)isonicotinamide

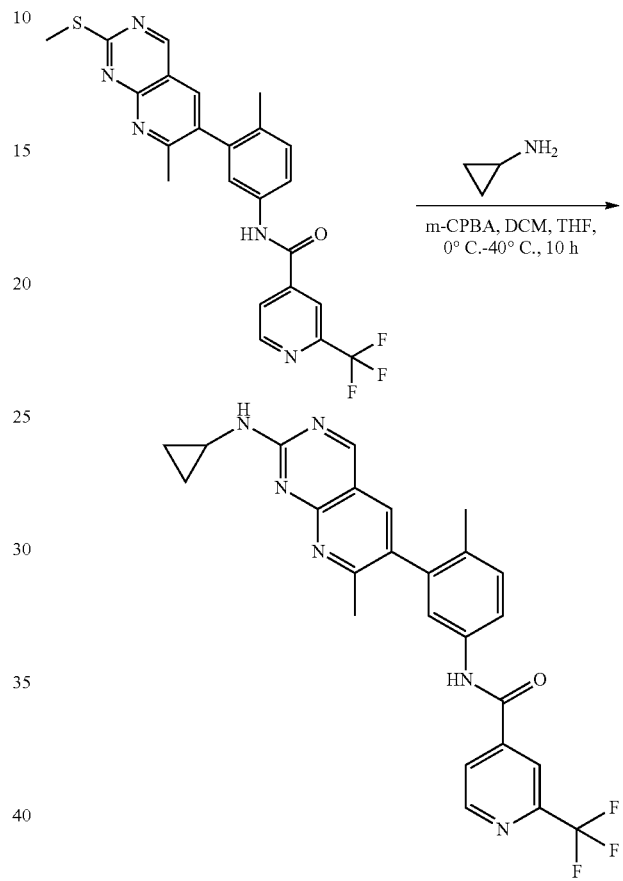

Step 1

To a mixture of N-(4-methyl-3-(7-methyl-2-(methylthio)pyrido[2,3-d]pyrimidin-6-yl)phenyl)-2-(trifluoromethyl)isonicotinamide (250 mg, 0.53 mmol) in DCM (5 mL) was added m-CPBA (108 mg, 0.53 mmol) at −5° C. The reaction mixture was stirred at room temperature for 2 h. A solution of cyclopropanamine (91 mg, 1.59 mmol) in THF (5 mL) was dropwised to the mixture which was stirred at 40° C. for 8 h. The reaction mixture was diluted with water (20 mL) and extracted with DCM (20 mL) for four times. The combined organic layers were washed with brine (20 mL), dried over Na₂SO₄, filtered and concentrated. The residue was purified by prep-HPLC to afford N-(3-(2-(cyclopropylamino)-7-methylpyrido[2,3-d]pyrimidin-6-yl)-4-methylphenyl)-2-(trifluoromethyl)isonicotinamide (96.6 mg, 37.9%). ¹H NMR (400 MHz, DMSO-d₆): δ 10.70 (s, 1H), 9.12 (s, 1H), 8.99 (d, J=4.8 Hz, 1H), 8.36 (s, 1H), 8.18 (d, J=4.8 Hz, 1H), 7.97 (s, 1H), 7.93 (d, J=2.0 Hz, 1H), 7.76 (dd, J=2.0, 8.0 Hz, 1H), 7.63 (d, J=1.6 Hz, 1H), 7.39 (d, J=8.4 Hz, 1H), 2.89-2.86 (m, 1H), 2.35 (s, 3H), 2.04 (s, 3H), 0.76-0.75 (m, 2H), 0.58-0.55 (m, 2H). MS Calcd.: 478, MS Found: 479 ([M+H]⁺).

Example 38: Synthesis of N-(4-methyl-3-(7-methyl-2-((2-morpholinoethyl)amino)pyrido[2,3-d]pyrimidin-6-yl)phenyl)-2-(trifluoromethyl)isonicotinamide

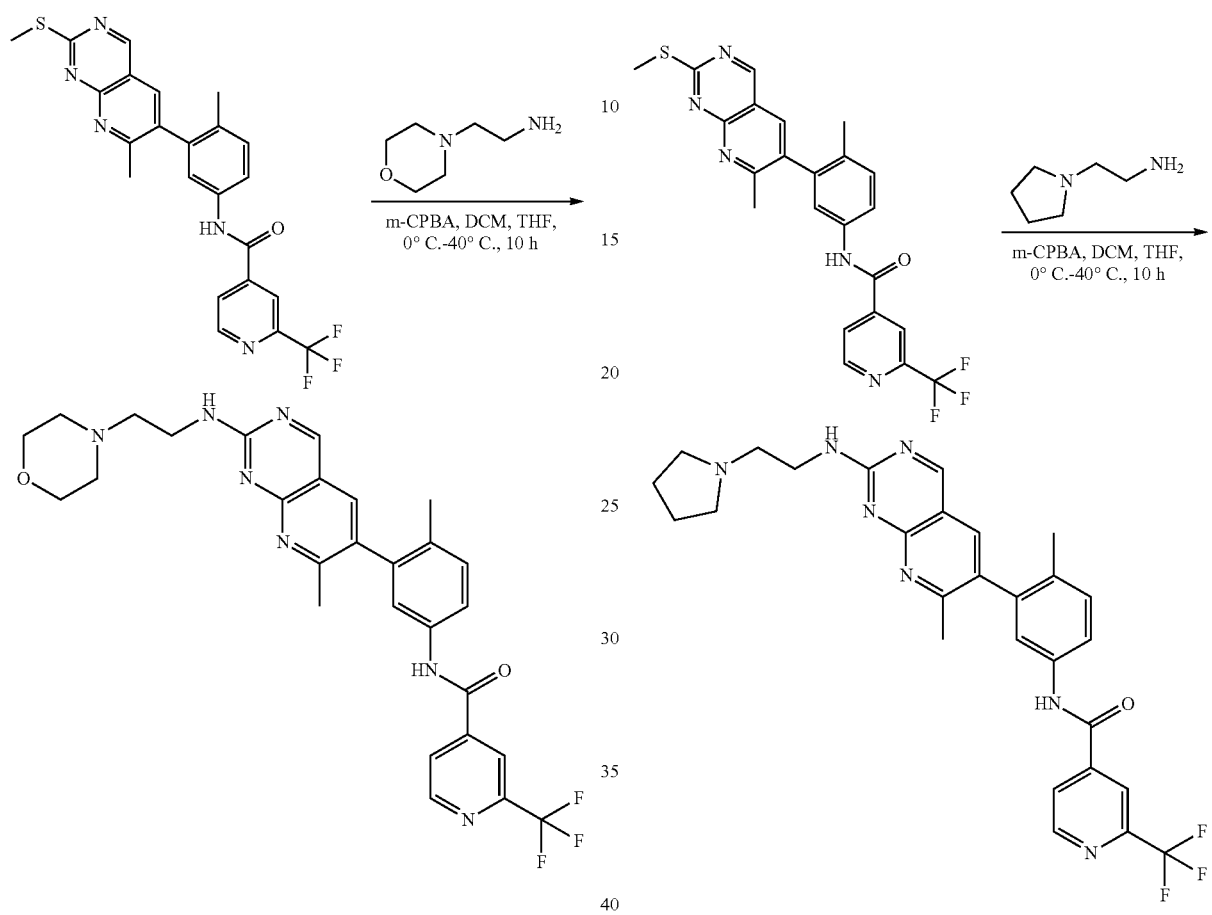

Step 1

To a mixture of N-(4-methyl-3-(7-methyl-2-(methylthio)pyrido[2,3-d]pyrimidin-6-yl)phenyl)-2-(trifluoromethyl)isonicotinamide (250 mg, 0.53 mmol) in DCM (10 mL) was added m-CPBA (108 mg, 0.53 mmol). The reaction mixture was stirred at room temperature for 2 h. A solution of 2-Morpholinoethanamine (207 mg, 1.59 mmol) in THF (10 mL) was dropwised to the mixture at −5° C. which was stirred at 40° C. for 8 h. The reaction mixture was diluted with water (20 mL) and extracted with DCM (20 mL) for four times. The combined organic layers were washed with brine (20 mL), dried over $Na_2SO_4$, filtered and concentrated. The residue was purified by prep-HPLC to afford N-(4-methyl-3-(7-methyl-2-((2-morpholinoethyl)amino)pyrido[2,3-d]pyrimidin-6-yl)phenyl)-2-(trifluoromethyl)isonicotinamide (157.1 mg, 53.4%). $^1$H NMR (400 MHz, DMSO-$d_6$): δ 10.70 (s, 1H), 9.11 (s, 1H), 8.99 (d, J=4.8 Hz, 1H), 8.36 (s, 1H), 8.18 (d, J=4.8 Hz, 1H), 7.96 (s, 1H), 7.75 (dd, J=2.0, 8.0 Hz, 1H), 7.63-7.60 (m, 2H), 7.39 (d, J=8.4 Hz, 1H), 3.59-3.53 (m, 6H), 2.57-2.54 (m, 2H), 2.49-2.45 (m, 4H), 2.34 (s, 3H), 2.04 (s, 3H). MS Calcd.: 551, MS Found: 552 ([M+H]$^+$).

Example 39: Synthesis of N-(4-methyl-3-(7-methyl-2-((2-(pyrrolidin-1-yl)ethyl)amino)pyrido[2,3-d]pyrimidin-6-yl)phenyl)-2-(trifluoromethyl)isonicotinamide

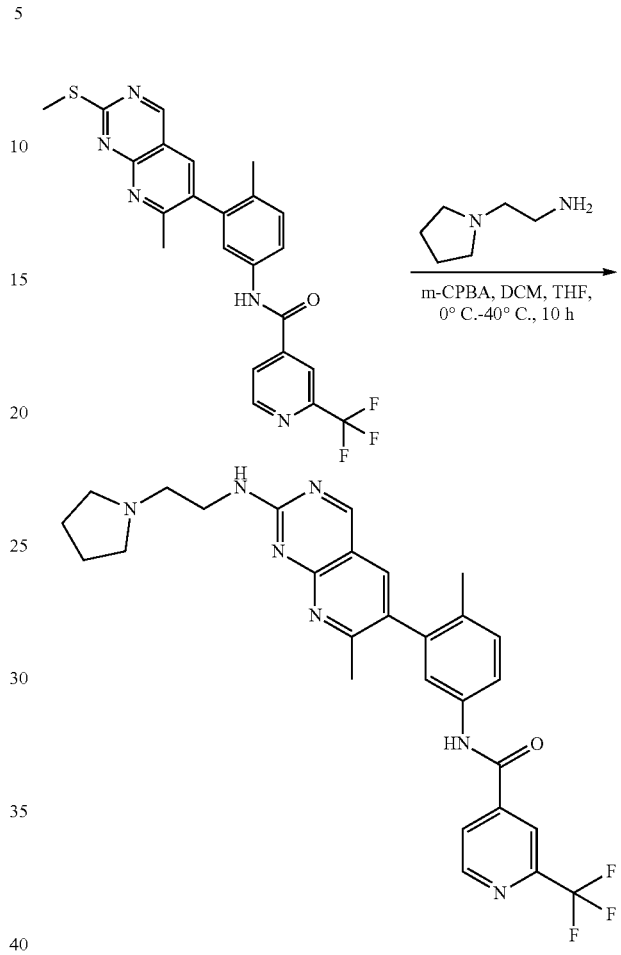

Step 1

To a mixture of N-(4-methyl-3-(7-methyl-2-(methylthio)pyrido[2,3-d]pyrimidin-6-yl)phenyl)-2-(trifluoromethyl)isonicotinamide (250 mg, 0.53 mmol) in DCM (10 mL) was added m-CPBA (108 mg, 0.53 mmol). The reaction mixture was stirred at room temperature for 2 h. A solution of 2-(Pyrrolidin-1-yl)ethanamine (182 mg, 1.59 mmol) in THF (10 mL) was dropwised to the mixture at −5° C. The reaction mixture was stirred at 40° C. for 8 h. The reaction mixture was diluted with water (20 mL) and extracted with DCM (20 mL) for four times. The combined organic layers were washed with brine (20 mL), dried over $Na_2SO_4$, filtered and concentrated. The residue was purified by prep-HPLC to afford N-(4-methyl-3-(7-methyl-2-((2-(pyrrolidin-1-yl)ethyl)amino)pyrido[2,3-d]pyrimidin-6-yl)phenyl)-2-(trifluoromethyl)isonicotinamide (170.5 mg, 60%). $^1$H NMR (400 MHz, DMSO-$d_6$): δ 10.70 (s, 1H), 9.11 (s, 1H), 8.99 (d, J=5.2 Hz, 1H), 8.36 (s, 1H), 8.18 (d, J=4.8 Hz, 1H), 7.96 (s, 1H), 7.75 (dd, J=2.0, 8.0 Hz, 1H), 7.63-7.60 (m, 2H), 7.39 (d, J=8.4 Hz, 1H), 3.55-3.52 (m, 2H), 2.71-2.68 (m, 2H), 2.53-2.50 (m, 4H), 2.34 (s, 3H), 2.04 (s, 3H), 1.72-1.68 (m, 4H). MS Calcd.: 535, MS Found: 536 ([M+H]$^+$).

Example 40: Synthesis of N-(3-(2-((2-hydroxy-ethyl)amino)-7-methylpyrido[2,3-d]pyrimidin-6-yl)-4-methylphenyl)-2-(trifluoromethyl)isonicotinamide

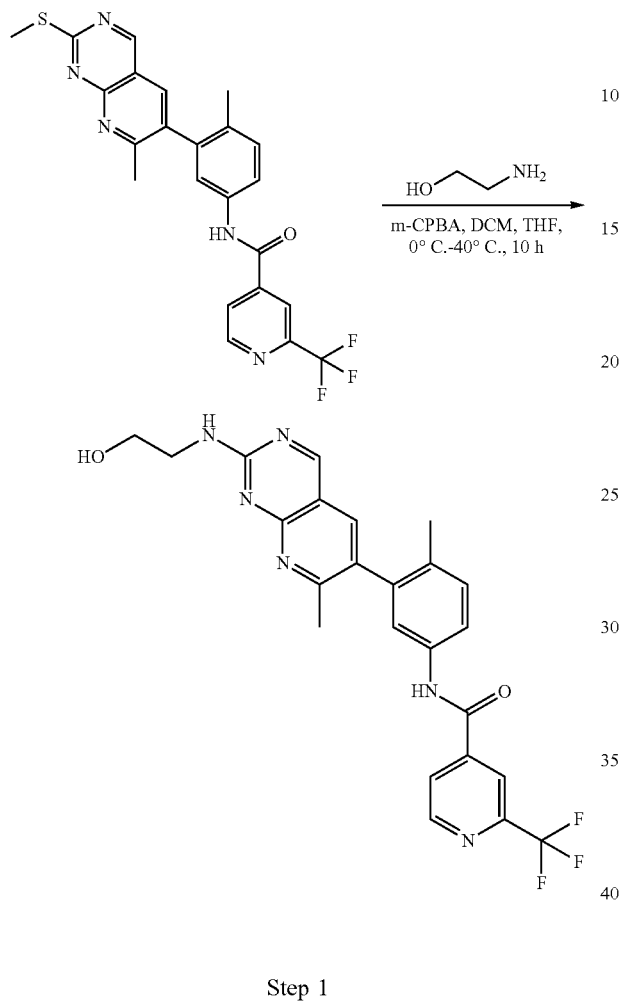

Example 41: Synthesis of 3-methyl-N-(4-methyl-3-(7-methyl-2-(methylamino)pyrido[2,3-d]pyrimidin-6-yl)phenyl)-2-(trifluoromethyl)isonicotinamide

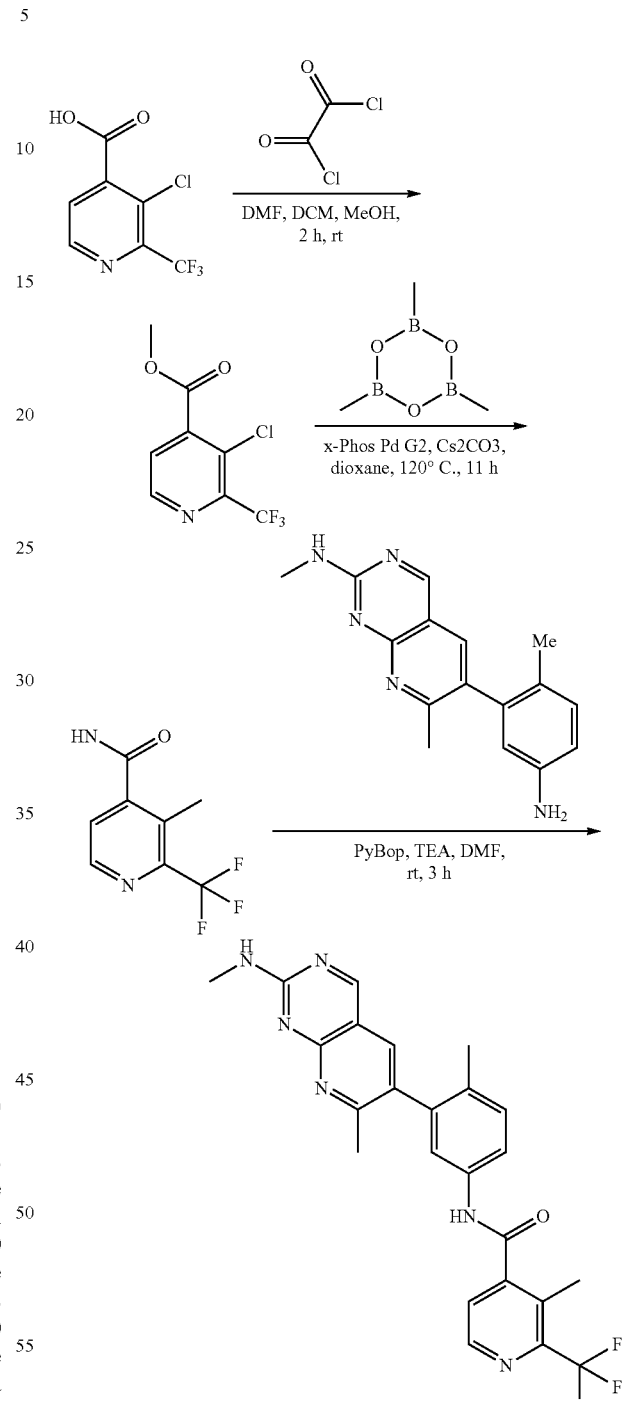

Step 1

To a mixture of N-(4-methyl-3-(7-methyl-2-(methylthio)pyrido[2,3-d]pyrimidin-6-yl)phenyl)-2-(trifluoromethyl)isonicotinamide (250 mg, 0.53 mmol) in DCM (10 mL) was added m-CPBA (108 mg, 0.53 mmol) at −5° C. Then The reaction mixture was stirred at room temperature for 2 h. A solution of 2-Aminoethanol (97 mg, 1.59 mmol) in THF (10 mL) was dropwised to the mixture. The reaction mixture was stirred at 40° C. for 8 h. The reaction mixture was diluted with water (20 mL) and extracted with DCM (20 mL) for four times. The combined organic layers were washed with brine (20 mL), dried over $Na_2SO_4$, filtered and concentrated. The residue was purified by prep-HPLC to afford N-(3-(2-((2-hydroxyethyl)amino)-7-methylpyrido[2,3-d]pyrimidin-6-yl)-4-methylphenyl)-2-(trifluoromethyl)isonicotinamide (101.5 mg, 39.5%). $^1$H NMR (400 MHz, DMSO-$d_6$): 10.70 (s, 1H), 9.11 (s, 1H), 8.99 (d, J=4.8 Hz, 1H), 8.36 (s, 1H), 8.18 (d, J=4.0 Hz, 1H), 7.96 (s, 1H), 7.75 (dd, J=2.0, 8.0 Hz, 1H), 7.66-7.62 (m, 2H), 7.39 (d, J=8.4 Hz, 1H), 4.80-4.78 (m, 1H), 3.62-3.60 (m, 2H), 3.51-3.47 (m, 2H), 2.34 (s, 3H), 2.04 (s, 3H). MS Calcd.: 482, MS Found: 483 ([M+H]$^+$).

Step 1

To a solution of 3-chloro-2-(trifluoromethyl)isonicotinic acid (330 mg, 1.46 mmol) in DCM (20 mL) was added one drop of DMF and oxalyl dichloride (373 mg, 2.94 mmol) slowly. The reaction mixture was stirred at RT for 1 h. The reaction mixture was concentrated in vacuum. The residue was dissolved in MeOH (20 mL) which was stirred for another 1 h at RT. The mixture was concentrated in vacuum. The residue was purified by FCC (PE:EA=3:1) to afford methyl 3-chloro-2-(trifluoromethyl)isonicotinate (300 mg, 86%).

MS Calcd.: 239, MS Found: 240 ([M+H]$^+$).

Step 2

To a solution of methyl 3-chloro-2-(trifluoromethyl)isonicotinate (250 mg, 1.05 mmol) and 2,4,6-trimethyl-1,3,5,2,4,6-trioxatriborinane (0.6 mL, 2.10 mmol) in dioxane (30 mL) was added Cs$_2$CO$_3$ (700 mg, 2.22 mmol) and x-Phos Pd G2 (8 mg, 0.011 mmol), The reaction mixture was stirred at 120° C. for 11 h under N$_2$. The reaction mixture was diluted with water (30 mL) and extracted with EA (30 mL) for three times. The combined organic layers were washed with brine (30 mL), dried over Na$_2$SO$_4$, filtered and concentrated. The residue was purified by silica gel column chromatography (PE:EA=1:1) to afford 3-methyl-2-(trifluoromethyl)isonicotinic acid (40 mg, 2%). MS Calcd.: 205, MS Found: 206 ([M+H]$^+$).

Step 3

To a solution of 6-(5-amino-2-methylphenyl)-N,7-dimethylpyrido[2,3-d]pyrimidin-2-amine (46 mg, 0.16 mmol) and 3-methyl-2-(trifluoromethyl)isonicotinic acid (26 mg, 0.13 mmol) in DMF (4 mL) was added TEA (36 mg, 0.36 mmol) and PyBop (112 mg, 0.21 mmol). The reaction mixture was stirred at room temperature for 3 h. The reaction mixture was poured into water (10 mL) and extracted with EA (10 mL) for three times. The combined organic layers were washed with brine (20 mL), dried over Na$_2$SO$_4$, filtered and concentrated in vacuum. The residue was purified by FCC (100% EA) to afford 3-methyl-N-(4-methyl-3-(7-methyl-2-(methylamino)pyrido[2,3-d]pyrimidin-6-yl)phenyl)-2-(trifluoromethyl)isonicotinamide (8.4 mg, 14%). $^1$H NMR (400 MHz, DMSO-d$_6$): δ 10.70 (s, 1H), 9.09 (s, 1H), 8.68 (d, J=4.8 Hz, 1H), 7.96 (s, 1H), 7.80 (d, J=5.2 Hz, 1H), 7.69-7.59 (m, 3H), 7.36 (d, J=8.4 Hz, 1H), 2.92 (d, J=4.4 Hz, 3H), 2.46 (d, J=1.6 Hz, 3H), 2.33 (s, 3H), 2.03 (s, 3H).

MS Calcd.: 466, MS Found: 467 ([M+H]$^+$).

Example 42: Synthesis of N-(4-methyl-3-(7-methyl-2-((1-methylpiperidin-4-yl)amino)pyrido[2,3-d]pyrimidin-6-yl)phenyl)-2-(trifluoromethyl)isonicotinamide

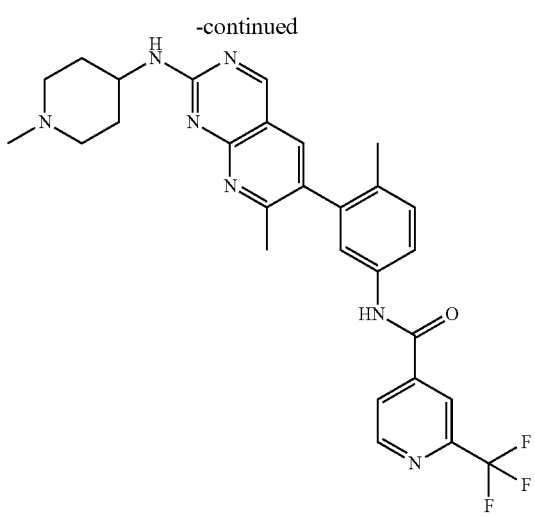

-continued

Step 1

To a mixture of N-(4-methyl-3-(7-methyl-2-(methylthio)pyrido[2,3-d]pyrimidin-6-yl)phenyl)-2-(trifluoromethyl)isonicotinamide (250 mg, 0.53 mmol) in DCM (10 mL) was added m-CPBA (108 mg, 0.53 mmol) at −5° C. The reaction mixture was stirred at room temperature for 2 h. A solution of 1-Methylpiperidin-4-amine (182 mg, 1.59 mmol) in THF (10 mL) was dropwised to the mixture which was stirred at 40° C. for 8 h. The reaction mixture was diluted with water (20 mL) and extracted with DCM (20 mL) for four times. The combined organic layers were washed with brine (20 mL), dried over Na$_2$SO$_4$, filtered and concentrated. The residue was purified by prep-HPLC to afford N-(4-methyl-3-(7-methyl-2-((1-methylpiperidin-4-yl)amino)pyrido[2,3-d]pyrimidin-6-yl)phenyl)-2-(trifluoromethyl)isonicotinamide (68.7 mg, 12%). $^1$H NMR (400 MHz, DMSO-d$_6$): δ 10.69 (s, 1H), 9.11 (s, 1H), 8.99 (d, J=5.2 Hz, 1H), 8.36 (s, 1H), 8.18 (dd, J=0.8, 4.8 Hz, 1H), 7.95 (d, J=1.2 Hz, 1H), 7.76-7.71 (m, 2H), 7.62 (d, J=2.0, Hz, 1H), 7.38 (d, J=8.4 Hz, 1H), 3.88-3.96 (m, 1H), 2.85-2.82 (m, 2H), 2.34 (s, 3H), 2.29-2.16 (m, 8H), 2.03-1.93 (m, 2H), 1.62-1.59 (m, 2H). MS Calcd.: 535, MS Found: 536 ([M+H]$^+$).

Example 43: Synthesis of N-(4-methyl-3-(7-methyl-2-((trideuteromethyl)amino)pyrido[2,3-d]pyrimidin-6-yl)phenyl)-2-(trifluoromethyl)isonicotinamide

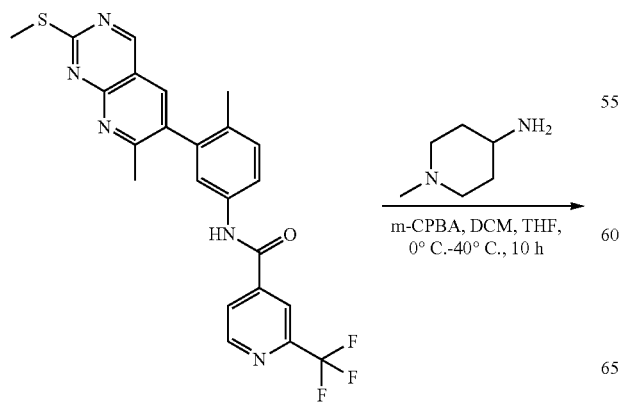

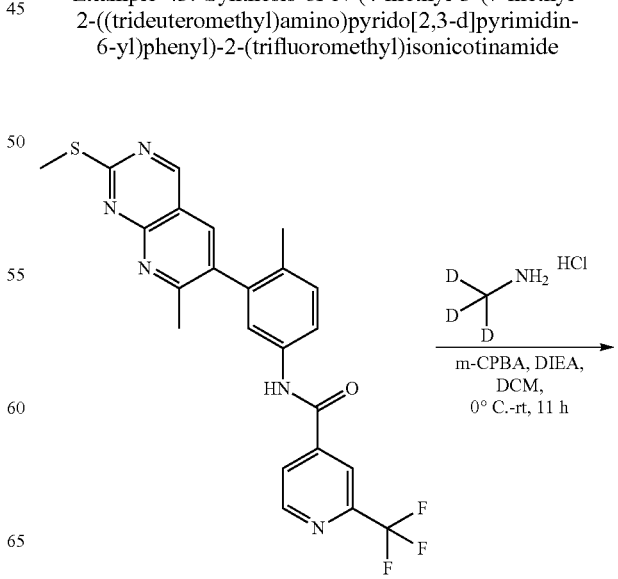

-continued

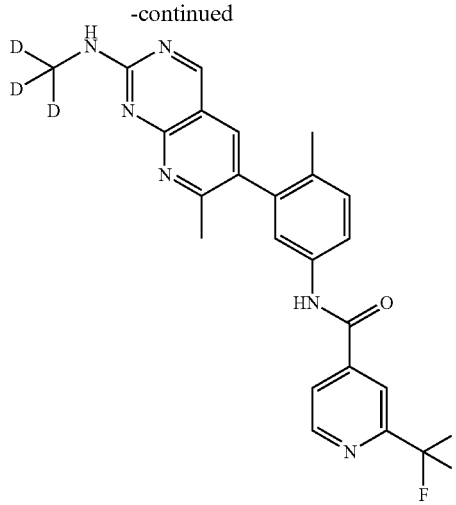

Step 1

To a mixture of N-(4-methyl-3-(7-methyl-2-(methylthio)pyrido[2,3-d]pyrimidin-6-yl)phenyl)-2-(trifluoromethyl)isonicotinamide (300 mg, 0.64 mmol) in DCM (15 mL) was added m-CPBA (130 mg, 0.64 mmol) at −5° C. The reaction mixture was stirred at room temperature for 3 h. Trideuteromethanamine hydrochloride (182 mg, 1.59 mmol) and DIEA (496 mg, 3.84 mmol) was added to the mixture which was stirred at room temperature for 8 h. The reaction mixture was diluted with water (20 mL) and extracted with DCM (20 mL) for four times. The combined organic layers were washed with brine (20 mL), dried over $Na_2SO_4$, filtered and concentrated. The residue was purified by prep-HPLC to afford N-(4-methyl-3-(7-methyl-2-((trideuteromethyl)amino)pyrido[2,3-d]pyrimidin-6-yl)phenyl)-2-(trifluoromethyl)isonicotinamide (71.5 mg, 24.6%). $^1$H NMR (400 MHz, DMSO-$d_6$): δ 10.69 (s, 1H), 9.10 (s, 1H), 8.99 (d, J=5.2 Hz, 1H), 8.36 (s, 1H), 8.18 (d, J=5.2 Hz, 1H), 7.96 (s, 1H), 7.75 (dd, J=2.0, 8.0 Hz, 1H), 7.66-7.62 (m, 2H), 7.39 (d, J=8.4 Hz, 1H), 2.34 (s, 3H), 2.04 (s, 3H). MS Calcd.: 455, MS Found: 456 ([M+H]$^+$).

Example 44: Synthesis of N-(6-methyl-5-(7-methyl-2-(methylamino)pyrido[2,3-d]pyrimidin-6-yl)pyridin-3-yl)-3-(trifluoromethyl)benzamide

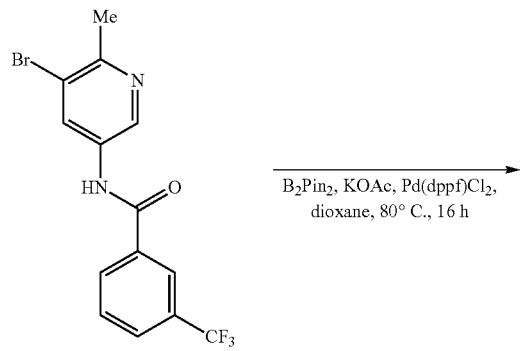

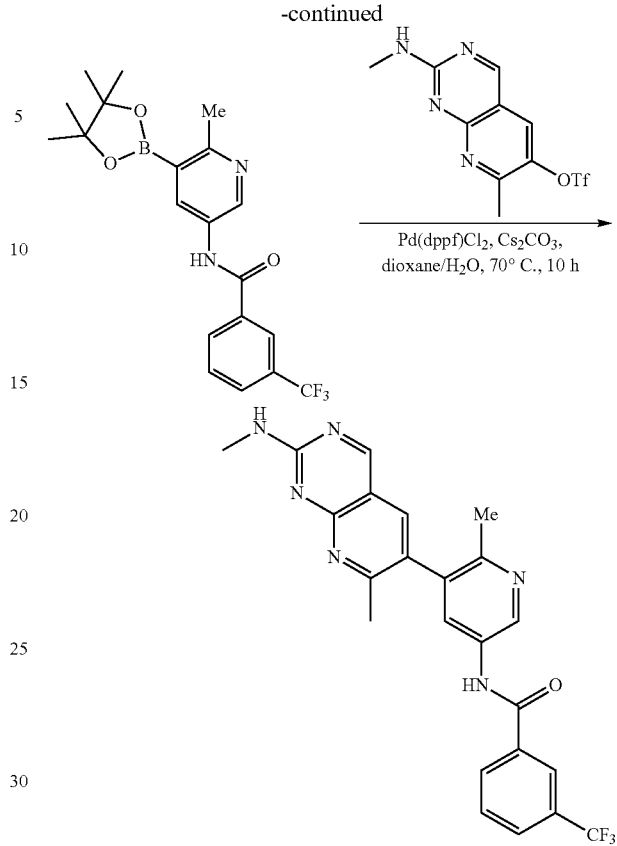

Step 1

To a solution of N-(5-bromo-6-methylpyridin-3-yl)-3-(trifluoromethyl)benzamide (1.0 g, 2.78 mmol), 4,4,4',4',5,5,5',5'-octamethyl-2,2'-bi(1,3,2-dioxaborolane) (777 mg, 3.06 mmol) and KOAc (545 mg, 5.56 mmol) in dioxane (20 mL) was added Pd(dppf)C12 (203 mg, 0.28 mmol) under nitrogen atmosphere. Then the reaction mixture was stirred at 80° C. for 16 h under nitrogen atmosphere. After the reaction mixture was cooled down to room temperature, filtered and concentrated to give N-(6-methyl-5-(4,4,5,5-tetramethyl-1,3,2-dioxaborolan-2-yl)pyridin-3-yl)-3-(trifluoromethyl)benzamide (1.12 g, crude) which was used to the next step without further purification. MS Calcd.: 406, MS Found: 407 ([M+H]$^+$).

Step 2

To a solution of N-(4-methyl-3-(4,4,5,5-tetramethyl-1,3,2-dioxaborolan-2-yl)phenyl)-3-(trifluoromethyl)pyrrolidine-1-carboxamide (748 mg, 2.32 mmol), N-(6-methyl-5-(4,4,5,5-tetramethyl-1,3,2-dioxaborolan-2-yl)pyridin-3-yl)-3-(trifluoromethyl)benzamide (1.1 g, 2.78 mmol) and $Cs_2CO_3$ (1.5 g, 4.64 mmol) in dioxane (30 mL) and water (5 mL) was added Pd(dppf)C12 (170 mg, 0.23 mmol) at room temperature under nitrogen atmosphere. The reaction mixture was stirred at 70° C. for 10 h under nitrogen atmosphere. The reaction mixture was cooled down to room temperature, filtered and concentrated. The residue was purified by FCC (EA:MeOH=20:1) to afford N-(6-methyl-5-(7-methyl-2-(methylamino)pyrido[2,3-d]pyrimidin-6-yl)pyridin-3-yl)-3-(trifluoromethyl)benzamide (300.5 mg, 28%) as a yellow solid. $^1$H NMR (400 MHz, DMSO-$d_6$): δ 10.69 (s, 1H), 9.10 (s, 1H), 8.90 (d, J=2.4 Hz, 1H), 8.32 (s, 1H), 8.28 (d, J=8.0 Hz, 1H), 8.05-7.98 (m, 3H), 7.81 (t, J=8.0 Hz, 1H), 7.74-7.73 (m, 1H), 2.93 (d, J=4.8 Hz, 3H), 2.36 (s, 3H), 2.25 (s, 3H). MS Calcd.: 452, MS Found: 453 ([M+H]$^+$).

Example 45: Synthesis of N-(6-methyl-5-(2-(methylamino)pyrido[2,3-d]pyrimidin-6-yl)pyridin-3-yl)-3-(trifluoromethyl)benzamide

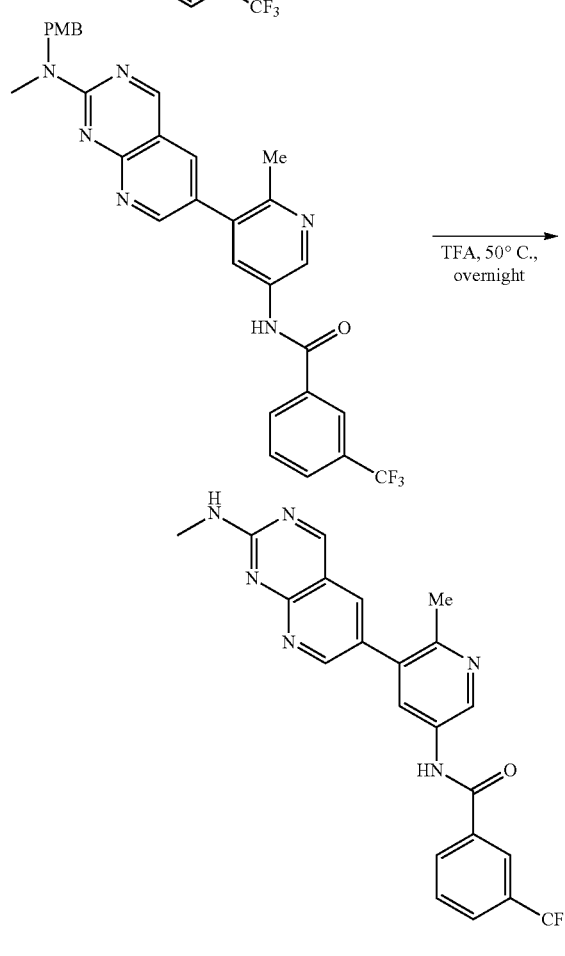

Step 1

To a solution of 6-bromo-N-(4-methoxybenzyl)-N-methylpyrido[2,3-d]pyrimidin-2-amine (1.08 g, 3.00 mmol), N-(6-methyl-5-(4,4,5,5-tetramethyl-1,3,2-dioxaborolan-2-yl)pyridin-3-yl)-3-(trifluoromethyl)benzamide (1.94 g, 5.99 mmol) and $Cs_2CO_3$ (1.96 g, 6.01 mmol) in dioxane (30 mL) and water (5 mL) was added Pd(dppf)Cl2 (220 mg, 0.30 mmol) at room temperature under nitrogen atmosphere. The reaction mixture was stirred at 70° C. for 8 h under nitrogen atmosphere. The reaction mixture was cooled down to room temperature, filtered and concentrated. The residue was purified by FCC (EA:PE=1:1) to afford N-(5-(2-((4-methoxybenzyl)(methyl)amino)pyrido[2,3-d]pyrimidin-6-yl)-6-methylpyridin-3-yl)-3-(trifluoromethyl)benzamide (1.2 g, 71%) as a yellow solid. MS Calcd.: 558, MS Found: 559 ([M+H]$^+$).

Step 2

A solution of N-(5-(2-((4-methoxybenzyl)(methyl)amino)pyrido[2,3-d]pyrimidin-6-yl)-6-methylpyridin-3-yl)-3-(trifluoromethyl)benzamide (1.2 g, 2.15 mmol) in TFA (12 mL) was stirred at 50° C. overnight. The reaction mixture was cooled down to room temperature and concentrated in vacuum. The residue was dissolved in ice water (20 mL), basified to pH=7 with saturated sodium bicarbonate aqueous solution and extracted with DCM (20 mL*3). The combined organic layers were washed with brine (20 mL), dried over $Na_2SO_4$, filtered and concentrated. The residue was purified by FCC (EA:PE=1:1) to afford N-(6-methyl-5-(2-(methylamino)pyrido[2,3-d]pyrimidin-6-yl)pyridin-3-yl)-3-(trifluoromethyl)benzamide (561.2 mg, 50%) as a yellow solid. $^1$H NMR (400 MHz, DMSO-d$_6$): δ 10.71 (s, 1H), 9.22 (s, 1H), 8.94 (d, J=2.4 Hz, 1H), 8.91 (d, J=2.4 Hz, 1H), 8.35-8.29 (m, 3H), 8.17 (d, J=2.4 Hz, 1H), 8.00 (d, J=3.6 Hz, 1H), 7.87-7.80 (m, 2H), 2.95 (d, J=4.8 Hz, 3H), 2.49 (s, 3H). MS Calcd.: 438, MS Found: 439 ([M+H]$^+$).

Example 46: Synthesis of N-(6-methyl-5-(2-(methylamino)pyrido[2,3-d]pyrimidin-6-yl)pyridin-3-yl)-2-(trifluoromethyl)isonicotinamide

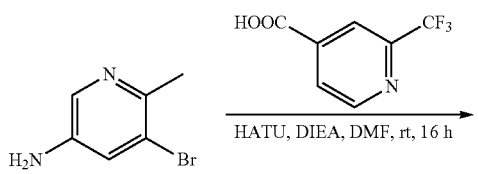

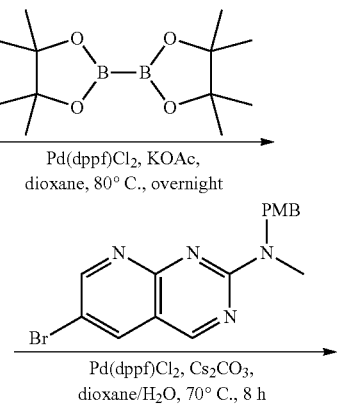
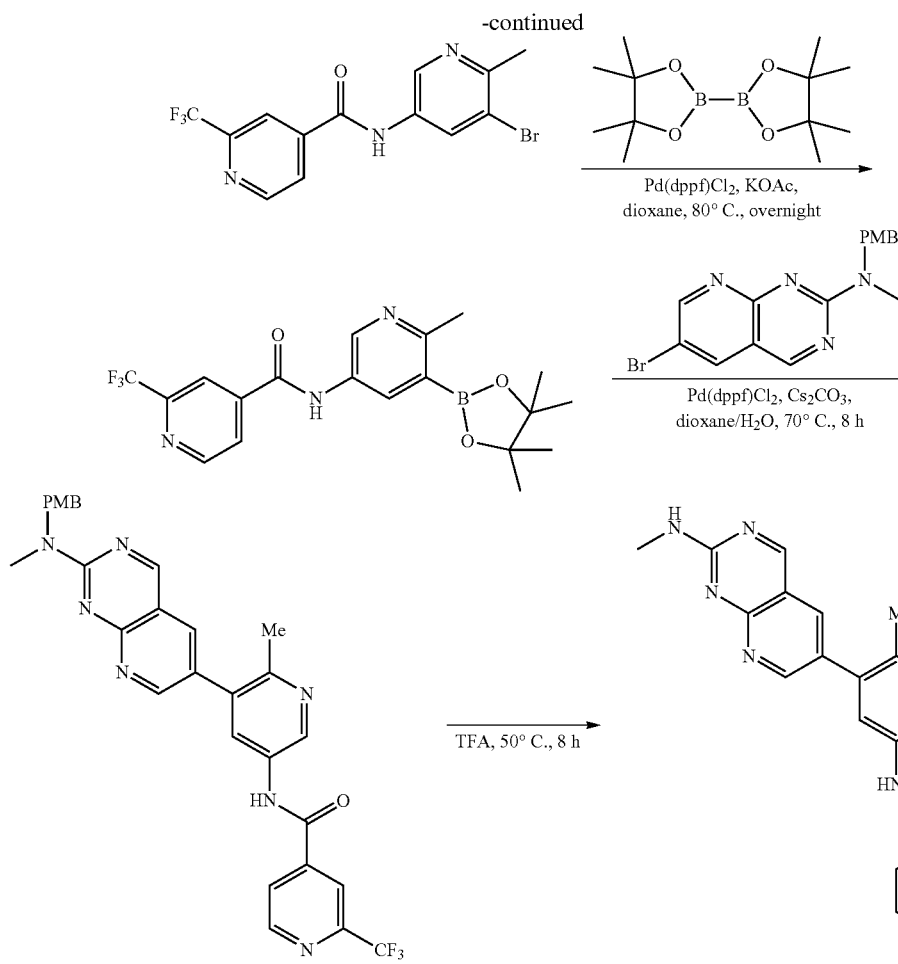

Step 1

A solution of 5-bromo-6-methylpyridin-3-amine (1.0 g, 5.3 mmol), 2-(trifluoromethyl)isonicotinic acid (1.1 g, 5.9 mmol), HATU (3.06 g, 8.0 mmol) and DIEA (3.47 g, 26.9 mmol) in DMF (20 mL) was stirred at room temperature for 16 h. Then the mixture was poured into water (60 mL) and extracted with EA (20 mL*3). The combined organic layers were washed with brine (20 mL), dried over $Na_2SO_4$, filtered and concentrated. The residue was purified by FCC (EA:PE=1:1) to afford N-(5-bromo-6-methylpyridin-3-yl)-2-(trifluoromethyl)isonicotinamide (800 mg, 42%) as a yellow solid. MS Calcd.: 359, MS Found: 360 ([M+H]$^+$).

Step 2

To a solution of N-(5-bromo-6-methylpyridin-3-yl)-2-(trifluoromethyl)isonicotinamide (500 mg, 1.40 mmol), 4,4,4',4',5,5,5',5'-octamethyl-2,2'-bi(1,3,2-dioxaborolane) (391 mg, 1.54 mmol) and KOAc (274 mg, 2.80 mmol) in dioxane (20 mL) was added Pd(dppf)Cl2 (102 mg, 0.14 mmol) under nitrogen atmosphere. Then the reaction mixture was stirred at 80° C. overnight under nitrogen atmosphere. After the reaction mixture was cooled down to room temperature, filtered and concentrated to give N-(6-methyl-5-(4,4,5,5-tetramethyl-1,3,2-dioxaborolan-2-yl)pyridin-3-yl)-2-(trifluoromethyl)isonicotinamide (570 mg, crude) which was used to the next step without further purification. MS Calcd.: 407, MS Found: 408 ([M+H]$^+$).

Step 3

To a solution of 6-bromo-N-(4-methoxybenzyl)-N-methylpyrido[2,3-d]pyrimidin-2-amine (200 mg, 0.56 mmol), N-(6-methyl-5-(4,4,5,5-tetramethyl-1,3,2-dioxaborolan-2-yl)pyridin-3-yl)-2-(trifluoromethyl)isonicotinamide (570 mg, 1.40 mmol) and $Cs_2CO_3$ (365 mg, 1.12 mmol) in dioxane (30 mL) and water (5 mL) was added Pd(dppf)C12 (41 mg, 0.056 mmol) at room temperature under nitrogen atmosphere. The reaction mixture was stirred at 70° C. for 8 h under nitrogen atmosphere. The reaction mixture was cooled down to room temperature, filtered and concentrated. The residue was purified by FCC (EA:PE=1:3) to afford N-(5-(2-((4-methoxybenzyl)(methyl)amino)pyrido[2,3-d]pyrimidin-6-yl)-6-methylpyridin-3-yl)-2-(trifluoromethyl)isonicotinamide (250 mg, 80%) as a yellow solid. MS Calcd.: 559, MS Found: 560 ([M+H]$^+$).

Step 4

A solution of N-(5-(2-((4-methoxybenzyl)(methyl)amino)pyrido[2,3-d]pyrimidin-6-yl)-6-methylpyridin-3-yl)-2-(trifluoromethyl)isonicotinamide (250 mg, 0.45 mmol) in TFA (2 mL) was stirred at 50° C. for 8 h. The reaction mixture was cooled down to room temperature and concentrated in vacuum. The residue was dissolved in ice water (20 mL), basified to pH=8 with saturated sodium bicarbonate aqueous solution and extracted with DCM (20 mL*3). The combined organic layers were washed with brine (20 mL), dried over Na$_2$SO$_4$, filtered and concentrated. The residue was purified by prep-HPLC to afford N-(6-methyl-5-(2-(methylamino)pyrido[2,3-d]pyrimidin-6-yl)pyridin-3-yl)-2-(trifluoromethyl)isonicotinamide (41 mg, 21%) as a yellow solid. $^1$H NMR (400 MHz, DMSO-d$_6$): δ 10.94 (s, 1H), 9.22 (s, 1H), 9.02 (d, J=4.8 Hz, 1H), 8.94 (d, J=2.0 Hz, 1H), 8.90 (d, J=2.4 Hz, 1H), 8.40 (s, 1H), 8.34 (d, J=2.4 Hz, 1H), 8.22 (d, J=5.2 Hz, 1H), 8.16 (d, J=2.4 Hz, 1H), 7.87-7.86 (m, 1H), 2.95 (d, J=4.8 Hz, 3H), 2.51 (s, 3H). MS Calcd.: 439, MS Found: 440 ([M+H]$^+$).

Example 47: Synthesis of 2-methyl-N-(6-methyl-5-(2-(methylamino)pyrido[2,3-d]pyrimidin-6-yl)pyridin-3-yl)-3-(trifluoromethyl)benzamide

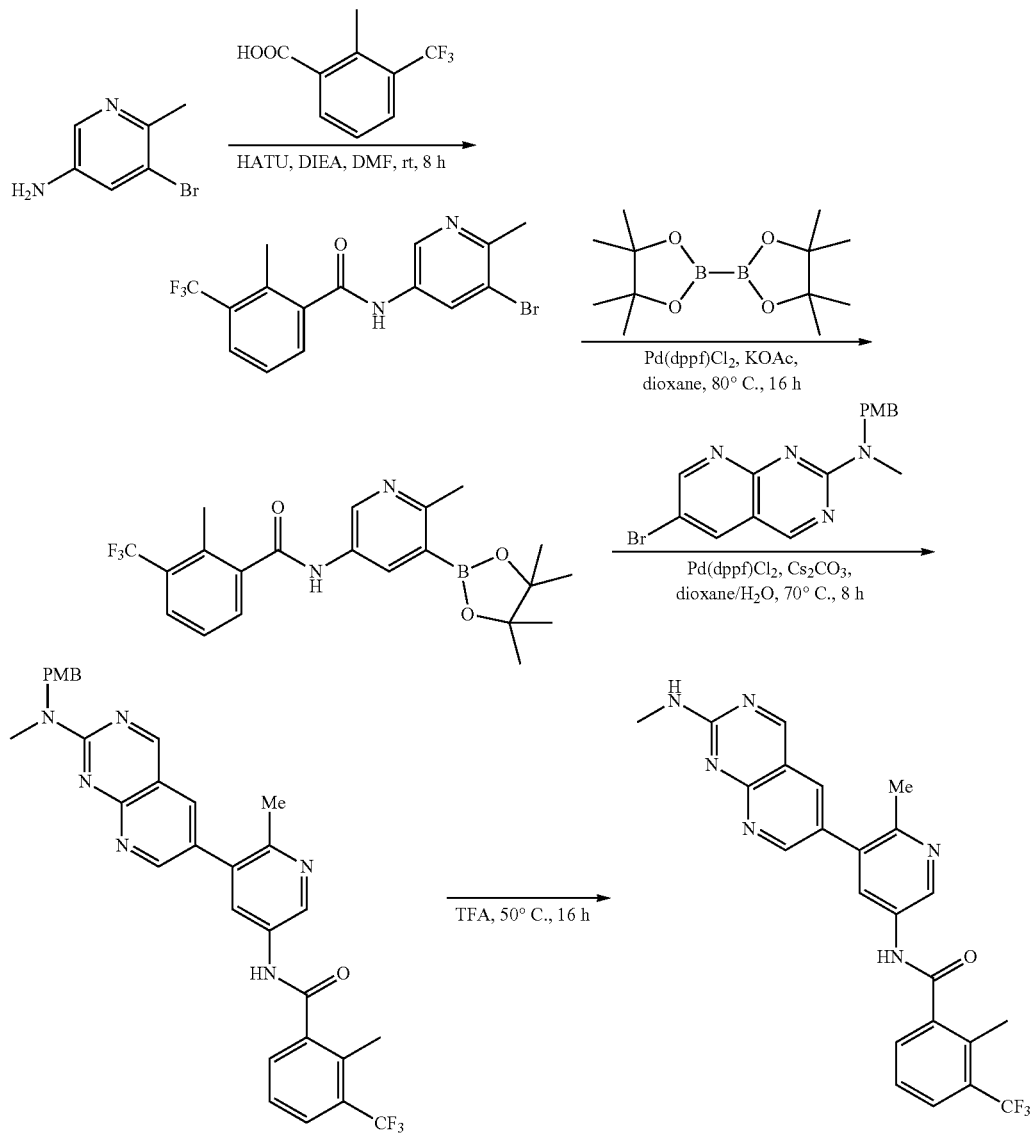

Step 1

A solution of 5-bromo-6-methylpyridin-3-amine (730 mg, 3.01 mmol), 2-methyl-3-(trifluoromethyl)benzoic acid (875 mg, 4.29 mmol), HATU (1.78 g, 4.68 mmol) and DIEA (2.52 g, 19.5 mmol) in DMF (20 mL) was stirred at room temperature for 8 h. Then the mixture was poured into water (60 mL) and extracted with EA (20 mL*3). The combined organic layers were washed with brine (20 mL), dried over Na$_2$SO$_4$, filtered and concentrated. The residue was purified by FCC (EA:PE=1:2) to afford N-(5-bromo-6-methylpyridin-3-yl)-2-methyl-3-(trifluoromethyl)benzamide (1.26 g, 77%) as a yellow solid. MS Calcd.: 372, MS Found: 373 ([M+H]$^+$).

Step 2

To a solution of N-(5-bromo-6-methylpyridin-3-yl)-2-methyl-3-(trifluoromethyl)benzamide (1.76 g, 3.38 mmol), 4,4,4',4',5,5,5',5'-octamethyl-2,2'-bi(1,3,2-dioxaborolane) (1.03 g, 4.06 mmol) and KOAc (663 mg, 6.76 mmol) in dioxane (20 mL) was added Pd(dppf)Cl2 (247 mg, 0.33 mmol) under nitrogen atmosphere. Then the reaction mixture was stirred at 80° C. for 16 h under nitrogen atmosphere. After the reaction mixture was cooled down to room temperature, filtered and concentrated to give 2-methyl-N-(6-methyl-5-(4,4,5,5-tetramethyl-1,3,2-dioxaborolan-2-yl)pyridin-3-yl)-3-(trifluoromethyl)benzamide (1.4 g, crude) which was used to the next step without further purification. MS Calcd.: 420, MS Found: 421 ([M+H]⁺).

Step 3

To a solution of 6-bromo-N-(4-methoxybenzyl)-N-methylpyrido[2,3-d]pyrimidin-2-amine (360 mg, 1.00 mmol), 2-methyl-N-(6-methyl-5-(4,4,5,5-tetramethyl-1,3,2-dioxaborolan-2-yl)pyridin-3-yl)-3-(trifluoromethyl)benzamide (714 mg, 1.70 mmol) and Cs₂CO₃ (652 mg, 2.00 mmol) in dioxane (30 mL) and water (5 mL) was added Pd(dppf)Cl2 (73 mg, 0.10 mmol) at room temperature under nitrogen atmosphere. Then the reaction mixture was stirred at 70° C. for 8 h under nitrogen atmosphere. The reaction mixture was cooled down to room temperature, filtered and concentrated. The residue was purified by FCC (EA:PE=1:1) to afford N-(5-(2-((4-methoxybenzyl)(methyl)amino)pyrido[2,3-d]pyrimidin-6-yl)-6-methylpyridin-3-yl)-2-methyl-3-(trifluoromethyl)benzamide (300 mg, 52%) as yellow oil.
MS Calcd.: 572, MS Found: 573 ([M+H]⁺).

Step 4

A solution of N-(5-(2-((4-methoxybenzyl)(methyl)amino)pyrido[2,3-d]pyrimidin-6-yl)-6-methylpyridin-3-yl)-2-methyl-3-(trifluoromethyl)benzamide (300 mg, 0.52 mmol) in TFA (15 mL) was stirred at 50° C. for 16 h. The reaction mixture was cooled down to room temperature and concentrated in vacuum. The residue was dissolved in ice water (20 mL), basified to pH=8 with saturated sodium bicarbonate aqueous solution and extracted with DCM (20 mL*3). The combined organic layers were washed with brine (20 mL), dried over Na₂SO₄, filtered and concentrated. The residue was purified by prep-HPLC to afford 2-methyl-N-(6-methyl-5-(2-(methylamino)pyrido[2,3-d]pyrimidin-6-yl)pyridin-3-yl)-3-(trifluoromethyl)benzamide (74.7 mg, 31%) as a yellow solid. ¹H NMR (400 MHz, DMSO-d₆): δ 10.77 (s, 1H), 9.22 (s, 1H), 8.92 (s, 1H), 8.79 (d, J=2.0 Hz, 1H), 8.33 (d, J=2.4 Hz, 1H), 8.16 (d, J=2.4 Hz, 1H), 7.85-7.71 (m, 3H), 7.55 (t, J=7.6 Hz, 1H), 2.95 (d, J=4.4 Hz, 3H), 2.48 (s, 3H), 2.47 (s, 3H). MS Calcd.: 452, MS Found: 453 ([M+H]⁺).

Example 48: Synthesis of N-(3-(2-amino-7-methylpyrido[2,3-d]pyrimidin-6-yl)-4-methylphenyl)-2-(trifluoromethyl)isonicotinamide

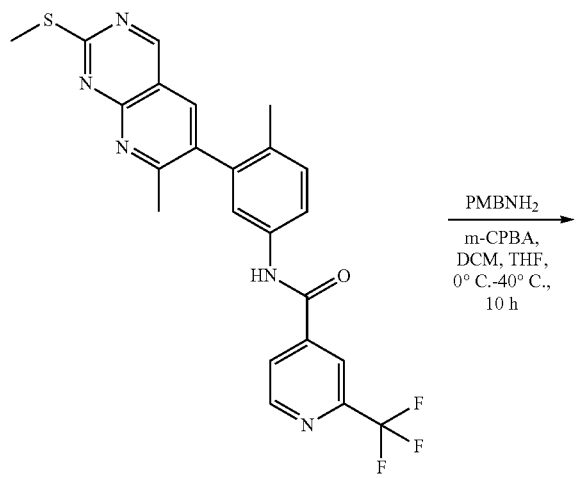

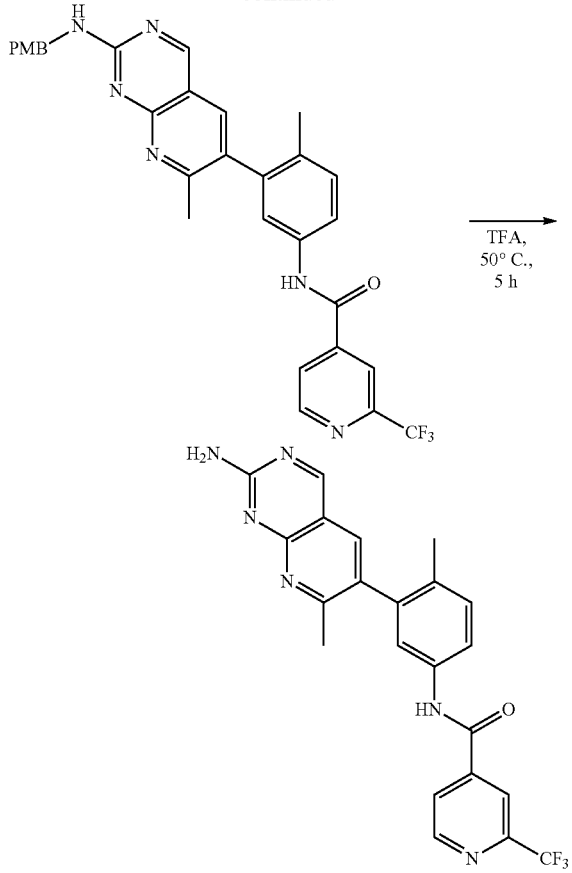

Step 1

To a mixture of N-(4-methyl-3-(7-methyl-2-(methylthio)pyrido[2,3-d]pyrimidin-6-yl)phenyl)-2-(trifluoromethyl)isonicotinamide (500 mg, 1.06 mmol) in DCM (20 mL) was added m-CPBA (183 mg, 1.06 mmol) at −5° C. The reaction mixture was stirred at room temperature for 2 h. A solution of PMBNH2 (455 mg, 3.18 mmol) in THF (20 mL) was dropwised to the mixture which was stirred at 40° C. for 8 h. The reaction mixture was diluted with water (20 mL) and extracted with DCM (20 mL) for four times. The combined organic layers were washed with brine (20 mL), dried over Na₂SO₄, filtered and concentrated. The residue was purified by prep-HPLC to afford N-(3-(2-((4-methoxybenzyl)amino)-7-methylpyrido[2,3-d]pyrimidin-6-yl)-4-methylphenyl)-2-(trifluoromethyl)isonicotinamide (600 mg, 90%). MS Calcd.: 558, MS Found: 559 ([M+H]⁺).

Step 2

A solution of N-(3-(2-((4-methoxybenzyl)amino)-7-methylpyrido[2,3-d]pyrimidin-6-yl)-4-methylphenyl)-2-(trifluoromethyl)isonicotinamide (250 mg, 0.45 mmol) in TFA (5 mL) was stirred at 50° C. for 5 h. The reaction mixture was cooled down to room temperature and concentrated in vacuum. The residue was dissolved in ice water (20 mL), basified to pH=7 with saturated sodium bicarbonate aqueous solution and extracted with DCM (20 mL*3). The combined organic layers were washed with brine (20 mL), dried over Na₂SO₄, filtered and concentrated. The residue was purified by prep-HPLC to afford N-(3-(2-amino-7-methylpyrido[2,3-d]pyrimidin-6-yl)-4-methylphenyl)-2-(trifluoromethyl)isonicotinamide (52.8 mg, 27%) as a white solid. ¹H NMR (400 MHz, DMSO-d₆): δ 10.69 (s, 1H), 9.13 (s, 1H), 8.98 (d, J=5.2 Hz, 1H), 8.36 (s, 1H), 8.18 (d, J=4.8 Hz, 1H), 7.96 (s, 1H), 7.55 (dd, J=2.4, 8.4 Hz, 1H), 7.62 (d, J=2.0 Hz, 1H), 7.39 (d, J=8.8 Hz, 1H), 7.16 (s, 2H), 2.33 (s, 3H), 2.01 (s, 3H).

MS Calcd.: 438, MS Found: 439 ([M+H]⁺).

Example 49: Synthesis of N-(3-(2-(cyclopropanecarboxamido)-7-methylpyrido[2,3-d]pyrimidin-6-yl)-4-methylphenyl)-2-(trifluoromethyl)isonicotinamide

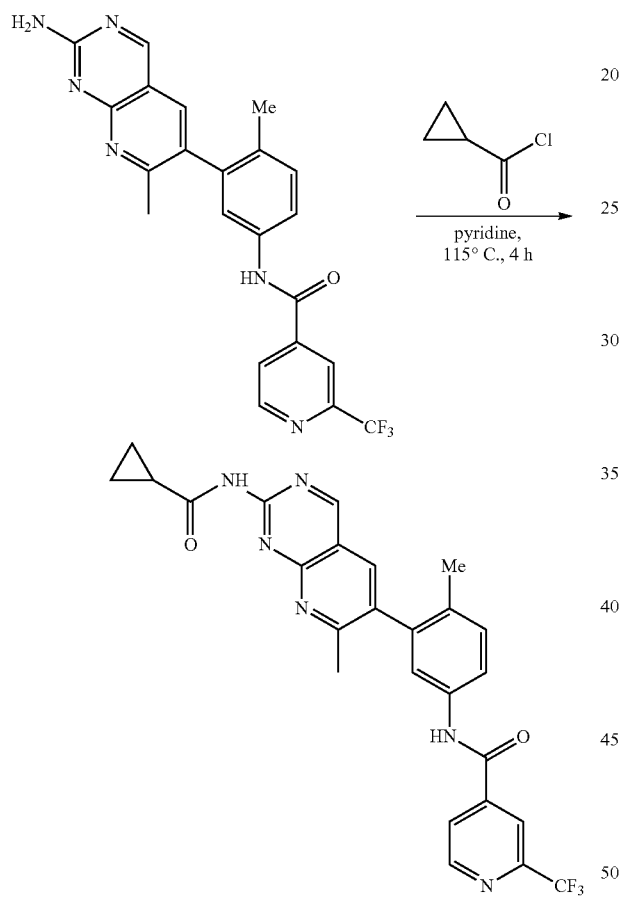

Step 1

To a solution of N-(3-(2-amino-7-methylpyrido[2,3-d]pyrimidin-6-yl)-4-methylphenyl)-2-(trifluoromethyl)isonicotinamide (70 mg, 0.16 mmol) in pyridine (10 mL) was added cyclopropanecarbonyl chloride (33 mg, 0.32 mmol) at room temperature. The reaction mixture was stirred at 115° C. for 4 h. The reaction mixture was cooled down to room temperature and concentrated. The residue was purified by prep-HPLC to give N-(3-(2-(cyclopropanecarboxamido)-7-methylpyrido[2,3-d]pyrimidin-6-yl)-4-methylphenyl)-2-(trifluoromethyl)isonicotinamide (8.6 mg, 11%) as a white solid. (R)—N-(2-fluoro-4-methyl-5-(7-methyl-2-(methylamino)pyrido[2,3-d]pyrimidin-6-yl)phenyl)-3-(2,2,2-trifluoroethyl)pyrrolidine-1-carboxamide. ¹H NMR (400 MHz, DMSO-d₆): δ 11.15 (s, 1H), 10.73 (s, 1H), 9.51 (s, 1H), 8.99 (d, J=4.8 Hz, 1H), 8.36 (s, 1H), 8.26 (s, 1H), 8.19 (d, J=5.2 Hz, 1H), 7.78 (dd, J=2.0, 8.0 Hz, 1H), 7.68 (d, J=2.0 Hz, 1H), 7.43 (d, J=8.8 Hz, 1H), 2.46 (s, 3H), 2.42-2.32 (m, 1H), 2.05 (s, 3H), 0.90-0.88 (m, 4H). MS Calcd.: 506, M Found: 507 ([M+H]⁺).

Example 50: Synthesis of N-(4-methyl-3-(7-methyl-2-(methylamino)pyrido[2,3-d]pyrimidin-6-yl)phenyl)-6-(trifluoromethyl)pyridazine-4-carboxamide

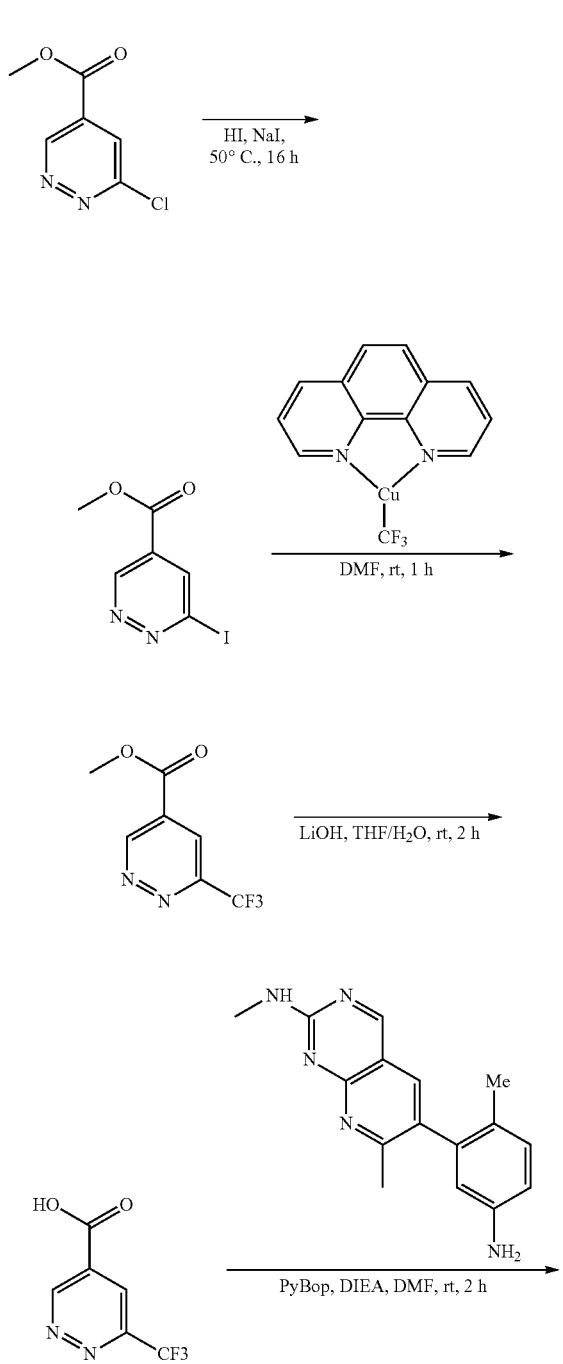

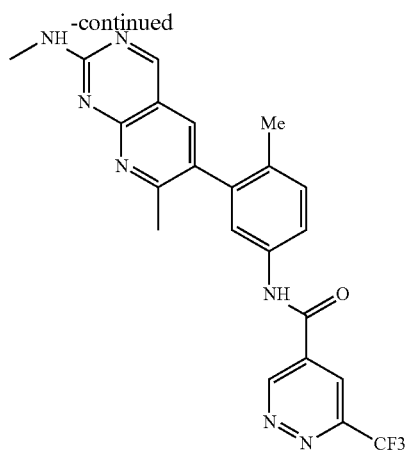

Step 1

A solution of methyl 6-chloropyridazine-4-carboxylate (500 mg, 2.85 mmol) and NaI (629 mg, 4.21 mmol) in HI (4 mL) was stirred at 50° C. for 16 h. The reaction mixture was cooled down to room temperature and diluted with water (30 mL). The mixture was basified to pH=7 with saturated sodium bicarbonate aqueous solution and extracted with DCM (20 mL*3). The combined organic layers were washed with brine (20 mL), dried over $Na_2SO_4$, filtered and concentrated. The residue was purified by prep-HPLC to afford methyl 6-iodopyridazine-4-carboxylate (500 mg, 58%) as an off-white solid. MS Calcd.: 264, MS Found: 265 ($[M+H]^+$).

Step 2

To a solution of methyl 6-iodopyridazine-4-carboxylate (200 mg, 0.68 mmol) and 1,10-phenanthroline ($CuCF_3$) (211 mg, 0.68 mmol) in DMF (5 mL) was stirred at room temperature for 1 h under dark. The reaction mixture was quenched with water (20 mL) and extracted with EA (10 mL*3). The combined organic layers were washed with brine (10 mL), dried over $Na_2SO_4$, filtered and concentrated. The residue purified by FCC (PE:EA=10:1) to give methyl 6-(trifluoromethyl)pyridazine-4-carboxylate (50 mg, 35%,) as an off-white solid. MS Calcd.: 206, M Found: 207 ($[M+H]^+$).

Step 3

A solution of methyl 6-(trifluoromethyl)pyridazine-4-carboxylate (50 mg, 0.24 mmol) and LiOH $H_2O$ (25 mg, 0.61 mmol) in THF (2.5 mL) and $H_2O$ (2.5 mL) was stirred at room temperature for 2 h. The mixture was acidified to pH=5 with 3M HCl. The mixture was filtered and the solid was dried to afford 6-(trifluoromethyl)pyridazine-4-carboxylic acid (46 mg, 100%) as an off-white solid. MS Calcd.: 192, MS Found: 193 ($[M+H]^+$).

Step 4

To a solution of 6-(5-amino-2-methylphenyl)-N,7-dimethylpyrido[2,3-d]pyrimidin-2-amine (60 mg, 0.22 mmol) and 6-(trifluoromethyl)pyridazine-4-carboxylic acid (46 mg, 0.22 mmol) in DMF (2 mL) was added DIEA (139 mg, 1.08 mmol) and PyBop (111 mg, 0.22 mmol). The reaction mixture was stirred at room temperature for 2 h. The reaction mixture was concentrated in vacuum and purified by prep-HPLC to afford N-(4-methyl-3-(7-methyl-2-(methylamino)pyrido[2,3-d]pyrimidin-6-yl)phenyl)-6-(trifluoromethyl)pyridazine-4-carboxamide (6.5 mg, 6.7%) as an off-white solid. $^1$H NMR (400 MHz, DMSO-$d_6$): δ 10.87 (s, 1H), 9.91 (d, J=1.6 Hz, 1H), 9.10 (s, 1H), 8.68 (d, J=2.0 Hz, 1H), 7.97 (s, 1H), 7.76-7.69 (m, 2H), 7.62 (d, J=2.0 Hz, 1H), 7.41 (d, J=8.4 Hz, 1H), 2.93 (d, J=4.4 Hz, 3H), 2.34 (s, 3H), 2.05 (s, 3H). MS Calcd.: 453, MS Found: 454 ($[M+H]^+$).

The following compounds in Table 8 were prepared using procedures similar to those described in Example 1 and 2 using appropriate starting materials.

TABLE 8

| Example # | Structure | Exact Mass $[M + H]^+$ |
|---|---|---|
| 51 | ![structure] | Calc'd 493.19, found 493.15 |
| 52 | ![structure] | Calc'd 449.18, found 449.25 |

Example 53: N-[4-methyl-3-[2-(methylamino)pyrido[2,3-d]pyrimidin-6-yl]phenyl]-2-(trifluoromethyl)pyridine-4-carboxamide Step 1: N-[3-(2-[[(4-methoxyphenyl)methyl](methyl)amino]pyrido[2,3-d]pyrimidin-6-yl)-4-methylphenyl]-2-(trifluoromethyl)pyridine-4-carboxamide

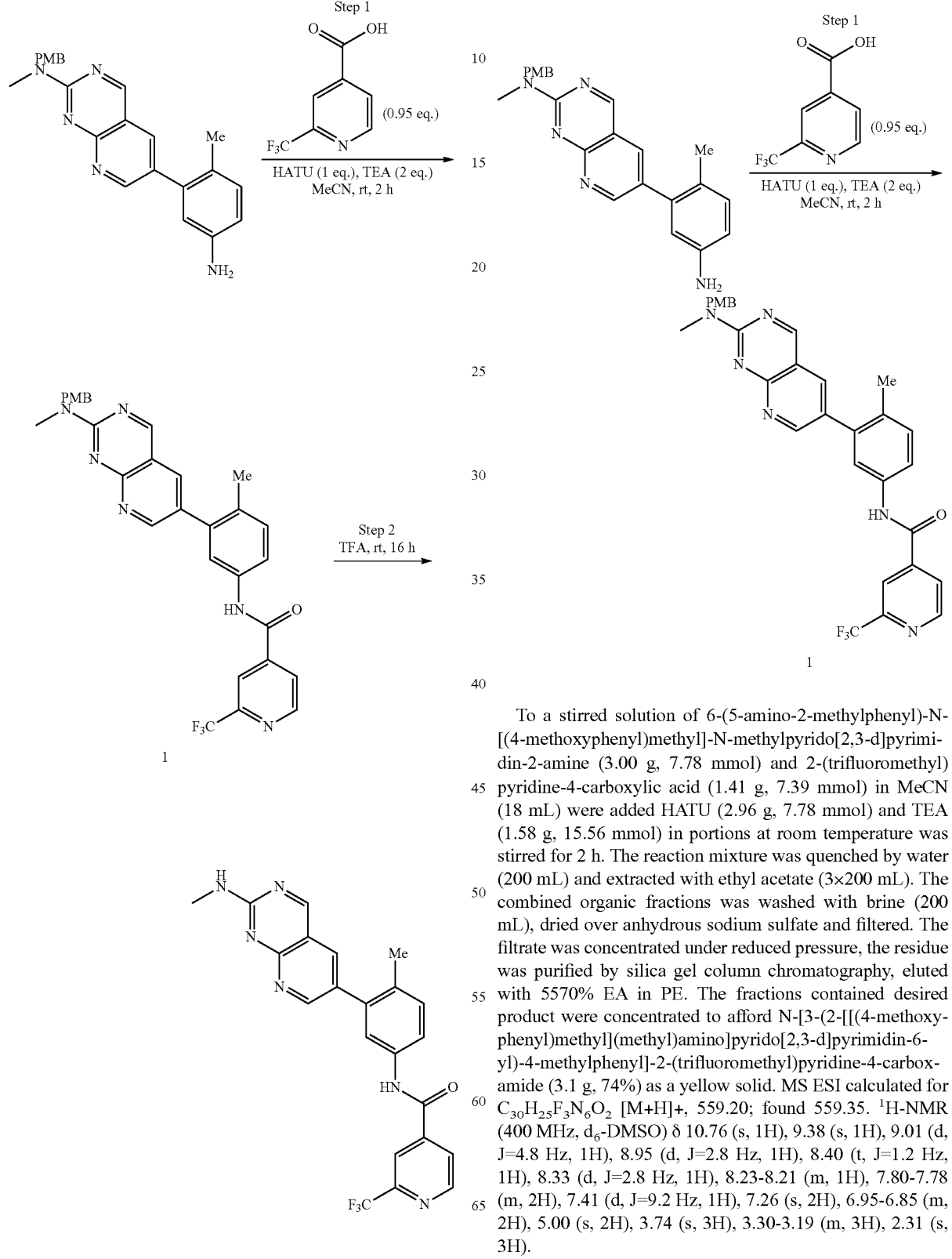

To a stirred solution of 6-(5-amino-2-methylphenyl)-N-[(4-methoxyphenyl)methyl]-N-methylpyrido[2,3-d]pyrimidin-2-amine (3.00 g, 7.78 mmol) and 2-(trifluoromethyl)pyridine-4-carboxylic acid (1.41 g, 7.39 mmol) in MeCN (18 mL) were added HATU (2.96 g, 7.78 mmol) and TEA (1.58 g, 15.56 mmol) in portions at room temperature was stirred for 2 h. The reaction mixture was quenched by water (200 mL) and extracted with ethyl acetate (3×200 mL). The combined organic fractions was washed with brine (200 mL), dried over anhydrous sodium sulfate and filtered. The filtrate was concentrated under reduced pressure, the residue was purified by silica gel column chromatography, eluted with 5570% EA in PE. The fractions contained desired product were concentrated to afford N-[3-(2-[[(4-methoxyphenyl)methyl](methyl)amino]pyrido[2,3-d]pyrimidin-6-yl)-4-methylphenyl]-2-(trifluoromethyl)pyridine-4-carboxamide (3.1 g, 74%) as a yellow solid. MS ESI calculated for $C_{30}H_{25}F_3N_6O_2$ [M+H]+, 559.20; found 559.35. $^1$H-NMR (400 MHz, $d_6$-DMSO) δ 10.76 (s, 1H), 9.38 (s, 1H), 9.01 (d, J=4.8 Hz, 1H), 8.95 (d, J=2.8 Hz, 1H), 8.40 (t, J=1.2 Hz, 1H), 8.33 (d, J=2.8 Hz, 1H), 8.23-8.21 (m, 1H), 7.80-7.78 (m, 2H), 7.41 (d, J=9.2 Hz, 1H), 7.26 (s, 2H), 6.95-6.85 (m, 2H), 5.00 (s, 2H), 3.74 (s, 3H), 3.30-3.19 (m, 3H), 2.31 (s, 3H).

Step 2: N-[4-methyl-3-[2-(methylamino)pyrido[2,3-d]pyrimidin-6-yl]phenyl]-2-(trifluoromethyl)pyridine-4-carboxamide

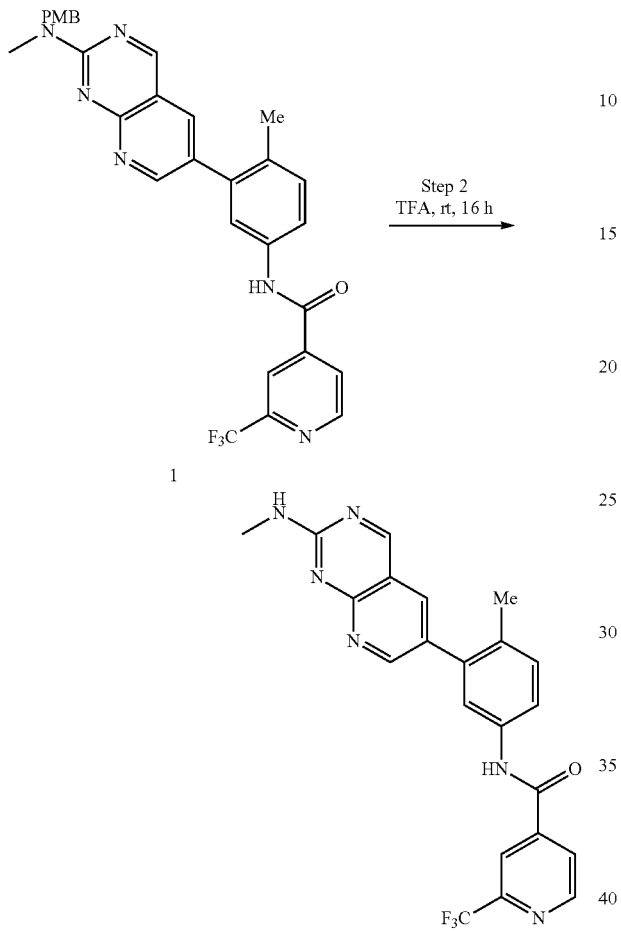

To a stirred solution of N-[3-(2-[[(4-methoxyphenyl)methyl](methyl)amino]pyrido[2,3-d]pyrimidin-6-yl)-4-methylphenyl]-2-(trifluoromethyl)pyridine-4-carboxamide (3.10 g, 5.55 mmol) in TFA (80 mL) at 25 degrees C. under nitrogen atmosphere. The resulting mixture was stirred overnight at room temperature. The reaction mixture was quenched by aqueous NaHCO$_3$ (200 mL) and extracted with ethyl acetate (3×200 mL). The combined organic fractions was washed with brine (200 mL), dried over anhydrous sodium sulfate and filtered. The filtrate was concentrated under reduced pressure, the residue was purified by silica gel column chromatography, eluted with 5070% (EtOH/EA=1/3) in PE. The fractions contained desired products were concentrated to afford 2.0 g of product. The product (2.0 g) was triturated with MeOH to afford 1.6 g product (The purity of 99% on LCMS, but H-NMR contained methanol). A solution of product (1.6) in DCM (100 mL) and it was concentrated under reduced pressure. The residue was dried under infrared light, N-[4-methyl-3-[2-(methylamino)pyrido[2,3-d]pyrimidin-6-yl]phenyl]-2-(trifluoromethyl)pyridine-4-carboxamide (1.4235 g, 58%) was obtained. MS ESI calculated for C$_{22}$H$_{17}$F$_3$N$_6$O [M+H]+, 439.14; found 439.10. $^1$H-NMR (400 MHz, d$_6$-DMSO) δ 10.74 (s, 1H), 9.22 (s, 1H), 9.00 (d, J=6.4 Hz, 1H), 8.89 (s, 1H), 8.38 (s, 1H), 8.28 (d, J=3.6 Hz, 1H), 8.21 (d, J=6.8 Hz, 1H), 7.87-7.73 (m, 3H), 7.40 (d, J=8.4 Hz, 1H), 2.95 (d, J=5.6 Hz, 3H), 2.29 (s, 3H).

Examples 54 and 55: (3R)—N-[4-methyl-3-[2-(methylamino)pyrido[2,3-d]pyrimidin-6-yl]phenyl]3(trifluoromethyl)pyrrolidine-1-carboxamide and (3S)—N-[4-methyl-3-[2-(methylamino)pyrido[2,3-d]pyrimidin-6-yl]phenyl]-3-(trifluoromethyl)pyrrolidine-1-carboxamide

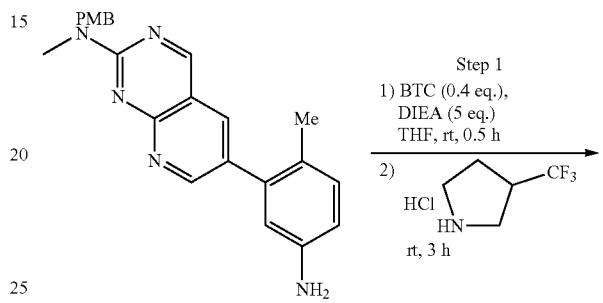

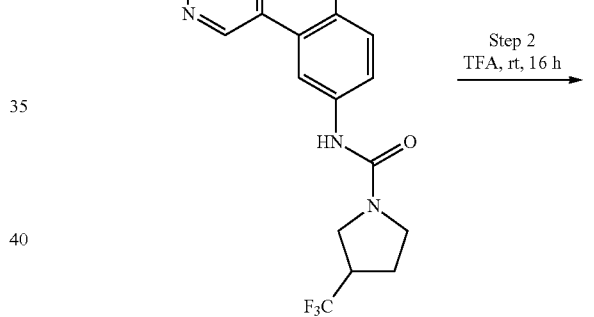

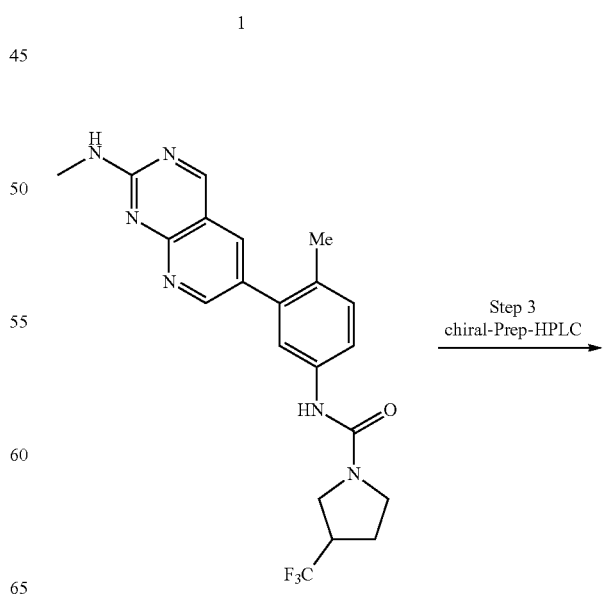

181

-continued

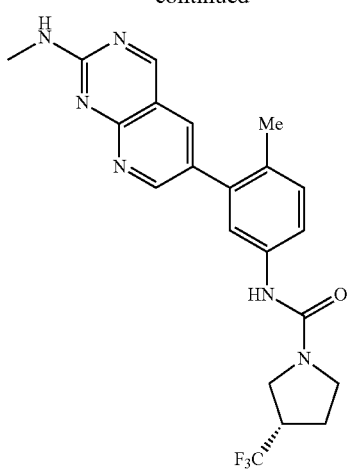

+

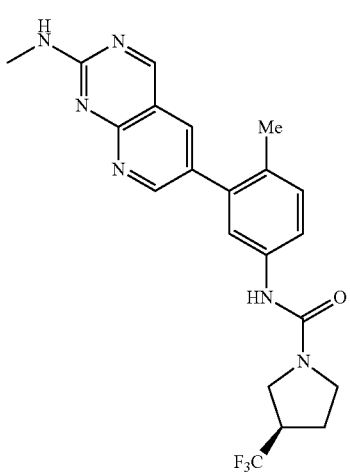 [SMILES: CNc1ncc2cc(-c3cc(NC(=O)N4CC[C@@H](C(F)(F)F)C4)ccc3C)cnc2n1]

182

-continued

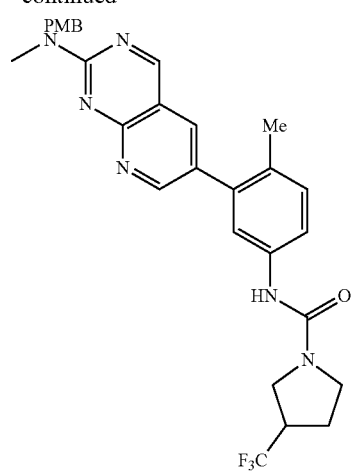

1

To a stirred mixture of 6-(5-amino-2-methylphenyl)-N-[(4-methoxyphenyl)methyl]-N-methylpyrido[2,3-d]pyrimidin-2-amine (0.60 g, 1.56 mmol) in THF (8 mL) were added triphosgene (185 mg, 0.62 mmol) and DIEA (1.29 mL, 7.78 mmol) at 0 degree under nitrogen atmosphere. The mixture was stirred at room temperature for 0.5 h. To the above mixture was added 3-(trifluoromethyl)pyrrolidine hydrochloride (327.96 mg, 1.87 mmol) in THF (2 mL) at room temperature. The resulting mixture was stirred for additional 3 h at room temperature. The resulting mixture was concentrated under reduced pressure to afford N-[3-(2-[[(4-methoxyphenyl)methyl](methyl)amino]pyrido[2,3-d]pyrimidin-6-yl)-4-methylphenyl]-3-(trifluoromethyl)pyrrolidine-1-carboxamide (0.600 g, crude) as a brown oil. MS ESI calculated for $C_{29}H_{29}F_3N_6O_2$ [M+H]$^+$, 551.23, found 551.40.

Step 2: N-[4-methyl-3-[2-(methylamino)pyrido[2,3-d]pyrimidin-6-yl]phenyl]-2-(trifluoromethyl)pyridine-4-carboxamide Step 1: N-[3-(2-[[(4-methoxyphenyl)methyl](methyl)amino]pyrido[2,3-d]pyrimidin-6-yl)-4-methylphenyl]-3-(trifluoromethyl)pyrrolidine-1-carboxamide

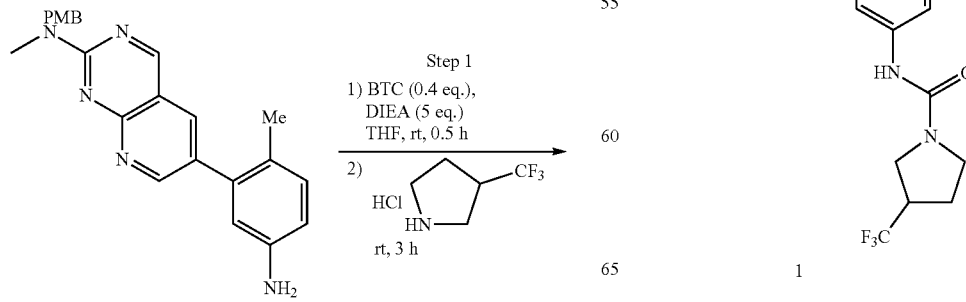

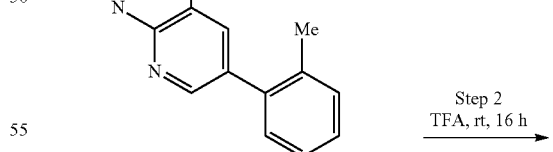

1

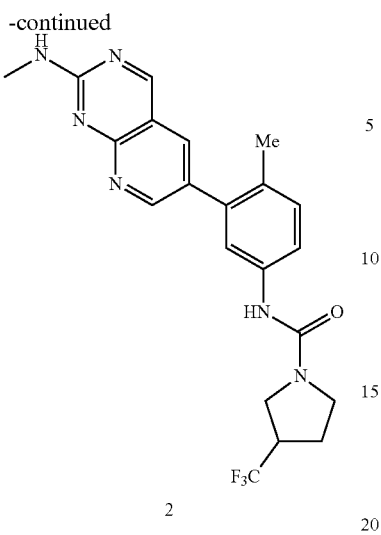

2

To a mixture of N-[3-(2-[[(4-methoxyphenyl)methyl](methyl)amino]pyrido[2,3-d]pyrimidin-6-yl)-4-methylphenyl]-3-(trifluoromethyl)pyrrolidine-1-carboxamide (0.600 mg, crude) was added trifluoroacetic acid (10 mL) at room temperature. The reaction mixture was stirred for 16 h at room temperature. The resulting mixture was concentrated under reduced pressure. The crude product was purified by Prep-HPLC with the following conditions (Column: XBridge C18 OBD Prep Column, 100 Å, 10 μm, 19 mm×250 mm; Mobile Phase A: water (10 mmol/L NH$_4$HCO$_3$), Mobile Phase B:ACN; Flow rate: 20 mL/min; Gradient: 50 B to 80 B in 5.8 min; 210/254 nm; RT: 5.23 min to afford N-[4-methyl-3-[2-(methylamino)pyrido[2,3-d]pyrimidin-6-yl]phenyl]-3-(trifluoromethyl)pyrrolidine-1-carboxamide (230 mg, 47%) as a yellow solid. MS ESI calculated for C$_{21}$H$_{21}$F$_3$N$_6$O [M+H]$^+$, 431.17, found 431.15. H-NMR (400 MHz, d$_6$-DMSO) δ 9.22 (s, 1H), 8.85 (s, 1H), 8.33 (s, 1H), 8.24 (d, J=2.8 Hz, 1H), 7.84 (s, 1H), 7.51-7.47 (m, 2H), 7.23 (d, J=8.8 Hz, 1H), 3.71-3.64 (m, 1H), 3.58-3.42 (m, 4H), 2.96 (d, J=4.7 Hz, 3H), 2.24-2.15 (m, 4H), 2.05-1.97 (m, 1H), 1.31-1.22 (m, 1H). F-NMR (376 MHz, d$_6$-DMSO) δ −69.77 (3F).

Step 3: (3R)—N-[4-methyl-3-[2-(methylamino)pyrido[2,3-d]pyrimidin-6-yl]phenyl]3(trifluoromethyl)pyrrolidine-1-carboxamide and (3S)—N-[4-methyl-3-[2-(methylamino)pyrido[2,3-d]pyrimidin-6-yl]phenyl]-3-(trifluoromethyl)pyrrolidine-1-carboxamide

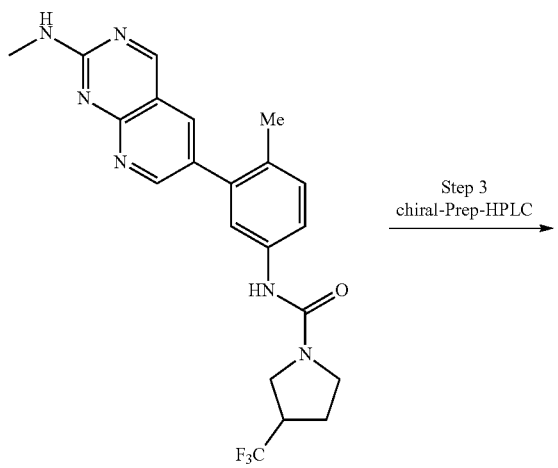

2

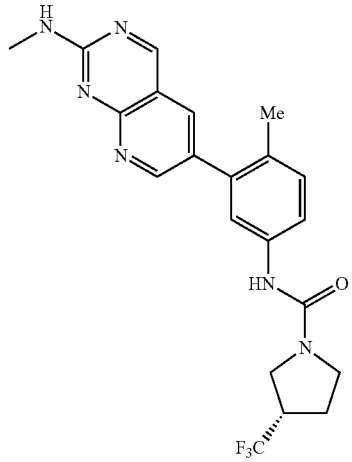

+

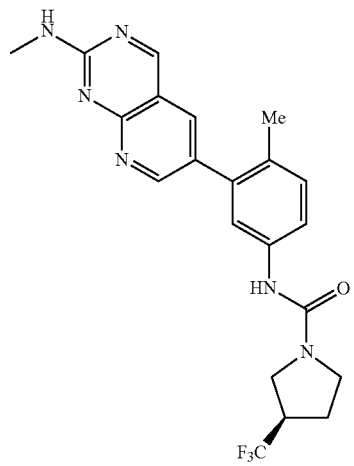

(N-[4-methyl-3-[2-(methylamino)pyrido[2,3-d]pyrimidin-6-yl]phenyl]-3-(trifluoromethyl)pyrrolidine-1-carboxamide (230 mg) was resolved by CHIRAL-HPLC with the following conditions (Column: CHIRALPAK-AD-H-UL001, 20×250 mm, 5 um; Mobile Phase A: hexane (8 mmol/L NH$_3$.MeOH), Mobile Phase B: IPA; Flow rate: 20 mL/min; Gradient: 30 B to 30 B in 35 min; 220/254 nm;

First eluting peak: RT1: 22.991 min, 106.4 mg (46%) of a yellow solid. MS ESI calculated for C$_{21}$H$_{21}$F$_3$N$_6$O [M+H]$^+$, 431.17, found 431.10. H-NMR (400 MHz, d$_6$-DMSO) δ 9.23 (s, 1H), 8.86 (s, 1H), 8.34 (s, 1H), 8.27 (d, J=2.8 Hz, 1H), 7.91 (s, 1H), 7.51 (d, J=7.6 Hz, 2H), 7.25-7.20 (m, 1H), 3.72-3.67 (m, 1H), 3.58-3.41 (m, 4H), 3.35-3.28 (m, 1H), 2.96 (d, J=4.4 Hz, 3H), 2.27-2.16 (m, 4H), 2.08-1.99 (m, 1H). F-NMR (376 MHz, d$_6$-DMSO) δ 69.78 (3F).

Second eluting peak: RT2: 30.019 min, 92.1 mg, (39%) of a yellow solid. MS ESI calculated for C$_{21}$H$_{21}$F$_3$N$_6$O [M+H]$^+$, 431.17, found 431.05. H-NMR (400 MHz, d$_6$-DMSO) δ 9.21 (s, 1H), 8.85 (s, 1H), 8.33 (s, 1H), 8.22 (d, J=2.8 Hz, 1H), 7.80 (s, 1H), 7.53-7.48 (m, 2H), 7.23 (d, J=9.0 Hz, 1H), 3.72-3.67 (m, 1H), 3.60-3.41 (m, 3H), 2.95 (d, J=4.8 Hz, 3H), 2.25-2.16 (m, 4H), 2.09-1.98 (m, 1H). F-NMR (376 MHz, d$_6$-DMSO) δ 69.78 (3F).

The compounds in Table 9 were prepared using procedures similar to those described in Examples 54 and 55 using appropriate starting materials.

TABLE 9

| Example # | Structure | Exact Mass [M + H]+ |
|---|---|---|
| 56 | 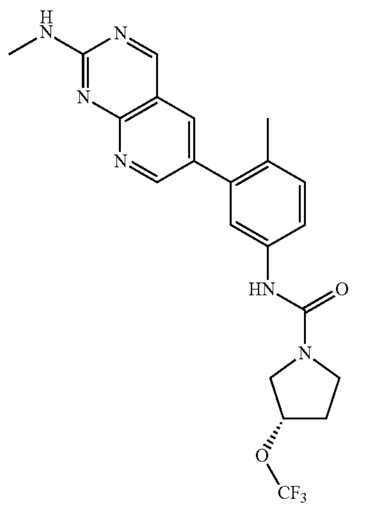 [SMILES: CNc1ncc2cc(-c3cc(NC(=O)N4CC[C@H](OC(F)(F)F)C4)ccc3C)cnc2n1] | Calc'd 447.17, found 447.20 |
| 57 | 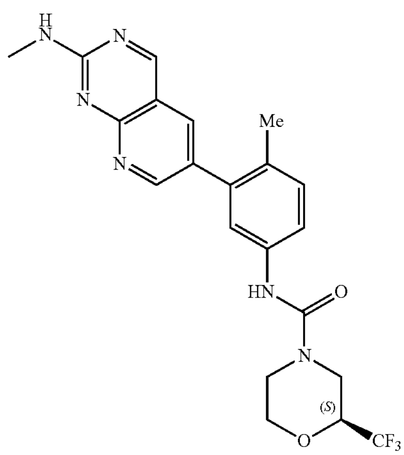 | Calc'd 447.17; found 447.20. |
| 58 | 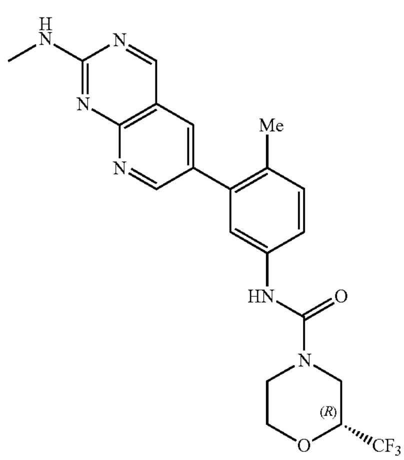 | Calc'd 447.17; found 447.20. |

TABLE 9-continued

| Example # | Structure | Exact Mass [M + H]+ |
|---|---|---|
| 59 | 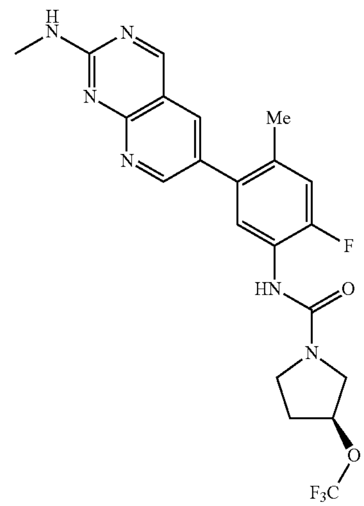 [SMILES: CNc1ncc2cc(-c3cc(NC(=O)N4CC[C@H](OC(F)(F)F)C4)c(F)cc3C)cnc2n1] | Calc'd 465.16, found 465.15 |
| 60 | 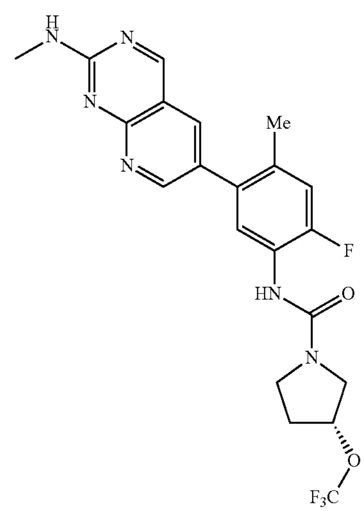 [SMILES: CNc1ncc2cc(-c3cc(NC(=O)N4CC[C@@H](OC(F)(F)F)C4)c(F)cc3C)cnc2n1] | Calc'd 465.16, found 465.10 |
| 61 | 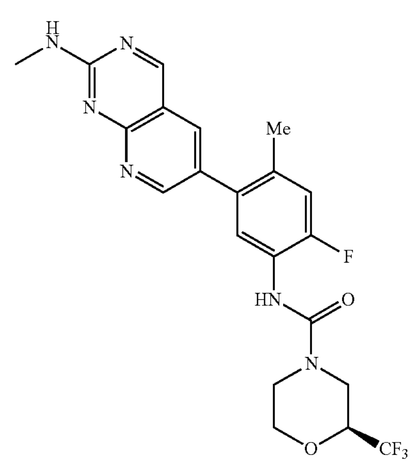 [SMILES: CNc1ncc2cc(-c3cc(NC(=O)N4CCO[C@H](C(F)(F)F)C4)c(F)cc3C)cnc2n1] | Calc'd 465.16; found 465.05. |

TABLE 9-continued

| Example # | Structure | Exact Mass [M + H]+ |
|---|---|---|
| 62 | (structure: methylamino-pyrido[2,3-d]pyrimidine linked to methyl-fluoro-phenyl with HN-C(O)-morpholine-CF3) | Calc'd 465.16; found 465.00. |
| 63 | (structure: methylamino-pyrido[2,3-d]pyrimidine linked to methyl-pyridine with HN-C(O)-pyrrolidine-OCF3) | Calc'd 448.16, found 448.15 |

Example 64: N-[3-[7-chloro-2-(methylamino)pyrido[2,3-d]pyrimidin-6-yl]-4-methylphenyl]-2-(trifluoromethyl) pyridine-4-carboxamide

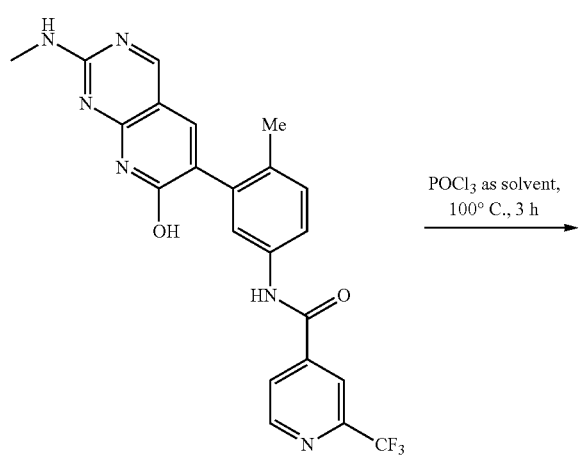

A mixture of N-[3-[7-hydroxy-2-(methylamino)pyrido[2,3-d]pyrimidin-6-yl]-4-methylphenyl]-2-(trifluoromethyl)pyridine-4-carboxamide (3.20 g, 7.04 mmol) in POCl$_3$ (32.00 mL) was stirred for 3.5 h at 100° C. under nitrogen atmosphere. The resulting mixture was concentrated under reduced pressure. The residue was diluted with EtOAc (50 mL) and poured into aqueous NaHCO$_3$ (sat., 100 mL). The resulting mixture was extracted with EtOAc (3×100 mL). The combined organic layers was washed with brine (150 mL), dried over anhydrous Na$_2$SO$_4$ and filtered. The filtrate was concentrated under reduced pressure. The residue was purified by silica gel column chromatography, eluted with 70% EtOAc in PE. The fractions contained desired product were combined and concentrated to afford N-[3-[7-chloro-2-(methylamino)pyrido[2,3-d]pyrimidin-6-yl]-4-methylphenyl]-2-(trifluoromethyl)pyridine-4-carboxamide (1.3 g, 39%) as a yellow solid. MS ESI calculated for C$_{22}$H$_{16}$ClF$_3$N$_6$O [M+H]+, 473.10, found 473.15. H-NMR (400 MHz, CDCl$_3$) δ 8.93-8.80 (m, 2H), 8.66 (s, 1H), 8.21 (s, 1H), 8.04-8.03 (m, 1H), 7.85 (s, 1H), 7.72-7.70 (m, 1H), 7.47 (s, 1H), 7.33-7.26 (m, 1H), 5.70 (s, 1H), 3.18-3.09 (m, 3H), 2.14 (s, 3H).

Example 65: N-[3-[7-ethenyl-2-(methylamino)pyrido[2,3-d]pyrimidin-6-yl]-4-methylphenyl]-2-(trifluoromethyl)pyridine-4-carboxamide

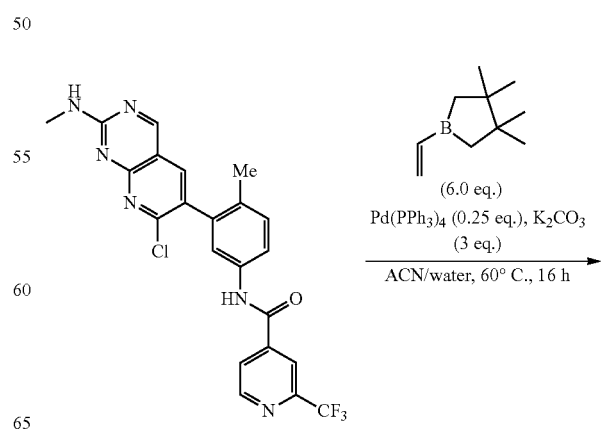

-continued

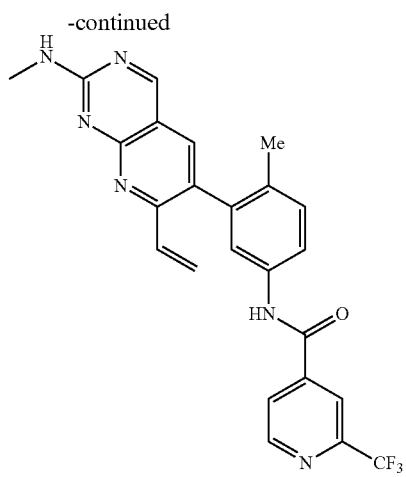

To a mixture of N-[3-[7-chloro-2-(methylamino)pyrido[2,3-d]pyrimidin-6-yl]-4-methylphenyl]-2-(trifluoromethyl)pyridine-4-carboxamide (0.25 g, 0.53 mmol), 1-ethenyl-3,3,4,4-tetramethylborolane (0.48 g, 3.17 mmol) and $K_2CO_3$ (219.21 mg, 1.59 mmol) in ACN (5.00 mL) and water (5.00 mL) was added $Pd(PPh_3)_4$ (0.15 g, 0.13 mmol). The reaction mixture was degassed with nitrogen for three times and stirred for 16 h at 60° C. The resulting mixture was diluted with EA (50 mL). The resulting mixture was washed with brine (2×20 mL), dried over anhydrous $Na_2SO_4$ and filtered. The filtrate was concentrated under reduced pressure. The residue was purified by silica gel column chromatography, eluted with 70% EA in PE. The fractions contained desired product were combined and concentrated to afford ~200 mg crude product which was further purified by Prep-HPLC with the following conditions: XBridge C18 OBD Prep Column, 100 Å, 10 μm, 19 mm×250 mm; Mobile Phase A: water (10 mmol/L $NH_4HCO_3$), Mobile Phase B: ACN; Flow rate: 20 mL/min; Gradient: 40 B to 75 B in 5.8 min. The fractions contained desired product were combined and concentrated to afford N-[3-[7-ethenyl-2-(methylamino)pyrido[2,3-d]pyrimidin-6-yl]-4-methylphenyl]-2-(trifluoromethyl)pyridine-4-carboxamide (0.11 g, 42%) as a yellow solid. MS ESI calculated for $C_{24}H_{19}F_3N_6O$ [M+H]+, 465.16, found 465.25. H-NMR (400 MHz, $CD_3OD$) δ 9.05 (s, 1H), 8.89 (d, J=4.8 Hz, 1H), 8.29 (s, 1H), 8.11 (d, J=4.8 Hz, 1H), 8.01 (s, 1H), 7.76-7.73 (m, 1H), 7.60 (d, J=2.0 Hz, 1H), 7.37 (d, J=8.4 Hz, 1H), 6.68-6.56 (m, 2H), 5.57-5.53 (m, 1H), 3.10 (s, 3H), 2.07 (s, 3H).

Example 66: N-[3-[7-ethyl-2-(methylamino)pyrido[2,3-d]pyrimidin-6-yl]-4-methylphenyl]-2-(trifluoromethyl)pyridine-4-carboxamide

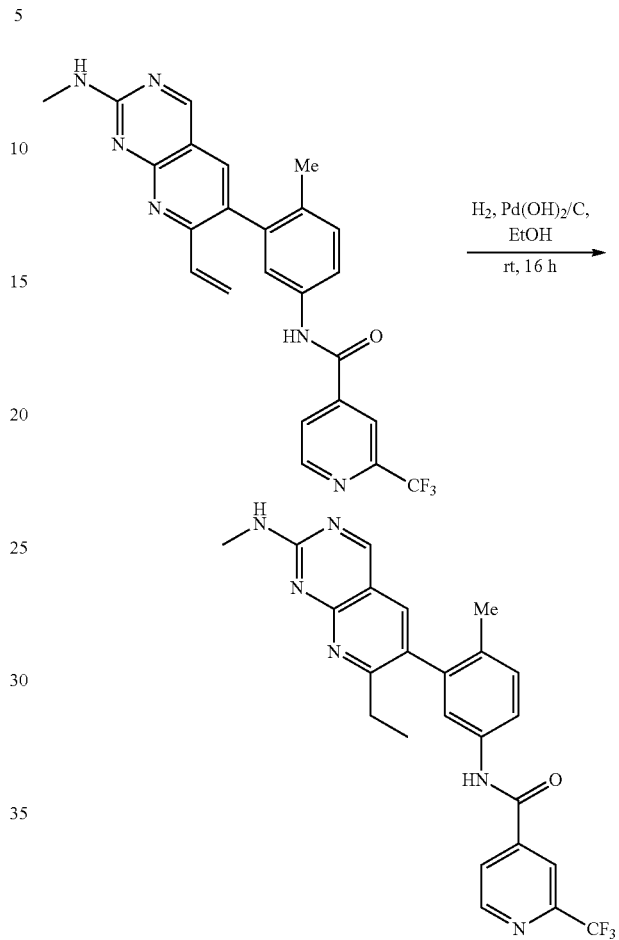

To a solution of N-[3-[7-ethenyl-2-(methylamino)pyrido[2,3-d]pyrimidin-6-yl]-4-methylphenyl]-2-(trifluoromethyl)pyridine-4-carboxamide (60.00 mg, 0.13 mmol) in EtOH (4.00 mL) was added $Pd(OH)_2/C$ (30.00 mg). The reaction mixture was degassed with hydrogen for three times and stirred for 16 h at room temperature. The resulting mixture was filtered and the filtrate was concentrated under reduced pressure. The residue was purified by Prep-HPLC with the following conditions: Column: SunFire Prep C18 OBD Column, 19×150 mm 5 um 10 nm; Mobile Phase A: water (0.1% FA), Mobile Phase B: ACN; Flow rate: 20 mL/min; Gradient: 15 B to 50 B in 4.3 min. The fractions contained desired product were combined and concentrated to afford N-[3-[7-ethyl-2-(methylamino)pyrido[2,3-d]pyrimidin-6-yl]-4-methylphenyl]-2-(trifluoromethyl)pyridine-4-carboxamide (20.6 mg, 34%) as a yellow solid. MS ESI calculated for $C_{24}H_{21}F_3N_6O$ [M+H]+, 467.17, found 467.25. H-NMR (300 MHz, $d_6$-DMSO) δ 10.72 (s, 1H), 9.12 (s, 1H), 9.00 (d, J=5.1 Hz, 1H), 8.38 (s, 1H), 8.20 (d, J=4.5 Hz, 1H), 7.97 (s, 1H), 7.66-7.65 (m, 3H), 7.40 (d, J=8.4 Hz, 1H), 2.96 (d, J=4.5 Hz, 3H), 2.65-2.61 (m, 2H), 2.05 (s, 3H), 1.16 (d, J=7.4 Hz, 3H).

Example 67: N-[3-[7-ethynyl-2-(methylamino)pyrido[2,3-d]pyrimidin-6-yl]-4-methylphenyl]-2-(trifluoromethyl)pyridine-4-carboxamide

Step 1: N-[4-methyl-3-[2-(methylamino)-7-[2-(trimethylsilyl)ethynyl]pyrido[2,3-d]pyrimidin-6-yl]phenyl]-2-(trifluoromethyl)pyridine-4-carboxamide

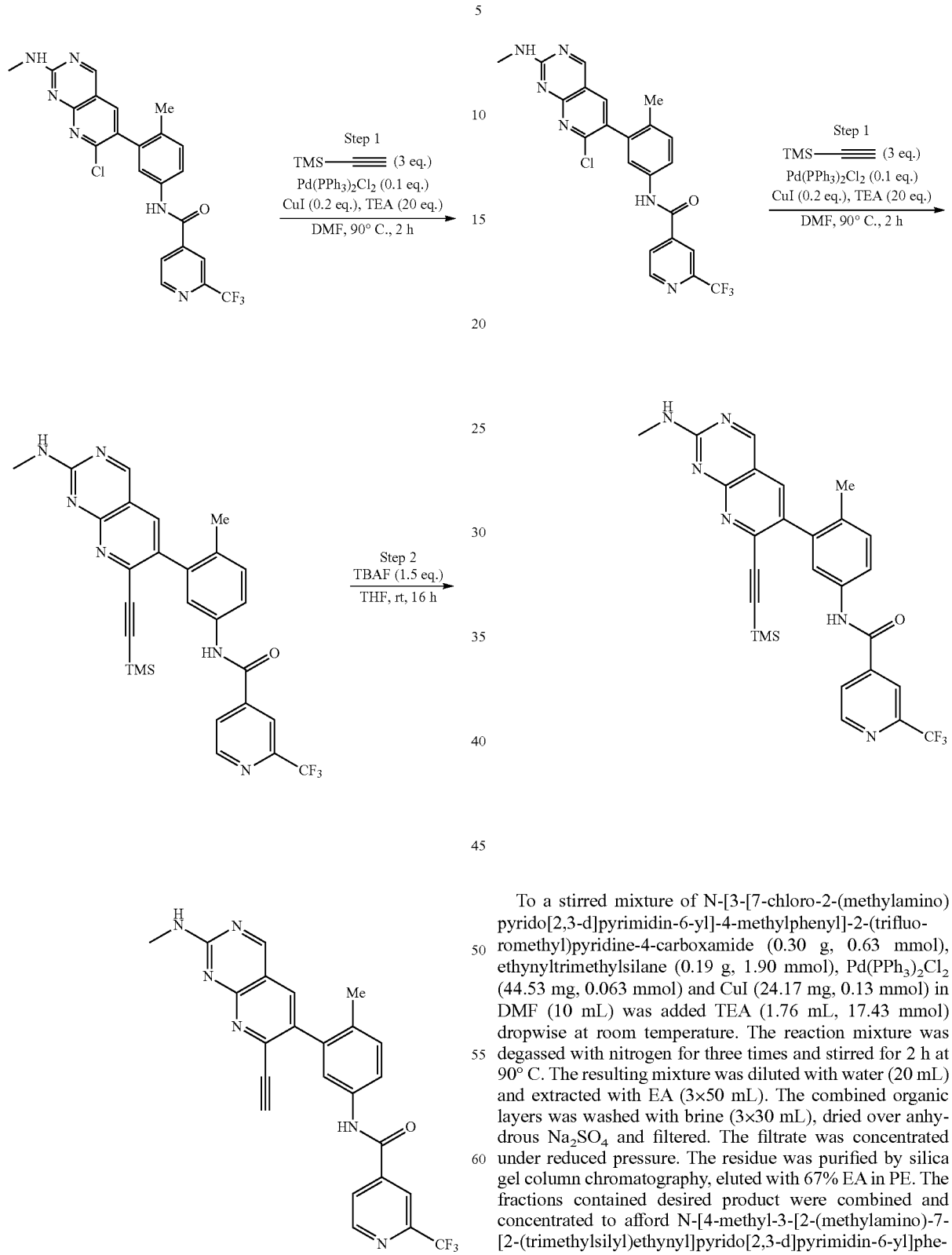

To a stirred mixture of N-[3-[7-chloro-2-(methylamino)pyrido[2,3-d]pyrimidin-6-yl]-4-methylphenyl]-2-(trifluoromethyl)pyridine-4-carboxamide (0.30 g, 0.63 mmol), ethynyltrimethylsilane (0.19 g, 1.90 mmol), Pd(PPh$_3$)$_2$Cl$_2$ (44.53 mg, 0.063 mmol) and CuI (24.17 mg, 0.13 mmol) in DMF (10 mL) was added TEA (1.76 mL, 17.43 mmol) dropwise at room temperature. The reaction mixture was degassed with nitrogen for three times and stirred for 2 h at 90° C. The resulting mixture was diluted with water (20 mL) and extracted with EA (3×50 mL). The combined organic layers was washed with brine (3×30 mL), dried over anhydrous Na$_2$SO$_4$ and filtered. The filtrate was concentrated under reduced pressure. The residue was purified by silica gel column chromatography, eluted with 67% EA in PE. The fractions contained desired product were combined and concentrated to afford N-[4-methyl-3-[2-(methylamino)-7-[2-(trimethylsilyl)ethynyl]pyrido[2,3-d]pyrimidin-6-yl]phenyl]-2-(trifluoromethyl)pyridine-4-carboxamide (52 mg, 14%) as a yellow solid. MS ESI calculated for C$_{27}$H$_{25}$F$_3$N$_6$OSi [M+H]$^+$, 535.18, found 535.25.

Step 2: N-[3-[7-ethynyl-2-(methylamino)pyrido[2,3-d]pyrimidin-6-yl]-4-methylphenyl]-2-(trifluoromethyl)pyridine-4-carboxamide

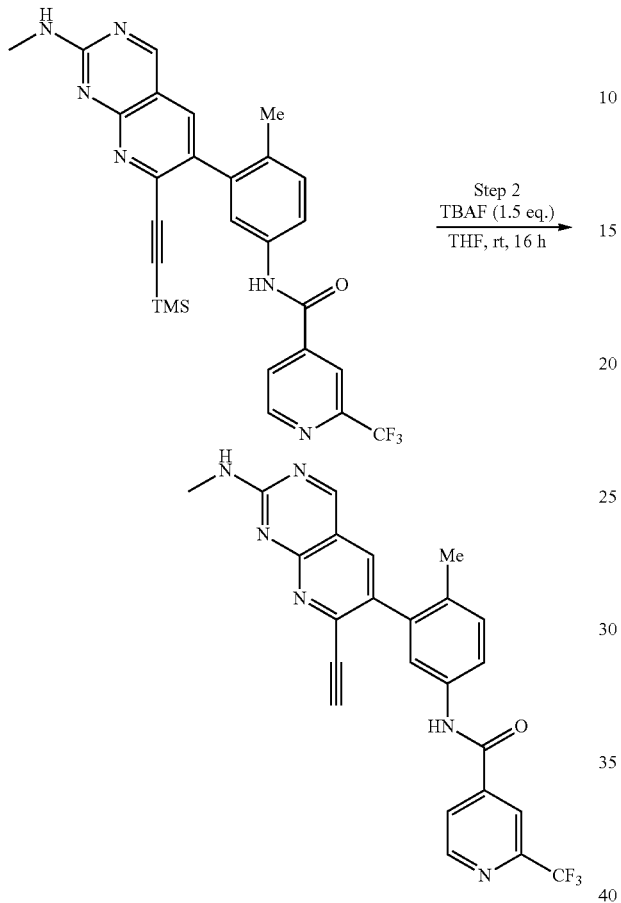

To a stirred solution of N-[4-methyl-3-[2-(methylamino)-7-[2-(trimethylsilyl)ethynyl]pyrido[2,3-d]pyrimidin-6-yl]phenyl]-2-(trifluoromethyl)pyridine-4-carboxamide (52 mg, 0.097 mmol) in THF (2.00 mL) was added TBAF (0.15 mL, 0.15 mmol) dropwise at 0° C. under nitrogen atmosphere. The reaction mixture was stirred for 16 h at room temperature under nitrogen atmosphere. The resulting mixture was diluted with water (10 mL) and extracted with EA (3×15 mL). The combined organic layers was washed with brine (2×10 mL), dried over anhydrous $Na_2SO_4$ and filtered. The filtrate was concentrated under reduced pressure. The residue was purified by silica gel column chromatography, eluted with 70% EA in PE to afford the crude product which was further purified by Prep-HPLC with the following conditions: Column: XBridge C18 OBD Prep Column, 100 Å, 10 μm, 19 mm×250 mm; Mobile Phase A: Water (10 mmol/L $NH_4HCO_3$), Mobile Phase B: ACN; Flow rate: 20 mL/min; Gradient: 40 B to 80 B in 5.8 min. The fractions contained desired product were combined and concentrated to afford N-[3-[7-ethynyl-2-(methylamino)pyrido[2,3-d]pyrimidin-6-yl]-4-methylphenyl]-2-(trifluoromethyl)pyridine-4-carboxamide (27.9 mg, 62%) as a yellow solid. MS ESI calculated for $C_{24}H_{17}F_3N_6O$ [M+H]$^+$, 463.14, found 463.10. H-NMR (400 MHz, $d_6$-DMSO) δ 10.71 (s, 1H), 9.19 (s, 1H), 8.99 (d, J=5.2 Hz, 1H), 8.37 (s, 1H), 8.20-8.17 (m, 2H), 7.93 (d, J=4.8 Hz, 1H), 7.80-7.77 (m, 1H), 7.68 (d, J=2.0 Hz, 1H), 7.37 (d, J=8.4 Hz, 1H), 4.38 (s, 1H), 2.94 (d, J=4.4 Hz, 3H), 2.12 (s, 3H).

Example 68: N-[3-[7-methoxy-2-(methylamino)pyrido[2,3-d]pyrimidin-6-yl]-4-methylphenyl]-2-(trifluoromethyl)pyridine-4-carboxamide

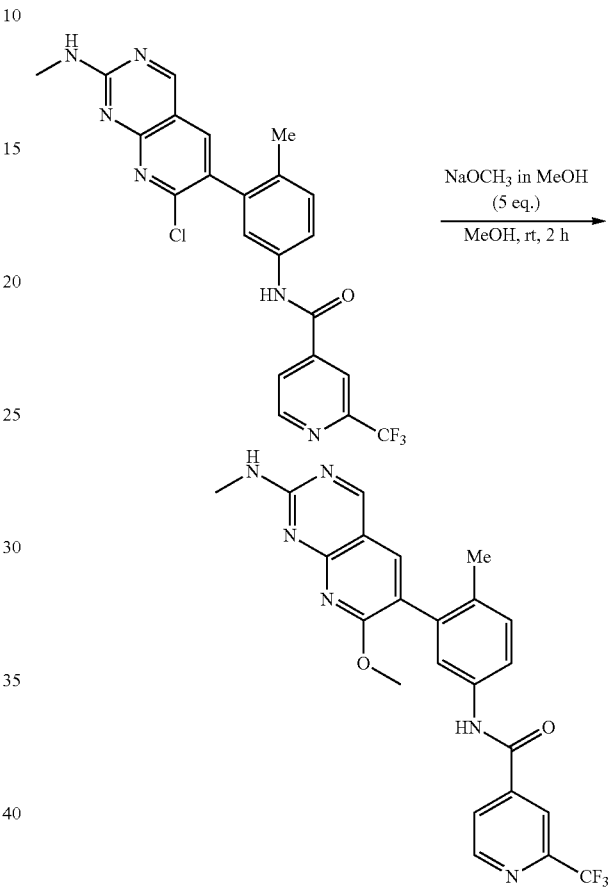

To a solution of N-[3-[7-chloro-2-(methylamino)pyrido[2,3-d]pyrimidin-6-yl]-4-methylphenyl]-2-(trifluoromethyl)pyridine-4-carboxamide (0.2 g, 0.42 mmol) in MeOH (4.00 mL, 0.13 mmol) was added sodium methoxide in MeOH (33%) (6.41 mL, 2.12 mmol) at 0° C. The reaction mixture was stirred for 2 h at room temperature. The resulting mixture was concentrated under reduced pressure. The residue was diluted with water (40 mL). The resulting mixture was extracted with EtOAc (3×40 mL). The combined organic layers was washed with brine (50 mL), dried over anhydrous $Na_2SO_4$ and filtered. The filtrate was concentrated under reduced pressure. The residue was purified by Prep-HPLC with the following conditions Column: XBridge C18 OBD Prep Column, 100 Å, 10 μm, 19 mm×250 mm; Mobile Phase A: Water (10 mmol/L $NH_4HCO_3$), Mobile Phase B: ACN; Flow rate: 20 mL/min; Gradient: 30 B to 70 B in 5.8 min. The fractions contained desired product were combined and concentrated to afford N-[3-[7-methoxy-2-(methylamino)pyrido[2,3-d]pyrimidin-6-yl]-4-methylphenyl]-2-(trifluoromethyl)pyridine-4-carboxamide (81.2 mg, 39%) as a white solid. MS ESI calculated for $C_{23}H_{19}F_3N_6O_2$ [M+H]$^+$, 469.15, found 469.25. $^1$H NMR (400 MHz, CDCl$_3$) δ 10.70 (s, 1H), 8.98 (d, J=5.2 Hz, 2H), 8.37 (s, 1H), 8.19 (d, J=4.8 Hz, 1H), 7.96 (s, 1H), 7.73-7.63 (m, 3H), 7.31 (d, J=8.4 Hz, 1H), 3.96 (s, 3H), 2.93 (s, 3H), 2.08 (s, 3H).

The compounds in Table 10 were prepared using procedures similar to those described in Example 68 using appropriate starting materials.

TABLE 10

| Example # | Structure | Exact Mass [M + H]+ |
|---|---|---|
| 69 | 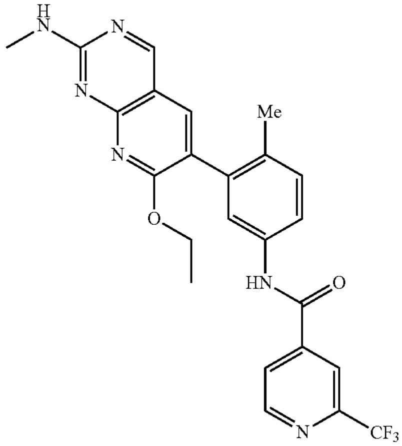 [SMILES: CCOc1nc2nc(NC)ncc2cc1-c1cc(NC(=O)c2ccnc(C(F)(F)F)c2)ccc1C] | Calc'd 483.17, found 483.20 |
| 70 | 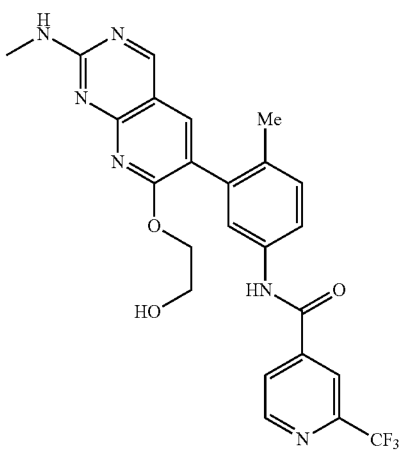 [SMILES: CNc1ncc2cc(-c3cc(NC(=O)c4ccnc(C(F)(F)F)c4)ccc3C)c(OCCO)nc2n1] | Calc'd 499.16, found 499.15 |
| 71 | 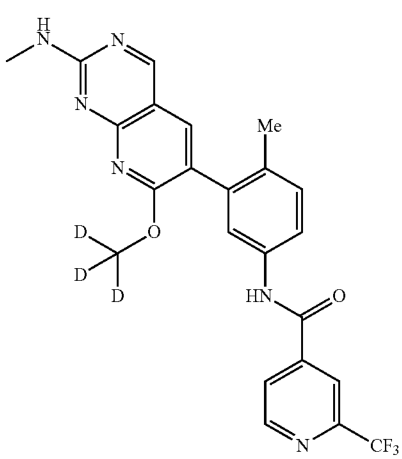 [SMILES: [2H]C([2H])([2H])Oc1nc2nc(NC)ncc2cc1-c1cc(NC(=O)c2ccnc(C(F)(F)F)c2)ccc1C] | Calc'd 472.17; found 472.15 |

Example 72: N-[3-[7-cyano-2-(methylamino)pyrido[2,3-d]pyrimidin-6-yl]-4-methylphenyl]-2-(trifluoromethyl)pyridine-4-carboxamide

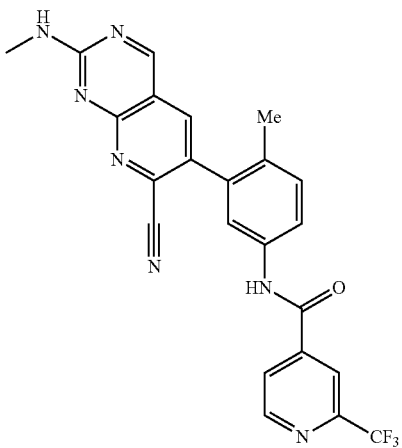 [SMILES: CNc1ncc2cc(-c3cc(NC(=O)c4ccnc(C(F)(F)F)c4)ccc3C)c(C#N)nc2n1]

Step 1: N-[3-[7-bromo-2-(methylamino)pyrido[2,3-d]pyrimidin-6-yl]-4-methylphenyl]-2-(trifluoromethyl)pyridine-4-carboxamide

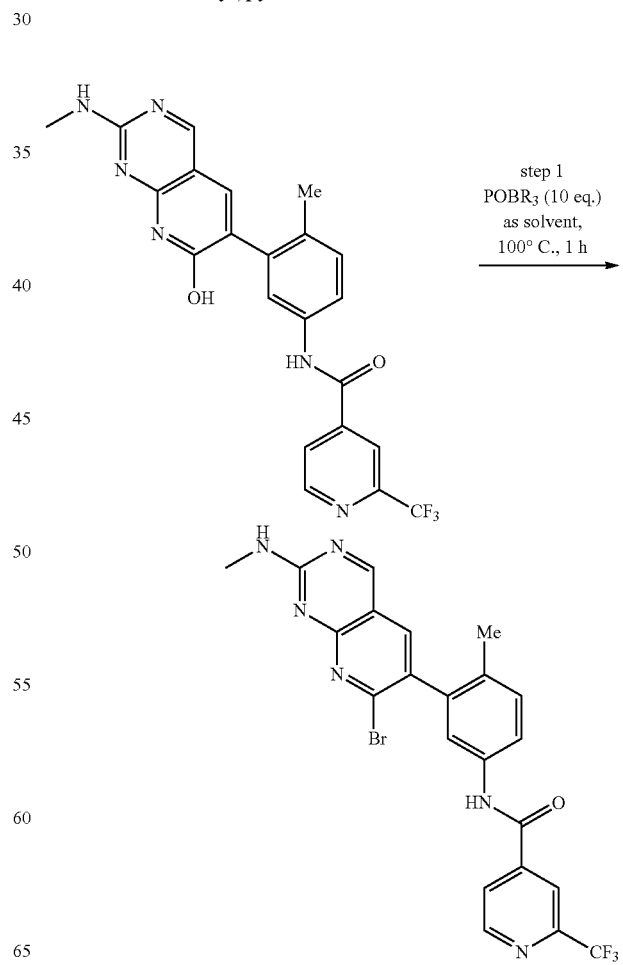

A mixture of N-[3-[7-hydroxy-2-(methylamino)pyrido[2,3-d]pyrimidin-6-yl]-4-methylphenyl]-2-(trifluoromethyl)pyridine-4-carboxamide (0.30 g, 0.66 mmol) in POBr$_3$ (1.89 g, 6.60 mmol) was stirred at 100° C. for 1 h under nitrogen atmosphere. After cooled to 0° C., the resulting mixture was quenched with sat. aqueous NaHCO$_3$. The resulting mixture was extracted with EtOAc (3×20 mL). The combined organic layer was washed with brine (20 mL), dried over anhydrous Na$_2$SO$_4$ and filtered. The filtrate was concentrated under reduced pressure. The residue was purified by silica gel column chromatography, eluted with hexane/(EtOAc:EtOH=3:1)=(1:1). The fractions contained desired product were combined and concentrated to afford N-[3-[7-bromo-2-(methylamino)pyrido[2,3-d]pyrimidin-6-yl]-4-methylphenyl]-2-(trifluoromethyl)pyridine-4-carboxamide (0.20 g, 59% yield) as a yellow solid. MS ESI calculated for C$_{22}$H$_{16}$BrF$_3$N$_6$O [M+H]$^+$, 517.05, 519.05; found 517.15, 519.15.

Step 2: N-[3-[7-cyano-2-(methylamino)pyrido[2,3-d]pyrimidin-6-yl]-4-methylphenyl]-2-(trifluoromethyl)pyridine-4-carboxamide

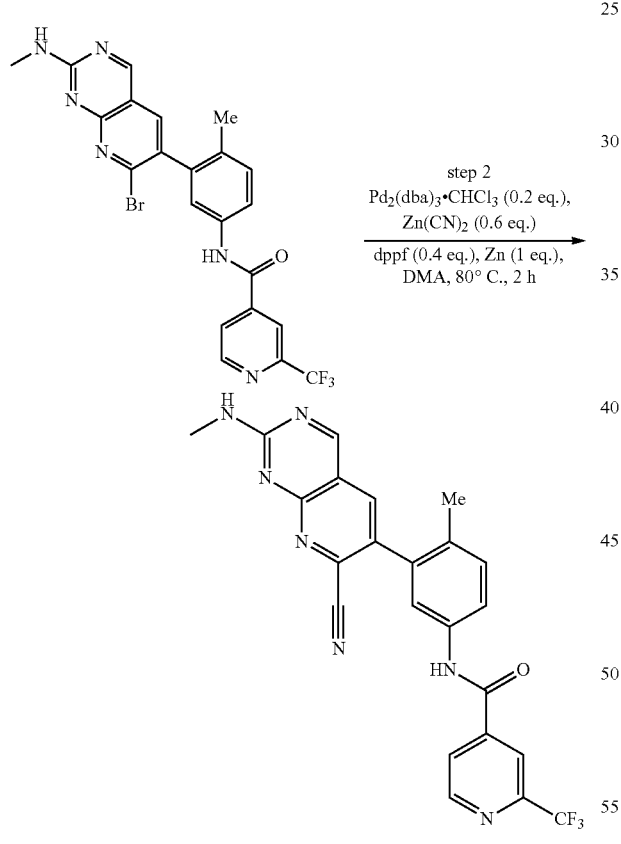

To a stirred mixture of N-[3-[7-bromo-2-(methylamino)pyrido[2,3-d]pyrimidin-6-yl]-4-methylphenyl]-2-(trifluoromethyl)pyridine-4-carboxamide (80.00 mg, 0.16 mmol) and Zn dust (10.12 mg, 0.16 mmol), Zn(CN)$_2$ (10.90 mg, 0.093 mmol), dppf (34.17 mg, 0.062 mmol) in DMA (2.00 mL, 22.96 mmol) was added Pd$_2$(dba)$_3$.CHCl$_3$ (32.01 mg, 0.031 mmol) in portions at room temperature. The reaction mixture was degassed with nitrogen for three times and stirred for 2 h at 80° C. The resulting mixture was concentrated under reduced pressure. The residue was diluted with EA (10 mL). The resulting mixture was washed with water (3×10 mL) and brine (10 mL). The organic layers was dried over anhydrous Na$_2$SO$_4$ and filtered. The filtrate was concentrated under reduced pressure. The residue was purified by silica gel column chromatography, eluted with hexane/EtOAc (2:1) to afford 178 mg crude product as a yellow solid. The crude product (178 mg) was further purified by Prep-HPLC with the following conditions (Column: XBridge Shield RP18 OBD Column, 19×250 mm, 10 um; Mobile Phase A: Water (10 mmol/L NH$_4$HCO$_3$), Mobile Phase B: ACN; Flow rate: 20 mL/min; Gradient: 60 B to 75 B in 5.5 min. The fractions contained desired product were combined and concentrated to afford N-[3-[7-cyano-2-(methylamino)pyrido[2,3-d]pyrimidin-6-yl]-4-methylphenyl]-2-(trifluoromethyl)pyridine-4-carboxamide (25.7 mg, 36%) as a yellow solid. MS ESI calculated for C$_{23}$H$_{16}$F$_3$N$_7$O [M+H]$^+$, 464.14; found 464.20. $^1$H NMR (400 MHz, DMSO-d$_6$) δ 10.80 (s, 1H), 9.33 (s, 1H), 9.01-8.99 (m, 1H), 8.48-8.44 (m, 2H), 8.40-8.36 (m, 2H), 7.85-7.80 (m, 2H), 7.47-7.40 (m, 1H), 2.97 (d, J=4.8 Hz, 3H), 2.18 (s, 3H).

Example 73: N-[4-methyl-3-[2-(methylamino)-7-(trifluoromethyl)pyrido[2,3-d]pyrimidin-6-yl]phenyl]-2-(trifluoromethyl)pyridine-4-carboxamide

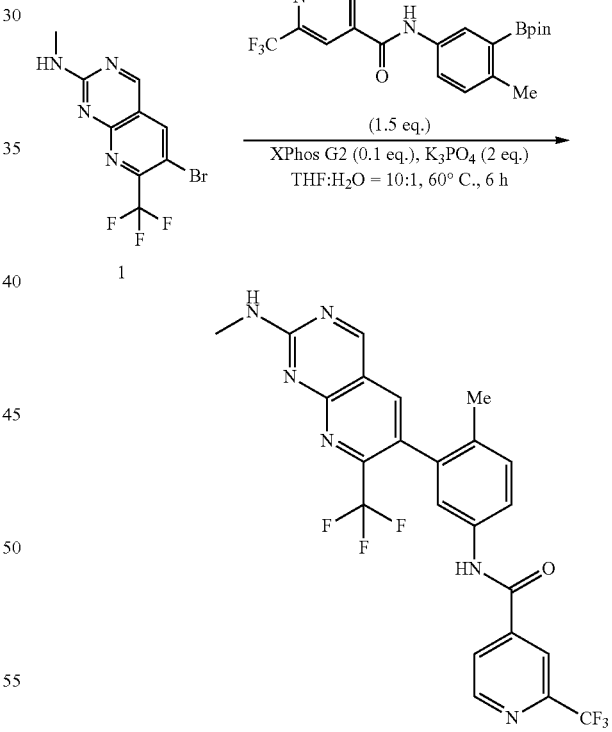

To a mixture of 6-bromo-N-methyl-7-(trifluoromethyl)pyrido[2,3-d]pyrimidin-2-amine (50.00 mg, 0.16 mmol) and N-[4-methyl-3-(4,4,5,5-tetramethyl-1,3,2-dioxaborolan-2-yl)phenyl]-2-(trifluoromethyl)pyridine-4-carboxamide (99.21 mg, 0.24 mmol) in THF: H$_2$O=10:1 (0.55 mL) were added XPhos palladium(II) biphenyl-2-amine chloride (12.81 mg, 0.016 mmol) and K$_3$PO$_4$ (69.13 mg, 0.326 mmol). The reaction mixture was degassed with nitrogen for three times and stirred for 6 h at 60° C. The resulting mixture was concentrated under reduced pressure. The residue was diluted with EA (10 mL). The resulting mixture was washed with water (3×10 mL) and brine (10 mL). The organic layers was dried over anhydrous $Na_2SO_4$ and filtered. The filtrate was concentrated under reduced pressure. The residue was purified by silica gel column chromatography, eluted with PE/EA (2:1). The fractions contained desired product were combined and concentrated to afford the crude product (98 mg). The crude was further purified by Prep-HPLC with the following conditions: Column: XBridge C18 OBD Prep Column, 100 Å, 5 um, 19 mm×250 mm; Mobile Phase A: Water (10 mmol/L $NH_4HCO_3$), Mobile Phase B: ACN; Flow rate: 20 mL/min; Gradient: 68 B to 90 B in 5.3 min. The fractions contained desired product were combined and concentrated to afford N-[4-methyl-3-[2-(methylamino)-7-(trifluoromethyl)pyrido[2,3-d]pyrimidin-6-yl]phenyl]-2-(trifluoromethyl)pyridine-4-carboxamide (60.0 mg, 73%) as an off-white solid. MS ESI calculated for $C_{23}H_{16}F_6N_6O$ $[M+H]^+$, 507.13, found 507.15. $^1$H-NMR (400 MHz, DMSO-$d_6$) δ 10.72 (s, 1H), 9.30 (s, 1H), 8.99-8.98 (m, 1H), 8.36-8.33 (m, 2H), 8.21-8.18 (m, 2H), 7.79-7.77 (m, 1H), 7.68 (s, 1H), 7.39-7.37 (m, 1H), 3.00-2.97 (m, 3H), 2.02 (s, 3H). F-NMR (376 MHz, DMSO-$d_6$) δ −62.71 (3F), −66.47 (3F).

The compounds in Table 11 were prepared using procedures similar to those described in Example 73 using appropriate starting materials.

Example 76: 4-([4-methyl-3-[7-methyl-2-(methylamino)pyrido[2,3-d]pyrimidin-6-yl]phenyl]carbamoyl)-2-(trifluoromethyl)pyridin-1-ium-1-olate

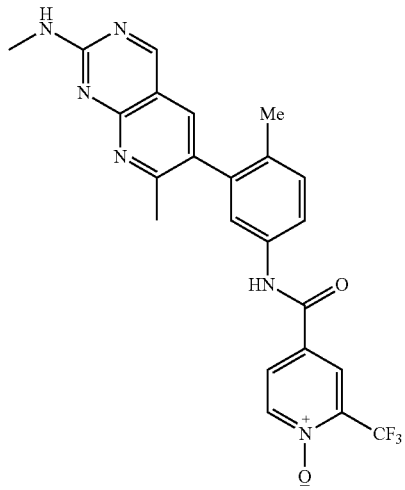

Step 1:
4-carboxy-2-(trifluoromethyl)pyridin-1-ium-1-olate

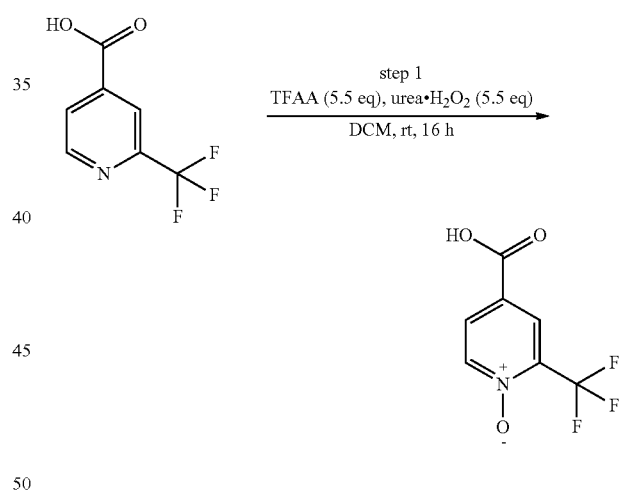

To a stirred mixture of 2-(trifluoromethyl)pyridine-4-carboxylic acid (1.00 g, 5.23 mmol) and peroxol; urea (2.74 g, 29.09 mmol) in DCM (25.00 mL) was added TFAA (4.05 mL, 19.267 mmol) dropwise at 0° C. under nitrogen atmosphere. The reaction mixture was stirred for 16 h at room temperature under nitrogen atmosphere. The resulting mixture was filtered. The filter cake was washed with DCM (3×5 mL). The filtrate was washed with water (3×20 mL). The aqueous layers were combined and extracted with EtOAc (3×50 mL). The combined organic layers was dried over anhydrous $Na_2SO_4$. After filtration, the filtrate was concentrated under reduced pressure to afford 4-carboxy-2-(trifluoromethyl)pyridin-1-ium-1-olate (0.49 g, 45%) as an off-white solid which was used directly to next step without further purification. MS ESI calculated for $C_7H_4F_3NO_3$ $[M-H]^-$, 206.01, found 206.00.

TABLE 11

| Example # | Structure | Exact Mass $[M + H]^+$ |
|---|---|---|
| 74 | 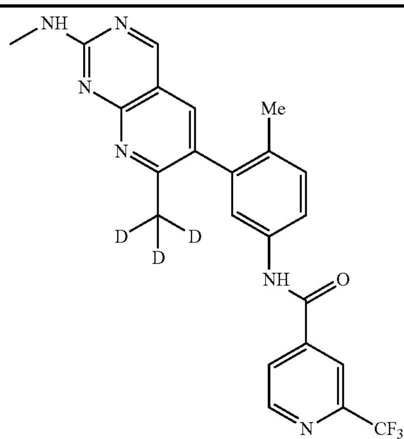 | Calc'd 456.18; found 456.10. |
| 75 | 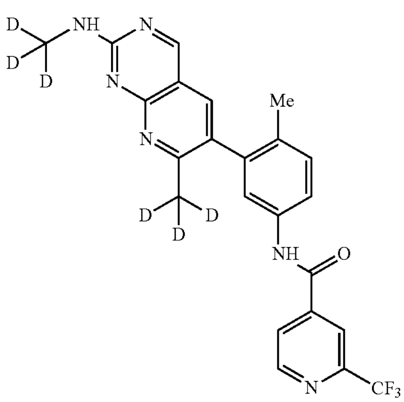 [SMILES: [2H]C([2H])([2H])Nc1ncc2cc(-c3cc(NC(=O)c4ccnc(C(F)(F)F)c4)ccc3C)c(C([2H])([2H])[2H])nc2n1] | Calc'd 459.19; found 459.05 |

Step 2: 4-([4-methyl-3-[7-methyl-2-(methylamino) pyrido[2,3-d]pyrimidin-6-yl]phenyl]carbamoyl)-2-(trifluoromethyl)pyridin-1-ium-1-olate

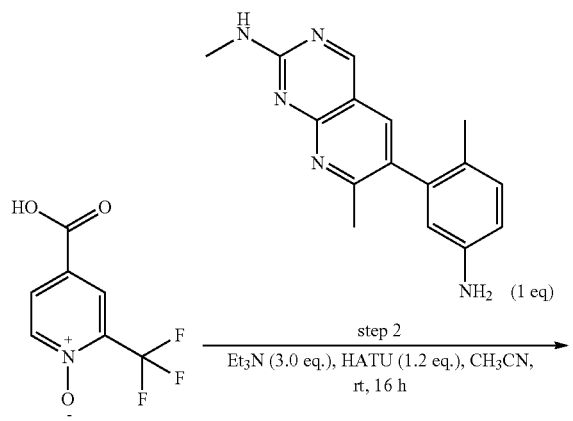

To a stirred mixture of 6-(5-amino-2-methylphenyl)-N,7-dimethylpyrido[2,3-d]pyrimidin-2-amine (0.25 g, 0.90 mmol), 4-carboxy-2-(trifluoromethyl)pyridin-1-ium-1-olate (0.19 g, 0.94 mmol), HATU (0.41 g, 1.07 mmol) and ACN (5.00 mL) was added TEA (0.27 g, 2.69 mmol) dropwise at 0° C. under nitrogen atmosphere. The reaction mixture was stirred for 16 h at room temperature. The resulting mixture was concentrated under reduced pressure. The residue was purified by silica gel column chromatography, eluted with EA/EtOH (3/1) in PE (90%). The fractions contained desired product were combined and concentrated to afford the crude product. The crude product was further purified by trituration with ACN to afford 4-([4-methyl-3-[7-methyl-2-(methylamino)pyrido[2,3-d]pyrimidin-6-yl]phenyl]carbamoyl)-2-(trifluoromethyl)pyridin-1-ium-1-olate (0.11 g, 26%) as a light yellow solid. MS ESI calculated for $C_{23}H_{19}F_3N_6O_2$ [M+H]$^+$, 469.15, found 469.00. H-NMR (400 MHz, $d_6$-DMSO) δ 10.59 (s, 1H), 9.10 (s, 1H), 8.62 (d, J=6.8 Hz, 1H), 8.47-8.46 (m, 1H), 8.21-8.19 (m, 1H), 7.96 (s, 1H), 7.76-7.73 (m, 2H), 7.60-7.59 (m, 1H), 7.39-7.37 (m, 1H), 2.93 (d, J=4.4 Hz, 3H), 2.34 (s, 3H), 2.04 (s, 3H).

Example 77: (3S)—N-[3-[7-cyano-2-(methylamino) pyrido[2,3-d]pyrimidin-6-yl]-4-methylphenyl]-3-(2, 2,2-trifluoroethyl)pyrrolidine-1-carboxamide Step 1: (3S)—N-[4-methyl-3-[2-(methylamino)-7-oxo-8H-pyrido[2,3-d]pyrimidin-6-yl]phenyl]-3-(2,2, 2-trifluoroethyl)pyrrolidine-1-carboxamide

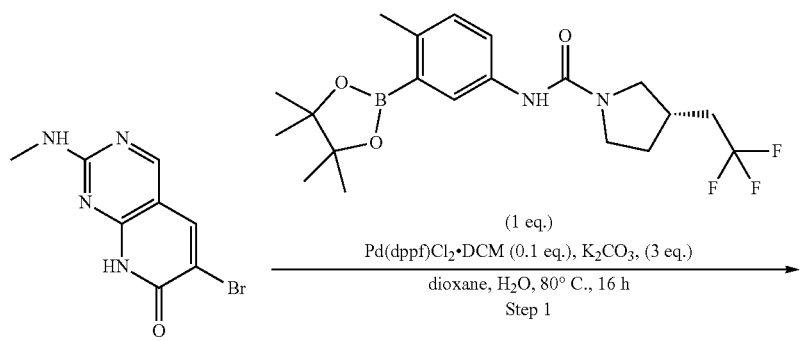

-continued

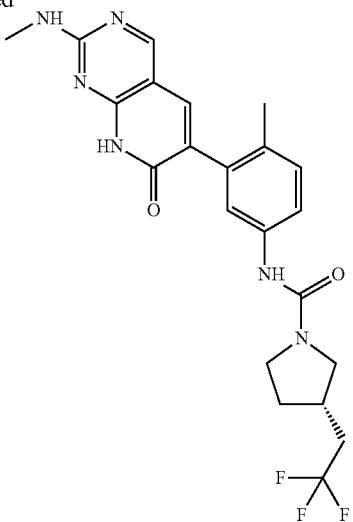

To a stirred solution of (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide (0.20 g, 0.49 mmol) and 6-bromo-2-(methylamino)-8H-pyrido[2,3-d]pyrimidin-7-one (0.14 g, 0.53 mmol), $K_2CO_3$ (0.20 g, 1.46 mmol) in dioxane (4.80 mL), $H_2O$ (1.20 mL) was added Pd(dppf)$Cl_2 \cdot CH_2Cl_2$ (39.62 mg, 0.05 mmol). The reaction mixture was degassed with nitrogen for three times and stirred for 16 h at 80° C. The resulting mixture was concentrated under reduced pressure. The residue was purified by silica gel column chromatography, eluted with hexane/(EtOAc:EtOH=3:1) (1:1). The fractions contained desired product were combined and concentrated to afford (3S)—N-[4-methyl-3-[2-(methylamino)-7-oxo-8H-pyrido[2,3-d]pyrimidin-6-yl]phenyl]-3-(2,2,2-trifluoroethyl)pyrrolidine-1-carboxamide (0.27 g, crude) as a yellow solid. MS ESI calculated for $C_{22}H_{23}F_3N_6O_2$ [M+H]$^+$, 461.18, found 461.20.

Step 2: (3S)—N-[3-[7-bromo-2-(methylamino)pyrido[2,3-d]pyrimidin-6-yl]-4-methylphenyl]-3-(2,2,2-trifluoroethyl)pyrrolidine-1-carboxamide

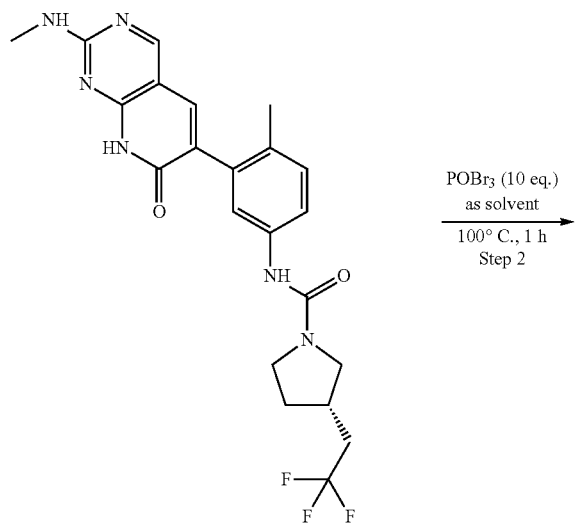

POBr$_3$ (10 eq.)
as solvent
$\xrightarrow{\text{100° C., 1 h}}$
Step 2

-continued

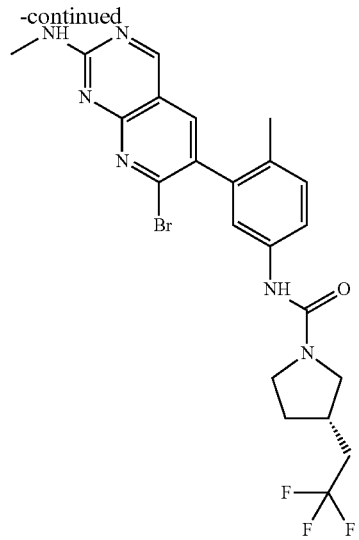

To a mixture of (3S)—N-[4-methyl-3-[2-(methylamino)-7-oxo-8H-pyrido[2,3-d]pyrimidin-6-yl]phenyl]-3-(2,2,2-trifluoroethyl)pyrrolidine-1-carboxamide (0.25 g, 0.54 mmol) was added POBr$_3$ (1.56 g, 5.43 mmol) at room temperature. The reaction mixture was stirred for 1 h at 100° C. The resulting mixture was quenched with NaHCO$_3$ at 0° C. The resulting mixture was extracted with EtOAc (3×20 mL). The combined organic layers was washed with brine (15 mL), dried over anhydrous Na$_2$SO$_4$ and filtered. The filtrate was concentrated under reduced pressure. The residue was purified by silica gel column chromatography, eluted with hexane/(EtOAc:EtOH=3:1) (1:1). The fractions contained desired product were combined and concentrated to afford (3S)—N-[3-[7-bromo-2-(methylamino)pyrido[2,3-d]pyrimidin-6-yl]-4-methylphenyl]-3-(2,2,2-trifluoroethyl)pyrrolidine-1-carboxamide (80 mg, 28%) as a yellow solid. MS ESI calculated for $C_{22}H_{22}BrF_3N_6O$ [M+H]$^+$, 523.10, found 523.15.

Step 3: (3S)—N-[3-[7-cyano-2-(methylamino)pyrido[2,3-d]pyrimidin-6-yl]-4-methylphenyl]-3-(2,2,2-trifluoroethyl)pyrrolidine-1-carboxamide

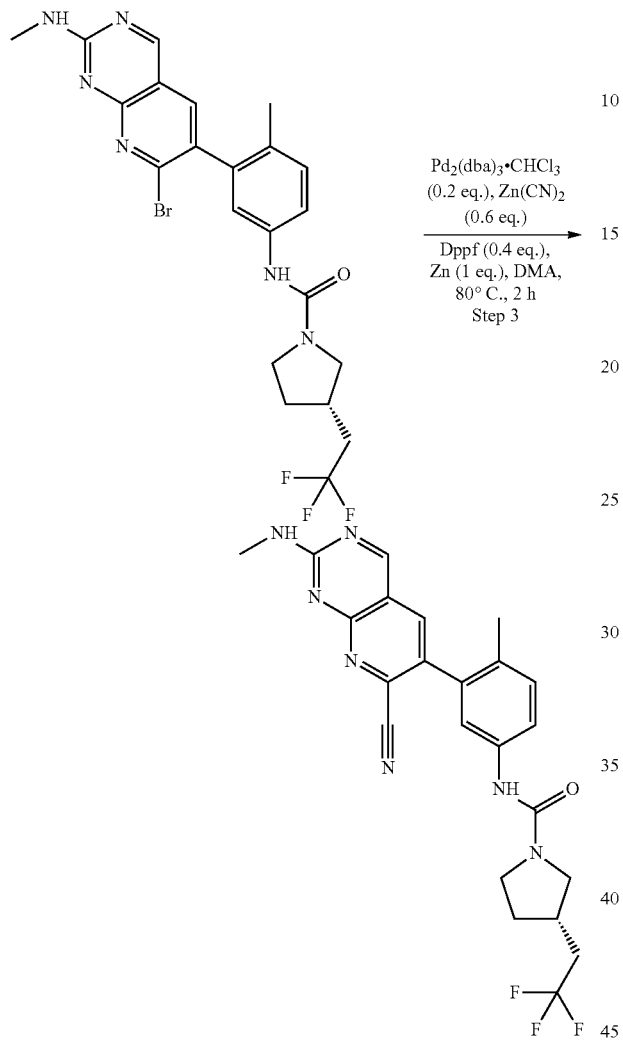

To a stirred mixture of (3S)—N-[3-[7-bromo-2-(methylamino)pyrido[2,3-d]pyrimidin-6-yl]-4-methylphenyl]-3-(2,2,2-trifluoroethyl)pyrrolidine-1-carboxamide (60.00 mg, 0.12 mmol), Zn (7.50 mg, 0.12 mmol), Dppf (25.33 mg, 0.05 mmol), Zn(CN)$_2$ (8.08 mg, 0.07 mmol) in DMA (1.50 mL) was added Pd$_2$(dba)$_3$·CHCl$_3$ (23.73 mg, 0.02 mmol). The reaction mixture was degassed with nitrogen for three times and stirred for 2 h at 80° C. The resulting mixture was filtered. The filtrate was concentrated under reduced pressure. The residue was purified by silica gel column chromatography, eluted with hexane/(EtOAc:EtOH=3:1) (1:1). The fractions contained desired product were combined and concentrated to afford the crude product (50 mg) which was purified by Prep-HPLC with the following conditions Column: XBridge C18 OBD Prep Column, 100 Å, 10 μm, 19 mm×250 mm; Mobile Phase A: Water (10 mmol/L NH$_4$HCO$_3$), Mobile Phase B: ACN; Flow rate: 20 mL/min; Gradient: 30 B to 50 B in 5.8 min; 254/210 nm; RT: 5.52 min. The fractions contained desired product were combined and concentrated to afford (3S)—N-[3-[7-cyano-2-(methylamino)pyrido[2,3-d]pyrimidin-6-yl]-4-methylphenyl]-3-(2,2,2-trifluoroethyl)pyrrolidine-1-carboxamide (15 mg, 28%) as a yellow solid. MS ESI calculated for C$_{23}$H$_{22}$F$_3$N$_7$O [M+H]$^+$, 470.18, found 0.470.25. $^1$H-NMR (400 MHz, d6-DMSO) δ 9.32 (s, 1H), 8.41 (s, 1H), 8.28-8.25 (m, 2H), 7.58-7.54 (m, 2H), 7.27-7.25 (m, 1H), 3.70-3.66 (m, 1H), 3.56-3.52 (m, 1H), 3.33-3.31 (m, 1H), 3.06-2.96 (m, 4H), 2.51-2.41 (m, 3H), 2.12-2.10 (m, 4H), 1.67-1.61 (m, 1H).

Example 78: (3R)—N-[3-[7-cyano-2-(methylamino)pyrido[2,3-d]pyrimidin-6-yl]-4-methylphenyl]-3-(trifluoromethoxy)pyrrolidine-1-carboxamide

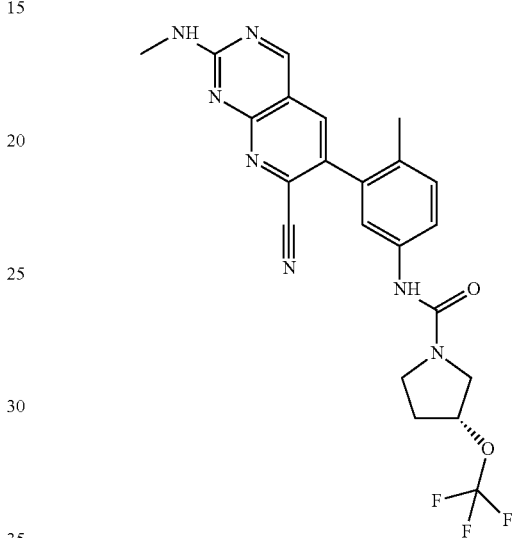

The title compound was prepared using procedures similar to those described in Example 79 using (3R)—N-[4-methyl-3-(4,4,5,5-tetramethyl-1,3,2-dioxaborolan-2-yl)phenyl]-3-(trifluoromethoxy)pyrrolidine-1-carboxamide instead of (3S)—N-[4-methyl-3-(4,4,5,5-tetramethyl-1,3,2-dioxaborolan-2-yl)phenyl]-3-(2,2,2-trifluoroethyl)pyrrolidine-1-carboxamide to afford the title compound as a solid.

II. Biological Evaluation

Example 1: Kinase Assay Protocol

Protein kinase assay: Assay platform was used to measure kinase/inhibitor interactions as described previously (Anastassiadis et al., 2011). In brief, for each reaction, kinase and substrate were mixed in a buffer containing 20 mM HEPES (pH 7.5), 10 mM MgCl2, 1 mM EGTA, 0.02% Brij35, 0.02 mg/mL BSA, 0.1 mM Na3VO4, 2 mM DTT, and 1% DMSO. All compounds were solubilized in DMSO. Compounds were then added to each reaction mixture via acoustic dispense using an ECHO 550 nanoliter dispenser. For human RAF1 testing, human MEK1 (K97R) was used as a substrate at a concentration of 3 micromolar, with a final ATP concentration of 10 micromolar. For human BRAF testing, human MEK1 (K97R) was used as a substrate at 1 micromolar concentration, with a final ATP concentration of 25 micromolar. Compounds were tested in 10-dose IC$_{50}$ mode with a 3-fold serial dilution starting at 10 micromolar. After a 20-min incubation, ATP (Sigma-Aldrich, St. Louis, Mo. 63178) and [g33P] ATP (specific activity 10 microCi/microliter) purchased at PerkinElmer (Boston, Mass., 02118

Cat #BLU 003H250UC) were added at a final total concentration of 10 mM. Reactions were carried out at room temperature for 2 hr and spotted onto P81 ionexchange cellulose chromatography paper (Reaction Biology). Filter paper was washed in 0.75% phosphoric acid to remove unincorporated ATP. The percent remaining kinase activity relative to a vehicle-containing (DMSO) kinase reaction was calculated for each kinase/inhibitor pair. $IC_{50}$ values were calculated using Prism 5 (GraphPad).

Representative data for exemplary compounds is presented in Table 12.

TABLE 12

| Synthetic Chemistry Example | RAF-1 $IC_{50}$ |
| --- | --- |
| 1 | A |
| 2 | A |
| 3 | A |
| 4 | B |
| 5 | B |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |

Note:
Biochemical assay $IC_{50}$ data are designated within the following ranges:
A: ≤0.010 μM
B: >0.010 μM to ≤0.100 μM
C: >0.100 μM to ≤1 μM III. Preparation of Pharmaceutical Dosage Forms Example 1: Oral Capsule The active ingredient is a compound of Table 1, or a pharmaceutically acceptable salt or solvate thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example 2: Solution for Injection

The active ingredient is a compound of Table 1, or a pharmaceutically acceptable salt thereof, and is formulated as a solution in sesame oil at a concentration of 50 mg-eq/mL.

The examples and embodiments described herein are for illustrative purposes only and various modifications or changes suggested to persons skilled in the art are to be included within the spirit and purview of this application and scope of the appended claims.

We claim:

1. A compound, or pharmaceutically acceptable salt or solvate thereof, having the structure of Formula (I):

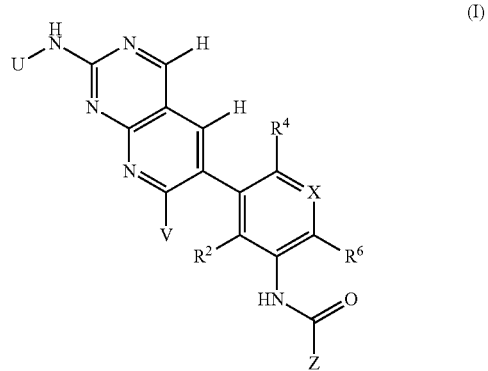

wherein,
V is hydrogen, halogen, —CN, optionally substituted C1-C4 alkyl, —CD$_3$, optionally substituted C1-C4 alkoxy, optionally substituted C1-C4 alkenyl, or optionally substituted C1-C4 alkynyl;
U is selected from optionally substituted alkyl, —CD$_3$, optionally substituted cycloalkyl, optionally substituted cycloalkylalkyl, optionally substituted heterocyclyl, optionally substituted heterocyclylalkyl, optionally substituted heteroaryl, optionally substituted heteroaralkyl group, optionally substituted —COalkyl, optionally substituted —COcycloalkyl;
X is C—H, C-D, or C—F;
R$^2$ is H, D or F;
R$^4$ is halogen, optionally substituted C1-C3 alkyl, —CD$_3$, or optionally substituted C1-C3 alkoxy;
R$^6$ is H, D, Cl or F; and
Z is an optionally substituted nitrogen-containing heteroaryl group.

2. The compound of claim 1, or pharmaceutically acceptable salt or solvate thereof, wherein V is H.

3. The compound of claim 1, or pharmaceutically acceptable salt or solvate thereof, wherein V is Me.

4. The compound of claim 1, or pharmaceutically acceptable salt or solvate thereof, wherein X is C—H.

5. The compound of claim 1, or pharmaceutically acceptable salt or solvate thereof, wherein R$^2$ is H.

6. The compound of claim 1, or pharmaceutically acceptable salt or solvate thereof, wherein R$^4$ is optionally substituted C1-C3 alkyl.

7. The compound of claim 1, or pharmaceutically acceptable salt or solvate thereof, wherein R$^4$ is methyl.

8. The compound of claim 1, or pharmaceutically acceptable salt or solvate thereof, wherein R$^6$ is H.

9. The compound of claim 1, or pharmaceutically acceptable salt or solvate thereof, wherein R$^6$ is F.

10. The compound of claim 1, or pharmaceutically acceptable salt or solvate thereof, wherein U is optionally substituted alkyl.

11. The compound of claim 1, or pharmaceutically acceptable salt or solvate thereof, wherein U is optionally substituted cycloalkyl.

12. The compound of claim 1, or pharmaceutically acceptable salt or solvate thereof, wherein Z is an optionally substituted monocyclic nitrogen-containing heteroaryl group.

13. The compound of claim 12, or pharmaceutically acceptable salt or solvate thereof, wherein the optionally substituted monocyclic nitrogen-containing heteroaryl group is a 5-membered optionally substituted monocyclic nitrogen-containing heteroaryl group.

14. The compound of claim 13, or pharmaceutically acceptable salt or solvate thereof, wherein the 5-membered optionally substituted monocyclic nitrogen-containing heteroaryl group is selected from an optionally substituted pyrrole, optionally substituted oxazole, optionally substituted thiazole, optionally substituted imidazole, optionally substituted pyrazole, optionally substituted isoxazole, or optionally substituted isothiazole.

15. The compound of claim 13, or pharmaceutically acceptable salt or solvate thereof, wherein the 5-membered optionally substituted monocyclic nitrogen-containing heteroaryl group is an optionally substituted pyrazole.

16. The compound of claim 12, or pharmaceutically acceptable salt or solvate thereof, wherein the optionally substituted monocyclic nitrogen-containing heteroaryl group is a 6-membered optionally substituted monocyclic nitrogen-containing heteroaryl group.

17. The compound of claim 16, or pharmaceutically acceptable salt or solvate thereof, wherein the 6-membered optionally substituted monocyclic nitrogen-containing heteroaryl group is selected from an optionally substituted pyridine, optionally substituted pyridazine, optionally substituted pyrimidine, optionally substituted pyrazine or optionally substituted triazene.

18. The compound of claim 16, or pharmaceutically acceptable salt or solvate thereof, wherein the 6-membered optionally substituted monocyclic nitrogen-containing heteroaryl group is an optionally substituted pyridine.

19. The compound of claim 1, or pharmaceutically acceptable salt or solvate thereof, wherein Z is substituted with a halogen, or an optionally substituted C1-C4 alkyl.

20. The compound of claim 19, or pharmaceutically acceptable salt or solvate thereof, wherein the optionally substituted C1-C4 alkyl is an optionally substituted C1-C2 alkyl.

21. The compound of claim 19, or pharmaceutically acceptable salt or solvate thereof, wherein the optionally substituted C1-C4 alkyl is an optionally substituted Cl alkyl.

22. The compound of claim 21, or pharmaceutically acceptable salt or solvate thereof, wherein the optionally substituted Cl alkyl is a —CF$_3$ group.

23. The compound of claim 18, or pharmaceutically acceptable salt or solvate thereof, wherein the optionally substituted pyridine is substituted with at least a —CF$_3$ group.

24. The compound of claim 23, or pharmaceutically acceptable salt or solvate thereof, wherein the optionally substituted pyridine is a 2-trifluoromethylpyridin-4-yl group.

25. The compound of claim 1, or pharmaceutically acceptable salt or solvate thereof, wherein V is Me, U is optionally substituted alkyl, and Z is a 6-membered optionally substituted monocyclic nitrogen-containing heteroaryl group.

26. The compound of claim 25, or pharmaceutically acceptable salt or solvate thereof, wherein the 6-membered optionally substituted nitrogen-containing heteroaryl group is substituted with a halogen, or an optionally substituted C1-C4 alkyl.

27. The compound of claim 26, or pharmaceutically acceptable salt or solvate thereof, wherein the 6-membered optionally substituted monocyclic nitrogen-containing heteroaryl group is an optionally substituted pyridine.

28. The compound of claim 27, or pharmaceutically acceptable salt or solvate thereof, wherein the optionally substituted pyridine is substituted with at least a —CF$_3$ group.

29. A pharmaceutical composition comprising at least one pharmaceutically acceptable excipient and a compound of Formula (I), or pharmaceutically acceptable salt or solvate thereof, as described in claim 1.

* * * * *